United States Patent
Donohoue et al.

(10) Patent No.: US 9,580,727 B1
(45) Date of Patent: Feb. 28, 2017

(54) COMPOSITIONS AND METHODS OF ENGINEERED CRISPR-CAS9 SYSTEMS USING SPLIT-NEXUS CAS9-ASSOCIATED POLYNUCLEOTIDES

(71) Applicant: Caribou Biosciences, Inc., Berkeley, CA (US)

(72) Inventors: Paul Daniel Donohoue, Berkeley, CA (US); Andrew Paul May, San Francisco, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 48 days.

(21) Appl. No.: 14/835,675

(22) Filed: Aug. 25, 2015

Related U.S. Application Data

(60) Provisional application No. 62/202,715, filed on Aug. 7, 2015, provisional application No. 62/209,334, filed on Aug. 24, 2015.

(51) Int. Cl.
*C12N 15/87* (2006.01)
*C12N 9/22* (2006.01)

(52) U.S. Cl.
CPC ............. *C12N 15/87* (2013.01); *C12N 9/22* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,795,965 B2 | 8/2014 | Zhang |
| 8,841,260 B2 | 9/2014 | Miller et al. |
| 8,865,406 B2 | 10/2014 | Zhang et al. |
| 8,871,445 B2 | 10/2014 | Cong et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2011/0223638 A1 | 9/2011 | Wiedenheft et al. |
| 2013/0130248 A1 | 5/2013 | Haurwitz et al. |
| 2014/0068797 A1 | 3/2014 | Doudna et al. |
| 2014/0294773 A1 | 10/2014 | Brouns et al. |
| 2014/0302563 A1 | 10/2014 | Doudna et al. |
| 2014/0315985 A1* | 10/2014 | May et al. ............... C12Q 1/68 514/44 R |
| 2015/0024499 A1 | 1/2015 | Brouns et al. |
| 2015/0045546 A1 | 2/2015 | Siksnys et al. |
| 2015/0050699 A1 | 2/2015 | Siksnys et al. |
| 2015/0059010 A1 | 2/2015 | Cigan et al. |
| 2015/0082478 A1 | 3/2015 | Cigan et al. |
| 2015/0152398 A1 | 6/2015 | Doudna et al. |

OTHER PUBLICATIONS

Briner et al. (2014) Guide RNA Functional Modules Direct Cas9 Activity and Orthogonality. Molecular Cell, 56:333-339.*
Jinek et al. (2012) A Programmable Dual-RNA—Guided DNA Endonuclease in Adaptive Bacterial Immunity. Science, 337:816-821.*
Jinek, M., et al., "A programmable dual-RNA-guided DNA endonuclease in adaptive bacterial immunity," Science 337 (6096):816-21 (2012).
Jinek, M., et al., "A programmable dual-RNA-guided DNA endonuclease in adaptive bacterial immunity," Science 337 (6096):816-21 (2012); Supplemental Materials.
Briner, A., et al., "Guide RNA Functional Modules Direct Cas9 Activity and Orthogonality," Molecular Cell 56(2):333-339 (2014).
Wright, A. V., et al., "Rational design of a split-Cas9 enzyme complex," PNAS 112(10):2984-2989 (2015).

* cited by examiner

*Primary Examiner* — Neil P Hammell
(74) *Attorney, Agent, or Firm* — Gary R. Fabian; Barbara G. McClung

(57) ABSTRACT

The present specification discloses engineered Type II CRISPR-Cas9 systems comprising split-nexus Cas9-associated polynucleotides (sn-casPNs), including systems comprising three split-nexus Cas9-associated polynucleotides (sn1-casPN/sn2-casPN/sn3-casPN) and systems comprising two split-nexus Cas9-associated polynucleotides (sn1-casPN/sn2-casPN). Together with a Cas9 protein, the sn-casPNs facilitate site-specific modifications, including cleavage and mutagenesis, of a target polynucleotide in vitro and in vivo. Furthermore, the engineered Type II CRISPR-Cas9 systems comprising sn-casPNs are useful in methods of regulating expression of a target nucleic acid. Methods are described herein for the creation of a variety of engineered Type II CRISPR-Cas9 systems comprising two or more sn-casPNs. Polynucleotide sequences, expression cassettes, vectors, compositions, and kits for carrying out a variety of methods are also described. Furthermore, the present specification provides genetically modified cells, compositions of modified cells, transgenic organisms, pharmaceutical compositions, as well as a variety of compositions and methods involving the engineered Type II CRISPR-Cas9 systems.

19 Claims, 22 Drawing Sheets

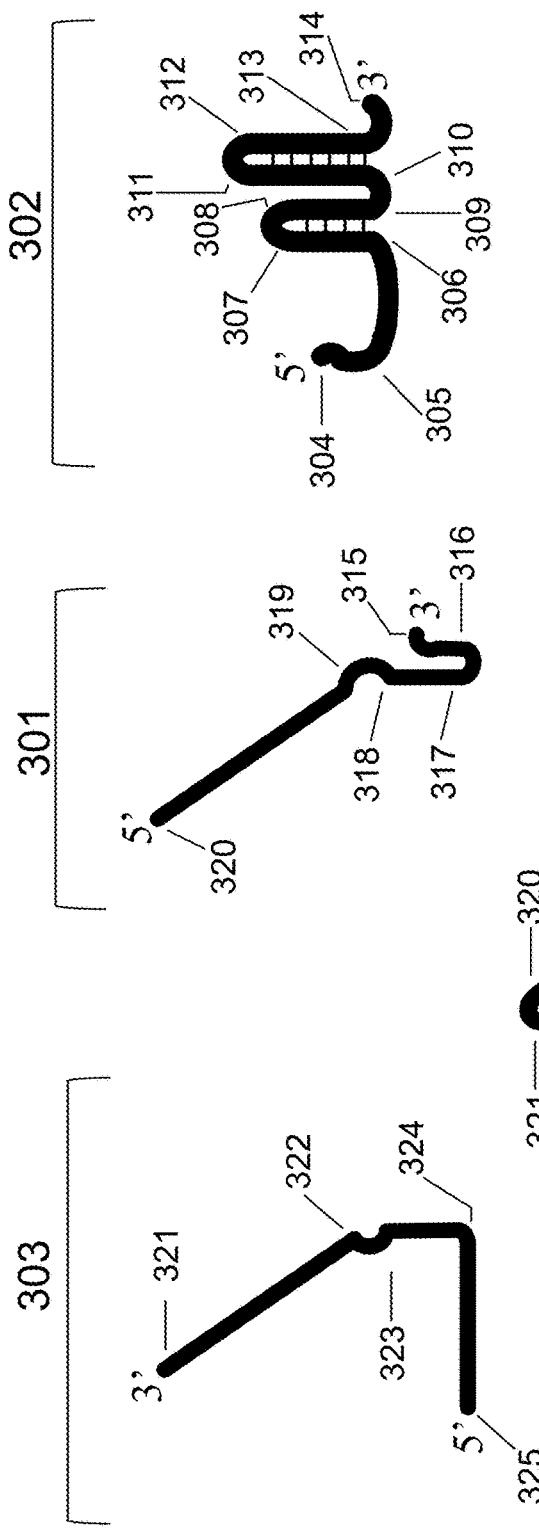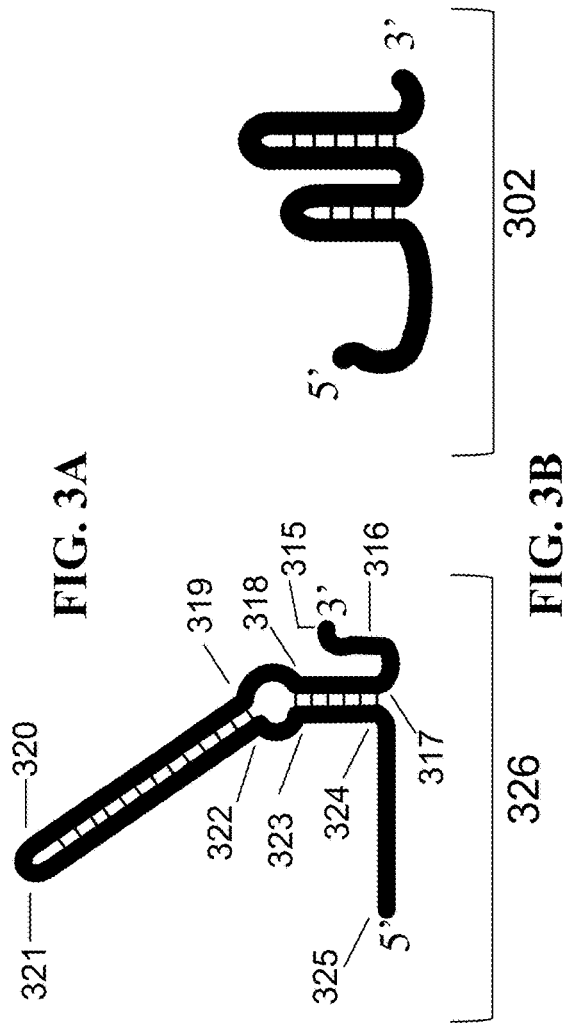
FIG. 3A
FIG. 3B

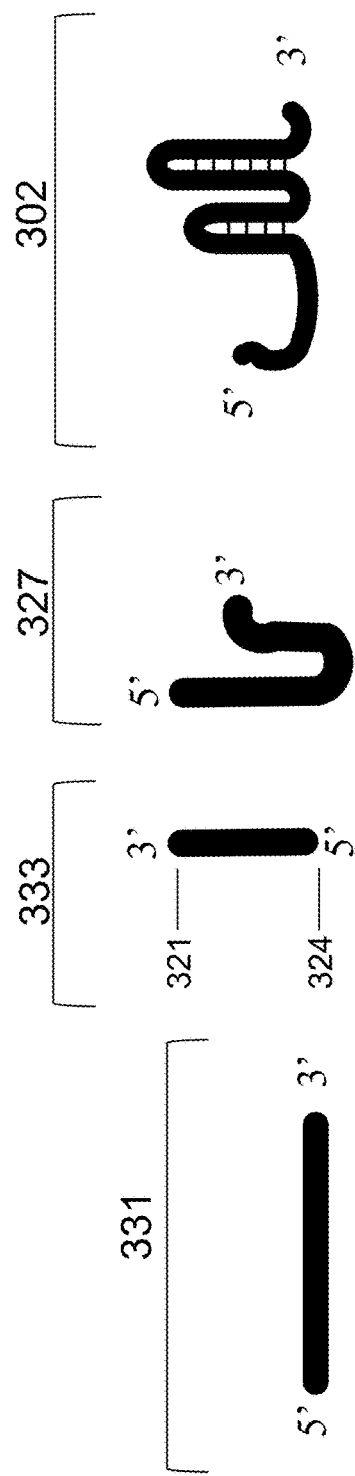
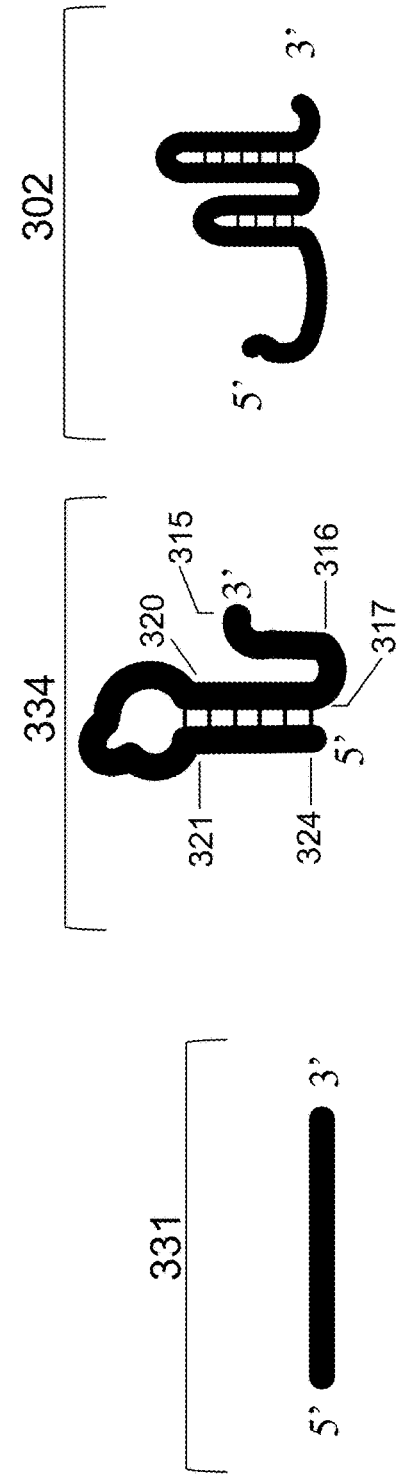
FIG. 3G
FIG. 3H

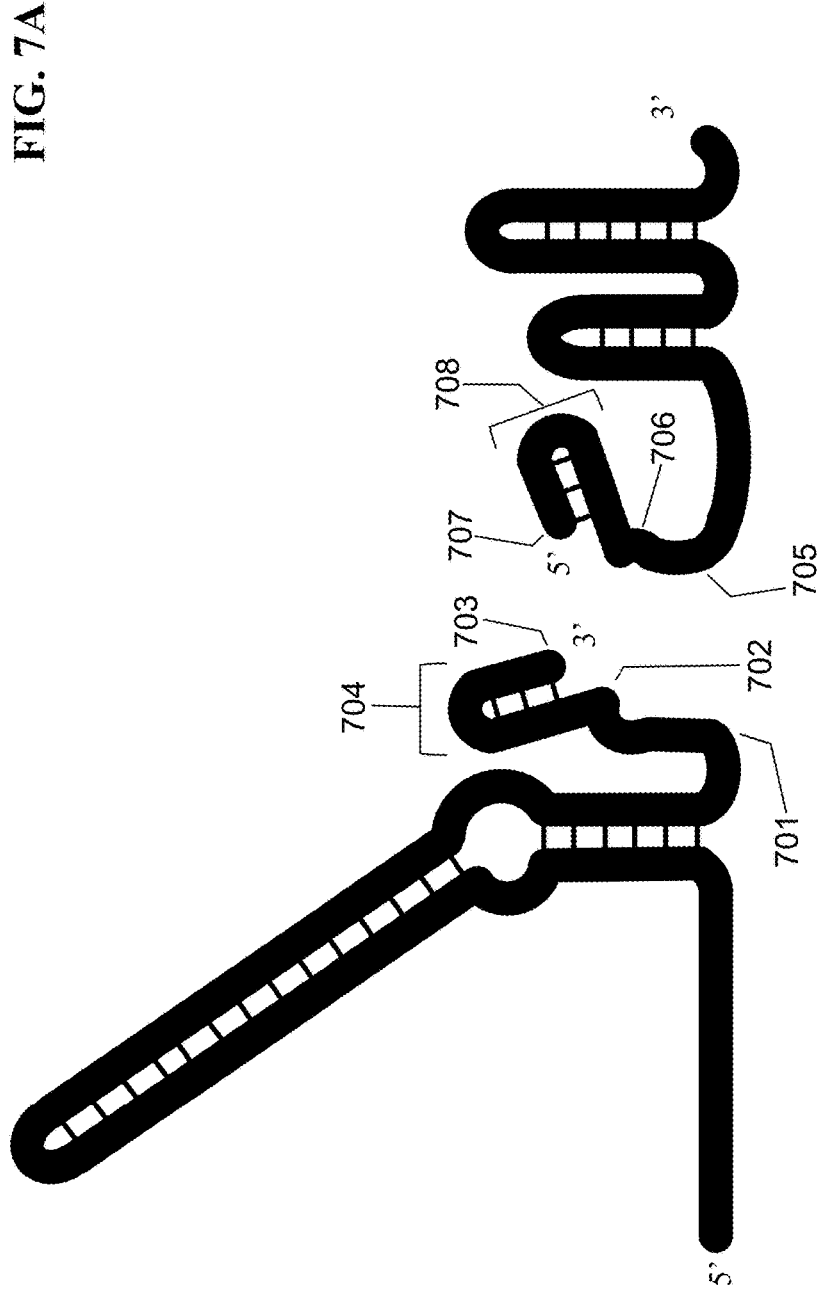

| 1 | CAAAACAGCAUAGCAAGUUAAAAUAAGGCUA/GUCC GUUAUCAACUUGAAAAGUGGCACCGAGUCGGUGCU UUUUUU | SEQ ID NO:1/ SEQ ID NO:2 |
|---|---|---|
| 2 | UAAAUCUUGCAGAAGCUACAACGAUAAGGCUUCA/U GCCGAAAUCAACACCCUGUCAUUUUAUGGCAGGGUG UUUUCGUUAUUUUUUU | SEQ ID NO:3/ SEQ ID NO:4 |
| 3 | CAAAAUAACAUAGCAAGUUAAAAUAAGGCUUU/GUC CGUUAUCAACUUUUAAUUAAGUAGCGCUGUUUCGGC GCUUUUUUU | SEQ ID NO:5/ SEQ ID NO:6 |
| 4 | CUGCGAAAUGAGAACCGUUGCUACAAUAAGGCCGUC UGAAAAGAU/GUGCCGCAACGCUCUGCCCCUUAAAGC UUCUGCUU | SEQ ID NO:7/ SEQ ID NO:8 |
| 5 | UUGGAGCUAUUCGAAACAACACAGCGAGUUAAAAUA AGGCUUU/GUCCGUACACAACUUGUAAAAGUGGCAC CCGAUUCGGGUGCGUUUUUUU | SEQ ID NO:9/ SEQ ID NO:10 |
| 6 | AUUGUACUUAUACCUAAAAUUACAGAAUCUACUAAA ACAAGGCAAA/AUGCCGUGUUUAUCUCGUCAACUUG UUGGCGAGAUUUUU | SEQ ID NO:11/ SEQ ID NO:12 |
| 7 | AGUCACUAACUUAAUUAAAUAGAACUGAACCUCAGU AAGCAUUGGCUC/GUUUCCAAUGUUGAUUGCUCCGCC GGUGCUCCUUAUUUUUAAGGGCGCCGGCUUUCUU | SEQ ID NO:13/ SEQ ID NO:14 |
| 8 | UAGCAAAUCGAGAGGCGGUCGCUUUCGCAAGCAAA UUGACCCCUU/GUGCGGGCUCGGCAUCCCAAGGUCAG CUGCCGGUUAUUAUCGAAAAGGCCCACCGCAAGCAG CGCGUGGGCCUUUUU | SEQ ID NO:15/ SEQ ID NO:16 |
| 9 | AAUUCUUGCUAAAGAAAUUUAAAAAGAGACUAAAA UAAGUGGUUUUUGGUC/AUCCACGCAGGGUUACAAU CCCUUUAAAACCAUUAAAAUUCAAAUAAACUAGGUU GUAUCAACUUAGUUUUUU | SEQ ID NO:17/ SEQ ID NO:18 |
| 10 | AUUGUCGCACUGCGAAAUGAGAACCGUUGCUACAAU AAGGCCGUCUGAAAAGAU/GUGCCGCAACGCUCUGCC CCUUAAAGCUUCUGCUUUAAGGGGCAUCGUUUAUUU CGGUUAAAAAUGCCGUCUGAAACCGGUUUUU | SEQ ID NO:19/ SEQ ID NO:20 |
| 11 | CUUGCACGGUUACUUAAAUCUUGCUGAGCCUACAAA GAUAAGGCUUU/AUGCCGAAUUCAAGCACCCCAUGU UUUGACAUGAGGUGCUUUU | SEQ ID NO:21/ SEQ ID NO:22 |

| A | AGTAATAATACGACTCACTATAG | SEQ ID NO:23 |
|---|---|---|
| B | AAGCACCGACTCGGTGCCACTTTT | SEQ ID NO:24 |
| C | TAATACGACTCACTATAGTCCGTTATCAACTTGAAAAAGTGGCACCGAGTCGGTGCTT | SEQ ID NO:25 |
| D | TAATACGACTCACTATAGCAGGACAGCATAGCAAGTTGAGATAAGGCTA | SEQ ID NO:26 |
| E | TAGCCTTATCTCAACTTGCTATGCTGTCCTGCTATAGTGAGTCGTATTA | SEQ ID NO:27 |
| F | TAATACGACTCACTATAGGGGCCACTAGGGACAGGATGTCTCAGAGCTATGCTGT | SEQ ID NO:28 |
| G | ACAGCATAGCTCTGAGACATCCTGTCCCTAGTGGCCCCTATAGTGAGTCGTATTA | SEQ ID NO:29 |
| H | CCCCGTTCTCCTGTGGATTC | SEQ ID NO:30 |
| I | ATCCTCTCTGGCTCCATCGT | SEQ ID NO:31 |
| J | CACTCTTTCCCTACACGACGCTCTTCCGATCTTCTGGCAAGGAGAGAGATGG | SEQ ID NO:32 |
| K | GGAGTTCAGACGTGTGCTCTTCCGATCTTATATTCCCAGGGCCGGTTA | SEQ ID NO:33 |
| L | CAAGCAGAAGACGGCATACGAGATTACGTGATGTGACTGGAGTTCAGACGTGTGCTC | SEQ ID NO:34 |
| M | AATGATACGGCGACCACCGAGATCTACACCGTCTAATACACTCTTTCCCTACACGACG | SEQ ID NO:35 |
| N | AATGATACGGCGACCACCGAGATCTACACTCTCTCCGACACTCTTTCCCTACACGACG | SEQ ID NO:36 |
| O | AATGATACGGCGACCACCGAGATCTACACTCGACTAGACACTCTTTCCCTACACGACG | SEQ ID NO:37 |
| P | AATGATACGGCGACCACCGAGATCTACACTTCTAGCTACACTCTTTCCCTACACGACG | SEQ ID NO:38 |
| Q | AATGATACGGCGACCACCGAGATCTACACCCTAGAGTACACTCTTTCCCTACACGACG | SEQ ID NO:39 |
| R | AATGATACGGCGACCACCGAGATCTACACCTATTAAGACACTCTTTCCCTACACGACG | SEQ ID NO:40 |
| S | GGCAGTAGCCTTATCTCAACTTGCTATGCTGTCCTGtttcCAGGACAGCATAGCTCTGAGAC | SEQ ID NO:41 |
| T | GGCAGTAGCCTTATCTCAAC | SEQ ID NO:42 |
| U | TAATACGACTCACTATAGGCAGGTCCGTTATCAACTTGAAAAAGTGGCACCGAGTCGGTGCTT | SEQ ID NO:43 |
| V | GGCAGtgaacTAGCCTTATCTCAACTTGCTATGCTGTCCTGttttcCAGGACAGCATAGCTCTGAGAC | SEQ ID NO:44 |
| W | GGCAGtgaacTAGCCTTATC | SEQ ID NO:45 |
| X | TAATACGACTCACTATAGGCAGctaagGTCCGTTATCAACTTGAAAAAGTGGCACCGAGTCGGTGCTT | SEQ ID NO:46 |

| Y | TAATACGACTCACTATAgggccactagggacaggatGTCTCAGAGCTATGCTGTC | SEQ ID NO:47 |
|---|---|---|
| Z | TAATACGACTCACTATAGTTTGTGTTTCCATAAACTGGTCTCAGAGCTATGCTGTC | SEQ ID NO:48 |
| AA | TAATACGACTCACTATAGCCCGCCACCACCAGGATGTGTCTCAGAGCTATGCTGTC | SEQ ID NO:49 |
| AB | TAATACGACTCACTATAGGCAGCCAGCATGATGAGACGTCTCAGAGCTATGCTGTC | SEQ ID NO:50 |
| AC | AAGCACCGACTCGGTGCCAC | SEQ ID NO:51 |
| AD | CACTCTTTCCCTACACGACGCTCTTCCGATCTACATGCACACCCATGTTTTG | SEQ ID NO:52 |
| AE | GGAGTTCAGACGTGTGCTCTTCCGATCTAACATTTCCAGGTGACAGGC | SEQ ID NO:53 |
| AF | CACTCTTTCCCTACACGACGCTCTTCCGATCTGTTCCGACGCTCCTTGAA | SEQ ID NO:54 |
| AG | GGAGTTCAGACGTGTGCTCTTCCGATCTCAGATGCGATGACCTTTGTG | SEQ ID NO:55 |
| AH | CACTCTTTCCCTACACGACGCTCTTCCGATCTaagaaaggCAAGAAGCCTGG | SEQ ID NO:56 |
| AI | GGAGTTCAGACGTGTGCTCTTCCGATCTGCTGGCCTGAGACATTCCTA | SEQ ID NO:57 |
| AJ | TAGCCTTATCTCAACTTGCTATGCTGTCCTGtttcCAGGACAGCATAGCTCTGAGAC | SEQ ID NO:58 |
| AK | TAATACGACTCACTATAGGGGCCACTAGGGACAGGATGTCTCAGAGCTATGCAGTCC | SEQ ID NO:59 |
| AL | CAGTAGCCTTATCTCAACTTGCTATGCAGTCCTGTTTCCAGGACTGCATAGCTCTGAGAC | SEQ ID NO:60 |
| AM | CTGCCTATACGGCAGTAGCCTTATCTCAACTTGCTATGCA | SEQ ID NO:61 |
| AN | TAATACGACTCACTATAGCTGCCGTATAGGCAGGTCCGTTATCAACTTGAAAAAGTG | SEQ ID NO:62 |
| AO | AAGCACCGACTCGGTGCCACTTTTTCAAGTTGATAACGGACCT | SEQ ID NO:63 |
| AP | GTCTAGCCTTATCTCAACTTGCTATGCAGTCCTGTTTCCAGGACTGCATAGCTCTGAGAC | SEQ ID NO:64 |
| AQ | CTGCCTATACGGCAGTGTCTAGCCTTATCTCAACTTGCTA | SEQ ID NO:65 |
| AR | TAATACGACTCACTATAGCTGCCGTATAGGCAGAGACAGTCCGTTATCAACTTGAAA | SEQ ID NO:66 |
| AS | AAGCACCGACTCGGTGCCACTTTTTCAAGTTGATAACGGACTGTCTCT | SEQ ID NO:67 |

FIG. 13 (cont.)

COMPOSITIONS AND METHODS OF ENGINEERED CRISPR-CAS9 SYSTEMS USING SPLIT-NEXUS CAS9-ASSOCIATED POLYNUCLEOTIDES

CROSS-REFERENCE TO RELATED APPLICATIONS

This application claims the benefit of U.S. Provisional Patent Application Ser. No. 62/202,715, filed 7 Aug. 2015, and U.S. Provisional Patent Application Ser. No. 62/209,334, filed 24 Aug. 2015, the contents of which are herein incorporated by reference in their entireties.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 24 Aug. 2015, is named CBI017-10_ST25.txt and is 20 kb in size.

TECHNICAL FIELD

The present invention relates to engineered Type II CRISPR-Cas9 systems.

BACKGROUND OF THE INVENTION

Genome engineering includes altering the genome by deleting, inserting, mutating, or substituting specific nucleic acid sequences. The alteration can be gene or location specific. Genome engineering can use nucleases to cut DNA, thereby generating a site for alteration. In certain cases, the cleavage can introduce double-stranded breaks in the target DNA. Double-stranded breaks can be repaired, e.g., by endogenous non-homologous end joining (NHEJ) or homology-directed repair (HDR). HDR relies on the presence of a template for repair. In some examples of genome engineering, a donor polynucleotide, or portion thereof, can be inserted into the break.

Clustered regularly interspaced short palindromic repeats (CRISPR) and associated Cas proteins constitute the CRISPR-Cas system. This system provides adaptive immunity against foreign DNA in bacteria (Barrangou, R., et al., "CRISPR provides acquired resistance against viruses in prokaryotes," Science 315, 1709-1712 (2007); Makarova, K. S., et al., "Evolution and classification of the CRISPR-Cas systems," Nat Rev Microbiol 9, 467-477 (2011); Garneau, J. E., et al., "The CRISPR/Cas bacterial immune system cleaves bacteriophage and plasmid DNA," Nature 468, 67-71 (2010); Sapranauskas, R., et al., "The *Streptococcus thermophilus* CRISPR/Cas system provides immunity in *Escherichia coli*," Nucleic Acids Res 39, 9275-9282 (2011)). The RNA-guided Cas9 endonuclease specifically targets and cleaves DNA in a sequence-dependent manner (Gasiunas, G., et al., "Cas9-crRNA ribonucleoprotein complex mediates specific DNA cleavage for adaptive immunity in bacteria," Proc Natl Acad Sci USA 109, E2579-E2586 (2012); Jinek, M., et al., "A programmable dual-RNA-guided DNA endonuclease in adaptive bacterial immunity," Science 337, 816-821 (2012); Sternberg, S. H., et al., "DNA interrogation by the CRISPR RNA-guided endonuclease Cas9," Nature 507, 62 (2014); Deltcheva, E., et al., "CRISPR RNA maturation by trans-encoded small RNA and host factor RNase III," Nature 471, 602-607 (2011)), and has been widely used for programmable genome editing in a variety of organisms and model systems (Cong, L., et al., "Multiplex genome engineering using CRISPR/Cas systems," Science 339, 819-823 (2013); Jiang, W., et al., "RNA-guided editing of bacterial genomes using CRISPR-Cas systems," Nat. Biotechnol. 31, 233-239 (2013); Sander, J. D. & Joung, J. K., "CRISPR-Cas systems for editing, regulating and targeting genomes," Nature Biotechnol. 32, 347-355. (2014)).

Jinek, M., et al., ("A programmable dual-RNA-guided DNA endonuclease in adaptive, bacterial immunity," Science 337(6096):816-21 (2012)) showed that in a subset of CRISPR-associated (Cas) systems the mature CRISPR (crRNA) that is base paired to trans-activating crRNA (tracrRNA) forms a two-part RNA structure that directs the CRISPR-associated protein Cas9 to introduce double-stranded breaks in target DNA. At sites complementary to the crRNA-guide (spacer) sequence, the Cas9 HNH nuclease domain cleaves the complementary strand and the Cas9 RuvC-like domain cleaves the non-complementary strand. Dual crRNA/tracrRNA molecules were engineered into single-chain crRNA/tracrRNA molecules. These single-chain crRNA/tracrRNA directed target sequence-specific Cas9 double-strand DNA cleavage.

Jinek, M., et al., designed two versions of single-chain crRNA/tracrRNA containing a target recognition sequence (spacer) at the 5' end followed by a hairpin structure retaining the base-pairing interactions that normally occur between the tracrRNA and the crRNA (see FIG. 5B of Jinek, M., et al.). For each single-chain crRNA/tracrRNA, the 3' end of crRNA was covalently attached to the 5' end of tracrRNA. In cleavage assays using plasmid DNA, Jinek, M., et al., observed that a 3' truncated single-chain crRNA/tracrRNA did not cleave target DNA as efficiently in the assay as a longer single-chain crRNA/tracrRNA that was not truncated at the 3' end (see FIG. 5B and FIG. S14 A, B, and C of Jinek, M., et al.). These data confirmed that the "5 to 12 positions beyond the tracrRNA:crRNA base-pairing interaction are important for efficient Cas9 binding and/or target recognition" (Jinek, M., et al., Science 337(6096):820 (2012)).

Briner, A., et al., ("Guide RNA Functional Modules Direct Cas9 Activity and Orthogonality," Molecular Cell 56(2), 2014, Pages 333-339) elucidated the molecular basis of selective Cas9/guide-RNA interactions by identifying and characterizing distinct sequence and structural modules within guide RNAs that direct Cas9 endonuclease activity and define orthogonality. They established six modules within native crRNA:tracrRNA duplexes and single guide RNAs (sgRNAs) across forty-one systems from three distinct Cas9 families. The six identified modules are the spacer, the lower stem, the bulge, the upper stem, the nexus hairpin, and 3' hairpins. These modules are illustrated with reference to an sgRNA in FIG. 2.

Using the sgRNA/Cas9 system from *Streptococcus pyogenes*, Briner, A., et al., showed that a bulge within the sgRNA is structurally necessary for DNA cleavage both in vitro and in vivo, whereas sequence substitutions are tolerated in other regions. Furthermore, expendable features can be removed to generate functional miniature sgRNAs. They also identified a conserved module "named the nexus; this feature exhibits sequence and structural features important for cleavage" (Briner, A., et al., page 2). They stated that this module, the nexus, is "necessary for DNA cleavage" (Briner, A., et al., Summary). The nexus hairpin confers activity to its cognate Cas9. The location of this nexus hairpin corresponds to the 5 to 12 positions beyond the tracrRNA:crRNA base-pairing interaction that are important for efficient Cas9 binding and/or target recognition as identified by Jinek, M., et al. (see above).

Briner, A., et al., showed that the general nexus hairpin shape with a GC-rich stem and an offset uracil was shared between the two *Streptococcus* families. In contrast, the idiosyncratic double stem of the nexus hairpin was unique to, and ubiquitous in, *Lactobacillus* systems. Some bases within the nexus hairpin were strictly conserved even between distinct families, including A52 and C55, further highlighting the important role of this module. In the crystal structure of SpyCas9 A52 interacts with the backbone of residues 1103-1107 close to the 5' end of the target strand in the in the crystal structure of SpyCas9, suggesting that the interaction of the nexus hairpin with the protein backbone may be required for protospacer-adjacent motif (PAM) binding.

Wright, A. V., et al., ("Rational design of a split-Cas9 enzyme complex," PNAS 112(10), 2015, pages 2984-2989) determined the RNA molecular determinants of sgRNA motifs that promote heterodimerization of the α-helical and nuclease lobes to form a ternary complex. Crystal structures of sgRNA/DNA-bound Cas9 showed that the spacer and the stem-loop motifs (i.e., the lower stem, the bulge, and the upper stem modules described by Briner, A., et al.) at the 5' end of the sgRNA primarily contact the α-helical lobe, whereas the two hairpins (i.e., the hairpins module described by Briner, A., et al.) at the 3' end bind the outside face of the nuclease lobe. They noted that "the nexus motif, recently shown to be critical for activity" (Wright, A. V., et al., page 2986, col. 1), occupies a central position between the lobes and forms extensive interactions with the bridge helix. Based on this interaction profile, Wright, et al., generated a full-length sgRNA and two shorter sgRNA constructs that were selectively truncated from either the 5' or 3' end (no modifications were made to the critical nexus hairpin) and determined their affinities for wild-type Cas9, the individual α-helical and nuclease lobes, and split-Cas9.

Contrary to the above-described teachings of the prior art, experiments performed in support of the present invention unexpectedly demonstrated that Cas9 functions (e.g., binding and cutting double-strand DNA) are supported by guide RNAs having a split nexus, as well as guide RNAs having modifications of the split nexus.

Results presented in the present specification open new design and engineering avenues for CRISPR technologies and set the stage for the development of next-generation CRISPR-based technologies.

SUMMARY OF THE INVENTION

Aspects of the present invention relate to engineered Type II CRISPR-Cas9 system wherein at least two polynucleotides are necessary to form a nexus stem element.

In one aspect, the present invention relates to an engineered Type II CRISPR-Cas9 system comprising three polynucleotides capable of forming a complex with a Cas9, protein to cause the Cas9 protein to bind a first DNA sequence comprising a DNA target sequence preferentially relative to a second DNA sequence without the DNA target binding sequence. At least two of the three polynucleotides are necessary to form a nexus stem element. In some embodiments, the engineered Type II CRISPR-Cas9 system further comprises a Cas9 protein or a DNA sequence encoding a Cas9 protein. In additional embodiments, the present invention relates to the three polynucleotides in complex with a Cas9 protein.

In one embodiment, an engineered Type II CRISPR-Cas9 system of the present invention comprises a first polynucleotide, a second polynucleotide, and a third polynucleotide that are separate polynucleotides each having a 5' end and a 3' end.

The first polynucleotide comprising in a 5' to 3' direction a first stem element nucleotide sequence I and a nexus stem element nucleotide sequence 1. The second polynucleotide comprising a nexus stem element nucleotide sequence II, wherein the nexus stem element nucleotide sequence I and the nexus stem element nucleotide sequence II are capable of forming the nexus stem element by base-pair hydrogen bonding between the nexus stem element nucleotide sequence I and the nexus stem element nucleotide sequence II. The third polynucleotide comprising in a 5' to 3' direction a DNA target binding sequence and a first stem element nucleotide sequence II, wherein the first stem element nucleotide sequence I and the first stem element nucleotide sequence II are capable of forming a first stem element by base-pair hydrogen bonding between the first stem element nucleotide sequence I and the first stem element nucleotide sequence II.

In another embodiment, an engineered Type II CRISPR-Cas9 system of the present invention comprises a first polynucleotide, a second polynucleotide, and a third polynucleotide that are separate polynucleotides each having a 5' end and a 3' end. The first polynucleotide comprising in a 5' to 3' direction an upper stem element nucleotide sequence I, a bulge element nucleotide sequence I, a lower stem element nucleotide sequence I, and a nexus stem element nucleotide sequence I. The second polynucleotide comprising a nexus stem element nucleotide sequence II, wherein the nexus stem element nucleotide sequence I and the nexus stem element nucleotide sequence II are capable of forming the nexus stem element by base-pair hydrogen bonding between the nexus stem element nucleotide sequence I and the nexus stem element nucleotide sequence II. The third polynucleotide comprising in a 5' to 3' direction a DNA target binding sequence, a lower stem element nucleotide sequence II, a bulge element nucleotide sequence II, and an upper stem element nucleotide sequence II, wherein the upper stem element nucleotide sequence I and the upper stem element nucleotide sequence II are capable of forming an upper stem element by base-pair hydrogen bonding between the upper stem element nucleotide sequence I and the upper stem element nucleotide sequence II, and the lower stem element nucleotide sequence I and the lower stem element nucleotide sequence II are capable of forming a lower stem element by base-pair hydrogen bonding between the lower stem element nucleotide sequence I and the lower stem element nucleotide sequence II.

In further embodiments the second polynucleotide comprises first and/or second adjunct polynucleotides. The second polynucleotide can further comprise in a 5' to 3' direction the nexus stem element nucleotide sequence II and a second stem element nucleotide sequence I, and a first adjunct polynucleotide that comprises a second stem element nucleotide sequence II. The second stem element nucleotide sequence I and the second stem element nucleotide sequence II are capable of forming a second stem element by base-pair hydrogen bonding between the second stem element nucleotide sequence I and the second stem element nucleotide sequence II. In some embodiments, the first adjunct polynucleotide further comprises in a 5' to 3' direction a loop element nucleotide sequence and the second stem element nucleotide sequence II, wherein 5' end of the loop element nucleotide sequence is covalently bonded to the 3' end of the second stem element nucleotide sequence I, thus forming a hairpin. In yet further embodiments, the first adjunct polynucleotide comprises in a 5' to 3' direction the second stem element nucleotide sequence II and a third stem element nucleotide sequence 1, and a second adjunct polynucleotide comprises in a 5' to 3' direction a third stem element nucleotide sequence II. The third stem element nucleotide sequence I and the third stem element nucleotide sequence II are capable of forming a third stem element by base-pair hydrogen bonding between the third stem element nucleotide sequence I and third stem element nucleotide sequence II. In some embodiments the second adjunct polynucleotide further comprises in a 5' to 3' direction a loop element nucleotide sequence and the third stem element nucleotide sequence II, wherein 5' end of the loop element nucleotide sequence is covalently bonded to the 3' end of the third stem element nucleotide sequence I.

Additional embodiments of the present invention include the first polynucleotide further comprising a first auxiliary polynucleotide 3' adjacent the nexus stem element nucleotide sequence I, the second polynucleotide further comprising a second auxiliary polynucleotide 5' adjacent the nexus stem element nucleotide sequence II, or both the first polynucleotide and the second polynucleotide each comprising an auxiliary sequence.

In some embodiments of the present invention, the first auxiliary polynucleotide comprises an effector binding element nucleotide sequence I, and the second auxiliary polynucleotide comprises an effector binding element nucleotide sequence II. The effector binding element nucleotide sequence I and the effector binding element nucleotide sequence II are capable of forming an effector binding element by base-pair hydrogen bonding between the effector binding element nucleotide sequence I and the effector binding element nucleotide sequence I. The effector binding element can be, for example, a double-stranded RNA and the effector protein is a double-stranded RNA binding protein capable of binding the effector binding element. In selected embodiments the effector protein is a catalytically inactive variant of a protein selected from the group consisting of Cas5, Cas6, and Csy4.

In additional embodiments, the first auxiliary polynucleotide further comprises in a 5' to 3' direction a linker element nucleotide sequence I and the effector binding element nucleotide sequence I, and the second auxiliary polynucleotide comprises in a 5' to 3' direction the effector binding element nucleotide sequence TI and a linker element nucleotide sequence II. The linker element nucleotide sequence I and the linker element nucleotide sequence II are capable of forming a linker element by base-pair hydrogen bonding between the effector binding element nucleotide sequence I and the effector binding element nucleotide sequence I.

In yet further embodiments, the first auxiliary polynucleotide, the second auxiliary polynucleotide, or both the first auxiliary polynucleotide and the second auxiliary polynucleotide each comprises a hairpin. Furthermore, the first auxiliary polynucleotide can further comprises in a 5' to 3' direction a linker element nucleotide sequence I and the hairpin, the second auxiliary polynucleotide comprises in a 5' to 3' direction the hairpin and a linker element nucleotide sequence II, or both the first auxiliary polynucleotide comprises in a 5' to 3' direction a linker element nucleotide sequence I and the hairpin and the second auxiliary polynucleotide comprises in a 5' to 3' direction the hairpin and a linker element nucleotide sequence II. The linker element nucleotide sequence I and the linker element nucleotide sequence II are capable of forming linker element by base-pair hydrogen bonding between the effector binding element nucleotide sequence I and the effector binding element nucleotide sequence I.

In another aspect an engineered Type II CRISPR-Cas9 system of the present invention comprises three polynucleotides. A first polynucleotide comprises in a 5' to 3' direction an upper stem element nucleotide sequence I, a bulge element nucleotide sequence I, a lower stem element nucleotide sequence I, and a nexus stem element nucleotide sequence I. A second polynucleotide comprises in a 5' to 3' direction a nexus stem element nucleotide sequence II, a second stem element comprising a hairpin, and a third stem element comprising a hairpin. The nexus stem element nucleotide sequence I and the nexus stem element nucleotide sequence II are capable of forming the nexus stem element by base-pair hydrogen bonding between the nexus stem element nucleotide sequence I and the nexus stem element nucleotide sequence II. A third polynucleotide comprises in a 5' to 3' direction a DNA target binding sequence, a lower stem element nucleotide sequence II, a bulge element nucleotide sequence II, and an upper stem element nucleotide sequence II. The upper stem element nucleotide sequence I and the upper stem element nucleotide sequence II are capable of forming an upper stem element by base-pair hydrogen bonding between the upper stem element nucleotide sequence I and the upper stem element nucleotide sequence II, and the lower stem element nucleotide sequence I and the lower stem element nucleotide, sequence II are capable of forming a lower stem element by base-pair hydrogen bonding between the lower stem element nucleotide sequence I and the lower stem element nucleotide sequence II. The engineered Type II CRISPR-Cas9 system can further comprise a Cas9 protein or a DNA sequence encoding a Cas9 protein.

In some embodiments of this aspect of the present invention the first polynucleotide further comprises a first auxiliary polynucleotide 3' adjacent the nexus stem element nucleotide sequence I, and the second polynucleotide further comprises a second auxiliary polynucleotide 5' adjacent the nexus stem element nucleotide sequence II.

These aspects and other embodiments of the present invention using the sn-casPNs/Cas9 protein systems of the present invention will readily occur to those of ordinary skill in the art in view of the disclosure herein.

BRIEF DESCRIPTION OF THE FIGURES

FIG. 3A, FIG. 3B, FIG. 3C, FIG. 3D, FIG. 3E, FIG. 3F, FIG. 3G, and FIG. 3H present a variety of polynucleotides of the engineered Type II CRISPR-Cas9 systems of the present invention.

FIG. 7A and FIG. 7B illustrate an example of a split-nexus Cas9-associated two polynucleotide system and its association with a Cas9 protein.

FIG. 12 presents examples of putative split nexus arrangements of known tracrRNA sequences from certain bacterial species.

FIG. 13 is an olionucleotide table that sets forth the sequences of olionucleotides used in the Examples of the present specification.

Incorporation by Reference

All patents, publications, and patent applications cited in this specification are herein incorporated by reference as if each individual patent, publication, or patent application was specifically and individually indicated to be incorporated by reference in its entirety for all purposes.

DETAILED DESCRIPTION OF THE INVENTION

Figure 1A:
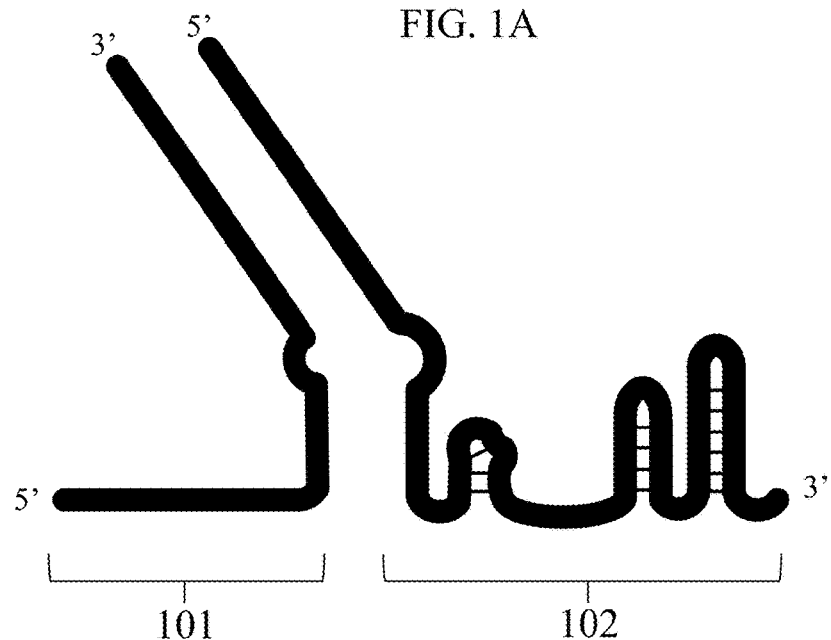
FIG. 1A and 1B present illustrative examples of dual guide Type II CRISPR-Cas9 associated RNAs.
Figure 1B:
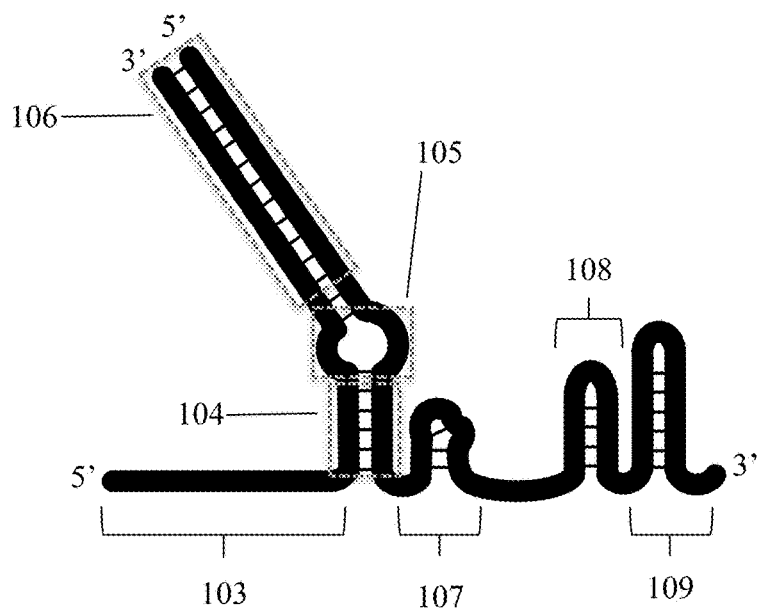

FIG. 1A and FIG. 1B present illustrative examples of dual guide Type II CRISPR-Cas9 associated RNAs. FIG. 1A shows a two-RNA component Type II CRISPR-Cas9 system comprising a crRNA (FIG. 1A, 101) and a tracrRNA (FIG. 1A, 102). FIG. 1B illustrates the formation of base-pair hydrogen bonds between the crRNA and the tracrRNA to form secondary structure (see U.S. Published Patent Application No. 2014-0068797, published 6 Mar. 2014; see also Jinek M., et al., "A programmable dual-RNA-guided DNA endonuclease in adaptive bacterial immunity," Science, 2012; 337:816-21). The figure presents an overview of and nomenclature for secondary structural elements of the crRNA and tracrRNA of the *Streptococcus pyogenes* Cas9 including the following: a spacer element (FIG. 1B, 103); a first stem element comprising a lower stem element (FIG. 1B, 104), a bulge element comprising unpaired nucleotides (FIG. 1B, 105), and an upper stem element (FIG. 1B, 106); a nexus element (FIG. 1B, 107); a second hairpin element comprising a second stem element (FIG. 1B, 108); and a third hairpin element comprising a third stem element (FIG. 1B, 109). The figures are not proportionally rendered nor are they to scale. The locations of indicators are approximate.

Figure 2:
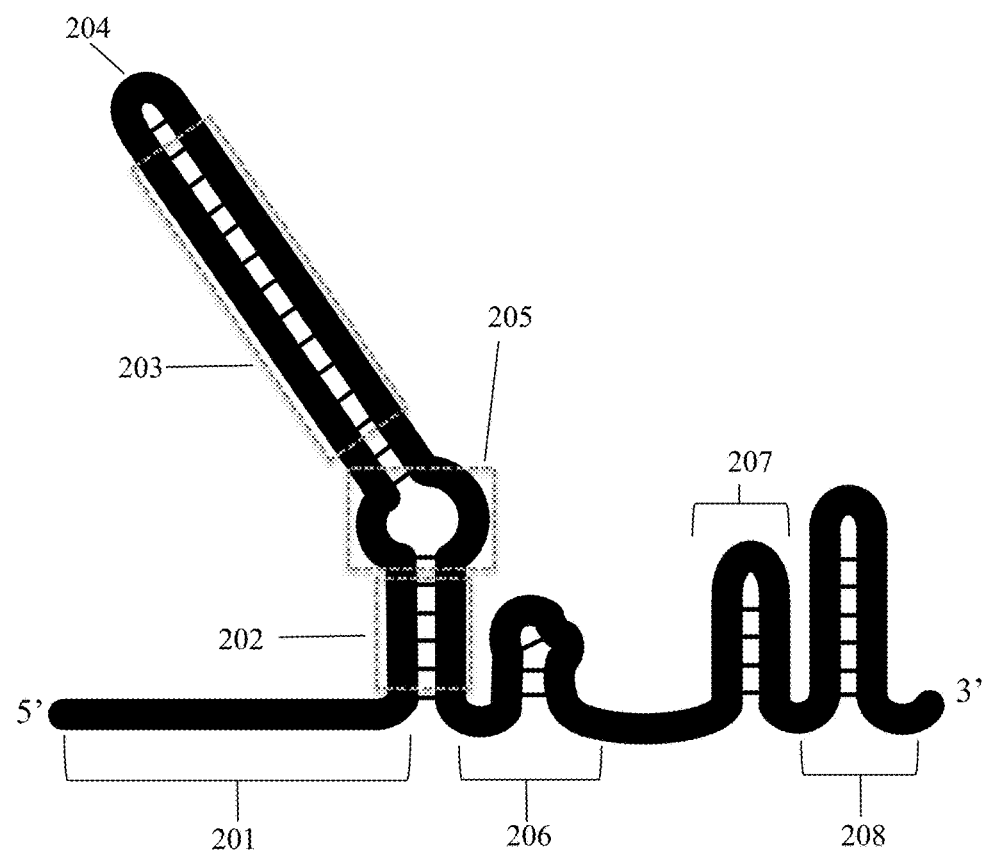
FIG. 2 shows another example of a CRISPR-Cas9 associated RNA.

FIG. 2 shows another example of a CRISPR-Cas9 associated RNA. The figure illustrates a single guide RNA (sgRNA) wherein the crRNA is covalently joined to the tracrRNA and forms a RNA polynucleotide secondary structure through base-pair hydrogen bonding (see, e.g., U.S. Published Patent Application No. 2014-0068797, published 6 Mar. 2014). The figure presents an overview of and nomenclature for secondary structural elements of a sgRNA of the *Streptococcus pyogenes* Cas9 including the following: a spacer element (FIG. 2, 201); a first stem element comprising a lower stem element (FIG. 2, 202), a bulge element comprising unpaired nucleotides (FIG. 2, 205), and an upper stem element (FIG. 2, 203); a loop element (FIG. 2, 204) comprising unpaired nucleotides; (a first hairpin element comprises the first stem element and the loop element); a nexus element (FIG. 2, 206); a second hairpin element comprising a second stem element (FIG. 2, 207); and a third hairpin element comprising a third stem element (FIG. 2, 208). (See, e.g., FIGS. 1 and 3 of Briner, A. E., et al., "Guide RNA Functional Modules Direct Cas9 Activity and Orthogonality," Molecular Cell Volume 56, Issue 2, 23 Oct. 2014, Pages 333-339.) The figure is not proportionally rendered nor is it to scale. The locations of indicators are approximate.

FIG. 3A, FIG. 3B, FIG. 3C, FIG. 3D, FIG. 3E, FIG. 3F, FIG. 3G, and FIG. 3H present a variety of polynucleotides of the engineered Type II CRISPR-Cas9 systems of the present invention. The "split-nexus Cas9-associated polynucleotides" (sn-casPNs) of the present invention comprise two or more polynucleotides, wherein the polynucleotide backbone is broken within the nexus element. These figures present exemplary sn-casPN structures. Other modifications of sn-casPNs are described in the present specification. The figures are not proportionally rendered nor are they to scale. The indicators for locations corresponding to elements are only illustrative to provide reference points in the example polynucleotides.

Table 1 presents a series of indicators used consistently in FIG. 3A, FIG. 3B, FIG. 3C, FIG. 3D, FIG. 3E, FIG. 3F, FIG. 3G, and FIG. 3H.

TABLE 1

Numerical Indicators Used to Illustrate Regions of Nucleotide Sequence Associated with Example sn-casPNs Indicators and Corresponding Elements Second Polynucleotide (sn2-casPN)

304 to 305 corresponds to a split nexus stem element nucleotide sequence II
305 to 306 corresponds to a second connective nucleotide sequence
306 to 307 corresponds to a second stem element nucleotide sequence I
307 to 308 corresponds to a loop element nucleotide sequence
308 to 309 corresponds to a second stem element nucleotide sequence II
309 to 310 corresponds to a third connective nucleotide sequence
310 to 311 corresponds to a third stem clement nucleotide sequence 1
311 to 312 corresponds to a loop element nucleotide sequence
312 to 313 corresponds to a third stem element nucleotide sequence II
313 to 314 corresponds to a 3' nucleotide sequence First Polynucleotide (sn1-casPN)

315 to 316 corresponds to a split nexus stem element nucleotide sequence I
316 to 317 corresponds to a first connective nucleotide sequence
317 to 320 corresponds to a first stem element nucleotide sequence I
317 to 318 corresponds to a lower stem element nucleotide sequence I
318 to 319 corresponds to a bulge element nucleotide sequence I
319 to 320 corresponds to an upper stem element nucleotide sequence I
320 to 321 corresponds to a loop element nucleotide sequence Additional Polynucleotides (sn3-casPN, sn4-casPN)

321 to 324 corresponds to a first stem element nucleotide sequence II
321 to 322 corresponds to an upper stem element nucleotide sequence II
322 to 323 corresponds to a bulge element nucleotide sequence II
323 to 324 corresponds to a lower stem element nucleotide sequence II
324 to 325 corresponds to a nucleic acid target binding sequence (a spacer element)

FIG. 3A illustrates an example of a split-nexus Cas9-associated three polynucleotide system. FIG. 3A, 301 illustrates a first polynucleotide (sn1-casPN) that comprises a first portion of the split nexus element. FIG. 3A, 302 illustrates a second polynucleotide (sn2-casPN) that comprises a second portion of the split nexus element. FIG. 3A, 303 illustrates a third polynucleotide (sn3-casPN) that comprises a spacer element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence I/sn2-casPN third stem element nucleotide sequence II form a third stem element; sn1-casPN first stem element nucleotide sequence I/sn3-casPN first stem element nucleotide sequence II form a first stem element, the first stem element comprising sn1-casPN lower stem element nucleotide sequence I/sn3-casPN lower stem element nucleotide sequence II form a lower stem element, and sn1-casPN upper stem element nucleotide sequence I/sn3-casPN upper stem element nucleotide sequence II form an upper stem element.

FIG. 3B illustrates an example of a split-nexus Cas9-associated two polynucleotide system. FIG. 3B, 326 illustrates a first polynucleotide (sn1-casPN) that comprises a first portion of the split nexus element. FIG. 3B, 302 illustrates a second polynucleotide (sn2-casPN) that comprises a second portion of the split nexus element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence IT form a second stem element; sn2-casPN third stem element nucleotide sequence I/sn2-casPN third stem element nucleotide sequence II form a third stem element; sn1-casPN first stem element nucleotide sequence I/sn1-casPN first stem element nucleotide sequence II form a first stem element, the first stem element comprising sn1-casPN lower stem element nucleotide sequence I/sn1-casPN lower stem element nucleotide sequence II forming a lower stem element, and sn1-casPN upper stem element nucleotide sequence I/sn1-casPN upper stem element nucleotide sequence II forming an upper stem element.

Figure 3C:
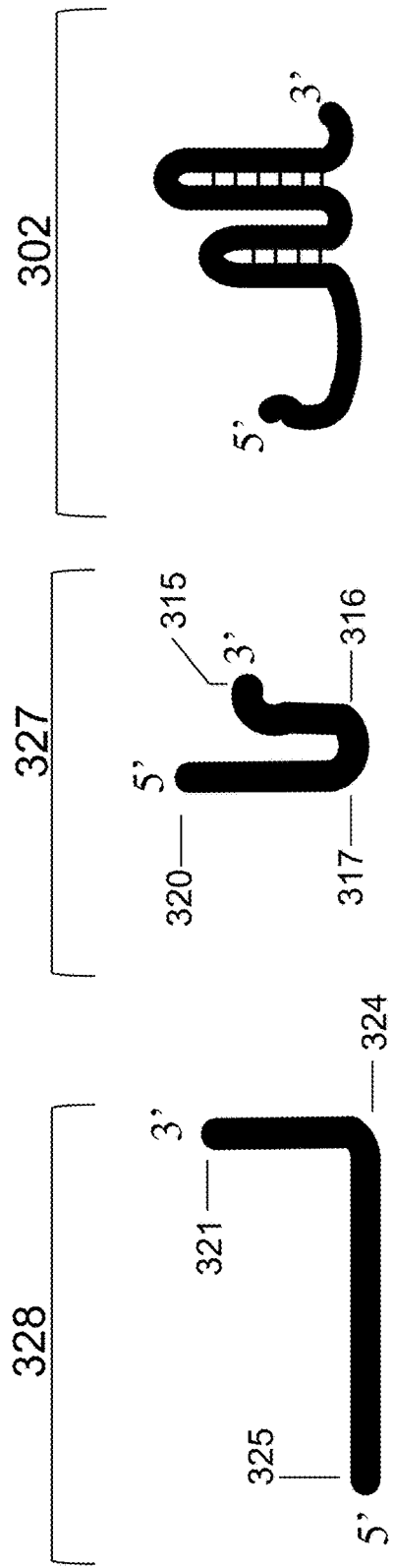

FIG. 3C illustrates an example of a split-nexus Cas9-associated three polynucleotide system. FIG. 3C, 327 illustrates a first polynucleotide (sn1-casPN) that comprises a first portion of the split nexus element. FIG. 3C, 302 illustrates a second polynucleotide (sn2-casPN) that comprises a second portion of the split nexus element. FIG. 3C, 328 illustrates a third polynucleotide (sn3-casPN) that comprises a spacer element. Examples of polynucleotide secondary structures that form through base-pair hydrogen bonding between indicated sequences include the following: sn1-casPN split nexus stem element nucleotide sequence 1/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence I/sn2-casPN third stem element nucleotide sequence II form a third stem element; sn1-casPN first stem element nucleotide sequence I/sn3-casPN first stem element nucleotide sequence II form a first stem element.

Figure 3D:
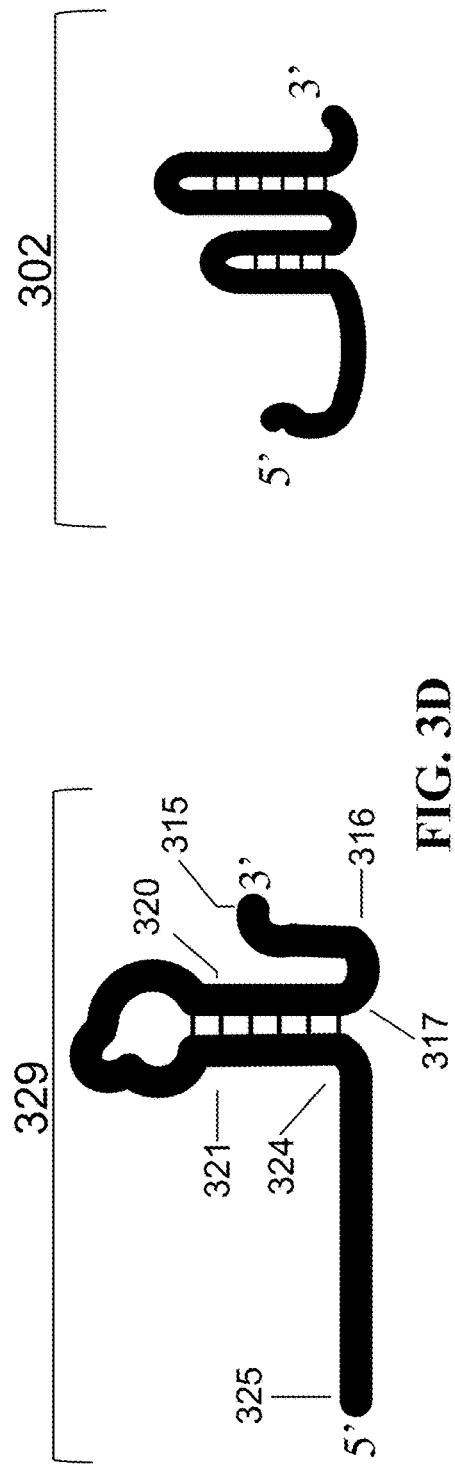

FIG. 3D illustrates an example of a split-nexus Cas9-associated two polynucleotide system. FIG. 3D, 329 illustrates a first polynucleotide (sn1-casPN) that comprises a first portion of the split nexus element. FIG. 3D, 302 illustrates a second polynucleotide (sn2-casPN) that comprises a second portion of the split nexus element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence 1/sn2-casPN third stem element nucleotide sequence II form a third stem element; sn1-casPN first stem element nucleotide sequence I/sn1-casPN first stem element nucleotide sequence II form a first stem element.

Figure 3E:
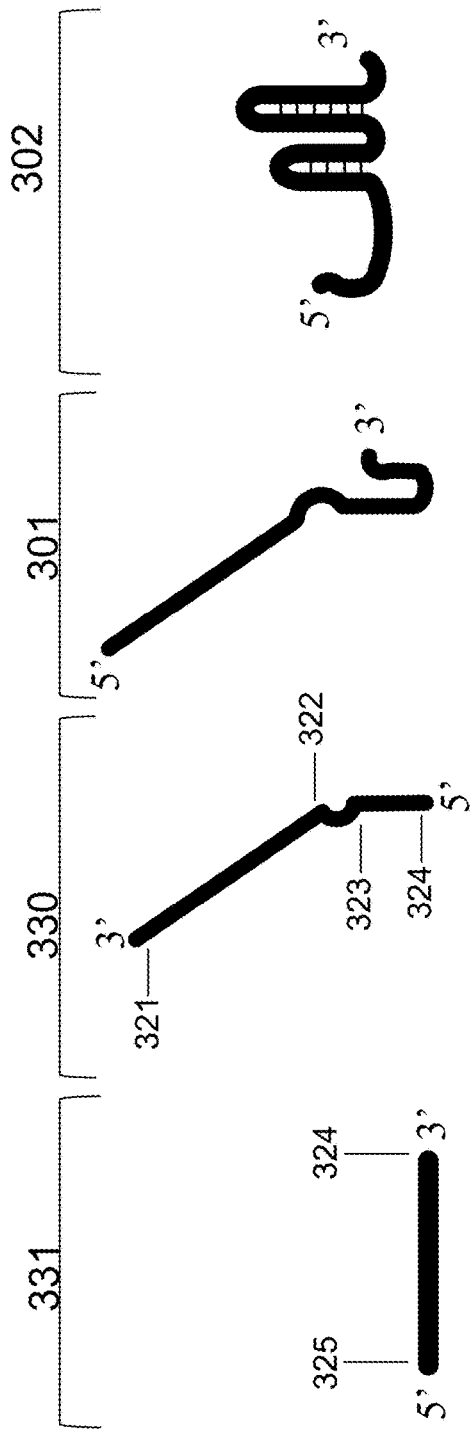

FIG. 3E illustrates an example of a split-nexus Cas9-associated four polynucleotide system. FIG. 3E, 301 illustrates a first polynucleotide (sn1-casPN) that comprises a first portion of the split nexus element. FIG. 3E, 302 illustrates a second polynucleotide (sn2-casPN) that comprises a second portion of the split nexus element. FIG. 3E, 330 illustrates a third polynucleotide (sn3-casPN). FIG. 3E, 331 illustrates a spacer polynucleotide (sn4-casPN) that comprises a spacer element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence 1/sn2-casPN third stem element nucleotide sequence II form a third stem element; sn1-casPN first stem element nucleotide sequence I/sn3-casPN first stem element nucleotide sequence II form a first stem element, the first stem element comprising sn1-casPN lower stem element nucleotide sequence I/sn3-casPN lower stem element nucleotide sequence II forming a lower stem element, and sn1-casPN upper stem element nucleotide sequence I/sn3-casPN upper stem element nucleotide sequence II forming an upper stem element.

Figure 3F:
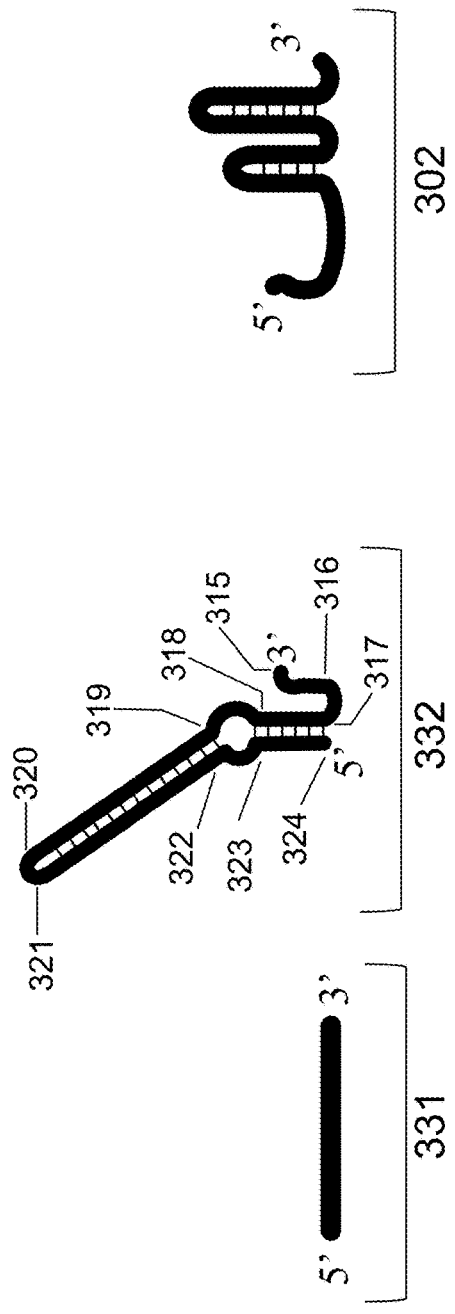

FIG. 3F illustrates an example of a split-nexus Cas9-associated three polynucleotide system. FIG. 3F, 332 illustrates a first polynucleotide (sn1-casPN) that comprises a first portion of the split nexus element. FIG. 3F, 302 illustrates a second polynucleotide (sn2-casPN) that comprises a second portion of the split nexus element. FIG. 3F, 331 illustrates a spacer polynucleotide (sn4-casPN) that comprises a spacer element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence I/sn2-casPN third stem element nucleotide sequence II form a third stem element; sn1-casPN first stem element nucleotide sequence I/sn1-casPN first stem element nucleotide sequence II form a first stem element, the first stem element comprising sn1-casPN lower stem element nucleotide sequence I/sn1-casPN lower stem element nucleotide sequence II forming a lower stem element, and sn1-casPN upper stem element nucleotide sequence I/sn1-casPN upper stem element nucleotide sequence II forming an upper stem element.

FIG. 3G illustrates an example of a split-nexus Cas9-associated four polynucleotide system. FIG. 3G, 327 illustrates a first polynucleotide (sn1-casPN) that comprises a first portion of the split nexus element. FIG. 3G, 302 illustrates a second polynucleotide (sn2-casPN) that comprises a second portion of the split nexus element. FIG. 3G, 333 illustrates a third polynucleotide (sn3-casPN). FIG. 3G, 331 illustrates a spacer polynucleotide (sn4-casPN) that comprises a spacer element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence I/sn2-casPN third stem element nucleotide sequence II form a third stem element; sn1-casPN first stem element nucleotide sequence I/sn3-casPN first stem element nucleotide sequence II form a first stem element.

FIG. 3H illustrates an example of a split-nexus Cas9-associated three polynucleotide system. FIG. 3H, 334 illustrates a first polynucleotide (sn1-casPN) that comprises a first portion of the split nexus element. FIG. 3H, 302 illustrates a second polynucleotide (sn2-casPN) that comprises a second portion of the split nexus element. FIG. 3H, 331 illustrates a spacer polynucleotide (sn4-casPN) that comprises a spacer element. Examples of polynucleotide secondary structures that form through base-pair hydrogen bonding between indicated sequences include the following: sn1-casPN split nexus stem element nucleotide sequence I/sn2-casPN split nexus stem element nucleotide sequence II form a split nexus stem element; sn2-casPN second stem element nucleotide sequence I/sn2-casPN second stem element nucleotide sequence II form a second stem element; sn2-casPN third stem element nucleotide sequence I/sn2-casPN third stem element nucleotide sequence II form a third stem element; sn1-casPN first stem element nucleotide sequence I/sn1-casPN first stem element nucleotide sequence II form a first stem element.

Figure 4A:
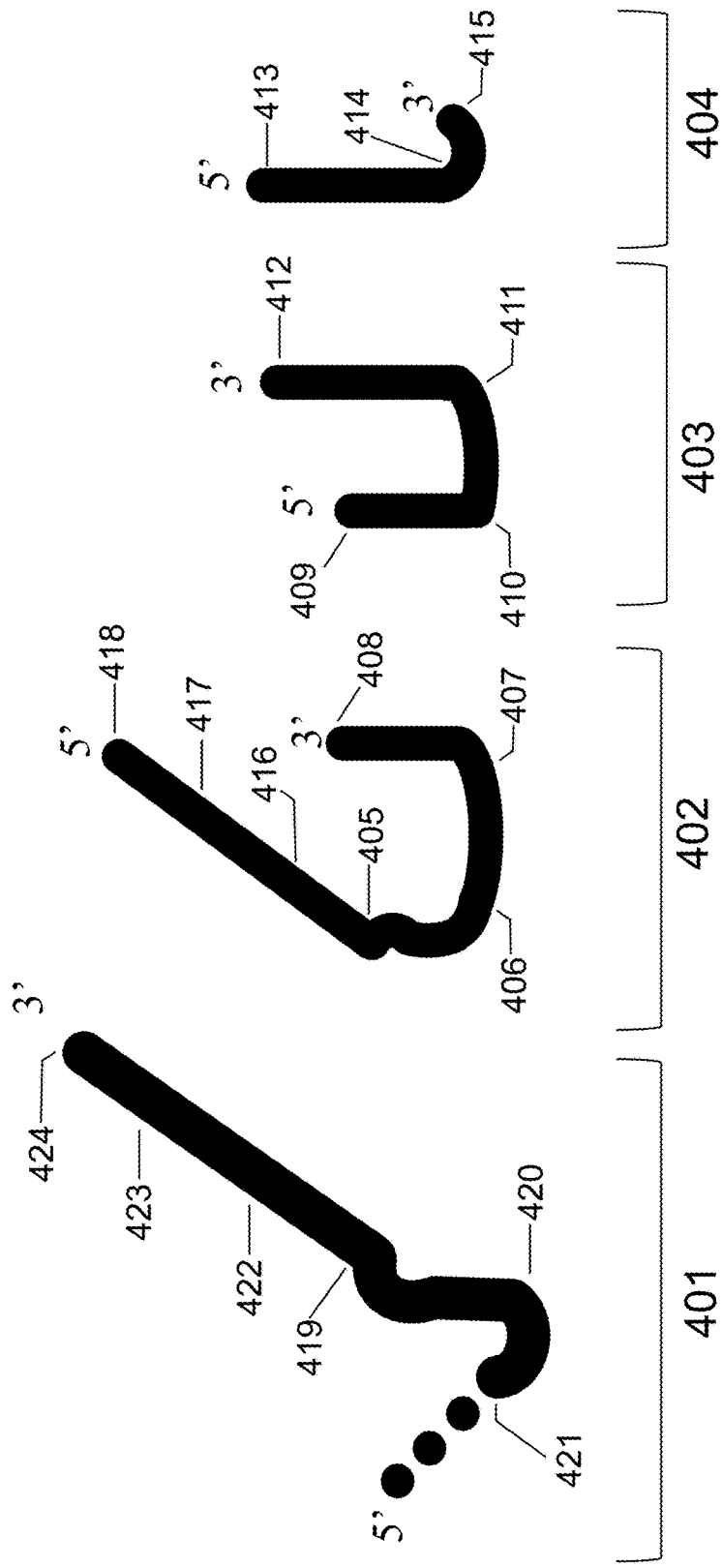
FIG. 4A and FIG. 4B present further modifications of the polynucleotides described in FIG. 3A through FIG. 3H.
Figure 4B:
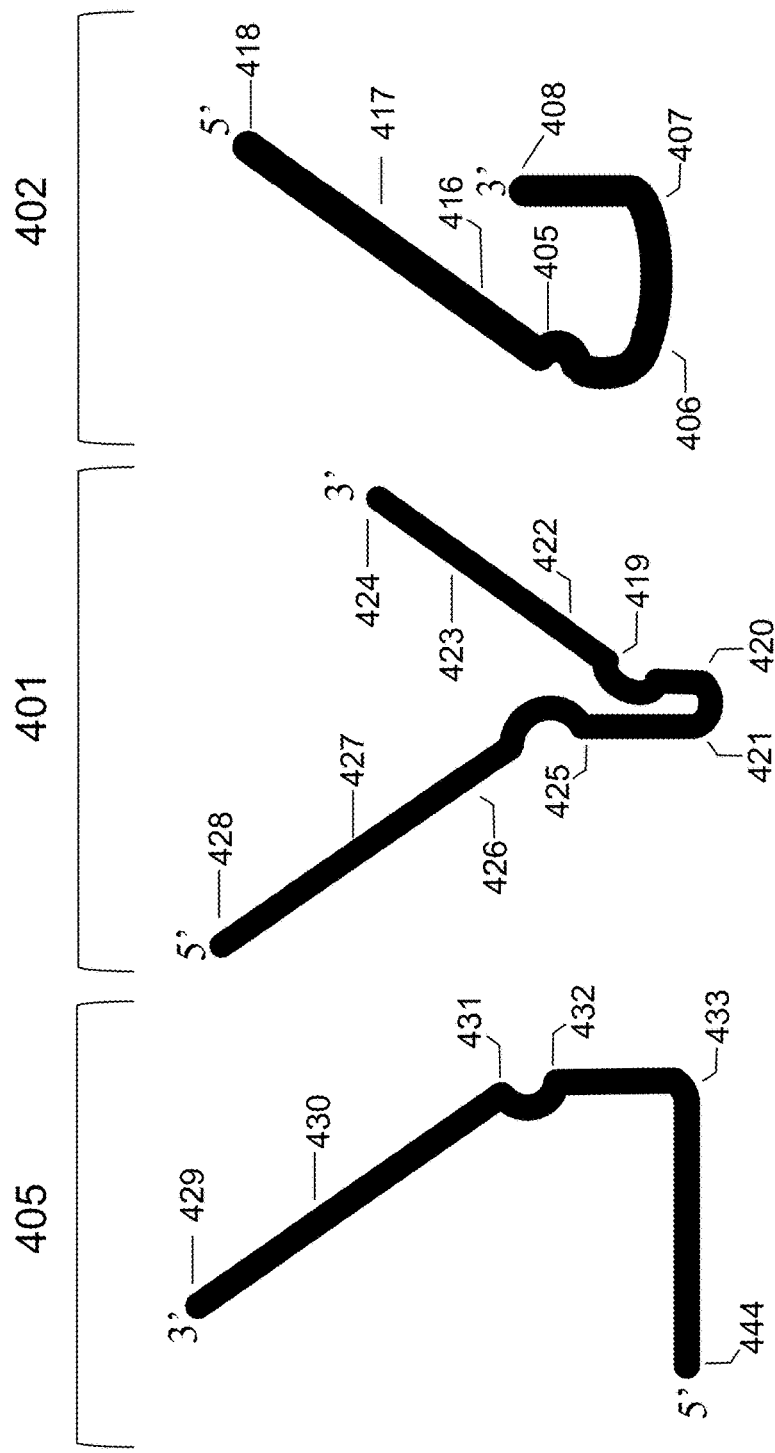

FIG. 4A presents modifications of Polynucleotide 1 (sn1-casPN) and Polynucleotide 2 (sn2-casPN) described above in FIG. 3A to FIG. 3H. FIG. 4B presents examples of further modifications to polynucleotide 1 (sn1-casRNA; described above in FIG. 3A to FIG. 3H) and polynucleotide 3 (sn3-casRNA; described above in FIG. 3A, FIG. C, FIG. E, and FIG. 3G) described above in FIG. FIG. 4A and FIG. 4B present examples of sn1-casPN, sn2-casPN, and sn3-casPN structures. Other modifications of sn1-casPN, sn2-casPN, and sn3-casPN are described in the present specification. The figures are not proportionally rendered nor are they to scale. The indicators for locations corresponding to elements are only illustrative to provide reference points in the example polynucleotides. Table 2 presents a series of indicators used consistently in FIG. 4A and FIG. 4B.

TABLE 2

Numerical Indicators Used to Illustrate Regions of Nucleotide Sequences Associated with Examples of sn1-casPNs, sn2-casPNs, an sn3-casPNs Indicators and Corresponding Elements Second Polynucleotide (sn2-casPN; second auxiliary polynucleotide; first adjunct polynucleotide; second adjunct polynucleotide)

405 to 406 corresponds to a split nexus stem element nucleotide sequence II

TABLE 2-continued

Numerical Indicators Used to Illustrate Regions of Nucleotide Sequences Associated with Examples of sn1-casPNs, sn2-casPNs, an sn3-casPNs Indicators and Corresponding Elements 406 to 407 corresponds to a second connective nucleotide sequence
407 to 408 corresponds to a second stem element nucleotide sequence I
408 to 409 corresponds to a loop element nucleotide sequence
409 to 410 corresponds to a second stem element nucleotide sequence II
410 to 411 corresponds to a third connective nucleotide sequence
411 to 412 corresponds to a third stem element nucleotide sequence I
412 to 413 corresponds to a loop element nucleotide sequence
413 to 414 corresponds to a third stem element nucleotide sequence II
414 to 415 corresponds to a 3' nucleotide sequence
405 to 418 corresponds to a second auxiliary polynucleotide
405 to 416 corresponds to a linker element nucleotide sequence II
416 to 417 corresponds to an affinity nucleotide sequence II
417 to 418 corresponds to an effector binding element nucleotide sequence II First Polynucleotide (sn1-casPN; auxiliary polynucleotide)

419 to 420 corresponds to a split nexus stem element nucleotide sequence I
420 to 421 corresponds to a first connective nucleotide sequence
419 to 424 corresponds to a first auxiliary polynucleotide
419 to 422 corresponds to a linker element nucleotide sequence I
422 to 423 corresponds to an affinity nucleotide sequence I
423 to 424 corresponds to an effector binding element nucleotide sequence I
421 to 425 corresponds to a lower stem element nucleotide sequence I
425 to 426 corresponds to a bulge element nucleotide sequence I
426 to 427 corresponds to an upper stem element nucleotide sequence I
427 to 428 corresponds to a first accessory polynucleotide Third Polynucleotide (sn3-casPN; accessory polynucleotide)

429 to 430 corresponds to a second accessory polynucleotide
430 to 431 corresponds to an upper stem element nucleotide sequence II
431 to 432 corresponds to a bulge element nucleotide sequence II
432 to 433 corresponds to a lower stem element nucleotide sequence II
433 to 434 corresponds to a nucleic acid target binding sequence (a spacer element)

FIG. 4A, 401 illustrates a first polynucleotide (sn1-casPN) that comprises a first portion of the split nexus element and an optional first auxiliary polynucleotide that is located 3' of the split nexus element. FIG. 4A, 402 illustrates an example of a second polynucleotide (sn2-casPN) that comprises a second portion of the split nexus element, an optional second connective sequence, and an optional second auxiliary polynucleotide that is located 5' of the split nexus element. FIG. 4A, 402, 403 illustrates a sn2-casPN comprising a first adjunct polynucleotide. FIG. 4A-402, 403, 404 illustrates a sn2-casPN further comprising second adjunct polynucleotide. In FIG. 4A, the 5' three dots represent further polynucleotide sequence.

In some embodiments, a sn2-casPN can comprises one or more of the following: a first adjunct polynucleotide, a second adjunct polynucleotide, a second auxiliary polynucleotide, or combinations thereof. A first adjunct polynucleotide comprises one or more of the following: a loop element nucleotide sequence, a second stem element nucleotide sequence II, a third connective nucleotide sequence, a third stem element nucleotide sequence I, or combinations thereof. A second adjunct polynucleotide comprises one or more of the following: a loop element nucleotide sequence, a third stem element nucleotide sequence II, a 3' nucleotide sequence, or combinations thereof.

In some embodiments, neither sn1-casPN nor sn2-casPN comprise an auxiliary polynucleotide. Combinations of sn1-casPN and/or sn2-casPN comprising an auxiliary polynucleotide include, but are not limited to, the following: sn1-casPN-first auxiliary polynucleotide/sn2-casPN; sn1-casPN/sn2-casPN-second auxiliary polynucleotide; or sn1-casPNfirst auxiliary polynucleotide/sn2-casPN-second auxiliary polynucleotide. Furthermore, the first auxiliary polynucleotide comprises one or more of the following: a linker element nucleotide sequence I, an affinity nucleotide sequence I, an effector binding element nucleotide sequence I, or combinations thereof. In addition, the second auxiliary polynucleotide comprises one or more of the following: a linker element nucleotide sequence II, an affinity nucleotide sequence II, an effector binding element nucleotide sequence II, or combinations thereof.

Examples of polynucleotide secondary structures that are capable of forming through base-pair hydrogen bonding between indicated sequences (when the sequences are present) include the following: sn1-casPN split nexus stem element nucleotide sequence I/sn2-casPN split nexus stem element nucleotide sequence II form a split nexus stem element; sn2-casPN second stem element nucleotide sequence I/first adjunct polynucleotide second stem element nucleotide sequence II form a second stem element; and first adjunct polynucleotide third stem element nucleotide sequence I/second adjunct polynucleotide third stem element nucleotide sequence II form a third stem element.

Furthermore, in some embodiments the first auxiliary polynucleotide and the second auxiliary polynucleotide are capable of forming secondary structure through base-pair hydrogen bonding between indicated sequences, for example, including one or more of the following: sn1-casPN first auxiliary polynucleotide/sn2-casPN second auxiliary polynucleotide form; sn1-casPN affinity nucleotide sequence I/sn2-casPN affinity nucleotide sequence II; sn1-casPN effector binding element nucleotide sequence I/sn2-casPN effector binding element nucleotide sequence II; and sn1-casPN linker element nucleotide sequence I/sn2-casPN linker element nucleotide sequence II.

However, in other embodiments base-pair hydrogen bonding between one or more of these sequences is not required. In addition, in some embodiments secondary structure forms through base-pair hydrogen bonding within an indicated sequence, for example, sn1-casPN first auxiliary polynucleotide can comprise a hairpin and/or sn2-casPN second auxiliary polynucleotide can comprise a hairpin.

Further modifications of the variations of sn2-casPN described above in FIG. 4A include a second hairpin element comprising a second stem element and a loop element, a third hairpin element comprising a third stem element and a loop element, and both the second hairpin element and the third hairpin element. For example, by connecting the 3' end of the second stem element nucleotide sequence I (FIG. 4, 408) to the 5' end of the second stem element nucleotide sequence II (FIG. 4, 409) a second hairpin element is formed. Similarly, by connecting the 3' end of the third stem element nucleotide sequence I (FIG. 4, 412) to the 5' end of the third stem element nucleotide sequence II (FIG. 4, 413) a third hairpin element is formed.

In some embodiments, a sn2-casPN can comprises one or more of the following: a first adjunct polynucleotide, a second adjunct polynucleotide, a second auxiliary polynucleotide, or combinations thereof. A first adjunct polynucleotide comprises one or more of the following: a loop element nucleotide sequence, a second stem element nucleotide sequence II, a third connective nucleotide sequence, a third stem element nucleotide sequence I, or combinations thereof. A second adjunct polynucleotide comprises one or more of the following: a loop element nucleotide sequence, a third stem element nucleotide sequence II, a 3' nucleotide sequence, or combinations thereof.

FIG. 4B, 401 illustrates a first polynucleotide (sn1-casPN) that comprises a first portion of the split nexus element, an optional first auxiliary polynucleotide that is located 3' of the split nexus element, and an optional first accessory polynucleotide that is located 5' of the upper stem element nucleotide sequence I. FIG. 4B, 405 illustrates an example of a third polynucleotide (sn3-casPN) that comprises an optional second accessory polynucleotide that is located 3' of the upper stem element nucleotide sequence II.

In some embodiments, neither sn1-casPN nor sn3-casPN comprises an accessory polynucleotide. Combinations of sn1-casPN and/or sn3-casPN comprising an auxiliary polynucleotide include, but are not limited to, the following: sn1-casPN-first accessory polynucleotide/sn3-casPN; sn1-casPN/sn3-casPN-second accessory polynucleotide; or sn1-casPN-first accessory polynucleotide/sn3-casPN-second accessory polynucleotide. Furthermore, the first accessory polynucleotide can comprise one or more of the following: a linker element, an affinity sequence (for example a ligand or ligand-binding moiety), an effector binding element, or combinations thereof. In addition, the second auxiliary polynucleotide can comprise one or more of the following: a linker element, an affinity sequence (e.g., a ligand or ligand-binding moiety), an effector binding element, or combinations thereof.

Figures 5A, 5B:
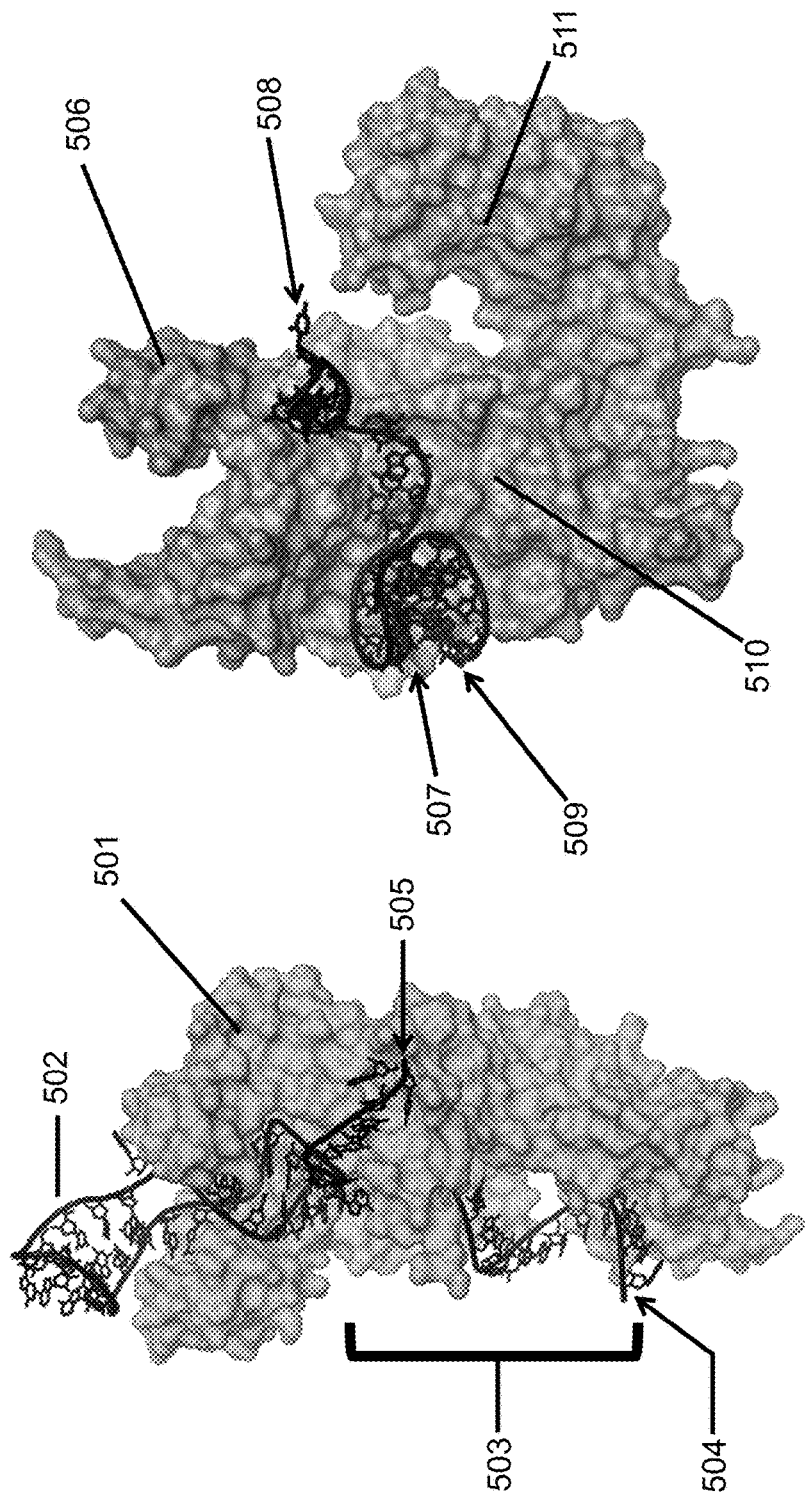
FIG. 5A, FIG. 5B, and FIG. 5C relate to structural information for an embodiment of a snl-casRNA/sn2-casRNA/Cas9 protein complex, wherein the snl-casRNA, sn2-casRNA correspond to snl-casPN and sn2-casPN of FIG. 3B.
Figure 5C:
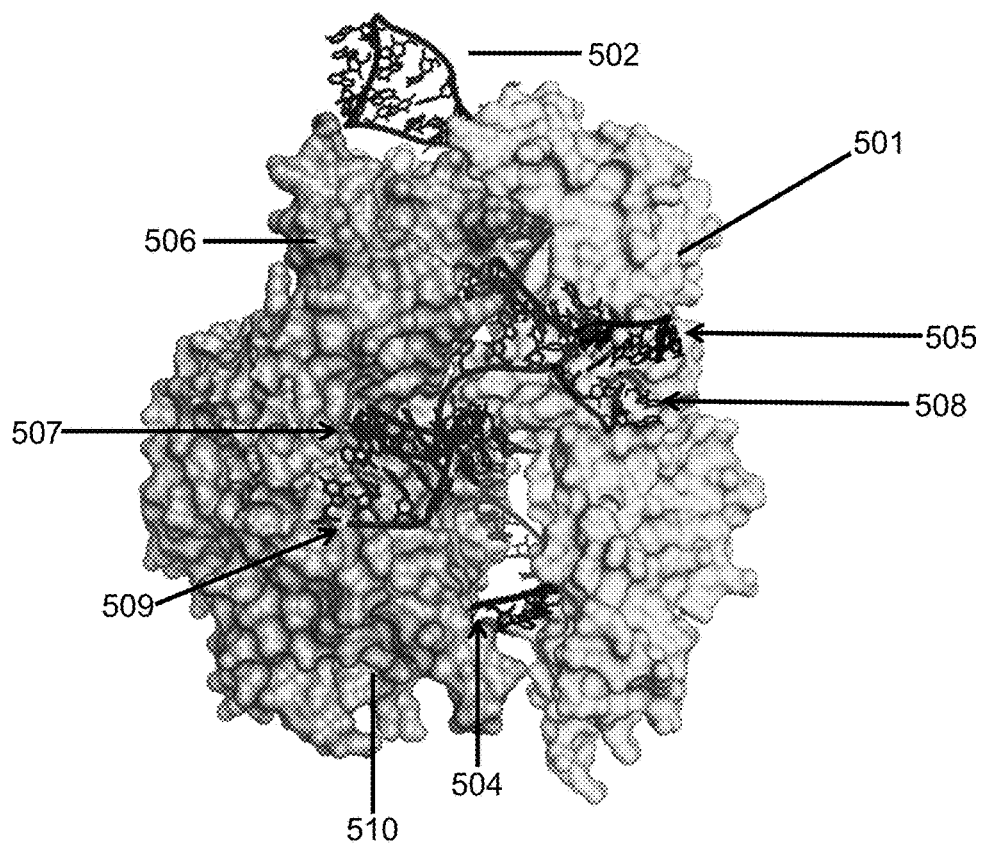

FIG. 5A, FIG. 5B, and FIG. 5C relate to structural information for an embodiment of a sn1-casRNA/sn2-casRNA/Cas9 protein complex, wherein the sn1-casRNA, sn2-casRNA correspond to sn1-casPN and sn2-casPN of FIG. 3B. FIG. 5A and FIG. 5B provide a close-up, open book view of SpyCas9. FIG. 5A presents a model of the α-Helical lobe of SpyCas9 (FIG. 5A, 501) in complex with sn1-casRNA (FIG. 5A, 502). The section of the sn1-casRNA corresponding to the spacer element (i.e., a nucleic acid target binding sequence) is indicated by a bracket (FIG. 5A, 503). The 5' end of the sn1-casRNA (FIG. 5A, 504) is also indicated. The 3' end of the sn1-casRNA is the location of the break in the nexus element, that is the 3' end of the first portion of the split nexus (FIG. 5A, 505). FIG. 5B presents a model of the Catalytic nuclease lobe (FIG. 5B, 506) of SpyCas9 in complex with sn2-casRNA (FIG. 5B, 507). The 5' end of the sn2-casRNA is the location of the break in the nexus element, that is, the 5' end of the second portion of the split nexus (FIG. 5A, 508). The 3' end of the sn2-casRNA (FIG. 5B, 509) is also indicated. The relative positions of the RuvC domain (FIG. 5B, 510; RNase H domain) and the HNH domain (FIG. 5B, 511; HNH nuclease domain) are indicated. FIG. 5C provide a view of an assembled sn1-casRNA/sn2-casRNA/Cas9 protein complex. The relative locations of the following elements are indicated: the α-Helical lobe of SpyCas9 (FIG. 5C, 501); the Catalytic nuclease lobe (FIG. 5C, 506) of SpyCas9; the sn1-casRNA (FIG. 5C, 502); the sn2-casRNA (FIG. 5C, 507); the 3' end of the sn2-casRNA (FIG. 5C, 509); the 5' end of the sn1-casRNA (FIG. 5C, 504) is also indicated; the relative position of the RuvC domain (FIG. 5C, 510); and the area of the 5' and 3' ends of the split nexus element (FIG. 5C 508, 505).

Figure 6A:
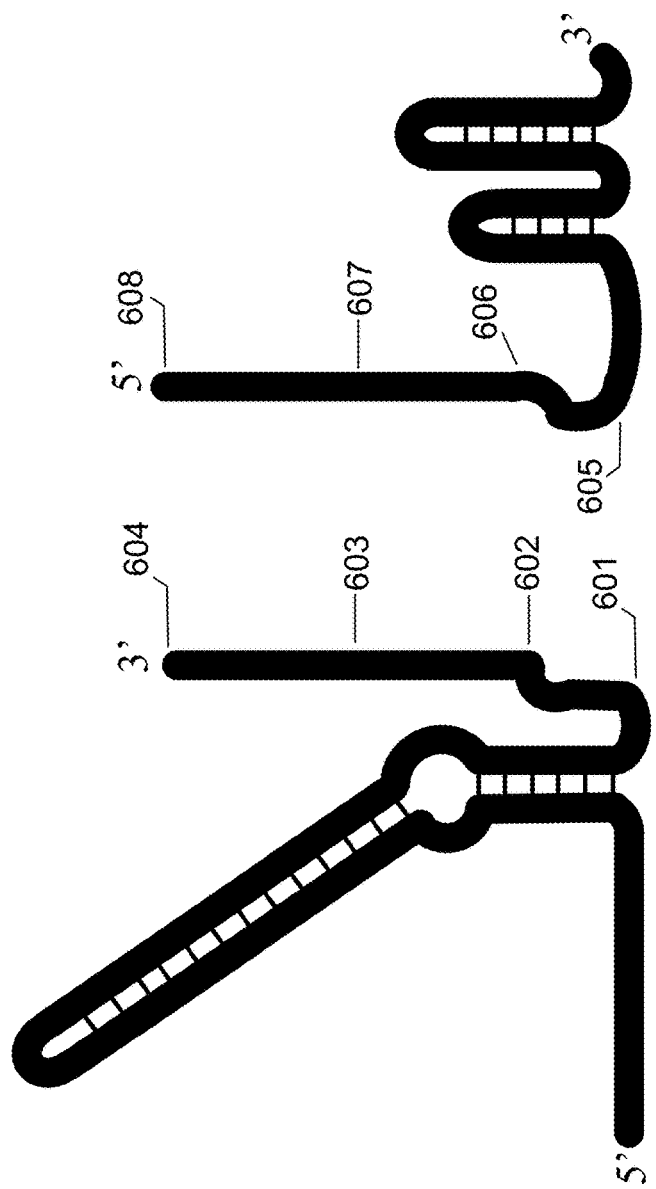
FIG. 6A, FIG. 6B, and FIG. 6C illustrate an example of a split-nexus Cas9-associated two polynucleotide system and its association with a Cas9 protein.
Figure 6B:
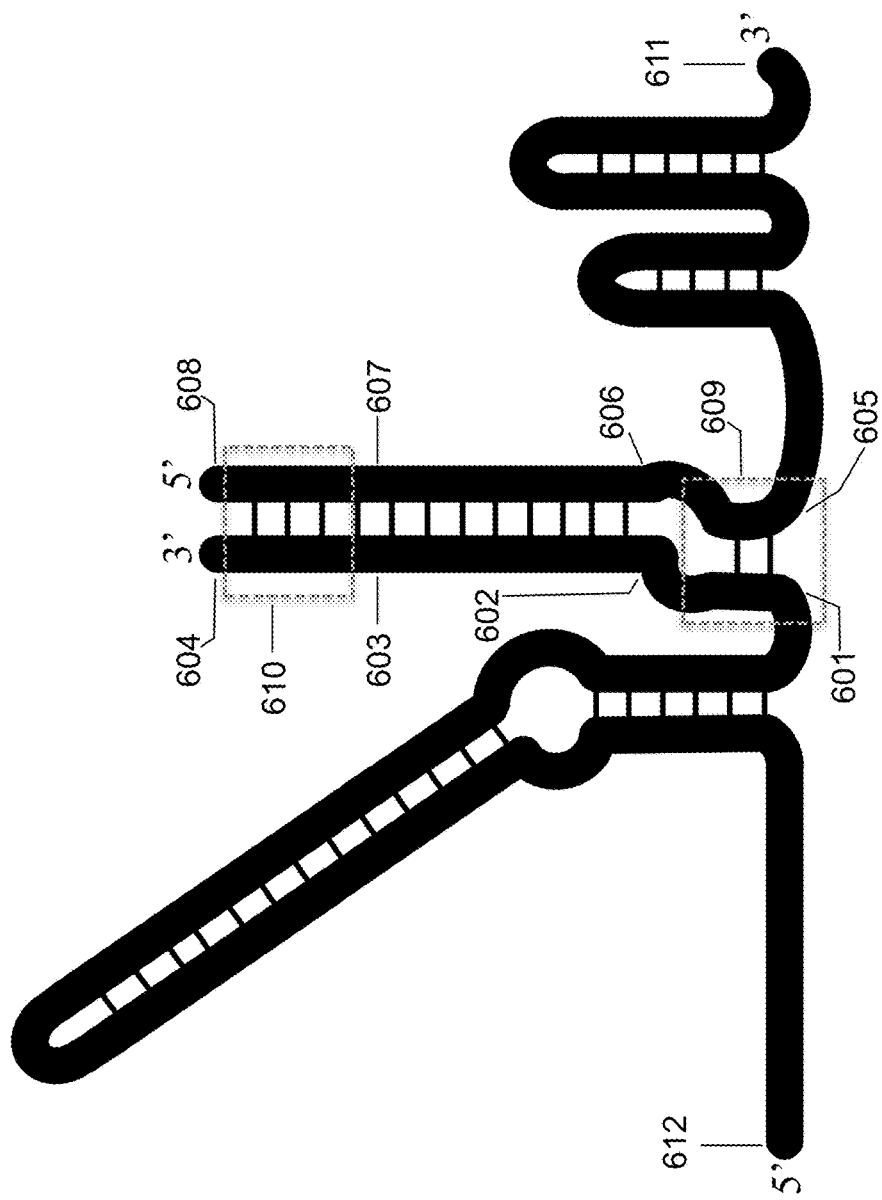
Figure 6C:
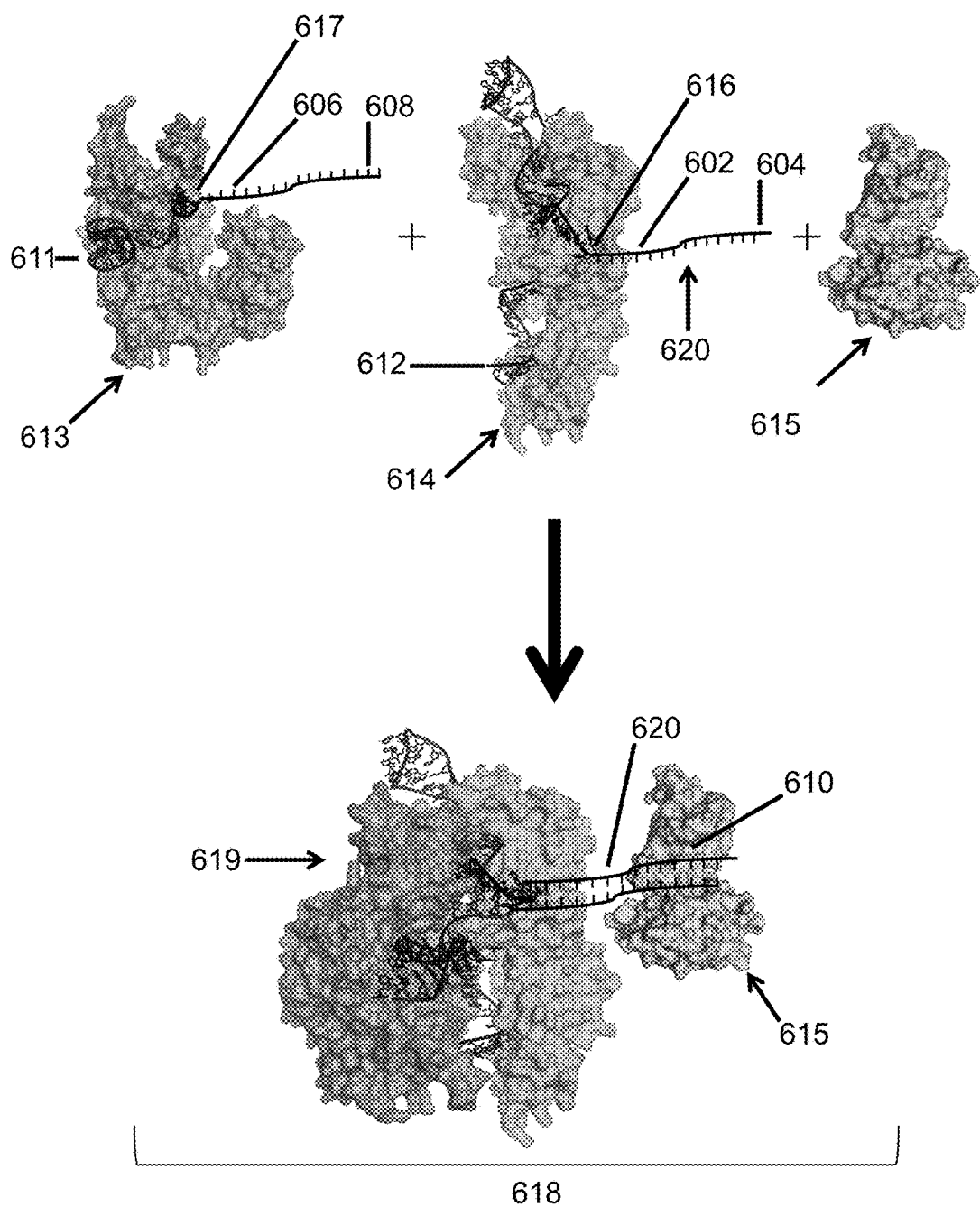

FIG. 6A, FIG. 6B and FIG. 6C illustrate an example of a split-nexus Cas9-associated two polynucleotide system. This system corresponds to a first polynucleotide (sn1-casPN) that comprises a first portion of the split nexus element (FIG. 3B, 326) and a second polynucleotide (sn2-casPN) that comprises a second portion of the split nexus element (FIG. 3B, 302). The figures are not proportionally rendered nor are they to scale. The indicators for locations corresponding to elements are only illustrative to provide reference points in the example polynucleotides. Table 3 presents a series of indicators used in FIG. 6A and FIG. 6B.

TABLE 3

Numerical Indicators Used to Illustrate Regions of Nucleotide Sequences Associated with Example sn1-casRNA and sn2-casRNA Indicators and Corresponding Elements 601 to 602 corresponds to a split nexus stem element nucleotide sequence I
602 to 604 corresponds to a first auxiliary polynucleotide
602 to 603 corresponds to a linker element nucleotide sequence I
603 to 604 corresponds to an effector binding element nucleotide sequence I
605 to 606 corresponds to a split nexus stem element nucleotide sequence II
606 to 608 corresponds to a second auxiliary polynucleotide
606 to 607 corresponds to a linker element nucleotide sequence II
607 to 608 corresponds to an effector binding element nucleotide sequence II FIG. 6A illustrates a sn1-casRNA comprising a first auxiliary polynucleotide (FIG. 6A, 602 to 604) and a sn2-casRNA comprising a second auxiliary polynucleotide (FIG. 6A, 606 to 608). The figure shows the sn1-casRNA and sn2-casRNA before association and formation of hydrogen bond base pairs (bp) between them. FIG. 6B illustrates the sn1-casRNA comprising a first auxiliary polynucleotide and the sn2-casRNA comprising a second auxiliary polynucleotide after formation of hydrogen bond base pairs between them. A linker element is formed between the linker element nucleotide sequence I (FIG. 6B, 602 to 603) and the linker element nucleotide sequence II (FIG. 6B, 606 to 607). The bottom dash-lined box (FIG. 6B, 609) shows formation of a nexus stem element. The top dashed-line box (FIG. 6B, 610) shows formation of an effector binding element, in this example a Csy4 RNA binding element. FIG. 6C illustrates the association of the sn2-casRNA with the catalytic nuclease lobe (FIG. 6C, 613) of SpyCas9 and the association of the sn1-casRNA with the α-Helical lobe (FIG. 6C, 614) of SpyCas9. Also shown is an effector protein Csy4* (FIG. 6C, 615), which is a variant of Csy4 without endoribonucleases activity. Furthermore, the first portion of the split nexus (FIG. 6C, 616), the second portion of the split nexus (FIG. 6C, 617), the 3' end of the sn2-casRNA (FIG. 6C, 611), the 5' end of the sn1-casRNA (FIG. 6C, 612), the first auxiliary polynucleotide (FIG. 6C, 602 to 604), and the second auxiliary polynucleotide (FIG. 6C, 606 to 608) are indicated. The thick downward pointing arrow indicates the assembly of the sn2-casRNA/catalytic nuclease lobe (FIG. 6C, 613) of SpyCas9, the sn1-casRNA/α-Helical lobe (FIG. 6C, 614) of SpyCas9, and the Csy4* protein (FIG. 6C, 615) into a complex (FIG. 6C, 618). In the complex (FIG. 6C, 618) the sn2-casRNA/catalytic nuclease lobe (FIG. 6C, 613) of SpyCas9 and the sn1-casRNA/α-Helical lobe (FIG. 6C, 614) of SpyCas9 have assembled into an active sn1-casRNA/sn2-casRNA/Cas9 complex (FIG. 6C, 619). The Csy4* protein (FIG. 6C, 615) has bound to Csy4 RNA binding element (FIG. 6C, 610). The linker element (620) is also indicated.

Figure 7B:
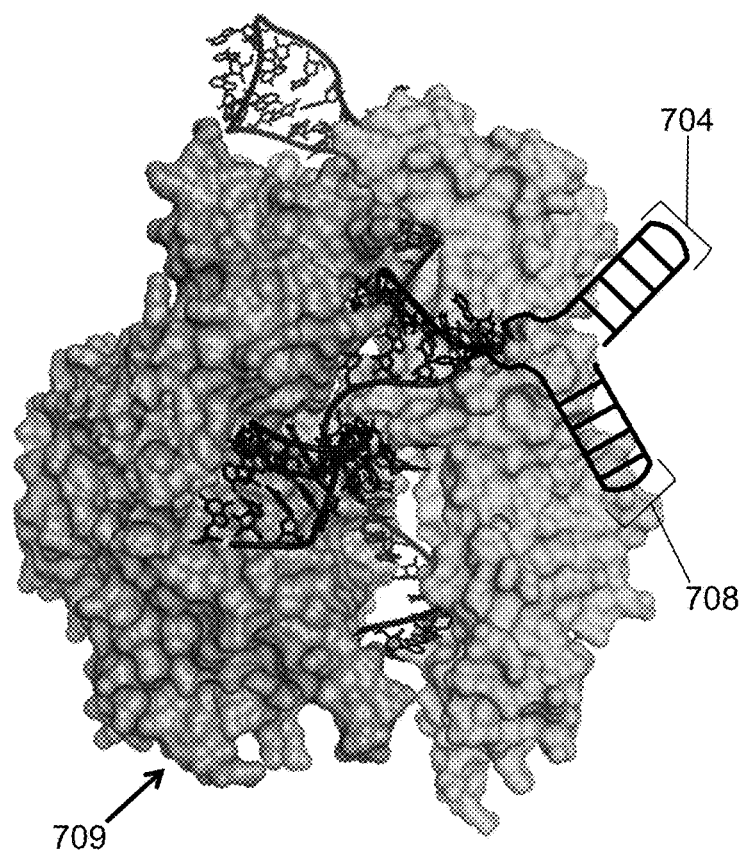

FIG. 7A and FIG. 7B illustrate an example of a split-nexus Cas9-associated two polynucleotide system. This system corresponds to a first polynucleotide (sn1-casPN) that comprises a first portion of the split nexus element (FIG. 3B, 326) and a second polynucleotide (sn2-casPN) that comprises a second portion of the split nexus element (FIG. 3B, 302). The figures are not proportionally rendered nor are they to scale. The indicators for locations corresponding to elements are only illustrative to provide reference points in the example polynucleotides. Table 4 presents a series of indicators used in FIG. 7A and FIG. 7B.

TABLE 4

Numerical Indicators Used to Illustrate Regions of Nucleotide Sequences Associated with Example sn1-casRNA and sn2-casRNA Indicators and Corresponding Elements 701 to 702 corresponds to a split nexus stem element nucleotide sequence I
702 to 703 corresponds to a first auxiliary polynucleotide
704 a hairpin element formed by hydrogen bond base pairing between bases within the first auxiliary polynucleotide
705 to 706 corresponds to a split nexus stem element nucleotide sequence II
706 to 707 corresponds to a second auxiliary polynucleotide
708 a hairpin element formed by hydrogen bond base pairing between bases within the second auxiliary polynucleotide FIG. 7A illustrates a sn1-casRNA comprising a first auxiliary polynucleotide (FIG. 7A, 702 to 703) and a sn2-casRNA comprising a second auxiliary polynucleotide (FIG. 7A, 706 to 707). The figure shows the sn1-casRNA and sn2-casRNA before association and formation of hydrogen bond base pairs between them. The figure shows a hairpin element formed by hydrogen bond base pairing between bases within the first auxiliary polynucleotide (FIG. 7A, 704) and a hairpin element formed by hydrogen bond base pairing between bases within the second auxiliary polynucleotide (FIG. 7A, 708). FIG. 7B illustrates the sn1-casRNA comprising a first auxiliary polynucleotide and the sn2-casRNA comprising a second auxiliary polynucleotide assembled into an active sn1-casRNA/sn2-casRNA/Cas9 complex. In FIG. 7B the Cas9 protein (FIG. 7B, 709), the first auxiliary polynucleotide comprising a hairpin element (FIG. 7B, 704), and the second auxiliary polynucleotide comprising a hairpin element (FIG. 7B, 708) are indicated.

Figure 8:
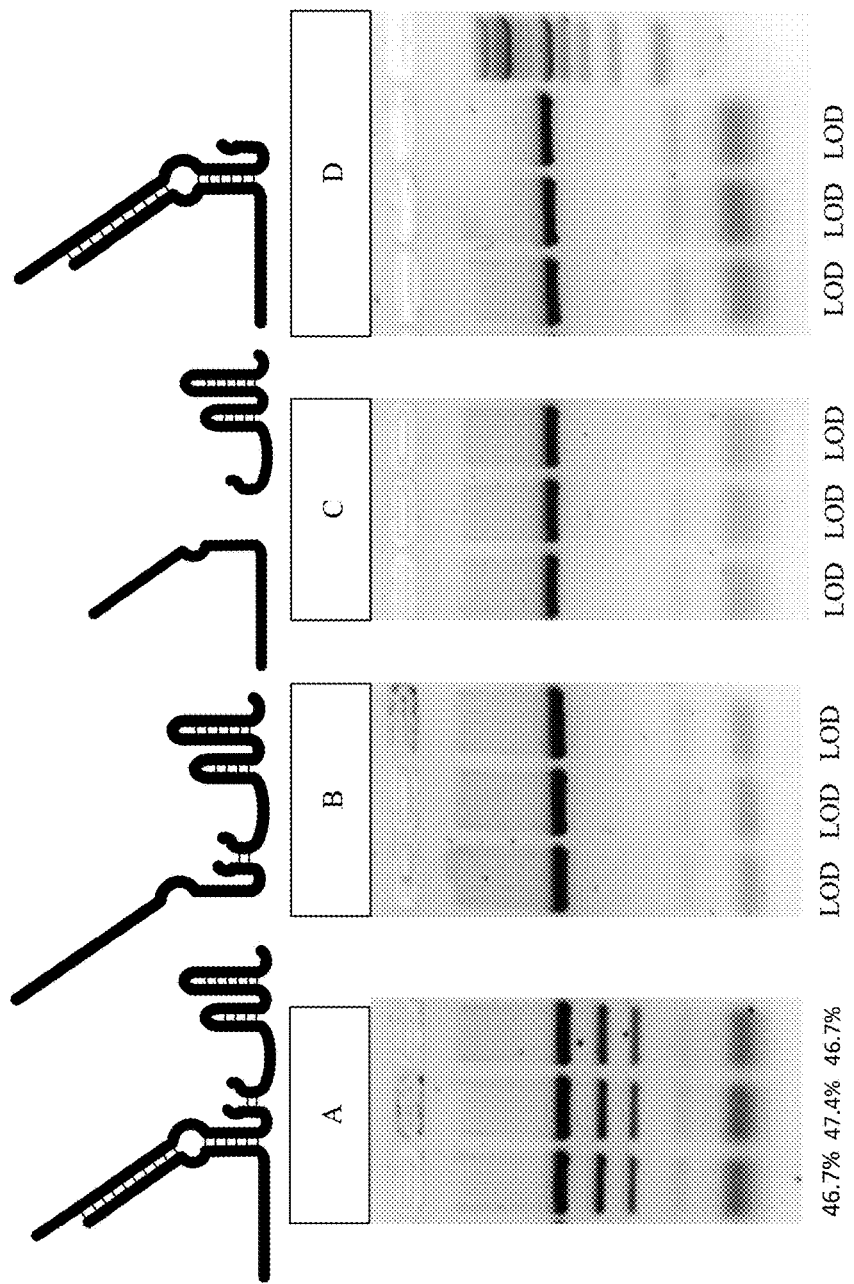
FIG. 8 presents the results of the Cas9 cleavage assay using the AAVS-1 target double-stranded DNA.

FIG. 8 presents the results of the Cas 9 cleavage assay using the AAVS-1 target double-stranded DNA. In the figure, replicates of three are shown for each combination of sn-casRNAs$^{EX}$. At the top of each panel is a graphical representation of the sn-casRNAs$^{EX}$ used in the assay. FIG. 8, Panel A shows the biochemical activity of sn1-casRNA$^{Ex}$, sn2-casRNA$^{EX}$, sn3-casRNA$^{EX}$-AAVS1. FIG. 8, Panel B shows the biochemical activity of sn1-casRNA$^{EX}$ and sn2-casRNA$^{EX}$. FIG. 8, Panel C shows the biochemical activity of sn2-casRNA$^{EX}$ and sn3-casRNA$^{EX}$-AAVS1, FIG. 8, Panel D shows the biochemical activity of sn1-casRNA$^{EX}$ and sn3-casRNA$^{EX}$-AAVS1. The last lane of FIG. 8, Panel D contains molecular weight standards. Cleavage percentages are shown at the bottom of each lane. For lanes indicated as LOD, any cleavage activity was below the limit of detection.

Figure 9:
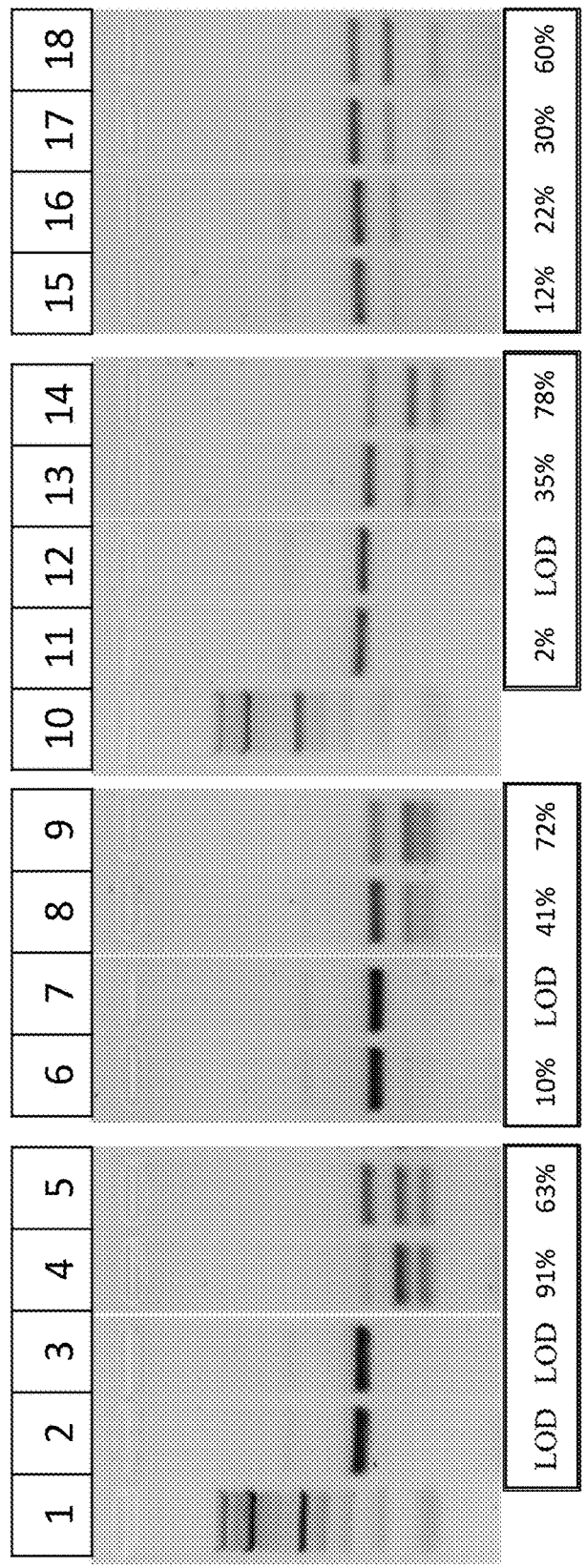
FIG. 9 presents the results of the Cas9 cleavage assay using the Csy4* protein to enhance the cleavage activity of the sn-casRNAs comprising an additional Csy4 RNA binding sequence.

FIG. 9 presents the results of the Cas9 cleavage assay using the Csy4* protein to enhance the cleavage activity of the sn-casRNAs comprising an additional Csy4 RNA binding sequence. The cleavage assays used two different split-nexus Cas9-associated two polynucleotide systems that were variants of the system present in FIG. 3B. In the first system the sn1-casRNA further comprised a first auxiliary polynucleotide comprising a Csy4 binding element nucleotide sequence I and the sn2-casRNA comprised a second auxiliary polynucleotide comprising a Csy4 binding element nucleotide sequence II, wherein the first auxiliary polynucleotide and the second auxiliary polynucleotide associate to form a Csy4 RNA binding element (sn1-casRNA$^{EXCsy}$-Csy/sn2-casRNA$^{EXCsy}$-Csy). In the second system the sn1-casRNA further comprised a first auxiliary polynucleotide comprising a linker element nucleotide sequence I and a Csy4 binding element nucleotide sequence I and the sn2-casRNA comprised a second auxiliary polynucleotide comprising a linker element nucleotide sequence II and a Csy4 binding element nucleotide sequence II, wherein the first auxiliary polynucleotide and the second auxiliary polynucleotide associate to form a linker element and a Csy4 RNA binding element (sn1-casRNA$^{EXCsy}$-lnkCsy/sn2-casRNA$^{EXCsy}$-lnkCsy). Each of the two systems was used to cleave four different targets, where the sn1-casRNAs each comprised a spacer complementary to one of the four targets: AAVS-1, CD-34, CD-151, and JAK-1. In the figure, the cleavage activity is shown at the bottom of each lane (except for lanes 1 and 10, which are molecular weight standards). For lanes indicated as LOD, any cleavage activity was below the limit of detection. The systems used in each of the Cas9 cleavage assay reactions were as shown in Table 5.

TABLE 5

Split Nexus Polynucleotide Components
Used in Cas9 Cleavage Assays

| Lane | sn-casRNAs$^{EXCsy}$ | Csy4* Protein Added? |
|---|---|---|
| 1 | No (Molecular Weight Standard) | n/a |
| 2 | sn1-casRNA$^{EXCsy}$-Csy-AAVS1/sn2-casRNA$^{EXCsy}$-Csy | NO |
| 3 | sn1-casRNA$^{EXCsy}$-lnkCsy-AAVS1/sn2-casRNA$^{EXCsy}$-lnkCsy | NO |
| 4 | sn1-casRNA$^{EXCsy}$-Csy-AAVS1/sn2-casRNA$^{EXCsy}$-Csy | YES |
| 5 | sn1-casRNA$^{EXCsy}$-lnkCsy-AAVS1/sn2-casRNA$^{EXCsy}$-lnkCsy | YES |
| 6 | sn1-casRNA$^{EXCsy}$-Csy-CD34/sn2-casRNA$^{EXCsy}$-Csy | NO |
| 7 | sn1-casRNA$^{EXCsy}$-lnkCsy-CD34/sn2-casRNA$^{EXCsy}$-lnkCsy | NO |
| 8 | sn1-casRNA$^{EXCsy}$-Csy-CD34/sn2-casRNA$^{EXCsy}$-Csy | YES |
| 9 | sn1-casRNA$^{EXCsy}$-lnkCsy-CD34/sn2-casRNA$^{EXCsy}$-lnkCsy | YES |
| 10 | No (Molecular Weight Standard) | n/a |
| 11 | sn1-casRNA$^{EXCsy}$-Csy-CD151/sn2-casRNA$^{EXCsy}$-Csy | NO |
| 12 | sn1-casRNA$^{EXCsy}$-lnkCsy-CD151/sn2-casRNA$^{EXCsy}$-lnkCsy | NO |
| 13 | sn1-casRNA$^{EXCsy}$-Csy-CD151/sn2-casRNA$^{EXCsy}$-Csy | YES |
| 14 | sn1-casRNA$^{EXCsy}$-lnkCsy-CD151/sn2-casRNA$^{EXCsy}$-lnkCsy | YES |
| 15 | sn1-casRNA$^{EXCsy}$-Csy-JAK-1/sn2-casRNA$^{EXCsy}$-Csy | NO |
| 16 | sn1-casRNA$^{EXCsy}$-lnkCsy-JAK-1/sn2-casRNA$^{EXCsy}$-lnkCsy | NO |
| 17 | sn1-casRNA$^{EXCsy}$-Csy-JAK-1/sn2-casRNA$^{EXCsy}$-Csy | YES |
| 18 | sn1-casRNA$^{EXCsy}$-lnkCsy-JAK-1/sn2-casRNA$^{EXCsy}$-lnkCsy | YES |

Figure 10:
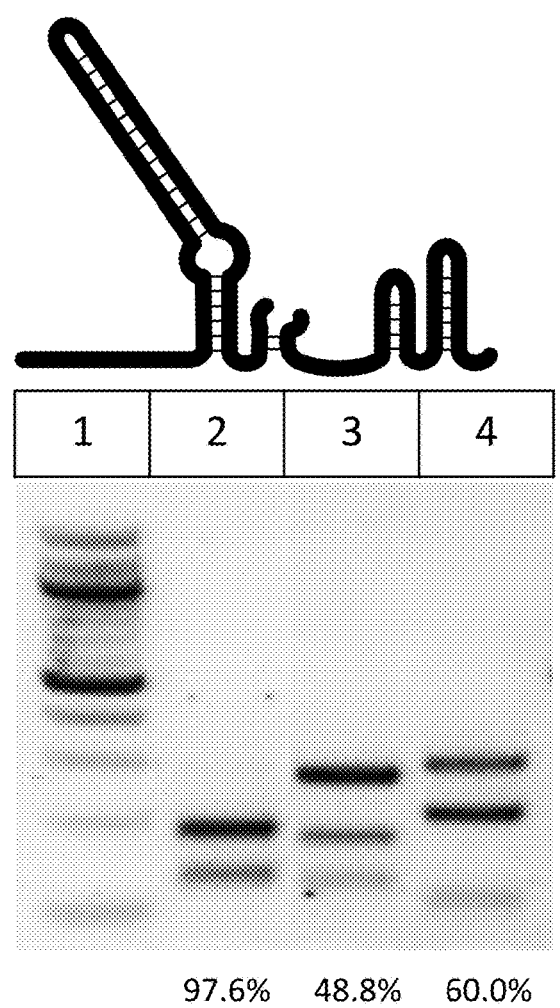
FIG. 10 presents the result of the Cas9 cleavage assay using sn1-casRNAs$^{EX2}$ and sn2-casRNA$^{EX2}$.

FIG. 10 presents the result of the Cas9 cleavage assay using sn1-casRNAs$^{EX2}$ and sn2-casRNA$^{EX2}$. Cleavage percentages are shown at the bottom of each lane except for lane 1, which is a molecular weight standard. FIG. 10, lane 2, presents cleavage results for a sn1-casRNA$^{EX2}$-AAVS1 and sn2-casRNA$^{EX2}$ system. FIG. 10, lane 3, presents cleavage results for a sn1-casRNA$^{EX2}$-CD151 and sn2-casRNA$^{EX2}$ system. FIG. 10, lane 4, presents the results for a sn1-casRNA$^{EX2}$-JAK1 and sn2-casRNA$^{EX2}$ system. At the top of the figure is a graphical representation of the sn-casRNAs$^{EX2}$ used in the assay.

Figure 11:
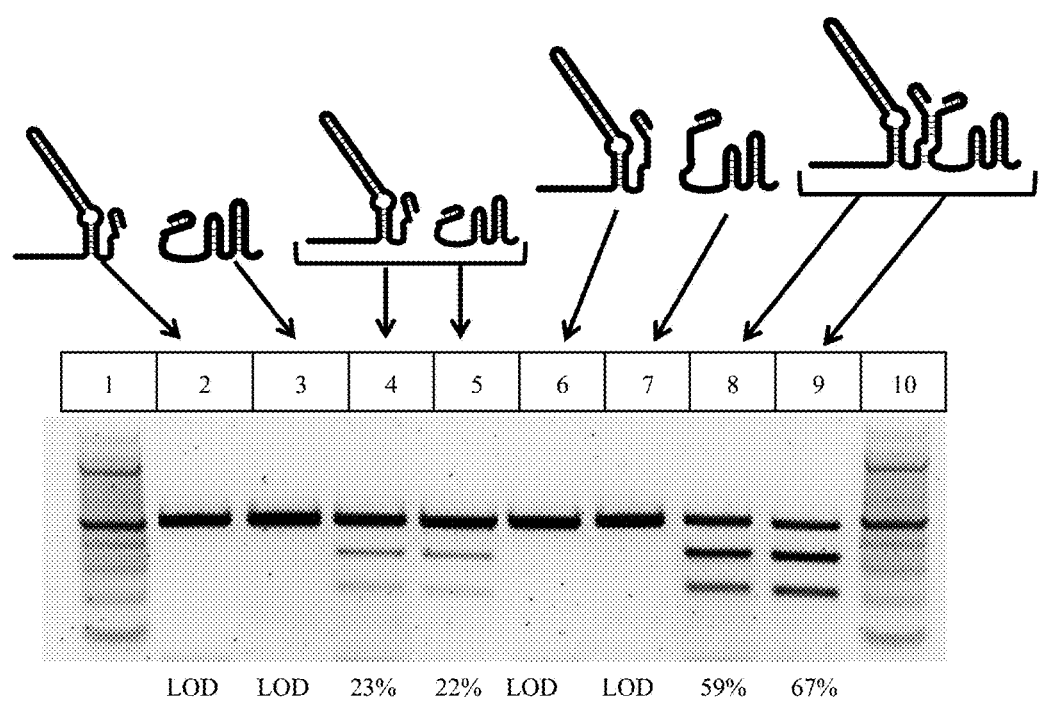
FIG. 11 presents the results of Cas9 cleavage assays.

FIG. 11 presents the results of Cas9 cleavage assays. The cleavage assays used two different split-nexus Cas9-associated two polynucleotide systems similar to the system illustrated in FIG. 7A. In the figure, the cleavage activity is shown at the bottom of each lane (except for lanes 1 and 10, which are molecular weight standards). For lanes indicated as LOD, any cleavage activity was below the limit of detection. Representations of the sn-casRNA(s) used in each assay are illustrated at the top of the figure. The systems used in each of the Cas9 cleavage assay reactions were as shown in Table 6.

TABLE 6

Split Nexus Polynucleotide Components Used in Cas9 Cleavage Assays

| Lane | sn-casRNAs$^{EX3Csy}$ | Csy4* Protein Added? |
|---|---|---|
| 1 | None (Molecular Weight Standard) | n/a |
| 2 | sn1-casRNA$^{EX3Csy}$-Csy-AAVS1 | NO |
| 3 | sn2-casRNA$^{EX3Csy}$-Csy | NO |
| 4 | sn1-casRNA$^{EX3Csy}$-Csy-AAVS1/sn2-casRNA$^{EX3Csy}$-Csy | NO |
| 5 | sn1-casRNA$^{EX3Csy}$-Csy-AAVS1/sn2-casRNA$^{EX3Csy}$-Csy | YES |
| 6 | sn1-casRNA$^{EX3Csy}$-lnkCsy-AAVS1 | NO |
| 7 | sn2-casRNA$^{EX3Csy}$-lnkCsy | NO |
| 8 | sn1-casRNA$^{EX3Csy}$-lnkCsy-AAVS1/sn2-casRNA$^{EX3Csy}$-lnkCsy | NO |
| 9 | sn1-casRNA$^{EX3Csy}$-lnkCsy-AAVS1/sn2-casRNA$^{EX3Csy}$-lnkCsy | YES |
| 10 | None (Molecular Weight Standard) | n/a |

FIG. 12 presents examples of putative split nexus arrangements of known tracrRNA sequences from the bacterial species listed in Table 7. In the figure, the first column is an identifying number for the bacterial species (as shown in Table 7, the second column is the sequence of the split nexus tracrRNA (an example of sn1-casRNA/sn2-casRNA), and the third column is the SEQ ID NO of the oligonucleotide. All bacterial species listed in Table 7 have at least one identified Type II CRISPR-Cas9 system.

TABLE 7

Bacterial Species and Putative Split-nexus tracrRNA Sequences

| ID | Genus/Species |
|---|---|
| 1 | *Streptococcus pyogenes* |
| 2 | *Streptococcus thermophilus* CRISPR-1 |
| 3 | *Listeria innocua* |
| 4 | *Neisseria meningitidis* |
| 5 | *Streptococcus gallolyticus* |
| 6 | *Staphylococcus aureus* |
| 7 | *Corynebacterium diphtheriae* |
| 8 | *Parvibaculum lavamentivorans* |
| 9 | *Campylobacter lari* |
| 10 | *Neisseria cinerea* |
| 11 | *Streptococcus pasteurianus* |

FIG. 13 is an oligonucleotide table that sets forth the sequences of oligonucleotides used in the Examples of the present specification: The first column is an identifying letter for the oligonucleotide, the second column is the sequence of the oligonucleotide, and the third column is the SEQ ID NO of the oligonucleotide.

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a primer" includes one or more primer, reference to "a recombinant cell" includes one or more recombinant cell, reference to "a cross-linking agent" includes one or more cross-linking agent, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, preferred materials and methods are described herein.

In view of the teachings of the present specification, one of ordinary skill in the art can apply conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, 2014, Cold Spring Harbor Laboratory Press, ISBN 978-1-936113-81-1; Culture of Animal Cells: A Manual of Basic Technique and Specialized Applications, 6th Edition, R. I. Freshney, 2010, Wiley-Blackwell, ISBN 978-0-470-52812-9; Transgenic Animal Technology, Third Edition: A Laboratory Handbook, 2014, C. A. Pinkert, Elsevier, ISBN 978-0124104907; The Laboratory Mouse, Second Edition, 2012, H. Hedrich, Academic Press, ISBN 978-0123820082; Manipulating the Mouse Embryo: A Laboratory Manual, 2013, R. Behringer, et al., Cold. Spring Harbor Laboratory Press, ISBN 978-1936113019; PCR 2: A Practical Approach, 1995, M. J. McPherson, et al., IRL Press, ISBN 978-0199634248; Methods in Molecular Biology (Series), J. M. Walker, ISSN 1064-3745, Humana Press; RNA: A Laboratory Manual, 2010, D. C. Rio, et al., Cold Spring Harbor Laboratory Press, ISBN 978-0879698911; Methods in Enzymology (Series), Academic Press; Molecular Cloning: A Laboratory Manual (Fourth Edition), 2012, M. R. Green, et al., Cold Spring Harbor Laboratory Press, ISBN 978-1605500560; Bioconjugate Techniques, Third Edition, 2013, G. T. Hermanson, Academic Press, ISBN 978-0123822390; Methods in Plant Biochemistry and Molecular Biology, 1997, W. V. Dashek, CRC Press, ISBN 978-0849394805; Plant Cell Culture Protocols (Methods in Molecular Biology), 2012, V. M. Loyola-Vargas, et al., Humana Press, ISBN 978-1617798177; Plant Transformation Technologies, 2011, C. N. Stewart, et al., Wiley-Blackwell, ISBN 978-0813821955; Recombinant Proteins from Plants (Methods in Biotechnology), 2010, C. Cunningham, et al., Humana Press, ISBN 978-1617370212; Plant Genomics: Methods and Protocols (Methods in Molecular Biology), 2009, D. J. Somers, et al., Humana Press, ISBN 978-1588299970; Plant Biotechnology: Methods in Tissue Culture and Gene Transfer, 2008, R. Keshavachandran, et al., Orient Blackswan, ISBN 978-8173716164.

As used herein and described in detail below, the term "sn-casPNs" refers to split-nexus Cas9-associated polynucleotides of the present invention. One distinguishing feature of the sn-casPNs is that at least two of the two or more Cas associated polynucleotides are necessary to form a nexus stem element.

The term "Cas protein" as used herein refers to Type II CRISPR Cas proteins (as described, e.g., in Chylinski, K., (2013) "The tracrRNA and Cas9 families of type II CRISPR-Cas immunity systems," RNA Biol. 2013 10(5): 726-737), including, but not limited to Cas9, Cas9-like, Cas1, Cas2, Cas3, Csn2, Cas4, proteins encoded by Cas9 orthologs, Cas9-like synthetic proteins, and variants and modifications thereof.

The term "Cas9 protein" as used herein refers to Cas9 wild-type proteins derived from Type II CRISPR-Cas9 systems, modifications of Cas9 proteins, variants of Cas9 proteins, Cas9 orthologs, and combinations thereof.

As used herein "sn-casPNs/Cas9 protein system" and "sn-casPNs/Cas9 system" are used interchangeably to refer to engineered Type II CRISPR-Cas9 systems comprising at least sn-casPNs and Cas9 protein components, expressible forms of the components thereof, or combinations of the components and expressible forms of the components. An engineered Type II CRISPR-Cas9 system of the present invention comprises at least a two polynucleotide system of sn-casPNs as described herein. sn-casPNs/Cas9 systems can comprise further CRISPR Cas components, such as additional Cas proteins.

As used herein, the terms "wild-type," "naturally-occurring" and "unmodified" are used to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in and can be isolated from a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," and "non-naturally occurring" are interchangeable and indicate intentional human manipulation.

As used herein, the terms "nucleic acid," "nucleotide sequence," "oligonucleotide," and "polynucleotide" are interchangeable. All refer to a polymeric form of nucleotides. The nucleotides may be deoxyribonucleotides (DNA) or ribonucleotides (RNA), or analogs thereof, and they may be of any length. Polynucleotides may perform any function and may have any secondary structure and three-dimensional structure. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides (e.g., many modified nucleotides are available from commercial providers like TriLink (San Diego, Calif.) and Integrated DNA Technologies (Coralville, Iowa)). Examples of modified nucleotides include methylated nucleotides and nucleotide analogs. Nucleotide structure may be modified before or after a polymer is assembled. Following polymerization, polynucleotides may be additionally modified via, for example, conjugation with a labeling component or target-binding component. A nucleotide sequence may incorporate non-nucleotide components. The terms also encompasses nucleic acids comprising modified backbone residues or linkages, that (i) are synthetic, naturally occurring, and non-naturally occurring, and (ii) have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids, and morpholino structures.

Peptide-nucleic acids (PNAs) are synthetic homologs of nucleic acids wherein the polynucleotide phosphate-sugar backbone is replaced by a flexible pseudo-peptide polymer. Nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation. In some embodiments, phosphorothioate bonds are introduced between the last 3-5 nucleotides at the 5'- or 3'-end of a polynucleotide sequence to inhibit exonuclease degradation. Placement of phosphorothioate bonds throughout an entire oligonucleotide helps reduce degradation by endonucleases as well.

Threose nucleic acid (TNA) is an artificial genetic polymer. TNA's backbone structure comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., www.ucalgary.ca/dnalab/synthesis/-modifications/linkages). Typically such polynucleotides have phosphoramidite groups on the 5'-OH position and a dimethoxytrityl (DMT) protecting group on the 3'-OH position. Normally, the DMT protecting group is on the 5'-OH and the phosphoramidite is on the 3'-OH. The most common use of linkage inversion is to add a 3'-3' linkage to the end of a polynucleotide with a phosphorothioate backbone. The 3'-3' linkage stabilizes the polynucleotide to exonuclease degradation by creating an oligonucleotide having two 5'-OH ends and no 3'-OH end.

Polynucleotide sequences are displayed herein in the conventional 5' to 3' orientation.

As used herein, the term "complementarity" refers to the ability of a nucleic acid sequence to form hydrogen bond(s) with another nucleic acid sequence (e.g., through traditional Watson-Crick base pairing). A percent complementarity indicates the percentage of residues in a nucleic acid molecule that can form hydrogen bonds with a second nucleic acid sequence. When two polynucleotide sequences have 100% complementary, the two sequences are perfectly complementary, i.e., all of a first polynucleotide's contiguous residues hydrogen bond with the same number of contiguous residues in a second polynucleotide.

As used herein, the term "sequence identity" generally refers to the percent identity of bases or amino comparing a first polynucleotide or polypeptide to a second polynucleotide or polypeptide using algorithms having various weighting parameters. Sequence identity between two polypeptides or two polynucleotides can be determined using sequence alignment by various methods and computer programs (e.g., BLAST, CS-BLAST, FASTA, HMMER, L-ALIGN, etc.), available through the worldwide web at sites including GENBANK (www.ncbi.nlm.nih.gov/genbank/) and EMBL-EBI (www.ebi.ac.uk.). Sequence identity between two polynucleotides or two polypeptide sequences is generally calculated using the standard default parameters of the various methods or computer programs.

As used herein "hybridization" or "hybridize" or "hybridizing" is the process of combining two complementary single-stranded DNA or RNA molecules and allowing them to form a single double-stranded molecule (DNA/DNA, DNA/RNA, RNA/RNA) through hydrogen base pairing. Hybridization stringency is typically determined by the hybridization temperature and the salt concentration of the hybridization buffer, for example, high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below Tm; moderate stringency, approximately 0.16M to approximately 0.33M salt, hybridization temperature 20° C. to 29° C. below Tm; low stringency, approximately 0.33M to approximately 0.82M salt, hybridization temperature 40° C. to 48° C. below Tm. Tm of duplex nucleic acids is calculated by standard methods well-known in the art (Maniatis, T., et al (1982) Molecular Cloning: A Laboratory Manual, Cold Spring Harbor Laboratory Press: New York; Casey, J., et al., (1977) Nucleic Acids Res., 4: 1539; Bodkin, D K., et al., (1985) J. Virol. Methods, 10: 45; Wallace, R. B., et al. (1979) Nucleic Acids Res. 6: 3545.) Algorithm prediction tools to estimate Tm are also widely available. High stringency conditions for hybridization typically refer to conditions under which a nucleic acid having complementarity to a target sequence predominantly hybridizes with the target sequence, and substantially does not hybridize to non-target sequences. Typically hybridization conditions are of moderate stringency, preferably high stringency.

As used herein a "stem-loop structure" or "stem-loop element" refers to a polynucleotide having a secondary structure that includes a region of nucleotides that are known or predicted to form a double strand region (the "stem element") that is linked on one side by a region of predominantly single-stranded nucleotides (the "loop element"). The term "hairpin" element is also used herein to refer to stem-loop structures. Such structures are well known in the art. The base pairing may be exact. However, as is known in the art, that a stem element does not require exact base pairing. Thus, the stem element may include one or more base mismatches or non-paired bases.

As used herein, the term "recombination" refers to a process of exchange of genetic information between two polynucleotides.

As used herein, the terms "donor polynucleotide," "donor template" and "donor oligonucleotide" are used interchangeably and refer to a polynucleotide that provides a nucleic acid sequence of which at least a portion is intended to be integrated into a selected nucleic acid target site. Typically, a donor polynucleotide is a single-strand polynucleotide or a double-strand polynucleotide. For example, an engineered Type II CRISPR-Cas9 system of the present invention can be used in combination with a donor DNA template to modify a DNA target sequence in a genomic DNA wherein the genomic DNA is modified to comprise at least a portion of the donor DNA template at the DNA target sequence. In some embodiments, a vector comprises a donor polynucleotide (e.g., a targeting vector). In other embodiments, a donor polynucleotide is an oligonucleotide.

As used herein, the term "homology-directed repair (HDR)" refers to DNA repair that takes place in cells, for example, during repair of double-strand breaks in DNA. HDR requires nucleotide sequence homology and uses a donor template (e.g., a donor DNA template) or donor oligonucleotide to repair the sequence wherein the double-strand break occurred (e.g., DNA target sequence). This results in the transfer of genetic information from, for example, the donor template DNA to the DNA target sequence. HDR may result in alteration of the DNA target sequence (e.g., insertion, deletion, mutation) if the donor template DNA sequence or oligonucleotide sequence differs from the DNA target sequence and part or all of the donor template DNA polynucleotide or oligonucleotide is incorporated into the DNA target sequence. In some embodiments, an entire donor template DNA polynucleotide, a portion of the donor template DNA polynucleotide, or a copy of the donor polynucleotide is integrated at the site of the DNA target sequence.

The terms "vector" and "plasmid" are used interchangeably and as used herein refer to a polynucleotide vehicle to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, viral vectors, cosmids, and artificial chromosomes.

As used herein the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein a "targeting vector" is a recombinant DNA construct typically comprising tailored DNA arms homologous to genomic DNA that flanks critical elements of a target gene or target sequence. When introduced into a cell the targeting vector integrates into the cell genome via homologous recombination. Elements of the target gene can be modified in a number of ways including deletions and/or insertions. A defective target gene can be replaced by a functional target gene, or in the alternative a functional gene can be knocked out. Optionally a targeting vector comprises a selection cassette comprising a selectable marker that is introduced into the target gene. Targeting regions adjacent or sometimes within a target gene can be used to affect regulation of gene expression.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like.

As used herein the term "operably linked" refers to polynucleotide sequences or amino acid sequences placed into a functional relationship with one another. For instance, a promoter or enhancer is operably linked to a coding sequence if it regulates, or contributes to the modulation of, the transcription of the coding sequence. Operably linked DNA sequences encoding regulatory sequences are typically contiguous to the coding sequence. However, enhancers can function when separated from a promoter by up to several kilobases or more. Accordingly, some polynucleotide elements may be operably linked but not contiguous.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product." Expression may include splicing the mRNA in a eukaryotic cell, if the polynucleotide is derived from genomic DNA.

As used herein, the term "gene" comprises a DNA region encoding a gene product (e.g., an RNA or a protein), as well as all DNA regions that regulate the production of the gene product, whether or not such regulatory sequences are adjacent to the DNA region encoding the gene product. For example, in addition to the DNA region encoding the gene product, a gene can include promoter sequences, termination sequences, translational regulatory sequences (e.g., ribosome binding sites and internal ribosome entry sites), enhancers, silencers, insulators, boundary elements, replication origins, matrix attachment sites, locus control regions, and combinations thereof.

As used herein the term "modulate" refers to a change in the quantity, degree. or amount of a function. For example, the sn-casPNs/Cas9 protein systems disclosed herein may modulate the activity of a promoter sequence by binding at or near the promoter. Depending on the action occurring after binding, the sn-casPNs/Cas9 protein systems can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, e.g., changes in RNA or protein levels, protein activity, product levels, associated gene expression, or activity level of reporter genes. Accordingly, the terms "modulating expression," "inhibiting expression," and "activating expression" of a gene can refer to the ability of a sn-casPNs/Cas9 protein system to change, activate, or inhibit transcription of a gene.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, cross-linking, and/or conjugation (e.g., with a labeling component or ligand). Polypeptide sequences are displayed herein in the conventional N-terminal to C-terminal orientation.

Polypeptides and polynucleotides can be made using routine techniques in the field of molecular biology (see, e.g., standard texts discussed above). Furthermore, essentially any polypeptide or polynucleotide can be custom ordered from commercial sources.

As used herein, "non-native" refers to a nucleic acid sequence or polypeptide sequence that is not found in the corresponding native (or wild-type) nucleic acid sequence or polypeptide sequence. Non-native can also refer to a naturally occurring nucleic acid or polypeptide sequence that comprises mutations, insertions, deletions, or other modifications. A non-native nucleic acid sequence or polypeptide sequence may be linked to a naturally occurring nucleic acid sequence or polypeptide sequence by genetic engineering to generate a chimeric nucleic acid sequence or polypeptide sequence.

As used herein, "fusion" refers to a polypeptide sequence ("fusion polypeptide") and/or nucleic acid sequence ("fusion polynucleotide," "fusion nucleic acids") comprising one or more non-native sequences. Fusion can also refer to the attachment of a moiety to a polypeptide sequence or nucleic acid sequence, wherein the moiety is not native to the corresponding nucleic acid sequence or polypeptide sequence (i.e., the corresponding wild-type nucleic acid sequence or polypeptide sequence does not comprise the moiety). Examples of sequences and moieties that can be useful in the generation of fusion polypeptides or fusion polynucleotides include: a subcellular localization signal or coding sequences therefore (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like); a small molecule such as biotin or a dye (e.g., alexa fluor dyes, Cyanine3 dye, Cyanine5 dye); a detectable label, including a moiety that can provide a detectable signal (e.g., an enzyme, a radioisotope, a member of a specific binding pair; a fluorophore; a fluorescent protein; a quantum dot; and the like); a member of a FRET pair (donor/acceptor) (e.g., EDANS/fluorescein, IAEDANS/fluorescein, fluorescein/tetramethylrhodamine, fluorescein/Cy5, EDANS/DABCYL, fluorescein/QSY-7, fluorescein/LC Red 640, fluorescein/Cy 5.5 and fluorescein/LC Red 705); a fluorophore/quantum dot donor/acceptor pair; fluorescent labels (e.g., fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY® FL, LC Red 640, Cy 5, Cy 5.5, LC Red 705 and Oregon green); an enzyme (horse radish peroxidase, luciferase, beta-galactosidase, and the like); a fluorescent protein (e.g., a green fluorescent protein (GFP), a red fluorescent protein, a yellow fluorescent protein, any of a variety of fluorescent and colored proteins); a nanoparticle (e.g., fluorescent or luminescent nanoparticles, and magnetic nanoparticles); quantum dots (QDs) (QDs can be rendered water soluble by applying coating layers comprising a variety of different materials. For example, QDs can be solubilized using amphiphilic polymers; QDs can be conjugated to a polypeptide via any of a number of different functional groups or linking agents that can be directly or indirectly linked to a coating layer); and radioisotopes.

The term "binding" as used herein refers to a non-covalent interaction between macromolecules (e.g., between a protein and a polynucleotide, between a polynucleotide and a polynucleotide, and between a protein and a protein). Such non-covalent interaction is also referred to as "associating" or "interacting" (e.g., when a first macromolecule interacts with a second macromolecule, the first macromolecule binds to second macromolecule in a non-covalent manner). Some portions of a binding interaction may be sequence-specific; however, all components of a binding interaction do not need to be sequence-specific, such as the contact points of the protein with phosphate residues in a DNA backbone. Binding interactions can be characterized by a dissociation constant (Kd). "Affinity" refers to the strength of binding. An increased binding affinity is correlated with a lower Kd. An example of non-covalent binding is hydrogen bond formation between base pairs.

As used herein, the term "effector protein" refers to any polypeptide with a functional effect that selectively or specifically binds to an effector protein binding element within a polynucleotide. Such effector protein binding elements can be single-stranded or double-stranded polynucleotides. For example, an effector protein can comprise enzymatic activity, remodel biological molecules (e.g., folding chaperones), or be a scaffolding protein. In addition to binding a cognate effector protein binding element, an effector protein can modify a polynucleotide comprising a cognate effector binding element (e.g., cleavage, enzymatic modification, transcriptional modification). Alternatively, an effector protein can just bind to its cognate effector protein binding element. Effector proteins with enzymatic activity can be modified to be enzymatically inactive, however, they maintain their ability to bind an effector protein binding element. For example, Csy4 binds a Csy4 double-strand RNA binding element. Csy4 is normally an active endoribonucleases but Csy4 has variants in which its endonuclease activity has been eliminated (e.g., Csy4*). Cas 7, Cas5, and Cas6 are also examples of effector proteins. Other examples of effector proteins include, but are not limited to single-strand RNA binding proteins (e.g., p19 siRNA Binding Protein), single-strand DNA binding proteins (e.g., adnovirus DBP, Extreme Thermostable Single-Stranded DNA Binding Protein), double-strand RNA binding proteins (e.g., DICER), double-strand DNA binding proteins (e.g., Zinc Finger proteins) and double-strand RNA/DNA hybrids (e.g., Ribonuclease H).

As used herein, the term "isolated" can refer to a nucleic acid or polypeptide that, by the hand of a human, exists apart from its native environment and is therefore not a product of nature. Isolated means substantially pure. An isolated nucleic acid or polypeptide can exist in a purified form and/or can exist in a non-native environment such as, for example, in a recombinant cell.

As used herein, "organism" refers to any living biological entity, such as a bacterium, protist, fungus, plant, or animal, composed of one or more cells.

As used herein, a "host cell" generally refers to a biological cell. A cell can be the basic structural, functional and/or biological unit of a living organism. A cell can originate from any organism having one or more cells. Examples of host cells include, but are not limited to: a prokaryotic cell, eukaryotic cell, a bacterial cell, an archacal cell, a cell of a single-cell eukaryotic organism, a protozoa cell, a cell from a plant (e.g. cells from plant crops (such as soy, tomatoes, sugar beets, pumpkin, hay, cannabis, tobacco, plantains, yams, sweet potatoes, cassava, potatoes, wheat, sorghum, soybean, rice, wheat, corn, oil-producing Brassica (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., Botryococcus braunii, Chlamydomonas reinhardtii, Nannochloropsis gaditana, Chlorella pyrenoidosa, Sargassum patens C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.). Furthermore, a cell can be a stem cell or progenitor cell.

As used herein, the term "transgenic organism" refers to an organism comprising a recombinantly introduced polynucleotide.

As used herein, the terms "transgenic plant cell" and "transgenic plant" are interchangeable and refer to a plant cell or a plant containing a recombinantly introduced polynucleotide. Included in the term transgenic plant is the progeny (any generation) of a transgenic plant or a seed such that the progeny or seed comprises a DNA sequence encoding a recombinantly introduced polynucleotide or a fragment thereof.

As used herein, the phrase "generating a transgenic plant cell or a plant" refers to using recombinant DNA methods and techniques to construct a vector for plant transformation to transform the plant cell or the plant and to generate the transgenic plant cell or the transgenic plant.

The term "excipient" as used herein typically refers to any pharmacologically inactive substance used for in the formulation or administration of pharmaceutical compositions of the present invention, for example, a carrier or vehicle. Examples of excipients useful in the practice of the present invention are described herein.

The term "physiological conditions" as used herein refers to conditions compatible with living cells, e.g., predominantly aqueous conditions of a temperature, pH, salinity, etc.

The terms "therapeutic composition," "pharmaceutical composition," "therapeutic preparation," and "pharmaceutical preparation" are used interchangeably herein and encompass compositions of the present invention suitable for application or administration to a subject, typically a human. In general such compositions are safe, sterile, and preferably free of contaminants that are capable of eliciting undesirable responses in the subject (i.e., the compound(s) comprising the composition are pharmaceutically acceptable). Compositions can be formulated for application or administration to a subject in need thereof by a number of different routes of administration including oral (i.e., administered by mouth or alimentary canal) or parenteral (e.g., buccal, rectal, transdermal, transmucosal, subcutaneous, intravenous, intraperitoneal, intradermal, intratracheal, intrathecal, pulmonary, and the like).

The term "subject" as used herein refers to any member of the subphylum Chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese; and the like. The term does not denote a particular age. Thus, adult, young, and newborn individuals are intended to be covered.

A CRISPR (Clustered Regularly Interspaced Short Palindromic Repeats) is a genomic locus found in the genomes of many prokaryotes (e.g., bacteria and archaea). CRISPR loci provide resistance to foreign invaders (e.g., virus, phage) in prokaryotes. In this way, the CRISPR system can be thought to function as a type of immune system to help defend prokaryotes against foreign invaders. There are three stages of CRISPR locus function: integration of new sequences into the locus, biogenesis of CRISPR RNA (crRNA), and silencing of foreign invader nucleic acid.

A CRISPR locus includes a number of short repeating sequences referred to as "repeats." Repeats can form hairpin structures and/or repeats can be unstructured single-stranded sequences. The repeats occur in clusters. Repeats frequently diverge between species. Repeats are regularly interspaced with unique intervening sequences, referred to as "spacers," resulting in a repeat-spacer-repeat locus architecture. Spacers are identical to or have high homology with known foreign invader sequences. A spacer-repeat unit encodes a crisprRNA (crRNA). A crRNA refers to the mature form of the spacer-repeat unit. A crRNA comprises a "seed" sequence that is involved in targeting a target nucleic acid (e.g., possibly as a surveillance mechanism against foreign nucleic acid). A seed sequence is typically located towards the 5' end of a crRNA (e.g. in the Cascade complex; for a description of the Cascade complex see, e.g., Jore, M. M. et al., "Structural basis for CRISPR RNA-guided DNA recognition by Cascade," Nature Structural & Molecular Biology 18, 529-536 (2011)) or at the 3' end of the spacer of a crRNA (e.g., in a Type II CRISPR-Cas9 system), directly adjacent to the first stem.

A CRISPR locus comprises polynucleotide sequences encoding for CRISPR Associated Genes (Cas) genes. Cas genes are involved in the biogenesis and/or the interference stages of crRNA function. Cas genes display extreme sequence (e.g., primary sequence) divergence between species and homologues. For example, Cas1 homologues can comprise less than 10% primary sequence identity between homologues. Some Cas genes comprise homologous secondary and/or tertiary structures. For example, despite extreme sequence divergence, many members of the Cas6-family of CRISPR proteins comprise a N-terminal ferredoxin-like fold. Cas genes are named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

The integration stage of a CRISPR system refers to the ability of the CRISPR locus to integrate new spacers into the crRNA array upon being infected by a foreign invader. Acquisition of the foreign invader spacers can help confer immunity to subsequent attacks by the same foreign invader. Integration typically occurs at the leader end of the CRISPR locus. Cas proteins (e.g., Cas1 and Cas2) are involved in integration of new spacer sequences. Integration proceeds similarly for some types of CRISPR systems (e.g., Type I-III).

Mature crRNAs are processed from a longer polycistronic CRISPR locus transcript (i.e., pre-crRNA array). A pre-crRNA array comprises a plurality of crRNAs. The repeats in the pre-crRNA array are recognized by Cas genes. Cas genes bind to the repeats and cleave the repeats. This action can liberate the plurality of crRNAs. crRNAs can be subjected to further events to produce the mature crRNA form such as trimming (e.g., with an exonuclease). A crRNA may comprise all, some, or none of the CRISPR repeat sequence.

Interference refers to the stage in the CRISPR system that is functionally responsible for combating infection by a foreign invader. CRISPR interference follows a similar mechanism to RNA interference (RNAi: e.g., wherein a target RNA is targeted (e.g., hybridized) by a short interfering RNA (siRNA)), which results in target RNA degradation and/or destabilization. CRISPR systems perform interference of a target nucleic acid by coupling crRNAs and Cas genes, thereby forming CRISPR ribonucleoproteins (crRNPs). crRNA of the crRNP guides the crRNP to foreign invader nucleic acid, (e.g., by recognizing the foreign invader nucleic acid through hybridization). Hybridized target foreign invader nucleic acid-crRNA units are subjected to cleavage by Cas proteins. Target nucleic acid interference typically requires a protospacer adjacent motif (PAM) in a target nucleic acid.

There are four types of CRISPR systems: Type I, Type II, Type III, and Type U. More than one CRISPR type system can be found in an organism. CRISPR systems can be complementary to each other, and/or can lend functional units in trans to facilitate CRISPR locus processing. Modifications of the components of CRISPR-Type II systems are extensively discussed in the present specification.

crRNA biogenesis in a Type II CRISPR system comprises a trans-activating CRISPR RNA (tracrRNA). A tracrRNA is typically modified by endogenous RNaseIII. The tracrRNA of the complex hybridizes to a crRNA repeat in the precrRNA array. Endogenous RNaseIII is recruited to cleave the pre-crRNA. Cleaved crRNAs is subjected to exoribonuclease trimming to produce the mature crRNA form (e.g., 5' trimming). The tracrRNA typically remains hybridized to the crRNA. The tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid activates a wild-type, cognate Cas9 for target nucleic acid cleavage. Target nucleic acid in a Type II CRISPR system comprises a PAM. In some embodiments, a PAM is essential to facilitate binding of a site-directed polypeptide (e.g., Cas9) to a target nucleic acid.

Type II CRISPR-Cas9 systems can be further subdivided into II-A (contains Csn2) and II-B (contains Cas4) and Type II-C (neither Csn2 nor Cas4, e.g. *N. meningitides*). A large number of Cas9 orthologs are known in the art as well as their associated tracrRNA and crRNA components (see, e.g., "Supplementary Table S2. List of bacterial strains with identified Cas9 orthologs," Fonfara, Ines, et al., "Phylogeny of Cas9 Determines Functional Exchangeability of Dual-RNA and Cas9 among Orthologous Type II CRISPR/Cas Systems," Nucleic Acids Research 42.4 (2014): 2577-2590, including all Supplemental Data; Chylinski K., et al., "Classification and evolution of type II CRISPR-Cas systems," Nucleic Acids Research, 2014; 42(10):6091-6105, including all Supplemental Data; Kevin M Esvelt, K. M., et al., (2013) "Orthogonal Cas9 proteins for RNA-guided gene regulation and editing," Nature Methods 10, 1116-1121, a number of orthogonal Cas9 proteins identified including a Cas9 protein from *Neisseria meningitidis*).

In addition, variants and modifications of Cas9 protein are known in the art. U.S. Published Patent Application 20140273226, published Sep. 18, 2014, discusses the *S. pyogenes* Cas9 gene, Cas9 protein, variants of the Cas9 protein including host-specific codon optimized Cas9 coding sequences (e.g., ¶¶0129-0137, U.S. Published Patent Application 20140273226) and Cas9 fusion proteins (e.g., ¶¶233-240, U.S. Published Patent Application 20140273226). U.S. Published Patent Application 20140315985, published Oct. 23, 2014, teaches a large number of exemplary wild-type Cas9 polypeptides (e.g., SEQ ID NO: 1-256, SEQ ID NO: 795-1346, U.S. Published Patent Application 2014031598) including the sequence of Cas9 from *S. pyogenes* (SEQ ID NO: 8, U.S. Published Patent Application 2014031598). Modifications and variants of Cas9 proteins are also discussed (e.g., ¶¶504-608, U.S. Published Patent Application 2014031598).

Aspects of the present invention can be practiced by one of ordinary skill in the art following the guidance of the specification to use Type II CRISPR Cas proteins and Cas-protein encoding polynucleotides, including, but not limited to Cas9, Cas9-like, Cas1, Cas2, Cas3, Csn2, Cas4, proteins encoded by Cas9 orthologs, Cas9-like synthetic proteins, and variants and modifications thereof. The cognate RNA components of these Cas proteins can be manipulated and modified for use in the practice of the present invention by one of ordinary skill in the art following the guidance of the present specification.

Cas9 is an exemplary Type II CRISPR Cas protein. Cas9 is an endonuclease that can be programmed by the tracrRNA/crRNA to cleave, site-specifically, target DNA using two distinct endonuclease domains (HNH and RuvC/RNase H-like domains) (see U.S. Published Patent Application No. 2014-0068797, published 6 Mar. 2014; see also Jinek M., et al., "A programmable dual-RNA-guided DNA endonuclease in adaptive bacterial immunity," Science, 2012; 337:816-21;). Two RNA components of a Type II CRISPR-Cas9 system are illustrated in FIG. 1A. Typically each CRISPR-Cas9 system comprises a tracrRNA and a crRNA. Cas9 is the signature protein characteristic for Type II CRISPR systems.

The crRNA has a region of complementarity to a potential DNA target sequence and a second region that forms base-pair hydrogen bonds with the tracrRNA to form a secondary structure, typically to form at least a stem structure. The region of complementarity to the DNA target is the spacer. The tracrRNA and a crRNA interact through a number of base-pair hydrogen bonds to form secondary RNA structures, for example, as illustrated in FIG. 1B. Complex formation between tracrRNA/crRNA and Cas9 protein results in conformational change of the Cas9 protein that facilitates binding to DNA, endonuclease activities of the Cas9 protein, and crRNA-guided site-specific DNA cleavage by the endonuclease. For a Cas9 protein/tracrRNA/crRNA complex to cleave a DNA target sequence, the DNA target sequence is adjacent to a cognate protospacer adjacent motif (PAM).

The term sgRNA typically refers to a single guide RNA (i.e., a single, contiguous polynucleotide sequence) that essentially comprises a crRNA connected at its 3' end to the 5' end of a tracrRNA through a "loop" sequence (see, e.g., U.S. Published Patent Application No. 2014-0068797, published 6 Mar. 2014). sgRNA interacts with a cognate Cas9 protein essentially as described for tracrRNA/crRNA polynucleotides, as discussed above. Similar to crRNA, sgRNA has a spacer element (FIG. 2, 201), a region of complementarity to a DNA target sequence, adjacent a second region that forms base-pair hydrogen bonds that form a secondary structure, typically a stem structure (e.g., in FIG. 2, 202, 203, 204, 205).

Using a sgRNA/Cas9 protein system, U.S. Published Patent Application No. 2014-0315985, published 23 Oct. 2014, and later published Briner, A. E., et al., ("Guide RNA Functional Modules Direct Cas9 Activity and Orthogonality," Molecular Cell Volume 56, Issue 2, 23 Oct. 2014, pages 333-339) demonstrated that expendable features can be removed to generate functional miniature sgRNAs. These publications discuss the importance of the "nexus," which is located in the portion of sgRNA that corresponds to tracrRNA (not crRNA), to confer cleavage activity to Cas9. The nexus confers the ability of a sgRNA or a tracrRNA to bind to its cognate cas9 protein and confer an apoenzyme to haloenzyme conformational transition.

The nexus is located immediately downstream of (i.e., located in the 3' direction from) the lower stem in Type II CRISPR-Cas9 systems. An example of the relative location of the nexus is illustrated in the sgRNA shown in FIG. 2, 206. U.S. Published Patent Application No. 2014-0315985 and Briner, et al., also disclose consensus sequences and secondary structures of predicted sgRNAs for several sgRNA/Cas9 families. These references show that the general arrangement of secondary structures in the predicted sgRNAs up to and including the nexus correspond to those shown FIG. 2 herein, that is, in a 5' to 3' direction, a spacer, a first stem, and the nexus. FIG. 2 presents an overview of and nomenclature for elements of a sgRNA of the *Streptococcus pyogenes* Cas9. Relative to FIG. 2, there are variations in the number and arrangement of stem structures located 3' of the nexus in the sgRNAs illustrated in U.S. Published Patent Application No. 2014-0315985 and Briner, et al.

Fonfara, et al., ("Phylogeny of Cas9 Determines Functional Exchangeability of Dual-RNA and Cas9 among Orthologous Type II CRISPR/Cas Systems," Nucleic Acids Research 42.4 (2014): 2577-2590, including all Supplemental Data, in particular Supplemental Figure S11) present the crRNA/tracrRNA sequences and secondary structures of eight Type II CRISPR-Cas9 systems. RNA duplex secondary structures were predicted using RNAcofold of the Vienna RNA package (Bernhart, S. H., et al., (2006) "Partition function and base pairing probabilities of RNA heterodimers," Algorithms Mol. Biol., 1, 3; Hofacker, I. L., et al., (2002) "Secondary structure prediction for aligned RNA sequences. J. Mol. Biol., 319, 1059-1066) and RNAhybrid (bibiserv.techfak.uni-bielefeld.de/rnahybrid/)). The structure predictions were then visualized using VARNA (Darty, K., et al., (2009) VARNA: Interactive drawing and editing of the RNA secondary structure Bioinformatics, 25, 1974-1975). Fonfara, et al., show that the crRNA/tracrRNA complex for *Campylobacter jejuni* does not have the bulge region illustrated in FIG. 1B, 105; however, it retains the general arrangement of secondary structures up to and including the nexus corresponding to those shown FIG. 1B herein, that is, in a 5' to 3' direction, a spacer, a first stem, and the nexus. Ran, F. A., et al., ("In vivo genome editing using *Staphylococcus aureus* Cas9," Nature, 2015, Apr. 9; 520 (7546):186-91, including all extended data) present the crRNA/tracrRNA sequences and secondary structures of eight Type II CRISPR-Cas9 systems (see Extended Data FIG. 1 of Ran, F. A., et al.). Predicted tracrRNA structures were based on the Constraint Generation RNA folding model (Zuker, M., "Mfold web server for nucleic acid folding and hybridization prediction," Nucleic Acids Res., 31, 3406-3415 (2003)). The crRNA/tracrRNA structures for the eight bacterial species presented in FIG. 1 of Ran, et al., show that the general arrangement of secondary structures in the predicted crRNA/tracrRNAs up to and including the nexus correspond to those shown FIG. 1B herein, that is, in a 5' to 3' direction, a spacer, a first stem, and the nexus.

As discussed above and in the Background of the present Specification, Jinek, M., et al., ("A programmable dual-RNA-guided DNA endonuclease in adaptive bacterial immunity," Science 337(6096):816-21 (2012)), Briner, A., et al., ("Guide RNA Functional Modules Direct Cas9 Activity and Orthogonality," Molecular Cell 56(2), 2014, Pages 333-339) and Wright, A. V., et al., ("Rational design of a split-Cas9 enzyme complex," PNAS 112(10), 2015, pages 2984-2989) all noted the importance of the nexus hairpin for guide RNA/Cas9 enzyme complex activity.

However, contrary to these teachings, experiments performed in support of the present invention unexpectedly demonstrated that the nexus hairpin structure can be broken and modified; thus providing new design and engineering avenues for CRISPR technologies as described herein.

In a first aspect, the present invention relates to an engineered Type II CRISPR-Cas9 system comprising two or more polynucleotides (sn-casPNs) capable of forming a complex with a Cas9 protein to cause the Cas9 protein to bind a first DNA sequence comprising a DNA target sequence preferentially relative to a second DNA sequence without the DNA target binding sequence. In some embodiments, the complex cuts the first DNA sequence. In the system, at least two of the two or more polynucleotides are necessary to form a nexus stem element. In addition to binding the first DNA sequence the sn-casPNs/Cas9 complex can cause the Cas9 protein to bind and cleave the first DNA sequence. A preferred embodiment comprises three sn-casPNs (sn1-casPN, sn2-casPN, and sn3-casPN; two examples are shown in FIG. 3A, FIG. 3C), wherein sn3-casPN comprises a spacer element (i.e., a DNA target binding sequence). Another preferred embodiment comprises two sn-casPNs (sn1-casPN, sn2-casPN; two examples are shown in FIG. 3B, FIG. 3D), wherein sn1-casPN comprises a spacer element (i.e., a DNA target binding sequence) and a first portion of the nexus element. Two variations of three sn-casPNs are presented in FIG. 3F, FIG. 3H. Two variations of four sn-casPNs are presented in FIG. 3E, FIG. 3G).

In one embodiment of the first aspect of the present invention, the two or more polynucleotides comprise a first polynucleotide (e.g., FIG. 3A, 301; FIG. 3C, 327; FIG. 3E, 301; FIG. 3G, 327) comprising a first nexus stem element nucleotide sequence I and a second polynucleotide (e.g., FIG. 3A, 302; FIG. 3C, 302; FIG. 3E, 302; FIG. 3G, 302) comprising a first nexus stem element nucleotide sequence II, wherein (i) the first nexus stem element nucleotide sequence II and the first nexus stem element nucleotide sequence II are capable of forming the nexus stem element by base-pair hydrogen bonding between the first nexus stem element nucleotide sequence I and the second nexus stem element nucleotide sequence II, and (ii) the first polynucleotide and the second polynucleotide are separate polynucleotides each having a 5' end and a 3' end.

In some embodiments of the first aspect of the present invention, the first polynucleotide (e.g., FIG. 3A, 301; FIG. 3C, 327) comprises in a 5' to 3' direction a first stem element nucleotide sequence I and the nexus stem element nucleotide sequence I and a third polynucleotide (e.g., FIG. 3A, 303; FIG. 3C, 328) comprises in a 5' to 3' direction a DNA target binding sequence and a first stem element nucleotide sequence II, wherein the first stem element nucleotide sequence I and the first stem element nucleotide sequence II are capable of forming a first stem element by base-pair hydrogen bonding between the first stem element nucleotide sequence I and the first stem element nucleotide sequence II, wherein the third polynucleotide is a separate polynucleotide having a 5' end and a 3' end.

In other embodiments of the first aspect of the present invention, the first polynucleotide (e.g., FIG. 3A, 301) comprises in a 5' to 3' direction an upper stem element nucleotide sequence I, a bulge element nucleotide sequence I, the first stem element nucleotide sequence I, and the nexus stem element nucleotide sequence I, and the third polynucleotide (e.g., FIG. 3A, 303) comprises in a 5' to 3' direction the DNA target binding sequence, the first stem element nucleotide sequence II, a bulge element nucleotide sequence II, and an upper stem element nucleotide sequence II, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the first stem element nucleotide sequence I and the first stem element nucleotide sequence II form the first stem element by base-pair hydrogen bonding between the first stem element nucleotide sequence I and the first stem element nucleotide sequence II.

In some embodiments of the first aspect of the present invention, the first polynucleotide (e.g., FIG. 3E, 301; FIG. 3G, 327) further comprises in a 5' to 3' direction a first stem element nucleotide sequence I and the nexus stem element nucleotide sequence I, a third polynucleotide (e.g., FIG. 3E, 330; FIG. 3G, 333) comprises a first stem element nucleotide sequence II, and a spacer polynucleotide (e.g., FIG. 3E, 331; FIG. 3G, 331) comprises a DNA target binding sequence, wherein the first stem element nucleotide sequence I and the first stem element nucleotide sequence II form a first stem element by base-pair hydrogen bonding between the first stem element nucleotide sequence I and the first stem element nucleotide sequence II. In this embodiment, the first polynucleotide, the second polynucleotide, the third polynucleotide, and the spacer polynucleotide are separate polynucleotides each having a 5' end and a 3' end.

In further embodiments of the first aspect of the present invention, the first polynucleotide (FIG. 3E, 301) comprises in a 5' to 3' direction an upper stem element nucleotide sequence I, a bulge element sequence I, a lower stem element nucleotide sequence I, and the nexus stem element nucleotide sequence I, a third polynucleotide (FIG. 3E, 330) comprises in a 5' to 3' direction a first lower stem element nucleotide sequence II, a bulge element nucleotide sequence II, and an upper stem element nucleotide sequence II, and a spacer polynucleotide (FIG. 3E, 331) comprises a DNA target binding sequence, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the lower stem element nucleotide sequence I and the lower stem element nucleotide sequence II form a lower stem element by base-pair hydrogen bonding between the lower stem element nucleotide sequence I and the lower stem element nucleotide sequence II.

Additional embodiments will be clear to one of ordinary skill in the art in view of the teachings of the present specification.

In a second aspect of the present invention, an engineered Type II CRISPR-Cas9 system comprises two or more polynucleotides. The two or more polynucleotides comprise a tracr element that is capable of forming a complex with a Cas9 protein to cause the Cas9 protein to bind DNA sequences containing protospacer adjacent motif (PAM) sequences preferentially relative to DNA sequences without PAM sequences. In some embodiments, the complex preferentially binds and cuts DNA sequences containing PAM sequences. The tracr element comprises a first polynucleotide (e.g., FIG. 3A, 301; FIG. 3C, 327; FIG. 3E, 301; FIG. 3G, 327) comprising a nexus stem element nucleotide sequence I and a second polynucleotide (e.g., FIG. 3A, 302; FIG. 3C, 302; FIG. 3E, 302; FIG. 3G, 302) comprising a nexus stem element nucleotide sequence II, wherein the nexus stem element nucleotide sequence I and the nexus stem element nucleotide sequence II are capable of forming a nexus stem element by base-pair hydrogen bonding between the nexus stem element nucleotide sequence I and the nexus stem element nucleotide sequence II, and (ii) the first polynucleotide and the second polynucleotide are separate polynucleotides each having a 5' end and a 3' end.

In some embodiments of the second aspect of the present invention, the first polynucleotide (e.g., FIG. 3A, 301; FIG. 3C, 327) comprises in a 5' to 3' direction a first stem element nucleotide sequence I and the nexus stem element nucleotide sequence I and a third polynucleotide (e.g., FIG. 3A, 303; FIG. 3C, 328) comprises in a 5' to 3' direction a DNA target binding sequence and a first stem element nucleotide sequence II, wherein the first stem element nucleotide sequence I and the first stem element nucleotide sequence II are capable of forming a first stem element by base-pair hydrogen bonding between the first stem element nucleotide sequence I and the first stem element nucleotide sequence II, wherein the third polynucleotide is a separate polynucleotide having a 5' end and a 3' end.

In other embodiments of the second aspect of the present invention, the first polynucleotide (e.g., FIG. 3A, 301) comprises in a 5' to 3' direction an upper stem element nucleotide sequence I, a bulge element nucleotide sequence I, the first stem element nucleotide sequence I, and the nexus stem element nucleotide sequence I, and the third polynucleotide (e.g., FIG. 3A, 303) comprises in a 5' to 3' direction the DNA target binding sequence, the first stem element nucleotide sequence II, a bulge element nucleotide sequence II, and an upper stem element nucleotide sequence II, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the first stem element nucleotide sequence I and the first stem element nucleotide sequence II form the first stem element by base-pair hydrogen bonding between the first stem element nucleotide sequence I and the first stem element nucleotide sequence II.

In some embodiments of the second aspect of the present invention, the first polynucleotide (e.g., FIG. 3E, 301; FIG. 3G, 327) further comprises in a 5' to 3' direction a first stem element nucleotide sequence I and the nexus stem element nucleotide sequence I, a third polynucleotide (e.g., FIG. 3E, 330; FIG. 3G, 333) comprises a first stem element nucleotide sequence II, and a spacer polynucleotide (e.g., FIG. 3E, 331; FIG. 3G, 331) comprises a DNA target binding sequence, wherein the first stem element nucleotide sequence I and the first stem element nucleotide sequence II form a first stem element by base-pair hydrogen bonding between the first stem element nucleotide sequence I and the first stem element nucleotide sequence II. In this embodiment, the first polynucleotide, the second polynucleotide, the third polynucleotide, and the spacer polynucleotide are separate polynucleotides each having a 5' end and a 3' end.

In further embodiments of the second aspect of the present invention, the first polynucleotide (FIG. 3E, 301) comprises in a 5' to 3' direction an upper stem element nucleotide sequence I, a bulge element sequence I, a lower stem element nucleotide sequence I, and the nexus stem element nucleotide sequence I, a third polynucleotide (FIG. 3E, 330) comprises in a 5' to 3' direction a first lower stem element nucleotide sequence II, a bulge element nucleotide sequence II, and an upper stem element nucleotide sequence II, and a spacer polynucleotide (FIG. 3E, 331) comprises a DNA target binding sequence, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the lower stem element nucleotide sequence I and the lower stem element nucleotide sequence II form a lower stem element by base-pair hydrogen bonding between the lower stem element nucleotide sequence I and the lower stem element nucleotide sequence II.

Additional embodiments will be clear to one of ordinary skill in the art in view of the teachings of the present specification.

With reference to the term "tracr element," as used herein the term refers to two or more sn-casPNs capable of forming a complex with a Cas9 protein to cause the Cas9 protein to bind DNA sequences containing PAM sequences preferentially relative to DNA sequences without PAM sequences. Sternberg, S. H. et al., ("DNA interrogation by the CRISPR RNA-guided endonuclease Cas9," Nature. 2014 Mar. 6; 507(7490): 62-67)) teach methods using double-tethered DNA curtains to examine the locations and corresponding lifetimes of all binding events for tracrRNA/crRNA/Cas with DNA. Following the guidance of the present specification, one of ordinary skill in the art can apply such methods to evaluate preferential binding (higher binding affinity) of, for example, sn-casPNs/Cas9 complexes to DNA sequences containing PAM sequences versus DNA sequences without PAM sequences to confirm presence of a tracr element comprising two or more of the sn-casPNs.

With reference to the sn-casPNs, a "spacer" or "spacer element" as used herein refers to a target binding sequence that can specifically hybridize to a complementary target nucleic acid sequence and a "spacer polynucleotide" refers to a polynucleotide sequence comprising a spacer element. The spacer element interacts with the target nucleic acid sequence through hydrogen bonding between complimentary base pairs (i.e., paired bases). Typically, a spacer element (a DNA target binding sequence) binds to a selected DNA target sequence. The spacer element determines the location of the Cas9 protein site-specific binding and endonucleolytic cleavage. Spacer elements range from approximately 17- to approximately 84 nucleotides long, depending on the Cas9 protein with which they are associated, and have an average length of 36 nucleotides (Marraffini, L. A., et al., "CRISPR interference: RNA-directed adaptive immunity in bacteria and archaea," Nature reviews Genetics. 2010; 11(3):181-190). In a Type II CRISPR-Cas9 system the spacer element typically comprises a "seed" sequence that is involved in targeting a target nucleic acid. For example, for SpyCas9 the functional length for a spacer element to direct specific cleavage is typically about 12-25 nucleotides. Variability of the functional length for a spacer element is known in the art (see, e.g., U.S. Published Patent Application No. 2014-0315985, published 23 Oct. 2014). Spacer polynucleotides in some embodiments have polynucleotide sequences in addition to the spacer element and such polynucleotide sequences are typically located at the 5' end of the spacer element, the 3' end of the spacer element, internal to the spacer element, or combinations thereof.

The creation of secondary structure between two polynucleotides through base-pair hydrogen bonding (e.g., stem elements and hairpins) can be determined by a number of methods known to those of ordinary skill in the art (e.g., experimental techniques, including but not limited to X-ray crystallography, Nuclear Magnetic Resonance (NMR) spectroscopy, Cryo-electron microscopy (Cryo-EM), Chemical/enzymatic probing, thermal denaturation (melting studies), and Mass spectrometry; predictive techniques, such as computational structure prediction; preferred methods include Chemical/enzymatic probing, thermal denaturation (melting studies)). Methods to predict secondary structures of single-stranded RNA or DNA sequences are known in the art, for example, the "RNAfold web server" (rna.tbi.univie.ac.at/cgi-bin/RNAfold.cgi) predicts secondary structures of single-stranded RNA or DNA sequences (see, e.g., Gruber A R, et al., The Vienna RNA Websuite, Nucleic Acids Res. 2008; Lorenz, R., et al., (2011) "ViennaRNA Package 2.0", Algorithms for Molecular Biology, 6, 26). A preferred method to evaluate RNA secondary structure is to use the combined experimental and computational SHAPE method (Low J. T., et al., "SHAPE-Directed RNA Secondary Structure Prediction," Methods (San Diego, Calif.) 2010; 52(2): 150-158).

In a third aspect of the present invention, an engineered Type II CRISPR-Cas9 system comprises two or more polynucleotides comprising a first polynucleotide and a second polynucleotide each having 5' and 3' ends. The first polynucleotide (e.g., FIG. 3A, 301; FIG. 3C, 327; FIG. 3E, 301; FIG. 3G, 327) comprises a nexus stem element nucleotide sequence I, the nexus stem element nucleotide sequence I comprising in a 5' to 3' direction Nw-N1-N2-Nx, where Nw is a first connective nucleotide sequence wherein w is the length of the connective nucleotide sequence and w is greater than or equal to two, N1 is a nucleotide, N2 is a nucleotide, and Nx is a first auxiliary polynucleotide wherein x is the length of the first auxiliary polynucleotide and x is greater than or equal to zero. In some embodiments, for Nw, w is greater than or equal to zero, preferably w is greater than or equal to 1, more preferably w is greater than or equal to 2. The second polynucleotide (e.g., FIG. 3A, 302; FIG. 3C, 302; FIG. 3E, 302; FIG. 3G, 302) comprises a nexus stem element nucleotide sequence II, the nexus stem element nucleotide sequence II comprising in a 5' to 3' direction Ny-Nc2-Nc1-Nz, where Ny is a second auxiliary polynucleotide wherein y is the length of the second auxiliary polynucleotide and y is greater than or equal to zero, Nc2 is a nucleotide that is complementary to N2, Nc1 is a nucleotide that is complementary to N1, and Nz is s second connective nucleotide sequence wherein z is the length of the second connective nucleotide sequence and z is greater than or equal to zero. In some embodiments, for Nz, z is greater than or equal to 1, preferably z is greater than or equal to 2. In this aspect, the first nexus stem element nucleotide sequence and the second nexus stem element nucleotide sequence are capable of forming a nexus stem element by base-pair hydrogen bonding between at least N1/Nc1 and N2/Nc2 and the first polynucleotide and the second polynucleotide are separate polynucleotides.

In some embodiments of the third aspect of the present invention, the first polynucleotide (e.g., FIG. 3A, 301; FIG. 3C, 327) comprises in a 5' to 3' direction a first stem element nucleotide sequence I and the nexus stem element nucleotide sequence I and a third polynucleotide (e.g., FIG. 3A, 303; FIG. 3C, 328) comprises in a 5' to 3' direction a DNA target binding sequence and a first stem element nucleotide sequence II, wherein the first stem element nucleotide sequence I and the first stem element nucleotide sequence II are capable of forming a first stem element by base-pair hydrogen bonding between the first stem element nucleotide sequence I and the first stem element nucleotide sequence II, wherein the third polynucleotide is a separate polynucleotide having a 5' end and a 3' end.

In other embodiments of the third aspect of the present invention, the first polynucleotide (e.g., FIG. 3A, 301) comprises in a 5' to 3' direction an upper stem element nucleotide sequence I, a bulge element nucleotide sequence I, the first stem element nucleotide sequence 1, and the nexus stem element nucleotide sequence I, and the third polynucleotide (e.g., FIG. 3A, 303) comprises in a 5' to 3' direction the DNA target binding sequence, the first stem element nucleotide sequence II, a bulge element nucleotide sequence II, and an upper stem element nucleotide sequence II, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the first stem element nucleotide sequence I and the first stem element nucleotide sequence II form the first stem element by base-pair hydrogen bonding between the first stem element nucleotide sequence I and the first stem element nucleotide sequence II.

In some embodiments of the third aspect of the present invention, the first polynucleotide (e.g., FIG. 3E, 301; FIG. 3G, 327) further comprises in a 5' to 3' direction a first stem element nucleotide sequence I and the nexus stem element nucleotide sequence I, a third polynucleotide (e.g., FIG. 3E, 330; FIG. 3G, 333) comprises a first stem element nucleotide sequence II, and a spacer polynucleotide (e.g., FIG. 3E, 331; FIG. 3G, 331) comprises a DNA target binding sequence, wherein the first stem element nucleotide sequence I and the first stem element nucleotide sequence II form a first stem element by base-pair hydrogen bonding between the first stem element nucleotide sequence I and the first stem element nucleotide sequence II. In this embodiment, the first polynucleotide, the second polynucleotide, the third polynucleotide, and the spacer polynucleotide are separate polynucleotides each having a 5' end and a 3' end.

In further embodiments of the third aspect of the present invention, the first polynucleotide (FIG. 3E, 301) comprises in a 5' to 3' direction an upper stem element nucleotide sequence I, a bulge element sequence I, a lower stem element nucleotide sequence I, and the nexus stem element nucleotide sequence I, a third polynucleotide (FIG. 3E, 330) comprises in a 5' to 3' direction a first lower stem element nucleotide sequence II, a bulge element nucleotide sequence II, and an upper stem element nucleotide sequence II, and a spacer polynucleotide (FIG. 3E, 331) comprises a DNA target binding sequence, wherein the upper stem element nucleotide sequence I and the upper stem element nucleotide sequence II form an upper stem element by base-pair hydrogen bonding between the upper stem element nucleotide sequence I and the upper stem element nucleotide sequence II, and the lower stem element nucleotide sequence I and the lower stem element nucleotide sequence II form a lower stem element by base-pair hydrogen bonding between the lower stem element nucleotide sequence I and the lower stem element nucleotide sequence II.

Additional embodiments will be clear to one of ordinary skill in the art in view of the teachings of the present specification.

A fourth aspect of the present invention comprises a modification of the first, second, and third aspects of the present invention, wherein the 5' end of the first polynucleotide and the 3' end of the third polynucleotide are joined by a loop element. Accordingly, in the fourth aspect of the invention there is no "third polynucleotide" because it has been subsumed into "a first polynucleotide comprising a first hairpin." In some embodiments, this first polynucleotide comprises in a 5' to 3' direction a DNA target binding sequence, a first stem element, and the nexus stem element nucleotide sequence I, wherein the first stem element comprises a first hairpin (e.g., FIG. 3D, 329). In further embodiments the first stem element further comprises a lower stem element, a bulge element, and an upper stem element, wherein the lower stem element is adjacent the bulge element, the bulge element is adjacent the upper stem element, the bulge element is interposed between the lower stem element and the upper stem element, and the upper stem element comprises the first hairpin (e.g., FIG. 3B, 326). In some embodiments the spacer element is separated from the first polynucleotide comprising the first hairpin (e.g., FIG. 3F, 332; FIG. 3H, 334) and a spacer polynucleotide (e.g., FIG. 3F, 331; FIG. 3H, 331) comprises the spacer element. The variations of sn-casPNs described below that use a first accessory polynucleotide or a second accessory polynucleotide do not apply to the sn-casPNs comprising a first polynucleotide comprising a first hairpin.

Additional embodiments will be clear to one of ordinary skill in the art in view of the teachings of the present specification.

Components of a sn1-casRNA/sn2-casRNA/Cas9 system is illustrated in FIG. 5A, FIG. 5B, and FIG. 5C. An example of sn1-casRNA/sn2-casRNA is presented in FIG. 3B, wherein the first polynucleotide is sn1-casRNA (FIG. 3B, 326) and the second polynucleotide is sn2-casRNA (FIG. 3B, 302). FIG. 5A presents a model of the α-Helical lobe of SpyCas9 (FIG. 5A, 501) in complex with sn1-casRNA (FIG. 5A, 502). The section of the sn1-casRNA corresponding to the spacer element (i.e., a nucleic acid target binding sequence) is indicated by a bracket (FIG. 5A, 503). 5B presents a model of the Catalytic nuclease lobe (FIG. 5B, 506) of SpyCas9 in complex with sn2-casRNA (FIG. 5B, 507). The relative positions of the RuvC domain (FIG. 5B, 510; RNase H domain) and the HNH domain (FIG. 5B, 511; HNH nuclease domain) are indicated. FIG. 5C provide a view of an assembled sn1-casRNA/sn2-casRNA/Cas9 protein complex. The relative locations of the 3' end of the sn1-casRNA split nexus element (FIG. 5C, 505) and 3' end of the split nexus element of the sn2-casRNA (FIG. 5C 508) are indicated.

A fifth aspect of the present invention comprises a modification of the first, second, and third aspects of the present invention, wherein the modification is the addition of an optional accessory polynucleotide to the first polynucleotide, the third polynucleotide, or both the first polynucleotide and the third polynucleotide. In some embodiments of the fifth aspect of the invention, the first polynucleotide further comprises a first accessory polynucleotide located 5' of the first stem element nucleotide sequence I. When the first stem element of the first polynucleotide comprises, in a 5' to 3' direction, the upper stem element nucleotide sequence I, the bulge element sequence I, the lower stem element nucleotide sequence I, and the nexus stem element nucleotide sequence I, then the first accessory polynucleotide is located 5' of the upper stem element nucleotide sequence I (e.g., FIG. 4B, 401-427 to 428).

In other embodiments of the fifth aspect of the present invention, the third polynucleotide further comprises a second accessory polynucleotide located 3' of the first stem element nucleotide sequence II. When the first stem element of the third polynucleotide comprises, in a 5' to 3' direction, the DNA target binding sequence, the first stem element nucleotide sequence II, the bulge element nucleotide sequence II, and the upper stem element nucleotide sequence II, then the second accessory polynucleotide is located 3' of the upper stem element nucleotide sequence II (e.g., FIG. 4B, 405-429 to 430).

The accessory polynucleotide can comprise a variety of moieties including, but not limited to, an affinity tag, a ligand, a ligand-binding sequence, a linker sequence, a hairpin, an affinity nucleotide sequences, an effector binding element, fused effector proteins, a subcellular localization signal or coding sequences therefore; a small molecule, a detectable label, a member of a FRET pair, a fluorophore/quantum dot donor/acceptor pair, fluorescent labels, an enzyme, a fluorescent protein, a nanoparticle, a quantum dot.

A sixth aspect of the present invention is directed to modifications of the second polynucleotide of sn-casPNs/Cas9 systems. In one embodiment, the second polynucleotide comprises, in a 5' to 3' direction, the nexus stem element nucleotide sequence II and a second stem element, wherein the second stem element comprises a hairpin. The second polynucleotide can also comprise in a 5' to 3' direction the nexus stem element nucleotide sequence II, the second stem element, and a third stem element, wherein the third stem element comprises a hairpin. Furthermore, the second polynucleotide comprises, in a 5' to 3' direction, the nexus stem element nucleotide sequence TI and a second stem element, wherein the second stem element comprises a hairpin, and a third stem element, wherein the third stem element comprises a hairpin (e.g., FIG. 3A, 302).

In another embodiment of the sixth aspect of the present invention, the second polynucleotide further comprises in a 5' to 3' direction the nexus stem element nucleotide sequence II, a second connective sequence, and a second stem element nucleotide sequence I (e.g., FIG. 4A, 402-406-407) and a first adjunct polynucleotide comprising a second stem element nucleotide sequence II (FIG. 4A, 403-409 to 410), wherein the second stem element nucleotide sequence I and the second stem element nucleotide sequence II form a second stem element by base-pair hydrogen bonding between the second stem element nucleotide sequence I and the second stem element nucleotide sequence II. In some embodiments, the 5' end of the second stem element nucleotide sequence II and the 3' end of the second stem element nucleotide sequence I are connected by a loop element to create a second hairpin.

Furthermore, the first adjunct polynucleotide can comprise in a 5' to 3' direction the second stem element nucleotide sequence II and a third stem element nucleotide sequence I (FIG. 4A, 403-411-412), and a second adjunct polynucleotide (FIG. 4A, 404) comprises in a 5' to 3' direction a third stem element nucleotide sequence II (FIG. 4A, 404-413 to 414), wherein the third stem element nucleotide sequence I and the third stem element nucleotide sequence II form a third stem element by base-pair hydrogen bonding between the third stem element nucleotide sequence I and third stem element nucleotide sequence II. In some embodiments, the 5' end of the third stem element nucleotide sequence II and the 3' end of the third stem element nucleotide sequence I are connected by a loop element to create a third hairpin.

In other embodiments the 3' end of the second polynucleotide comprises a 3' terminal sequence that can comprise a variety of moieties including, but not limited to, an affinity tag, a ligand, a ligand-binding sequence, a linker sequence, a hairpin, an affinity nucleotide sequences, an effector binding element, fused effector proteins, a subcellular localization signal or coding sequences therefore; a small molecule, a detectable label, a member of a FRET pair, a fluorophore/quantum dot donor/acceptor pair, fluorescent labels, an enzyme, a fluorescent protein, a nanoparticle, a quantum dot.

A seventh aspect of the present invention is directed to the modification of the 3' end of the split nexus of the first polynucleotide and the 5' end of the split nexus of the second polynucleotide wherein the modification is the addition of an optional auxiliary polynucleotide to the first polynucleotide, the second polynucleotide, or both the first polynucleotide and the second polynucleotide. In one embodiment, the first polynucleotide further comprises a first auxiliary polynucleotide 3' adjacent the nexus stem element nucleotide sequence I. In another embodiment, the second polynucleotide further comprises a second auxiliary polynucleotide 5' adjacent the nexus stem element nucleotide sequence II. In yet another embodiment, the first polynucleotide comprises a first auxiliary polynucleotide 3' adjacent the nexus stem element nucleotide sequence 1, and the second polynucleotide comprises a second auxiliary polynucleotide 5' adjacent the nexus stem element nucleotide sequence II. In some embodiments a linker element polynucleotide is interposed between the nexus element nucleotide sequence and the auxiliary polynucleotide. The first auxiliary polynucleotide and/or second auxiliary polynucleotide can comprise a binding site for a single-strand polynucleotide binding protein, such as a single-strand RNA binding protein.

In a further embodiment of the seventh aspect of the invention, the first polynucleotide comprises a first auxiliary polynucleotide 3' adjacent the nexus stem element nucleotide sequence I and the second polynucleotide comprises a second auxiliary polynucleotide 5' adjacent the nexus stem element nucleotide sequence II, and the first auxiliary polynucleotide comprises an effector binding element nucleotide sequence I, and the second auxiliary polynucleotide comprises an effector binding element nucleotide sequence II, wherein the effector binding element nucleotide sequence I and the effector binding element nucleotide sequence II are capable of forming an effector binding element by base-pair hydrogen bonding between the effector binding element nucleotide sequence I and the effector binding element nucleotide sequence I. Thus, providing a double-stranded polynucleotide effector binding element to which an effector protein can bind. In some embodiments the double-stranded polynucleotide is an RNA and the effector protein is a double-stranded RNA binding protein capable of binding the effector binding element. Examples of double-stranded RNA binding effector proteins include Cas5, Cas6, and Csy4. In some embodiments the effector binding protein is catalytically inactive (e.g., Csy4*) but still binds the effector binding element.

In some embodiments of the seventh aspect of the invention, the first auxiliary polynucleotide and/or second auxiliary polynucleotide further comprises one or more first affinity nucleotide sequence. An affinity nucleotide sequence can be covalently linked to a polypeptide. An affinity nucleotide sequence can comprise a ligand. In some embodiments, one of the affinity nucleotide sequences comprises a ligand and the other affinity nucleotide sequence comprises a cognate ligand-binding moiety.

FIG. 4A illustrates an example of a first polynucleotide (FIG. 4A, 401) comprising a first auxiliary polynucleotide (FIG. 4A, 401-419 to 424), wherein the first auxiliary polynucleotide comprises a linker element nucleotide sequence I (FIG. 4A, 401-419 to 422), an affinity nucleotide sequence I (FIG. 4A, 401-422 to 423), and an effector binding element nucleotide sequence I (FIG. 4A, 401-423 to 424), and a second polynucleotide (FIG. 4A, 402) comprising a second auxiliary polynucleotide (FIG. 4A, 402-405 to 418), wherein the second auxiliary polynucleotide comprises a linker element nucleotide sequence II (FIG. 4A, 402-405 to 416), an affinity nucleotide sequence II (FIG. 4A, 402-416 to 417), and an effector binding element nucleotide sequence II (FIG. 4A, 402-417 to 418).

An example of use of an effector protein is Csy4* with a cognate effector protein binding element can be given with reference to this figure. Effector binding effector binding element nucleotide sequence I (FIG. 4A, 401-423 to 424) and effector binding element nucleotide sequence II (FIG. 4A, 402-417 to 418) form a double-strand RNA structure through base-pair hydrogen bonding to form a Csy4* double-strand binding element. After formation of the double-strand RNA binding element Csy4* protein binds the binding element and stabilizes the interaction of the first auxiliary polynucleotide and the second auxiliary polynucleotide. Csy* and its cognate binding element is used in this manner in the Cas9 cleavage experiment presented in Example 5.

A related example of use of an effector protein is Csy4* with a cognate effector protein binding element is presented in FIG. 6A, FIG. 6B, and FIG. 6C for a two polynucleotide sn-casPNs/Cas9 system. This system corresponds to a first polynucleotide (sn1-casPN) that comprises a first portion of the split nexus element (FIG. 3B, 326) and a second polynucleotide (sn2-casPN) that comprises a second portion of the split nexus element (FIG. 3B, 302).

The ability of Csy4* to facilitate sn-casRNAs/Cas9 cleavage of four double-strand DNA targets is demonstrated in Example 5. The data presented in FIG. 9 demonstrate an effector protein (here Csy4*) enhanced cleavage of target double-stranded DNA by split-nexus Cas9-associated polynucleotide systems of the present invention comprising auxiliary polynucleotides having an effector binding element (here the Csy RNA binding sequence).

Wright, A. V., et al., ("Rational design of a split-Cas9 enzyme complex," PNAS 112(10), 2015, pages 2984-2989) designed a split-Cas9 enzyme in which the nuclease lobe and α-helical lobe are expressed as separate polypeptides. In this example, FIG. 6A shows the sn1-casRNA and sn2-casRNA before association and formation of hydrogen bond base pairs between them. FIG. 6B illustrates the sn1-casRNA comprising a first auxiliary polynucleotide and the sn2-casRNA comprising a second auxiliary polynucleotide after formation of hydrogen bond base pairs between them in order to illustrate formation of an effector binding element. The top dashed-line box (FIG. 6B, 610) shows formation of an effector binding element, in this example a Csy4* RNA binding element. FIG. 6C illustrates the association of the sn2-casRNA with the catalytic nuclease lobe (FIG. 6C, 613) of SpyCas9 and the association of the sn1-casRNA with the α-Helical lobe (FIG. 6C, 614) of SpyCas9. Also shown is an effector protein Csy4* (FIG. 6C, 615), which is a variant of Csy4 without endoribonuclease activity. The thick downward pointing arrow indicates the assembly of the sn2-casRNA/catalytic nuclease lobe (FIG. 6C, 613) of SpyCas9, the sn1-casRNA/α-Helical lobe (FIG. 6C, 614) of SpyCas9, and the Csy4* protein (FIG. 6C, 615) into a complex (FIG. 6C, 618). This example illustrates sn1-casRNA recruiting the α-Helical lobe and sn2-casRNA recruiting the catalytic nuclease lobe into a ternary complex further stabilized by the binding of the Csy4* protein to recapitulate the activity of Cas9 to catalyze site-specific DNA cleavage.

In further embodiments of the seventh aspect of the invention, the effector protein comprises at least one zinc finger domain.

The first auxiliary polynucleotide and/or second auxiliary polynucleotide can also comprise one or more hairpins. FIG. 7A illustrates a sn1-casRNA comprising a first auxiliary polynucleotide (FIG. 7A, 702 to 703) and a sn2-casRNA comprising a second auxiliary polynucleotide (FIG. 7A, 706 to 707). The figure shows the sn1-casRNA and sn2-casRNA before association and formation of hydrogen bond base pairs between them. The figure shows a hairpin element formed by hydrogen bond base pairing between bases within the first auxiliary polynucleotide (FIG. 7A, 704) and a hairpin element formed by hydrogen bond base pairing between bases within the second auxiliary polynucleotide (FIG. 7A, 708). FIG. 7B illustrates the sn1-casRNA/sn2-casRNA assembled into an active complex with Cas9.

All aspects of the invention can employ a Cas9 protein (or as needed nucleic acid sequences encoding a Cas9 protein) or a Cas9 fusion (or as needed nucleic acid sequences encoding a Cas9 fusion).

The term "affinity tag" as used herein refers to one or more moiety that increases the binding affinity of one sn-casPN to another sn-casPN and/or to a Cas9 protein. Some embodiments of the present invention use an "affinity sequence," which is a polynucleotide sequence comprising one or more affinity tag. Examples of affinity sequences that can be used to modify a first sn-casPN include using a MS2 binding sequence, U1A binding sequence, stem-loop sequence, eIF4A binding sequence, Transcription activator-like effector (TALE) binding sequence (Valton, J., et al., "Overcoming Transcription Activator-like Effector (TALE) DNA Binding Domain Sensitivity to Cytosine Methylation" J Biol Chem. 2012 Nov. 9; 287(46): 38427-38432), or zinc finger domain binding sequence (Font, J., et al., "Beyond DNA: zinc finger domains as RNA-binding modules," Methods Mol Biol. 2010; 649:479-91; Isalan, M., et al., "A rapid, generally applicable method to engineer zinc fingers illustrated by targeting the HIV-1 promoter," Nat Biotechnol. 2001 July; 19(7): 656-660). Other sn-casPNs and/or the Cas9 protein coding sequence can be modified to comprise a cognate affinity tag: an MS2 coding sequence, U1A coding sequence, stem-loop binding protein coding sequence, eIF4A coding sequence, TALE coding sequence, or a zinc finger domain coding sequence, respectively.

A wide variety of affinity tags are disclosed in U.S. Published Patent Application No. 2014-0315985 (published 23 Oct. 2014).

The terms "ligand" and "ligand-binding moiety" as used herein refer to moieties that facilitate the binding of one sn-casPN to another sn-casPN or to a Cas9 protein. Ligands and ligand-binding moieties are cognate affinity tags.

One embodiment of use of a ligand moiety is to build a ligand-binding moiety into the Cas9 protein or attach a ligand-binding moiety to a first sn-casPN and modify a polynucleotide sequence of a different sn-casPN to contain the ligand. A ligand/ligand-binding moiety useful in the practice of the present invention is Avidin or Streptavidin/Biotin (see, e.g., Livnah, O, et al., "Three-dimensional structures of avidin and the avidin-biotin complex," Proceedings of the National Academy of Sciences of the United States of America, 1993; 90(11):5076-5080; Airenne, K. J., et al., "Recombinant avidin and avidin-fusion proteins.," Biomol Eng. 1999 Dec. 31; 16(1-4):87-92.). One example of a Cas9 protein with a ligand-binding moiety is a Cas9 protein fused to a ligand Avidin or Streptavidin designed to bind a biotinylated sn-casPN, wherein the sn-casPN comprises an polynucleotide sequence with which the biotin is associated. Biotin is a high affinity and high specificity ligand for the Avidin or Streptavidin protein. By fusing an Avidin or Streptavidin polypeptide chain to the Cas9 protein, the Cas9 protein has a high affinity and specificity for a biotinylated sn-casPN-biotin.

Biotinylation is preferably in close proximity to the 5' or 3' ends of a sn-casPN. The sequence of the sn-casPN and location of the biotin is provided to commercial manufacturers for synthesis of the sn-casPN-biotin. Changes to cleavage percentage and specificity of a ligand-binding modified sn-casPNs/Cas9 system are evaluated as described, for example, in Example 3 and/or Example 9.

Examples of other ligands and ligand-binding moieties that can be similarly used include, but are not limited to (ligand/ligand-binding moiety): estradiol/estrogen receptor (see, e.g., Zuo, J., et al., "Technical advance: An estrogen receptor-based transactivator XVE mediates highly inducible gene expression in transgenic plants," Plant J. 2000 October; 24(2):265-73), rapamycin/FKBP12, and FK506/FKKBP (see, e.g., B. Setscrew, et al., "A split-Cas9 architecture for inducible genome editing and transcription modulation," Nature Biotechnology 33, 139-142 (2015); Chiu M. I., et al., "RAPT1, a mammalian homolog of yeast Tor, interacts with the FKBP12/rapamycin complex," PNAS 1994; 91(26):12574-12578).

Another example of a ligand and ligand-binding moiety is to provide one or more aptamer or modified aptamer in a polynucleotide sequence of a sn-casPN that has a high affinity and binding specificity for a selected region of a Cas9 protein. In one embodiment, a ligand-binding moiety is a polynucleotide comprising an aptamer (see, e.g., Navani, N. K., et al., "In vitro Selection of Protein-Binding DNA Aptamers as Ligands for Biosensing Applications," Biosensors and Biodetection, Methods in Molecular Biology™ Volume 504, 2009, pp 399-415; A. V. Kulbachinskiy, "Methods for Selection of Aptamers to Protein Targets," Biochemistry (Moscow), 2007, Vol. 72, No. 13, pp. 1505-1518.). Aptamers are single-stranded functional nucleic acids that possess cognate ligand recognition capability. Typically, the aptamer is located at the 5' or 3' end of a sn-casPN. In the practice of the present invention one example of a ligand is a casPN/Cas9 complex.

In another embodiment, a ligand-binding moiety comprises a modified polynucleotide wherein a nonnative functional group is introduced at positions oriented away from the hydrogen bonding face of the bases of the modified polynucleotide, such as the 5-position of pyrimidines and the 8-position of purines ("Slow Off-rate Modified Aptamers or SOMAmers"; see, e.g., Rohloff, J. C., et al., "Nucleic Acid Ligands With Protein-like Side Chains: Modified Aptamers and Their Use as Diagnostic and Therapeutic Agents," Molecular Therapy Nucleic Acids (2014) 3, e201). An aptamer with high specificity and affinity for Cas9 proteins could be obtained by in vitro selection and screening of an aptamer library.

In yet another embodiment, an established aptamer binding sequence/aptamer is used by introducing the aptamer-binding region into the Cas9 protein. For example, a biotin-binding aptamer can be introduced into a sn-casPN and the Cas9 protein can be selectively biotinylated to form a cognate binding site, for the biotin-binding aptamer.

The creation of a high affinity binding site for a selected ligand on a Cas9 protein can be achieved using several protein engineering methods known to those of ordinary skill in the art in view of the guidance of the present specification. Examples of such protein engineering methods include, rational protein design, directed evolution using different selection and screening methods for the library (e.g. phage display), DNA shuffling, computational methods (e.g. ROSETTA, www.rosettacommons.org/software), or introduction of a known high affinity ligand into Cas9. Libraries obtained by these methods can be screened to select for Cas9 protein high affinity binders using, for example, a phage display assay, a cell survival assay, or a binding assay.

In another aspect of the present invention, at least one of the sn-casPNs of a sn-casPNs/Cas9 system is a circular polynucleotide.

In yet another aspect of the present invention, at least one linear sn-casPN of a sn-casPNs/Cas9 system comprises a 5' terminal sequence and/or a 3' terminal sequence, and at least one 5' terminal sequence and/or 3' terminal sequence comprises an exonuclease resistance moiety associated with the 5' terminal sequence and/or 3' terminal sequence. Examples of exonuclease resistant moieties include, but are not limited to, a hairpin in the terminal sequence, a single-stranded polynucleotide binding sequence to which a single-stranded polynucleotide binds, and a linkage inversion.

One aspect of the invention relates to methods of manufacturing the sn-casPNs of the present invention. In one embodiment, the method of manufacturing comprises chemically synthesizing one or more of the sn-casPNs of a sn-casPNs/Cas9 system. In some embodiments, the sn-casPNs comprise RNA bases, DNA bases, or a combination of RNA bases and DNA bases. Furthermore, nucleobase backbones other than or in addition to a phosphodiester backbone can be synthesized, for example, using nucleic acids, peptide-nucleic acids, threose nucleic acid, or combinations thereof. In some embodiments, the method of manufacturing comprises producing one or more of the sn-casPNs of a sn-casPNs/Cas9 system by in vitro transcription.

In one aspect, the present invention relates to expression cassettes comprising polynucleotide coding sequences for two or more sn-casPNs and/or a Cas9 protein. An expression cassette of the present invention at least comprises a polynucleotide encoding a sn-casPN of the present invention. Expression cassettes useful in the practice of the present invention can further include Cas9 protein coding sequences. In one embodiment, an expression cassette comprises a sn-casPN coding sequence. In another embodiment, one or more expression cassette comprises sn-casPN coding sequence and a cognate Cas9 protein coding sequence. Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, insect cells, mammalian cells, and plant cells. Expression cassettes typically comprise functional regulatory sequences corresponding to the host cells or organism(s) into which they are being introduced.

One aspect of the present invention relates to vectors, including expression vectors, comprising polynucleotide coding sequences for a sn-casPN and/or a Cas9 protein. Vectors useful for practicing the present invention include plasmids, viruses (including phage), and integratable DNA fragments (e.g., fragments integratable into the host genome by homologous recombination). A vector replicates and functions independently of the host genome, or may, in some instances, integrate into the genome itself. Suitable replicating vectors will contain a replicon and control sequences derived from species compatible with the intended expression host cell. A vector can comprise one or more expression cassette of polynucleotide coding sequences for sn-casPNs and/or a Cas9 protein. Vectors include, but are not limited to, bacterial vectors, yeast vectors, algal vectors, insect cell vectors, mammalian vectors, and viral vectors.

Transformed host cells are cells that have been transformed or transfected with the vectors constructed using recombinant DNA techniques.

General methods for construction of expression vectors are known in the art. Expression vectors for most host cells are commercially available. There are several commercial software products designed to facilitate selection of appropriate vectors and construction thereof, such as bacterial plasmids for bacterial transformation and gene expression in bacterial cells, yeast plasmids for cell transformation and gene expression in yeast and other fungi, algal expression systems for use in algae cells, insect cell vectors for insect cell transformation and gene expression in insect cells, mammalian vectors for mammalian cell transformation and gene expression in mammalian cells or mammals, viral vectors (including retroviral, lentiviral, and adenoviral vectors) for cell transformation and gene expression, and methods to easily enable cloning of such polynucleotides. SnapGene™ (GSL Biotech LLC, Chicago, Ill.; snapgene.com/resources/plasmid_files/your_time_is_valuable/), for example, provides an extensive list of vectors, individual vector sequences, and vector maps, as well as commercial sources for many of the vectors.

Expression vectors can also include polynucleotides encoding protein tags (e.g., poly-His tags, hemagglutinin tags, fluorescent protein tags, bioluminescent tags). The coding sequences for such protein tags can be fused to a Cas9 protein coding sequence or can be included in an expression cassette, for example, in a targeting vector.

In some embodiments, polynucleotides encoding sn-casPNs and/or Cas9 protein are operably linked to an inducible promoter, a repressible promoter, or a constitutive promoter.

Aspects of the invention relate to vector systems comprising one or more vectors for expression of sn-casPNs and Cas9 proteins in prokaryotic or eukaryotic cells. Alternatively, sn-casPNs and Cas9 proteins can be transcribed in vitro, for example using T7 promoter regulatory sequences and T7 polymerase. Translation of Cas9 proteins can also be carried out in vitro.

Vectors comprising sn-casPNs/Cas9 systems can be introduced into and propagated in a prokaryote. Prokaryotic vectors are well known in the art. Typically a prokaryotic vector comprises an origin of replication suitable for the target host cell (e.g., oriC derived from *E. coli*, pUC derived from pBR322, pSC101 derived from *Salmonella*), 15A origin (derived from p15A) and bacterial artificial chromosomes). Vectors can include a selectable marker (e.g., genes encoding resistance for ampicillin, chloramphenicol, gentamicin, and kanamycin). Zeocin™ (Life Technologies, Grand Island, N.Y.) can be used as a selection in bacteria, fungi (including yeast), plants and mammalian cell lines. Accordingly, vectors can be designed that carry only one drug resistance gene for Zeocin for selection work in a number of organisms. Useful promoters are known for expression of proteins in prokaryotes, for example, T5, T7, Rhamnose (inducible), Arabinose (inducible), and PhoA (inducible). Furthermore, T7 promoters are widely used in vectors that also encode the T7 RNA polymerase. Prokaryotic vectors can also include ribosome binding sites of varying strength, and secretion signals (e.g., mal, sec, tat, ompC, and pelB). In addition, vectors can comprise RNA polymerase promoters for the expression of sn-casRNAs. Prokaryotic RNA polymerase transcription termination sequences are also well known (e.g., transcription termination sequences from *S. pyogenes*).

Integrating vectors for stable transformation of prokaryotes are also known in the art (see, e.g., Heap, J. T., et al., (2012) "Integration of DNA into bacterial chromosomes from plasmids without a counter-selection marker," Nucleic Acids Res. 2012 April; 40(8):e59).

Expression of proteins in prokaryotes is typically carried out in *Escherichia coli* with vectors containing constitutive or inducible promoters directing the expression of either fusion or non-fusion proteins.

A wide variety of RNA polymerase promoters suitable for expression of sn-casRNAs and Cas9 proteins are available in prokaryotes (see, e.g., Jiang, Y., et al., (2015) "Multigene editing in the *Escherichia coli* genome via the CRISPR-Cas9 system," Environ Microbiol. 81(7):2506-14); Estrem, S. T., et al., (1999) "Bacterial promoter architecture: subsite structure of UP elements and interactions with the carboxy-terminal domain of the RNA polymerase alpha subunit," Genes Dev. 15; 13(16):2134-47).

Fusion vectors add a number of amino acids to a protein encoded therein (e.g., to the amino terminus of the recombinant protein). Such fusion vectors serve one or more purposes. Examples include, but are not limited to, the following: (i) to increase expression of recombinant protein; (ii) to increase the solubility of the recombinant protein; and (iii) to aid in the purification of the recombinant protein by acting as a ligand in affinity purification. In fusion-expression vectors, a proteolytic cleavage site is sometimes introduced at the junction of the fusion moiety and the recombinant protein. This enables the separation of the recombinant protein from the fusion moiety following the purification of the fusion protein. Such enzymes, and their cognate proteolytic cleavage sites, include Factor Xa, thrombin and enterokinase. Examples of fusion-expression vectors include, but are not limited to, the following: pGEX, pMAL, and pRIT5 that fuse glutathione S-transferase (GST), maltose E binding protein, or protein A, respectively, to the target recombinant protein. Examples of suitable inducible non-fusion *E. coli* expression vectors include, but are not limited to, pTrc and pET 11d.

In some embodiments, a vector is a yeast expression vector comprising a sn-casPNs/Cas9 system. Examples of vectors for expression in yeast *Saccharomyces cerivisae* include, but are not limited to, the following: pYepSecI, pMFa, pJRY88, pYES2, and picZ. Methods for gene expression in yeast cells are known in the art (see, e.g., Methods in Enzymology, Volume 194, "Guide to Yeast Genetics and Molecular and Cell Biology, Part A," (2004) Christine Guthrie and Gerald R. Fink (eds.), Elsevier Academic Press, San Diego, Calif.). Typically, expression of protein encoding genes in yeast requires a promoter operably linked to a coding region of interest plus a transcriptional terminator. Various yeast promoters can be used to construct expression cassettes for expression of genes in yeast. Examples of promoters include, but are not limited to, promoters of genes encoding the following yeast proteins: alcohol dehydrogenase 1 (ADH1) or alcohol dehydrogenase 2 (ADH2), phosphoglycerate kinase (PGK), triose phosphate isomerase (TPI), glyceraldehyde-3-phosphate dehydrogenase (GAPDH; also known as TDH3, or triose phosphate dehydrogenase), galactose-1-phosphate uridyl-transferase (GALT), UDP-galactose epimerase (GAL10), cytochrome ci (CYC1), and acid phosphatase (PHO5). Hybrid promoters, such as the ADH2/GAPDH, CYC1/GAL10 and the ADH2/GAPDH promoter (which is induced at low cellular-glucose concentrations, e.g., about 0.1 percent to about 0.2 percent) also may be used. In *S. pombe*, suitable promoters include the thiamine-repressed nmtl promoter and the constitutive cytomegalovirus promoter in pTL2M.

Yeast RNA polymerase III promoters (e.g., promoters from 5S, U6 or RPR1 genes) as well as polymerase III termination sequences are known in the art (see, e.g., www.yeastgenome.org; Harismendy, O., et al., (2003) "Genome-wide location of yeast RNA polymerase III transcription machinery," The EMBO Journal. 22(18):4738-4747.)

A protein expression promoter may be inducible or constitutive. In some embodiments, a preferred promoter is a tightly regulated inducible promoter, such that a high copy number can be achieved in the absence of expression. Examples include, but are not limited to, the normally divergent GAL1p and GAL10p promoters, which are tightly suppressed in glucose media and highly induced by galactose after catabolite repression has been relieved by growth on a non-repressing carbon source such as glycerol or lactate. An open reading frame that encodes a polypeptide may be inserted into a GAL1p vector (see, e.g., Cartwright, et al., (1994) "Use of β-lactamase as a secreted reporter of promoter function in yeast," Yeast 10:497; and Harley, et al., (1998) "Transmembrane Protein Insertion Orientation in Yeast Depends on the Charge Difference across Transmembrane Segments, Their Total Hydrophobicity, and Its Distribution," J. Biol. Chem. 273:24963). Other vectors and promoters that can be used include the hybrid GAL1p-CYCp promoter in the Yep URA3 leu2d vector pPAP1488 in strain PAP1502 (see, e.g., Pedersen, et al. (1996) "Expression in High Yield of Pig α1β1 Na,K-ATPase and Inactive Mutants D369N and D807N in *Saccharomyces cerevisiae*," J. Biol. Chem. 1996 271: 2514-2522). This strain has plasmid pPAP1488 integrated at the Trp1 locus. This provides an additional copy of the GAL4 gene driven by the GAL10 promoter, and when GAL expression is induced, high levels of the Gal4p positive activator are produced.

In this vector system, growth in the absence of uracil produces a vector copy number of 15 to 20, determined by 2-micron replication functions. The copy number of the vector can be further increased, by at least 10 fold, by culturing the yeast cells in media lacking leucine, because of the very weak promoter associated with the defective leu2d allele. A proportional increase in GAL1p-driven expression requires the high galactose-induced levels of the Gal4p activator provided in strain PAP1502 by the integrated PAP1488 plasmid. Any other ura3 leu2 Gal+ *S. cerevisiae* strain into which this plasmid is inserted may be used instead of PAP1502.

Another yeast promoter that can be used is the promoter of the glycerol-3-phosphate dehydrogenase gene (GPD1). Expression of polypeptides using the GPD1 promoter can be regulated by the presence (repressed) or absence (derepressed) of high levels of glucose or sucrose in a fermentation medium. Alternatively, a non-repressing carbon source, such as ethanol or glycerol, can be added to the fermentation medium (see, e.g., U.S. Pat. No. 5,667,986).

Regulation of plasmid copy number can provide some control over the level of RNA products expressed from RNA polymerase III promoters. Furthermore, RNA polymerase III transcription can be regulated in yeast (Dingermann, T., et al., (1992) "RNA polymerase III catalysed transcription can be regulated in *Saccharomyces cerevisiae* by the bacterial tetracycline repressor-operator system," EMBO J. 11(4): 1487-92).

In addition to a promoter, several upstream activation sequences (UASs), also called enhancers, may be used to enhance polypeptide expression. Exemplary upstream activation sequences for expression in yeast include the UASs of genes encoding these proteins: CYC1, ADH2, GAL1, GALT, GAL10, and ADH2. Exemplary transcription termination sequences for expression in yeast include the termination sequences of the α-factor, CYC1, GAPDH, and PGK genes. One or multiple termination sequences can be used.

Any protein coding regions expressed in yeast cells can be codon-optimized for expression in the specific host yeast cell to be engineered, as is well known in the art.

Suitable promoters, terminators, and coding regions may be cloned into *E. coli*-yeast shuttle vectors and transformed into yeast cells. These vectors allow strain propagation in both yeast and *E. coli* strains. Typically, the vector contains a selectable marker and sequences enabling autonomous replication or chromosomal integration in each host. Examples of plasmids typically used in yeast are the shuttle vectors pRS423, pRS424, pRS425, and pRS426 (American Type Culture Collection, Manassas, Va.). These plasmids contain a yeast 2 micron origin of replication, an *E. coli* replication origin (e.g., pMB1), and a selectable marker.

Example 15 presents an illustration of genome engineering in *Saccharomyces cerevisiae* using the split-nexus Cas9-associated polynucleotides (sn-casPNs). A Cas9 vector and two sn1-casRNA/sn2-casRNA vector pairs are used to modifying the genome of the yeast. This protocol provides data to verify that the Cas9 and sn1-casRNA/sn2-casRNA system provide specific RNA-mediated endonuclease activity at targeted endogenous genomic loci in yeast. The constructs are also used in experiments to verify that the Cas9 and sn1-casRNA/sn2-casRNA system provides specific RNA-mediated endonuclease activity at targeted endogenous genomic loci in yeast and can stimulate homologous recombination events at such loci using donor DNA. Other chromosomal loci in *S. cerevisiae* can similarly targeted for modification by selection of appropriate spacer sequences and donor oligonucleotides. Functional genes can be introduced into the *S. cerevisiae* genome without disruption of endogenous genes. Furthermore, introduction of selectable markers into endogenous target genes can be used to provide selectable knock-out mutations of the target genes.

Integrating vectors are also widely available for stable transformation of yeast (Stearns T., et al., (1990) "Manipulating yeast genome using plasmid vectors," Methods Enzymol. 1990; 185:280-97).

For use of sn-casPNs/Cas9 systems in algal cells, suitable vectors and expression control sequences are well known in the art (see, e.g., Hallmann, A. (2007), "Algal Transgenics and Biotechnology," Transgenic Plant Journal 1(1), 81-98; Oey, M., et al., "Gateway-Assisted Vector Construction to Facilitate Expression of Foreign Proteins in the Chloroplast of Single Celled Algae," Feb. 11, 2014 DOI: 10.1371/journal.pone.0086841) including RNA polymerase III promoters (see, e.g., Dieci, G., et al., (2009) "Eukaryotic snoRNAs: A paradigm for gene expression flexibility," Genomics 94(2):83-88). Furthermore, algal expression systems are commercially available (Algae Expression & Engineering Products, ThermoFisher Scientific, Grand Island, N.Y.).

For use of sn-casPNs/Cas9 systems in insects or insect cells, suitable expression control sequences are well known in the art. In some embodiments, it is desirable that the expression control sequence comprises a. constitutive promoter. Examples of suitable strong promoters include, but are not limited to, the following: the baculovirus promoters for the piO, polyhedrin (polh), p 6.9, capsid, UAS (contains a Gal4 binding site), Ac5, cathepsin-like genes, the *B. mori* actin gene promoter; *Drosophila melanogaster* hsp70, actin, α-1-tubulin or ubiquitin gene promoters, RSV or MMTV promoters, copia promoter, gypsy promoter, and the cytomegalovirus IE gene promoter. Examples of weak promoters that can be used include, but are not limited to, the following: the baculovirus promoters for the ie1, ie2, ieO, etl, 39K (aka pp31), and gp64 genes. If it is desired to increase the amount of gene expression from a weak promoter, enhancer elements, such as the baculovirus enhancer element, hr5, may be used in conjunction with the promoter.

In some embodiments, the expression control sequence comprises an organ- or tissue-specific promoter. Many such expression control sequences. For example, suitable promoters that direct expression in insect silk glands include the *Bombyx mori* p25 promoter, which directs organ-specific expression in the posterior silk gland, and the silk fibroin heavy chain gene promoter, which directs specific expression of genes in the median silk gland.

Examples of insect regulatable expression control sequences (e.g., comprising an inducible promoter and/or enhancer element) include, but are not limited to, the following: *Drosophila* hsp70 promoters, *Drosophila* metallothionein promoter, an ecdysone-regulated promoter, and other well-known inducible systems. A Tet-regulatable molecular switch may be used in conjunction with any constitutive promoter (e.g., in conjunction with the CMV-IE promoter or baculovirus promoters). Another type of inducible promoter is a baculovirus late or very late promoter that is only activated following infection by a baculovirus.

For the expression of sn-casPNs in insects, RNA polymerase III promoters are known in the art, for example, the U6 promoter. Conserved features of RNA polymerase III promoters in insects are also known (see, e.g., Hernandez, G., (2007) "Insect small nuclear RNA gene promoters evolve rapidly yet retain conserved features involved in determining promoter activity and RNA polymerase specificity," Nucleic Acids Res. 2007 January; 35(1):21-34).

Methods for designing and preparing constructs suitable for generating transgenic insects or vectors for infection of an insect are conventional. Methods for transformation, culturing, and manipulation of insect cell lines are also conventional. Examples of insect cell lines include, but are not limited to, the following: Antheraea cells, Tn-368, *Drosophila* S2 Cells, High Five™ Cells (Life Technologies, Grand Island N.Y.), Sf21 Cells; and Sf9 cells. Insect cell lines are commercially available, for example, from the American Type Culture Collection (Manassas Va.).

A variety of immortalized lepidopteran insect cell lines are suitable for infection by vectors/constructs comprising the sn-casPNs/Cas9 proteins of the present invention. Examples of immortalized lepidopteran insect cell lines that are suitable for infection by the vectors/constructs of the invention include, but are not limited to, the following: Sf9 and Tn 5B1-4.

In another embodiment, the vector is a transposon-based vector. One transposon-based vector is a viral vector that further comprises inverted terminal repeats of a suitable transposon between which the gene of interest is cloned. One or more genes, under the control of a suitable expression control sequences, are cloned into the transposon-based vector. In some systems, the transposon-based vector carries its own transposase. However, typically the transposon-based vector does not encode a suitable transposase. In this case, the vector is co-infected into an insect (e.g., an insect larva) with a helper virus or plasmid that provides a transposase. The recombinant vector, generally with a helper, is introduced by conventional methods (e.g., microinjection) into an egg or early embryo. The transgenes become integrated at a transposon site (e.g., sequences corresponding to the inverted terminal repeat of the transposon) in the insect genome. Examples of suitable types of transposon-based vectors include, but are not limited to, the following: Minos, mariner, Hermes, sleeping beauty, and piggyBac.

TTAA-specific, short repeat elements are a group of transposons (Class II mobile elements) that have similar structures and movement properties. piggyBac vectors are the most extensively studied of these insertion elements. piggyBac is 2.4 kb long and terminates in 13 bp perfect inverted repeats, with additional internal 19 bp inverted repeats located asymmetrically with respect to the ends. A piggyBac vector may encode a trans-acting transposase that facilitates its own movement. Alternatively, the transposase encoding sequences can be deleted and this function supplied on a helper plasmid or virus. Some piggyBac vectors have deleted non-essential genes to facilitate cloning of large inserts. Inserts as large as 15 kB can be cloned into certain piggyBac vectors. For example, this allows for the insertion of approximately six or seven genes with their expression control sequences. For example, a collection of sn-casPNs can be introduced together via a single transposon vector into a single site in an insect genome.

Several piggyBac vectors have been developed for insect transgenesis. Two constructs were developed by analysis of deletion mutations within and outside of the boundaries of the transposon. Using such constructs, it is possible to increase the amount of genetic material mobilized by the piggyBac transposase by minimizing the size of the vector. The minimal requirements for movement include the 5' and 3' terminal repeat domains and attendant TTAA target sequences. A minimum of 50 bases separating the TTAA target sites of the element is typically required for efficient mobilization.

piggyBac can transpose in insect cells while carrying a marker gene and movement of the piggyBac element can occur in cells from lepidopteran species distantly related to the species from which it originated. For example, piggyBac has been shown to transform *D. melanogaster, Anastrepha suspena* (oriental fruit fly), *Bactrocera dorsalis, Bombyx mori, Pectinophora glossypiella, Tribolium castellani*, and several mosquito species. At least three lepidopteran species, *P. gossypiella, T. ni* and *B. mori*, have been successfully transformed using the piggyBac element.

Typically, a helper virus or plasmid that expresses a transposase is co-infected with the transposon-based vector. Expression of the transposase is determined by the choice of promoter for the insect system being tested. Examples of promoter-driven helper constructs that are useful for lepidopteran transformation include, but are not limited to, the following: *Drosophila* hsp70, baculovirus ie1 promoter, and *Drosophila* Actin 5C promoter. For further guidance on the use of baculovirus-based vectors, see, e.g., WO/2005/042753.

Methods for generating transgenic insects are conventional. For example, one or more genes to be introduced are placed under the control of a suitable expression control sequence and are cloned into a vector (e.g., an attenuated baculovirus vector or a non-permissive viral vector that is not infective for the target insect). The sequences to be introduced into the insect are flanked by genomic sequences from the insect. The construct is then introduced into an insect egg (e.g., by microinjection). The transgenes then integrate by homologous recombination of the flanking sequences into complementary sequences in the insect genome.

Methods for introducing constructs into an embryo to generate a transgenic insect (e.g., by microinjection) are known. Survivorship is typically high (up to 75%) for microinjected embryos. In general, pre-blastoderm eggs are stuck with a fine glass capillary holding a solution of the plasmid DNA and/or recombinant virus. G0 larvae hatched from the virus-injected eggs are screened for expression of the transfected genes. Breeding transgenic G1 insects with normal insects results in Mendelian inheritance.

Once a transgene is stably integrated into the genome of an insect egg or early embryo, conventional methods can be used to generate a transgenic insect, in which the transgene is present in all of the insect somatic and germ cells. Methods for producing homozygous transgenic insects (e.g., using suitable back-crosses) are conventional.

By selecting appropriate expression control sequences for each of the genes, a multiply transgenic insect that comprises genomically integrated copies of sn-casPNs and Cas9 protein genes can be designed such that the genes of are expressed at suitable levels, at the desired time during insect growth.

In another aspect, the sn-casPNs/Cas9 systems are incorporated into mammalian vectors for use in mammalian cells. A large number of mammalian vectors suitable for use with the sn-casPNs/Cas9 systems of the present invention are commercially available (e.g., from Life Technologies, Grand Island, N.Y.; NeoBiolab, Cambridge, Mass.; Promega, Madison, Wis.; DNA2.0, Menlo Park, Calif.; Addgene, Cambridge, Mass.).

Vectors derived from mammalian viruses can be used for expressing the sn-casPNs and Cas9 proteins of the present invention in mammalian cells. These include vectors derived from viruses such as adenovirus, papovirus, herpesvirus, polyomavirus, cytomegalovirus, lentivirus, retrovirus and simian virus 40 (SV40) (see, e.g., Kaufman, R. J., (2000) "Overview of vector design for mammalian gene expression," Molecular Biotechnology, Volume 16, Issue 2, pp 151-160; Cooray S., et al., (2012) "Retrovirus and lentivirus vector design and methods of cell conditioning," Methods Enzymol. 507:29-57). Regulatory sequences operably linked to the sn-casPNs/Cas9 components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGK1 (mouse or human), Ubc, CAG, CaMKIIa, and beta-Act. and others known in the art (Khan, K. H. (2013) "Gene Expression in Mammalian Cells and its Applications," Advanced Pharmaceutical Bulletin 3(2), 257-263). Furthermore, for expression of the sn-casPNs of the present invention, mammalian RNA polymerase III promoters, including H1 and U6, are used.

Adenovirus is a member of the Adenoviridae family. Adenovirus vectors are derived from adenovirus. Adenovirus is medium sized, non-enveloped icosahedral virus. It is composed of a nucleocapsid and a double-stranded linear DNA genome that can be used as a cloning vector. The extensive knowledge and data on adenovirus transcription regulation favored the engineering of adenovirus vectors modified for expression of inserted genes. For this purpose, the early regions E1 and E3 were deleted, thus making the virus incapable of replication, requiring the host cell to provide this function in trans. An expression cassette comprising protein coding sequences (e.g., a Cas9 protein) is typically inserted to replace the deleted E1 region. In the cassette, a gene is placed under control of an additional major late promoter or under control of an exogenous promoter, such as cytomegalovirus or selected regulatable promoter.

The genome of adenovirus can be manipulated in such a way that it encodes and expresses a gene product of interest while at the same time inactivating the adenovirus' ability to replicate via a normal lytic cycle. Some such adenoviral vectors include those derived from adenovirus strain Ad type 5 dl324 or other adenovirus strains (e.g., Ad2, Ad3, and Ad7). In certain circumstances, recombinant adenoviruses can be advantageous because they cannot infect non-dividing cells, and they can be used to infect epithelial cells and a variety of other cell types. In addition, the virus particle is relatively stable, and it is amenable to purification and concentration. The adenoviral genome's carrying capacity for foreign DNA is up to approximately 8 kilobases, which is large compared with other gene delivery vectors. Thr large double-stranded DNA adenovirus does not integrate into the genome, limiting its use to transient, episomal expression. Because it is not integrated into the genome of a host cell (unlike retroviral DNA) potential problems such as insertional mutagenesis are avoided.

Adeno-associated virus (AAV), an single-strand DNA member of the family Parvoviridae, is a naturally replication-deficient virus. Like adenovirus, it can infect non-dividing cells; however, it has the advantage of integration competence. AAV vectors are among the viral vectors most frequently used for gene therapy. Twelve human serotypes of AAV (AAV serotype 1 [AAV-1] to AAV-12) and more than 100 serotypes from non-human are known. A number of factors have increased AAV's potential as a delivery vehicle for gene therapy applications, including the lack of pathogenicity of the virus, the persistence of the virus, and the many available serotypes. AAV is a small (25-nm), non-enveloped virus that comprises a linear single-stranded DNA genome. Productive infection by AAV typically occurs only in the presence of a helper virus, for example, adenovirus or herpesvirus. In the absence of helper virus, AAV (serotype 2) can become latent by integrating into human chromosome 19q13.4 (locus AAVS-1) (see, e.g., Daya, S., et al., (2008) "Gene Therapy Using Adeno-Associated Virus Vectors," Clinical Microbiology Reviews, 21(4): 583-593).

Vaccinia virus is a member of the poxvirus family. Vaccinia vectors are derived from vaccinia virus. The vaccinia virus genome is comprised of a double stranded DNA of nearly 200,000 bp. It replicates in the cytoplasm of the host cell. Cells infected with the vaccinia virus produce up to 5000 virus particles per cell, leading to high levels of expression for encoded gene products. The vaccinia system has been efficiently used in very large scale culture (1000 L) to produce several proteins, including HIV-1 rgp160 and human pro-thrombin.

Retrovirus is a member of the Retroviridae family. Retroviral vectors are derived from retrovirus. Retroviruses are RNA viruses that replicate via a double-strand DNA intermediate. One advantage of using a retrovirus as vector is that most retroviruses do not kill the host, but instead produce progeny virons over an indefinite period of time. Therefore, retroviral vectors (i) can be used to make stably transformed cell lines, (ii) provide viral gene expression driven by strong promoters, which can be subverted to control the expression of transgenes; and (iii) include those derived from retroviruses having a broad host range (e.g., amphotropic strains of murine leukaemia virus (MLV)) thus allowing the transfection of many cell types.

Exogenous gene-expression systems based on the retroviral vector are also a method for generating stable, high-expressing mammalian cell lines.

Lentivirus is a member of the Retroviridae family. A single-strand RNA virus, it can infect both dividing and nondividing cells, as well as provide stable expression through integration into the genome. To increase the safety of lentivirus, components necessary to produce a viral vector are split across multiple plasmids. Transfer vectors are typically replication incompetent and may additionally contain a deletion in the 3'LTR, which renders the virus "self-inactivating" (SIN) after integration. Packaging and envelope plasmids are typically used in combination with a transfer vector. For example, a packaging plasmid can encode the Gag, Pol, Rev, and Tat genes. A transfer plasmid can comprise viral LTRs and the psi packaging signal. Usually one or more suitable promoter operably linked to the genes to be expressed (e.g., sn-casPNs and/or Cas9 protein coding sequences) because the 5'LTR is a weak promoter and requires the presence of Tat to activate expression. The envelope plasmid comprises an envelope protein (usually VSVG because of its wide infectivity range).

Lentiviral vectors based on human immunodeficiency virus type-1 (HIV-1) have additional accessory proteins that enable integration in the absence of cell division. HIV-1 vectors have been designed to address a number of safety concerns. These include separate expression of the viral genes in trans to prevent recombination events leading to the generation of replication-competent viruses. Furthermore, the development of self-inactivating (SIN) vectors reduces the potential for transactivation of neighboring genes and allows the incorporation of regulatory elements to target gene expression to particular cell types (see, e.g., Cooray, S., et al., (2012) "Retrovirus and lentivirus vector design and methods of cell conditioning," Methods Enzymol. 507:29-57).

In some embodiments, a recombinant mammalian expression vector is capable of preferentially directing expression of the nucleic acid in a particular cell type (e.g., using tissue-specific regulatory elements to express a polynucleotide). Tissue-specific regulatory elements are known in the art and include, but are not limited to, the albumin promoter, lymphoid-specific promoters, neuron-specific promoters (e.g., the neurofilament promoter), pancreas-specific promoters, mammary gland-specific promoters (e.g., milk whey promoter), and in particular promoters of T cell receptors and immunoglobulins. Developmentally-regulated promoters are also encompassed, e.g., the murine hox promoters and the alpha-fetoprotein promoter.

A number of vectors for use in mammalian cells are commercially available, for example: pcDNA3 (Life Technologies, Grand Island N.Y.); customizable expression vectors, transient vectors, stable vectors, and lentiviral vectors (DNA 2.0, Menlo Park Calif.); and pFN10A (ACT) Flexi® Vector (Promega, Madison, Wis.). Furthermore, the following elements can be incorporated into vectors for use in mammalian cells: RNA polymerase II promoters operatively linked to Cas9 coding sequences; RNA polymerase III promoters operably linked to coding sequences for sn-casRNAs; selectable markers (e.g., G418, gentamicin, kanamycin and Zeocin™ (Life Technologies, Grand Island, N.Y.)). Nuclear targeting sequences can also be added, for example, to Cas9 protein coding sequences.

Regulatory elements may also direct expression in a temporal-dependent manner, which may or may not also be tissue or cell-type specific (e.g., in a cell-cycle dependent or developmental stage-dependent manner). In some embodiments, vectors comprise one or more RNA polymerase III promoter (e.g., operably linked to sn-casPNs coding sequences), one or more RNA polymerase II promoters (e.g., operably linked to a Cas9 protein coding sequence), one or more RNA polymerase I promoters, or combinations thereof. As noted above, examples of mammalian RNA polymerase III promoters include, but are not limited to, the following: U6 and H1 promoters. Examples of RNA polymerase II promoters were discussed above. RNA polymerase I promoters are well known in the art.

Numerous mammalian cell lines have been utilized for expression of gene products including HEK 293 (Human embryonic kidney) and CHO (Chinese Hamster Ovary). These cell lines can be transfected by standard methods (e.g., using calcium phosphate or polyethyleneimine (PEI), or electroporation). Other typical mammalian cell lines include, but are not limited to: HeLa, U2OS, 549, HT1080, CAD, P19, NIH 3T3, L929, N2a, Human embryonic kidney 293 cells, MCF-7, Y79, SO-Rb50, Hep G2, DUKX-X11, J558L, and Baby hamster kidney (BHK) cells.

The sn-casPNs/Cas9 protein systems of the present invention can be used to manipulate mammalian cell bioprocesses for manufacturing. The Chinese Hamster Ovary (CHO) cells and mouse myeloma cells (including Sp2/0 and NS0 cells) are the most widely used host mammalian cells. Two derivatives of the CHO cell line, CHO-K1 and CHO pro-3, have given rise to the two most commonly used cell lines in bioprocessing today, DG44 and DUKX-X11 (both of these cell lines were engineered to be deficient in dihydrofolatereductase activity).

Example 14 describes the modification of CHO cells for industrial applications. This example describes use of the split-nexus Cas9-associated polynucleotides (sn-casPNs) of the present invention for modifying the genome of a CHO cell. Also described is an experimental for sequence validation and selection of sn-casPN modified cells for future uses in industrial applications (e.g., production of antibodies). The methods provide for modification of chromosomal loci within CHO cells by selection of appropriate spacer sequences for sn-casPNs. Selection is specific to a specific gene target and the procedure outlined in the example is readily modifiable by one of ordinary skill in the art for other gene targets.

Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAF-dextran mediated transfection, protoplast fusion, lipofection, liposome-mediated transfection, particle gun technology, direct microinjection, and nanoparticle-mediated delivery.

In some embodiments of the present invention it is useful to express all components of a sn-casPNs/Cas9 system in a host cell. Expression of sequences encoding sn-casRNAs and Cas9 protein in a host cell can be accomplished through use of expression cassettes as described above. However, expression of sn-casDNA in a target cell is not accomplished with the use of standard cloning vectors. Single-stranded DNA expression vectors, which can intracellularly generate single-stranded. DNA molecules, have been developed (Chen, Y., et al., "Intracellular production of DNA enzyme by a novel single-stranded DNA expression vector," Gene Ther. 2003 September; 10(20):1776-80; Miyata S., et al., "In vivo production of a stable single-stranded cDNA in *Saccharomyces cerevisiae* by means of a bacterial retron," Proc Natl Acad Sci USA 1992; 89: 5735-5739; Mirochnitchenko, O., et al., "Production of single-stranded DNA in mammalian cells by means of a bacterial retron," J Biol Chem 1994; 269: 2380-2383; Mao J., et al., "Gene regulation by antisense DNA produced in vivo. J Biol Chem 1995; 270: 19684-19687). Typically these single-stranded DNA expression vectors rely on transcription of a selected single-stranded DNA sequence to form an RNA transcript that is the substrate for a reverse transcriptase and RNaseH to generate the selected single-stranded DNA in a host cell. For example, components of single-stranded DNA expression vectors often comprise, a reverse transcriptase coding sequence (e.g., a mouse Moloney leukemia viral reverse transcriptase gene), a reverse transcriptase primer binding site (PBS) as well as regions of the promoter that are essential for the reverse transcription initiation, the coding sequence of interest (e.g., a sn-casDNA coding sequence), a stem loop structure designed for the termination of the reverse transcription reaction, and an RNA transcription promoter suitable for use in a host cell (used to create a mRNA template comprising the previous components). Reverse transcriptase expressed in cells uses endogenous tRNApro as a primer. After reverse transcription, single-stranded DNA is released when the template mRNA is degraded either by endogenous RNase H or the RNase H activity of the reverse transcriptase (Chen, Y., et al., "Expression of ssDNA in Mammalian Cells," BioTechniques 34:167-171 January 2003). Such expression vectors may be employed for expression of a sn-casDNAs of the present invention in a host cell.

The present invention also encompasses gene therapy methods for preventing or treating diseases, disorders, and conditions using the sn-casPNs/Cas9 systems described herein. In one embodiment, a gene therapy method uses the introduction of nucleic acid sequences into an organism or cells of an organism (e.g., patient) to achieve expression of sn-casPNs/Cas9 protein components of the present invention to provide modification of a target function. For example, cells from an organism may be engineered, ex vivo, by (i) introduction of vectors comprising expression cassettes expressing the sn-casPNs and Cas9 protein, (ii) direct introduction of sn-casPNs (e.g., sn-casPNs: DNA polynucleotides, RNA polynucleotides, RNA/DNA hybrid polynucleotides, nucleobases connected with alternative backbones, or combinations thereof) and Cas9 protein, or (iii) introduction of combinations of these components. The engineered cells are provided to an organism (e.g., patient) to be treated.

Examples of gene therapy and delivery techniques for therapy are known in the art (see, e.g., Kay, M. A., (2011) "State-of-the-art gene-based therapies: the road ahead," Nature Reviews Genetics 12, 316-328; Wang, D., et al., (2014) "State-of-the-art human gene therapy: part I. Gene delivery technologies," Discov Med. 18(97):67-77; Wang, D., et al., (2014) "State-of-the-art human gene therapy: part II. Gene therapy strategies and clinical applications," Discov Med. 18(98):151-61; "The Clinibook: Clinical Gene Transfer State of the Art," Odile Cohen-Haguenauer (Editor), EDP Sciences (Oct. 31, 2012), ISBN-10: 2842541715).

Example 11 illustrates illustrates the use of sn-casRNAs of the present invention to modify targets present in human genomic DNA and measure the level of cleavage activity at those sites. Target sites are first selected from genomic DNA and then sn-casRNAs are designed to target those selected sequences. Measurements are then carried out to determine the level of target cleavage that has taken place. Cleavage percentage data and specificity data provide criteria on which to base choices for a variety of applications. For example, in some situations the activity of the sn-casRNA may be the most important factor. In other situations, the specificity of the cleavage site may be relatively more important than the cleavage percentage.

In some aspects, components of the present invention are delivered using nanoscale delivery systems. Components to be delivered include, but are not limited to, polynucleotides encoding sn-casPNs and/or Cas9 protein, expression cassettes comprising sn-casPNs and/or Cas 9 proteins, sn-casPNs, Cas 9 protein, and combinations thereof. The components of the invention can be formulated as nanoparticles. Extensive libraries of nanoparticles, composed of an assortment of different sizes, shapes, and materials, and with various chemical and surface properties, are widely available. Examples of nanoparticles particularly useful in biotechnology and nanomedicine include: fullerenes (e.g., buckyballs and carbon tubes); liquid crystals; liposomes; silica and silicon-based nanoparticles (e.g., mesoporous silica nanoparticles); nanoshells; nanorods; metal and metal oxides nanoparticles (e.g., spherical nucleic acids, densely packed polynucleotides surrounding a gold core); polycations; and cationic cyclodextrins.

One example of nanoparticle formation includes the use of cationic cyclodextrins that can self-assemble into nanoparticles to form colloidal particles (Draz, M. S., et al., (2014) "Nanoparticle-Mediated Systemic Delivery of siRNA for Treatment of Cancers and Viral Infections," Theranostics. 2014; 4(9):872-892). Example 18 describes production of Cas9 protein and sn1-casRNA/sn2-casRNA/sn3-casRNA sn-casPNs/Cas9 system components. These sn-casPNs/Cas9 system components are formed into ribonucleoprotein complexes and are also prepared as particles with a SC12CDClickpropylamine vector. SC12CDClickpropylamine vectors have been described for use with siRNA (see, e.g., Aoife M. O'Mahony, A. M., et al., (2013) "Cationic and PEGylated Amphiphilic Cyclodextrins: Co-Formulation Opportunities for Neuronal Sirna Delivery," PLOSONE 8(6):e66413). Characterization of the SC12CDClickpropylamine vector sn-casRNAs/Cas9 particles is described in Example 18.

Cationic cyclodextrins include, but are not limited to, carboxyethyl-β-cyclodextrin, amphiphilic cyclodextrins (e.g., heptakis[2-(ω-amino-oligo(ethylene glycol))-6-deoxy-6-hexadecylthio]-β-cyclodextrin and heptakis[2-(ω-amino-oligo(ethylene glycol))-6-deoxy-6-dodecylthio]-β-cyclodextrin); and cationic multi-armed α-cyclodextrin (α-CD): PEG polyrotaxane.

Liposomes are another example of nanoparticle formation. sn-casPNs/Cas9 system component of the present invention can be entrapped in liposomes. Liposomes for use with the sn-casPNs/Cas9 system components typically comprise a cationic lipid. Examples of the cationic lipids include DODAC (dioctadecyldimethylammonium chloride), DOTMA (N-(2,3-dioleyloxy)propyl-N,N,N-trimethylammonium), DDAB (didodecylammonium bromide), DOTAP (1,2-dioleoyloxy-3-trimethylammonio propane), DC-Chol (3-beta-N—(N',N'-dimethyl-aminoethane)-carbamol cholesterol), DMRIE (1,2-dimyristoyloxypropyl-3-dimethylhydroxyethyl ammonium), DOSPA (2,3-dioleyloxy-N-[2(sperminecarboxamido)ethyl]-N,N-dimethyl-1-propanaminum trifluoroacetate), DSTAP (1,2-Distearoyl-3-Trimethylammonium Propane), DODAP (dioleoyl-3-dimethylammonium-propane), DOGS (dioctadecylamidoglycylcarboxyspermine), and the like. A single type of cationic lipid may be used alone, or a combination of two or more types of cationic lipids can be used. Cationic lipids are typically combined with other lipids (e.g., phospholipids and cholesterol) to form liposomes.

Examples of phospholipids for liposome formation include, but are not limited to, the following: phosphatidylcholine; L-α-phosphatidylcholine (egg phosphatidylcholine (EPC), or hydrogenated soy phosphatidylcholine (HSPC)); 1,2-distearoyl-sn-glycero-3-phosphocholine (DSPC); 1,2-dipalmitoyl-sn-glycero-3-phosphocholine (DPPC); phosphatidylserine (PS); phosphatidylinositol (PI); phosphatidylglycerol (PG); phosphatidylethanolamine (PE); dioleoyl phosphatidylglycerol (DOPG); 1,2-Dioleoyl-sn-glycero-3-phosphocholine (or dioleoyl phosphatidylcholine) (DOPC); dioleoyl phosphatidylserine (DOPS); 1,2-dileoyl-sn-glycero-3-phosphoethanolamine (DOPE); 1,2-Dioleoyl-sn-glycero-3-phosphate (DOPA); 1-Myristoyl-2-stearoyl-sn-glycero-3-phosphocholine (MSPC); 1,2-Dipalmitoyl-sn-glycero-3-phospho-rac-(1-glycerol) (DPPG); 1,2-Dimyristoyl-sn-glycero-3-phospho-rac-(1-glycerol) (DMPG); 1,2-Dimyristoyl-sn-glycero-3-yhosphocholine (DMPC); 1,2-Distearoyl-sn-glycero-3-phospho-rac-(1-glycerol) (DSPG); 1-Palmitoyl-2-oleoyl-sn-glyccro-3-phosphocholine (POPC); diacylphosphatidylcholine; diacylphosphatidic acid; N-dodecanoyl phosphatidylethanolamine: N-succinyl phosphatidylethanolamine: N-glutaryl phosphatidylethanolamine: lysylphosphatidylglycerol; sphingolipids (e.g., sphingomyelin); and mixtures thereof.

A variety of sterols and derivatives thereof (e.g., cholesterol) can be used to stabilize liposomes. Cholesterol can be chemically modified with a ligand designed to be recognized by a particular organ or cell type such as a long chain fatty acid, an amino acid, an amino acid derivative, a protein, glycoprotein, an oligosaccharide, a hormone, modified protein, or the like. Liposomes containing such modified cholesterols are suitable for being targeted to a specific organ or cell type (see, e.g., U.S. Pat. No. 4,544,545).

Hydrophilic polymers such as polyethylene glycol (PEG) and other polyethoxylated polymers can be used to shield liposomes to enhance the circulatory half-life of the liposome. Such hydrophilic polymers can be associated non-covalently with the liposomes or conjugated or covalently linked to a particular component of the liposome (e.g., PEG-derivatized lipids; such as 1,2-distearoyl-sn-glycero-3-phosphoethanolamine-N-[methoxy(polyethylene glycol)-2000] (ammonium salt) (mPEG-DSPE), and stearylated PEG2000). Additional exemplary hydrophilic polymers include, but are not limited to, polyvinyl alcohols, polylactic acids, polyglycolic acids, polyvinylpyrrolidones, polyacrylamides, polyglycerols, polyaxozlines, polyaminoacids (PAAs), and mixtures thereof.

Methods for the preparation of the liposomal compositions include liposomes formed by a thin film hydration method wherein rehydration uses an aqueous solution comprising a sn-casPN/Cas9 system of the present invention (see, e.g., Example 18).

Example 18 describes n-casRNAs/Cas9 protein complexes in non-viral delivery vectors comprising cationic molecules. In the example, production of Cas9 mRNA and sn1-casRNA/sn2-casRNA/sn3-casRNA components is described. These components are then formed into ribonucleoprotein complexes as well as ribonucleoprotein/SC12CDClickpropylamine particles. The complexes and particles are entrapped in liposomes. These liposomes are characterized using a number of criteria, including in vivo activity. The example establishes criteria for selecting optimal liposomal compositions for encapsulation of sn-casRNAs/Cas9 complexes of the present invention according to their advantages and limitations.

In other embodiments, liposomes are formed by a lipid solution injection method wherein a lipid solution is injected into an aqueous solution comprising components of the sn-casPN/Cas9 systems of the present invention. The lipids are typically dissolved in a solvent, for example, an organic solvent (such as an alcohol; e.g., ethanol), followed by injection into the aqueous solution comprising the sn-casPN/Cas9 system while stirring. Liposome vesicles are formed upon injection into the aqueous solution trapping small amounts of aqueous solution in the internal aqueous compartment(s) of the vesicles. One advantage of this method is that it is scalable.

Examples of sn-casPNs/Cas9 systems of the present invention that can be entrapped in liposomes include, but are not limited to, polynucleotides encoding sn-casPNs and/or Cas9 protein, expression cassettes comprising sn-casPNs and/or Cas 9 proteins, sn-casPNs, Cas9 protein, complexes of sn-casPNss and Cas9 protein, and combinations thereof.

Aspects of the present invention include, but are not limited to the following: one or more expression cassettes comprising polynucleotides encoding sn-casPNs and/or Cas9 protein; one or more vectors, including expression vectors, comprising polynucleotides encoding sn-casPNs and/or Cas9 protein; methods of manufacturing expression cassettes comprising production of polynucleotides comprising expression cassettes encoding sn-casPNs and/or Cas9 protein; methods of manufacturing vectors, including expression vectors, comprising production of vectors comprising polynucleotides encoding sn-casPNs and/or Cas9 protein; methods of introducing one ore more expression cassettes, comprising introducing polynucleotides encoding sn-casPNs and/or Cas9 protein into a selected host cell; methods of introducing one or more vectors, including expression vectors, comprising introducing vector(s) comprising polynucleotides encoding sn-casPNs and/or Cas9 protein into a selected host cell; host cells comprising one or more expression cassettes comprising polynucleotides encoding sn-casPNs and/or Cas9 protein (recombinant cells); host cells comprising one or more vectors, including expression vectors, comprising polynucleotides encoding sn-casPNs and/or Cas9 protein (recombinant cells); host cells comprising one or more polynucleotides encoding sn-casPNs and/or Cas9 protein (recombinant cells); host cells expressing the products of one or more polynucleotides encoding sn-casPNs and/or Cas9 protein (recombinant cells); methods for manufacturing sn-casPNs comprising producing sn-casPNs by in vitro transcription and/or producing Cas9 protein by in vitro translation; and methods for manufacturing sn-casPNs and/or Cas9 protein, comprising isolating the casPNs and/or Cas9 protein from host cells (recombinant cells) expressing the products of, one or more polynucleotides encoding sn-casPNs and/or Cas9 protein.

Another aspect of the present invention relates to methods to generate non-human genetically modified organisms. Generally, in these methods expression cassettes comprising polynucleotide sequences of the sn-casPNs and Cas9 protein, as well as a targeting vector are introduced into zygote cells to site-specifically introduce a selected polynucleotide sequence at a DNA target sequence in the genome to generate a modification of the genomic DNA. The selected polynucleotide sequence is present in the targeting vector. Modifications of the genomic DNA typically include, insertion of a polynucleotide sequence, deletion of a polynucleotide sequence, or mutation of a polynucleotide sequence, for example, gene correction, gene replacement, gene tagging, transgene insertion, gene disruption, gene mutation, mutation of gene regulatory sequences, and so on. In one embodiment of methods to generate non-human genetically modified organisms, the organism is a mouse. One embodiment of this aspect of the invention is the generation of genetically modified mice.

Generating transgenic mice involves five basic steps (Cho A., et al., "Generation of Transgenic Mice," Current protocols in cell biology, 2009; Chaper.Unit-19.11). First, purification of a transgenic construct (e.g., expression cassettes comprising polynucleotide sequences of the sn-casPNs and Cas9 protein, as well as a targeting vector). Second, harvesting donor zygotes. Third, microinjection of the transgenic construct into the mouse zygote. Fourth, implantation of microinjected zygotes into pseudo-pregnant recipient mice. Fifth, performing genotyping and analysis of the modification of the genomic DNA established in founder mice.

Example 17 describes use of the split-nexus Cas9-associated polynucleotides (sn-casPNs) of the present invention for creating genomic modifications in non-human animals. The example describes generation of transgenic mice using two-part sn-casRNA (sn1-casRNA and sn2-casRNA) system (see, e.g., FIG. 3B). The production of Cas9 mRNA and sn1-casRNA/sn2-casRNA is described. The mRNAs are use for one-cell embryo injection. The example describes the creation of double-gene mutant mice as well as the evaluation of in vivo off-target effects of the sn-casRNAs/Cas9 system. Furthermore, the example includes evaluation of in vivo gene repair using a donor oligonucleotide with the sn-casRNAs/Cas9 system. The results of these analyses are to demonstrate that mice with genomic repair modifications in multiple genes can be generated using the sn-casPNs/Cas9 systems described herein.

In another embodiment of methods to generate non-human genetically modified organisms, the organism is a plant. The sn-casPNs/Cas9 protein systems described herein are used to effect efficient, cost-effective gene editing and manipulation in plant cells. It is generally preferable to insert a functional recombinant DNA in a plant genome at a non-specific location. However, in certain instances, it may be useful to use site-specific integration to introduce a recombinant DNA construct into the genome. Such introduction of recombinant DNA into plants is facilitated using the sn-casPNs/Cas9 protein systems of the present invention. Recombinant vectors for use in plant are known in the art. The vectors can include, for example, scaffold attachment regions (SARs), origins of replication, and/or selectable markers.

For embodiments in which polynucleotides encoding sn-casPNs and/or Cas9 protein are used to transform a plant, a promoter demonstrating the ability to drive expression of the coding sequence in that particular species of plant is selected. Promoters that can be used effectively in different plant species are well known in the art, as well. Inducible, viral, synthetic, or constitutive promoters can be used in plants for expression of polypeptides. Promoters that are spatially regulated, temporally regulated, and spatio-temporally regulated can also be useful. A list of preferred promoters includes, but is not limited to, the FMV35S promoter, the enhanced CaMV35S promoters, CaMV 35S promoter, opine promoters, monocot promoters, plant ubiquitin promoter (Ubi), rice actin 1 promoter (Act-1), maize alcohol dehydrogenase 1 promoter (Adh-1).

Factors that determine which regulatory sequences to use in a recombinant construct, include, but are not limited to, desired expression level, and cell- or tissue-preferential expression, inducibility, efficiency, and selectability. One of skill in the art can modulate expression of a coding sequence by selecting and positioning regulatory sequences relative to the coding sequence.

Suitable regulatory sequences initiate mainly transcription or only transcription in certain cell types. Methods for identifying and characterizing regulatory sequences in plant genomic DNA are known. U.S. Patent Application Publication No. 20110177228, published Jul. 21, 2011, describes a large number of such regulatory sequences as follows.

Root-active promoters confer transcription in root tissue, e.g., root vascular tissues, root epidermis, or root endodermis. Some root-active promoters are root-preferential promoters and confer transcription predominantly in root tissue. Examples of root-preferential promoters include, but are not limited to, the following: PT0625, PT0660, PT0683, PT0758, YP0128, and YP0275. Other root-preferential promoters include the PT0613, PT0672, PT0688, and PT0837, which promote transcription primarily in root tissue but also to some extent in ovules and/or seeds. Other root-preferential promoters include the root-specific subdomains of the CaMV 35S promoter and the tobacco RD2 promoter.

In some embodiments, promoters specifically active in maturing endosperm can be used. Transcription from a maturing endosperm promoter generally begins after fertilization and occurs primarily in endosperm tissue during seed development. Transcription is commonly highest during the cellularization phase. Examples of maturing endosperm promoters that can be used in expression vector constructs include, but are not limited to, the napin promoter, the soybean trypsin inhibitor promoter, the soybean a' subunit of the beta-conglycinin promoter, the Arcelin-5 promoter, the ACP promoter, the phaseolin promoter, the stearoyl-ACP desaturase promoter, the oleosin promoter, the zein promoters (e.g., 15 kD, 16 kD, 19 kD, 22 kD, and 27 kD zein promoters), the Osgt-1 promoter from the rice glutelin-1 gene, the beta-amylase promoter, and the barley hordein promoter. Other maturing endosperm promoters include the PT0676, PT0708 and YP0092 promoters.

Examples of promoters active in ovary tissues include, but are not limited to, the following: the polygalacturonidase promoter, the banana TRX promoter, the melon actin promoter, YP0396, and PT0623. In addition, examples of promoters that are active primarily in ovules include YP0007, YP0008, YP0028, YP0039, YP0092, YP0103, YP0111, YP0115, YP0119, YP0120, YP0121, and YP0374.

To achieve expression in embryo sac/early endosperm, regulatory sequences are used that are active in polar nuclei and/or the central cell, or in precursors to polar nuclei, but not in egg cells or precursors to egg cells. A pattern of transcription that extends from polar nuclei into early endosperm development can also be found with embryo sac/early endosperm-preferential promoters (although transcription typically decreases significantly in later endosperm development during and after the cellularization phase). Expression in the zygote or developing embryo typically is not present with embryo sac/early endosperm promoters. Examples of such promoters include those derived from the following genes, but are not limited to, the following: *Arabidopsis* viviparous-1, *Arabidopsis* atmycl, *Arabidopsis* FIE, *Arabidopsis* MEA, *Arabidopsis* FIS2, FIE 1.1, maize MAC1, and maize Cat3. Additional *Arabidopsis* promoters include YP0039, YP0101, YP0102, YP0110, YP0117, YP0119, YP0137, DME, YP0285, and YP0212. Examples of rice promoters include p530c10, pOsFIE2-2, pOsMEA, pOsYp102, and pOsYp285.

Regulatory sequences that preferentially drive transcription in zygotic cells following fertilization can provide embryo-preferential expression. Examples of embryo-preferential promoters include, but are not limited to, the following: the barley lipid transfer protein (Ltp1) promoter, YP0088, YP0097, YP0107, YP0143, YP0156, PT0650, PT0695, PT0723, PT0740, PT0838, and PT0879.

Promoters active in photosynthetic tissue confer transcription in green tissues such as leaves and stems. Examples of photosynthetic tissue promoters include the ribulose-1,5-bisphosphate carboxylase (RbcS) promoters such as the RbcS promoter from eastern larch (*Larix laricina*), the pine cab6 promoter, the Cab-1 promoter from wheat, the CAB-1 promoter from spinach, the cab1R promoter from rice, the pyruvate orthophosphate dikinase (PPDK) promoter from corn, the tobacco Lhcb1*2 promoter, the *Arabidopsis thaliana* SUC2 sucrose-H+ symporter promoter, the thylakoid membrane protein promoters from spinach (psaD, psaF, psaE, PC, FNR, atpC, atpD, cab, and rbcS), and the PT0668, PT0886, YP0144, YP0380 and PT0585 promoters.

Examples of promoters that have high or preferential activity in vascular bundles include YP0022, YP0080, YP0087, YP0093, and YP0108. Other vascular tissue-preferential promoters include the glycine-rich cell wall protein GRP 1.8 promoter, the *Commelina* yellow mottle virus (CoYMV) promoter, and the rice tungro bacilliform virus (RTBV) promoter.

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include PD0901, PD1367, PT0710, PT0848, YP0286, YP0337, YP0356, YP0374, YP0377, YP0380, YP0381, YP0384, YP0385, YP0388, YP0396, PT0633, and PT0688. Examples of nitrogen-inducible promoters include PT0863, PT0829, PT0665, and PT0886. Examples of shade-inducible promoters include PRO924 and PT0678. An example of a promoter induced by salt is rd29A.

A stem promoter may be specific to one or more stem tissues or specific to stem and other plant parts. Stem promoters may have high or preferential activity in, for example, epidermis and cortex, vascular cambium, procambium, or xylem. Examples of stem promoters include the following: YP0018, CryIA(b), and CryIA(c).

Examples of other classes of promoters include shoot-preferential, callus-preferential, trichome cell-preferential, guard cell-preferential such as PT0678, tuber-preferential, parenchyma cell-preferential, and senescence-preferential promoters. In some embodiments, a promoter may preferentially drive expression in reproductive tissues.

A 5' untranslated region (UTR) can be included in vector constructs. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, the following: polyadenylation signals and transcription termination sequences, (e.g., a nopaline synthase termination sequence).

Additional regulatory sequences are described in U.S. Patent Application Publication No. 20110177228, published Jul. 21, 2011.

RNA Polymerase III promoters that can be used in plant vectors for the expression of sn-casPNs include 7SL, U6 (e.g., U6 snoRNA promoter) and U3 (e.g., U3 snoRNA promoter).

In any transformation experiment, DNA is introduced into a small percentage of target cells only. Genes that encode selectable markers are useful and efficient in identifying cells that are stably transformed when they receive and integrate a transgenic DNA construct into their genomes. Preferred marker genes provide selective markers that confer resistance to a selective agent, such as an antibiotic or herbicide. Any herbicide to which plants may be resistant is a useful agent for a selective marker.

Selectable markers can be used to select for plants or plant cells containing vectors comprising the sn-casPNs and/or Cas9 protein of the present invention. A selectable marker can provide a selectable phenotype on a plant cell. For example, a marker can provide resistance to an antibiotic (e.g., kanamycin, G418, bleomycin, or hygromycin), to an herbicide (a bar gene that codes for bialaphos resistance; a mutant EPSP synthase gene that encodes glyphosate resistance; a nitrilase gene that confers resistance to bromoxynil; a mutant acetolactate synthase gene (ALS) that confers imidazolinone or sulphonylurea resistance) or methotrexate (a methotrexate-resistant DHFR gene). Expression vectors can also include a tag sequence designed to promote detection or manipulation of the expressed polypeptide. Commonly expressed as a fusion with the encoded polypeptide are tag sequences. Examples of tag sequences include, but are not limited to, the following: luciferase, beta-glucuronidase (GUS), green fluorescent protein (GFP), glutathione S-transferase (GST), polyhistidine, c-myc, hemagglutinin, or epitope (e.g., a FLAG® epitope, Sigma-Aldrich, St. Louis, Mo.). Such tags can be inserted anywhere within the polypeptide, including at either the carboxyl or amino terminus.

Potentially transformed cells are exposed to the selective agent, and, among the surviving cells there will be cells in which the resistance-conferring gene has been integrated and is expressed at sufficient levels for cell survival. Cells may be tested further to confirm stable integration of the exogenous DNA.

A screenable marker, which may be used to monitor expression, may also be included in a recombinant vector or construct of the present invention. Screenable markers include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues; a β-lactamase gene, a gene that encodes an enzyme for which various chromogenic substrates are known (e.g., PADAC, a chromogenic cephalosporin); a luciferase gene; a xylE gene that encodes a catechol dioxygenase that can convert chromogenic catechols; an α-amylase gene; a tyrosinase that encodes an enzyme capable of oxidizing tyrosine to DOPA and dopaquinone, which in turn condenses to melanin; and an α-galactosidase, which catalyzes a chromogenic α-galactose substrate.

Polynucleotides of the present invention may be introduced into a plant cell, either permanently or transiently, together with other genetic elements, for example, promoters, enhancers, introns, and untranslated leader sequences.

Xing, H. L., et al., ((2014) "A CRISPR/Cas9 toolkit for multiplex genome editing in plants," BMC Plant Biology 2014, 14:327) have described module vectors for expression of CRISPR-Cas9 systems in dicots and monocots. Binary vectors with two types of backbones are utilized; the first based on pGreen vectors (Hellens, R. P., et al., (2000) "pGreen: a versatile and flexible binary Ti vector for *agrobacterium*-mediated plant transformation," Plant Mol Biol 42:819-832); and the second based on pCAMB1A vectors. The pGreen-like vectors are relatively small, allowing them to be used for transient Cas9 and sn-casRNA expression in protoplasts to test the effectiveness of target sites. The vectors can be directly used to generate transgenic plants after validation in protoplasts. In *Agrobacterium*, the pGreen-like vectors depend on their pSa origin for propagation, and they require a helper plasmid to provide replication protein (RepA). *Agrobacterium* containing pSoup helper plasmid can be used as hosts for pGreen-like vectors.

Among the pCAMBIA-derived binary vectors, those with a hygromycin-resistance gene as a selectable marker were derived from pCAMBIA1300, while those with a kanamycin-resistance gene were derived from pCAMBIA2300, and those with a Basta-resistance gene were derived from pCAMBIA3300. The vectors pCAMBIA1300/2300/3300 (Curtis, M. D., et al., (2003) "A gateway cloning vector set for high-throughput functional analysis of genes in plants," Plant Physiol 133:462-469; Lee, L. Y., Gelvin, S. B. (2008) "T-DNA binary vectors and systems," Plant Physiol 146: 325-332.) and their derivatives (including the Gateway-compatible pMDC series) are some of the most widely used binary vectors for a variety of plant species and with several plant transformation protocols specifically optimized based on these vectors.

Such binary vector systems can be used with the expression cassettes of the present invention to provide, for example, multiple sn-casRNAs for multiplex genome editing. For example, in a three polynucleotide split nexus system, sn1-casRNA and sn2-casRNA DNA coding sequences are placed under the control of RNA Polymerase. III promoters in the first vector. Multiple sn3-casRNA each comprising a different DNA targeting sequence are each placed under the control of RNA Polymerase III promoters and cloned into the same vector. A Cas9 protein coding sequence optimized for expression in the selected plant is also included in the vector.

Among preferred plant transformation vectors are those derived from a Ti plasmid of *Agrobacterium tumefaciens* (Lee, L. Y., et al., "T-DNA Binary Vectors and Systems," Plant Physiol. 2008 February; 146(2): 325-332). Also useful and known in the art are *Agrobacterium rhizogenes* plasmids. There are several commercial software products designed to facilitate selection of appropriate plant plasmids for plant cell transformation and gene expression in plants and methods to easily enable cloning of such polynucleotides. SnapGene™ (GSL Biotech LLC, Chicago, Ill.; www.snapgene.com/resources/plasmid_files/your_time_is_valuable/), for example, provides an extensive list of plant vectors including individual vector sequences and vector maps, as well as commercial sources for many of the vectors.

Methods and compositions for transforming plants by introducing a recombinant DNA construct into a plant genome includes any of a number of methods known in the art. One method for constructing transformed plants is microprojectile bombardment. *Agrobacterium*-mediated transformation is another method for constructing transformed plants. Alternatively, other non-*Agrobacterium* species (e.g., *Rhizobium*) and other prokaryotic cells that are able to infect plant cells and introduce heterologous nucleotide sequences into the infected plant cell's genome can be used. Further transformation methods include electroporation, liposomes, transformation using pollen or viruses, chemicals that increase free DNA uptake, or free DNA delivery by means of microprojectile bombardment. DNA constructs of the present invention can be introduced into the genome of a plant host using conventional transformation techniques that are well known to those skilled in the art (see, e.g., "Methods to Transfer Foreign Genes to Plants," Y Narusaka, et al., cdn.intechopen.com/pdfs-wm/30876.pdf).

Typically, a transgenic plant formed using *Agrobacterium* transformation methods contains one simple recombinant DNA sequence inserted into one chromosome; this is referred to as a transgenic event. Such transgenic plants are heterozygous because of the inserted exogenous sequence. It is possible to form a transgenic plant that is homozygous with respect to a transgene by sexually mating (i.e., selfing) an independent segregant transgenic plant containing a single exogenous gene sequence to itself, for example an F0 plant, to produce F1 seed. One quarter of the F1 seeds will be heterozygous for the transgene. Plants formed by germinating F1 seeds can be tested for heterozygosity. Typical zygosity assays include, but are not limited to, SNP assays and thermal amplification assays that distinguish between homozygotes and heterozygotes. The progeny resulting from crossing a heterozygous plant with itself or with another heterozygous plant are always heterozygous.

As an alternative to using a recombinant DNA construct for the direct transformation of a plant, transgenic plants can be formed by crossing a first plant that has been transformed with a recombinant DNA construct with a second plant that lacks the construct. As an example, a first plant line into which has been introduced a recombinant DNA construct for gene suppression can be crossed with a second plant line to introgress the recombinant DNA into the second plant line, thus forming a transgenic plant line.

The sn-casPNs/Cas9 protein systems of the present invention provide plant breeders with a new tool to induce mutations. Accordingly, one skilled in the art can analyze genomic sources and identify genes of interest having desired traits or characteristics (e.g., herbicide resistance genes) and use the sn-casPNs/Cas9 systems of the present invention to introduce such genes into plant varieties lacking the genes; this result can be achieved with more precision than by using previous mutagenic agents, thereby accelerating and enhancing plant breeding programs.

Example 16 describes targeted mutagenesis in *Zea mays* using a three-part sn-casRNA system (sn1-casRNA, sn-2-casRNA and sn3-casRNA) to create genomic modifications in plants. Three different maize genomic target sequences are targeted for cleavage. Vectors comprising expression cassettes of the sn1-casRNA/sn2-casRNA/sn3-casRNA/Cas9 systems are described. The generation of mutations at the targeted sites is used to demonstrate that the sn-casPNs/Cas9 systems as described herein cleave maize chromosomal DNA and can be used to generate genomic mutations.

Another aspect of the present invention comprises methods of modifying DNA using sn-casPNs and Cas9 proteins. Generally, a method of modifying DNA involves contacting a target DNA with a sn-casPNs/Cas9 protein complex (a "targeting complex"). In some cases, the Cas9 protein component exhibits nuclease activity that cleaves both strands of a double-stranded DNA target at a site in the double-stranded DNA that is complementary to a DNA target binding sequence in the sn-casPNs. With nuclease-active Type II Cas9 proteins, site-specific cleavage of the target DNA occurs at sites determined by (i) base-pair complementarity between the DNA target binding sequence in the sn-casPNs and the target DNA, and (ii) a protospacer adjacent motif (PAM) present in the target DNA. The nuclease activity cleaves the target DNA to produce double-strand breaks. In cells the double-strand breaks are repaired cellular mechanisms including, but not limited to: non-homologous end joining (NHEJ), and homology-directed repair (HDR).

Repair of double-strand breaks by NHEJ occurs by direct ligation of the break ends to one another. Typically no new polynucleotide sequences are inserted at the site of the double-strand break; however, insertions or deletions may occur when a small number of nucleotides are either randomly inserted or deleted at the site of the double-strand break. Furthermore, two different sn-casPNs that comprise DNA target binding sequences targeting two different DNA target sequences are used to provide deletion of an intervening DNA sequence (i.e., the DNA sequence between the two DNA target sequences). Deletion of the intervening sequence occurs when NHEJ rejoins the ends of the two cleaved DNA target sequences to each other. Similarly, NHEJ may be used to direct insertion of donor template DNA or portion thereof using donor template DNA, for example, containing compatible overhangs. Accordingly, one embodiment of the present invention includes methods of modifying DNA by introducing insertions and/or deletions at a target DNA site.

Repair of double-strand breaks by HDR uses a donor polynucleotide (donor template DNA) or oligonucleotide having homology to the cleaved target DNA sequence. The donor template DNA or oligonucleotide is used for repair of the double-strand break in the target DNA sequence resulting in the transfer of genetic information (i.e., polynucleotide sequences) from the donor template DNA or oligonucleotide at the site of the double-strand break in the DNA. Accordingly, new genetic information (i.e., polynucleotide sequences) may be inserted or copied at a target DNA site.

One aspect of the present invention is directed to a method of modifying a nucleic acid target binding sequence (e.g., DNA) comprising, contacting nucleic acid target binding sequence (e.g., a DNA target sequence in a DNA polynucleotide) with a sn-casPNs/Cas9 system of the present invention (e.g., an sn1-casPN/sn2-casPN/Cas9 protein complex (such as shown in FIG. 3B, sn1-casPN, FIG. 3B, 326, and sn2-casPN, FIG. 3B, 302; or FIG. 3A sn1-casPN, FIG. 3A, 301, sn2-casPN, FIG. 3a, 302, and sn3-casPN, FIG. 3A, 303), wherein the sn-casPNs/Cas9 protein form a complex that binds and cuts the nucleic acid target sequence (e.g., a DNA target sequence) resulting in a modification of the target nucleic acid (e.g., a DNA polynucleotide comprising the DNA target sequence). This method can be carried out in vitro or in vivo. The method can, for example, be used to modify DNA derived from a cell (e.g., a eukaryotic cell) isolated from an organism. Furthermore, in some embodiments the method comprises contacting a DNA target sequence in genomic DNA with a donor DNA template wherein the genomic DNA is modified in that it comprises that at least a portion of the donor DNA template integrated at the DNA target sequence.

Methods for bringing a donor polynucleotide into proximity to the site of a double-stranded break in a target nucleic acid are described in U.S. Published Patent Application No. 20140315985, published Oct. 23, 2014 (see, e.g., ¶0121, ¶¶0851-0860).

Example 1 describes production of exemplary sn-casPN components of the present invention. Example 2 describes production of double-stranded DNA target regions for use in Cas9 cleavage assays. Example 3 and Example 7 provide in vitro examples of a method of modifying DNA using a sn-casPNs/Cas9 system (sn1-casRNA/sn2-casRNA) of the present invention. Example 6 provides an in vitro example of a method of modifying DNA using a different sn-casPNs/Cas9 system (sn1-casRNA/sn2-casRNA/sn3-casRNA). Furthermore, the data presented in Example 4 demonstrate use of the sn-casPNs/Cas9 systems of the present invention for deep sequencing analysis for detection of target modifications in eukaryotic cells.

In some methods of the present invention, cells comprise polynucleotide sequences encoding a sn-casPNs and a Cas9 protein comprising active RuvC and HNH nuclease domains. Expression of these polynucleotide sequences is placed under the control of one or more inducible promoter. When the DNA binding sequence of an sn-casPN is complementary to a DNA target in, for example, a promoter of a gene, upon inducing expression of the sn-casPNs and Cas9 protein, expression from the gene is shut off (as a result of the cleavage of the promoter sequence by the sn-casPNs/Cas9 protein complex). The polynucleotides encoding the sn-casPNs and Cas9 protein can be integrated in the cellular genome, present on vectors, or combinations thereof.

In methods of modifying a target DNA using the sn-casPNs/Cas9 protein complexes of the present invention, repair of a double-stranded break by either NHEJ and/or HDR can lead to, for example, gene correction, gene replacement, gene tagging, gene disruption, gene mutation, transgene insertion, or nucleotide deletion. Methods of modifying a target DNA using the sn-casPNs/Cas9 protein complexes of the present invention in combination with a donor template DNA can be used to insert or replace polynucleotide sequences in a DNA target sequence, for example, to introduce a polynucleotide that encodes a protein or functional RNA (e.g., siRNA), to introduce a protein tag, to modify a regulatory sequence of a gene, or to introduce a regulatory sequence to a gene (e.g. a promoter, an enhancer, an internal ribosome entry sequence, a start codon, a stop codon, a localization signal, or polyadenylation signal), to modify a nucleic acid sequence (e.g., introduce a mutation), and the like.

In some embodiments of the sn-casPNs/Cas9 protein systems of the present invention, a mutated form of the Cas9 protein is used. Modified versions of the Cas9 protein can contain a single inactive catalytic domain (i.e., either inactive RuvC or inactive HNH). Such modified Cas9 proteins cleave only one strand of a target DNA thus creating a single-strand break. Modified Cas9 protein having a single inactive catalytic domain can bind DNA based on sn-casPN-conferred specificity; however, it will only cut one of the double-stranded DNA strands. As an example, in the Cas9 protein from *Streptococcus pyogenes* the RuvC domain can be inactivated by a D10A mutation and the HNH domain can be inactivated by an H840A mutation. When using a modified Cas9 protein having a single inactive catalytic domain in the sn-casPNs/Cas9 protein complexes of the present invention NHEJ is less likely to occur at the single-strand break site.

In other modified versions of the Cas9 protein both catalytic domains are inactive (i.e., inactive RuvC and inactive HNH; "dCas"). Such dCas9 proteins have no substantial nuclease activity; however, they can bind DNA based on sn-casPN-conferred specificity. As an example, in the Cas9 protein from *Streptococcus pyogenes* a D10A mutation and an H840A mutation result in a dCas 9 protein having no substantial nuclease activity.

The present invention also includes methods of modulating in vitro or in vivo transcription using sn-casPNs/Cas9 protein complexes described herein. In one embodiment, a sn-casPNs/Cas9 protein complex can repress gene expression by interfering with transcription when a sn-casPN directs DNA target binding of the sn-casPNs/Cas9 protein complex to the promoter region of a gene. Use of sn-casPNs/Cas9 protein complexes to reduce transcription also includes complexes wherein the dCas9 protein is fused to a known down regulator of a target gene (e.g., a repressor polypeptide). For example, expression of a gene is under the control of regulatory sequences to which a repressor polypeptide can bind. A sn-casPN can direct DNA target binding of a sn-casPNs/Cas9 protein-repressor protein complex to the DNA sequences encoding the regulatory sequences or adjacent the regulatory sequences such that binding of the sn-casPNs/Cas9 protein-repressor protein complex brings the repressor protein into operable contact with the regulatory sequences. This results in repression of expression of the target gene. Similarly, dCas9 is fused to an activator polypeptide to activate or increase expression of a gene under the control of regulatory sequences to which an activator polypeptide can bind.

In one aspect the present invention relates to a method of modulating the expression of a gene comprising transcriptional regulatory elements comprising, contacting a DNA target sequence in the gene with a sn-casPNs/Cas9 system of the present invention, wherein the sn-casPNs and the Cas9 protein form a complex that binds to the DNA target sequence resulting in modulation of the expression of the gene. In one embodiment, the Cas9 protein is a Cas9 that is nuclease-deficient. In other embodiments, the sn-casPNs/Cas9 complex further comprises a fusion protein.

Example 13 describes use of the split-nexus Cas9-associated polynucleotides (sn-casPNs) of the present invention for the repression or activation of endogenous genes in human cells. The nuclease deficient S. pyogenes Cas9 (dCas9) with mutation D10A and H840A is used. The sn1-casRNA-CD71 sequence comprises a 20 nucleotide spacer sequence that directs the sn-casRNAs/Cas9 protein complex to the upstream untranslated region of the of the transferrin receptor CD71. Activation of CD71 expression in dCas9-VP64 transfected samples is measured by the increase in detected fluorescence compared to the measured fluorescence of a non-transfected control population of HeLa cells as detected by FACS sorting. Repression of CD71 expression in dCas9-KRAB transfected samples is measured by the decrease in detected fluorescence compared to the measured fluorescence of a non-transfected control population of HeLa cells as detected by FACS sorting. This procedure provides data to verify that the sn-casPNs/Cas9 protein systems of the present invention can be used in the activation or repression of endogenous genes.

In some embodiments, a non-native sequence can confer new functions to a fusion protein. Examples of fusion proteins including a Cas9 protein (e.g., Cas9 protein) and other regulatory or functional domains include, but are not limited to a nuclease, a transposase, a methylase, a transcription factor repressor or activator domain (e.g., such as KRAB and VP16), co-repressor and co-activator domains, DNA methyl transferases, histone acetyltransferases, histone deacetylases, and DNA cleavage domains (e.g., a cleavage domain from the endonuclease FokI). Further examples include, but are not limited to the following: methyltransferase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, sumoylating activity, desumoylating activity, ribosylation activity, deribosylation activity, myristoylation activity, remodeling activity, protease activity, oxidoreductase activity, transferase activity, hydrolase activity, lyase activity, isomerase activity, synthase activity, synthetase activity, demyristoylation activity, and any combinations thereof.

In another aspect, the sn-casPNs/Cas9 systems of the present invention are used in methods for high-throughput functional genomics screening. Forward genetic screens are powerful tools for the discovery and functional annotation of genetic elements (see, e.g., Gilbert et al., (2013) "CRISPR-Mediated Modular RNA-Guided Regulation of Transcription in Eukaryotes," Cell 18; 154(2):442-51). The sn-casPNs/Cas9 systems can be used to generate genome-scale libraries of sn-casPNs for unbiased, phenotypic screening. Approaches for genome-scale screening include knockout approaches that inactivate genomic loci and approaches that modulate transcriptional activity. In knockout screening, loss-of-function mutations mediated by sn-casPNs/Cas9 systems are generated by double-strand break induction and NHEJ-mediated repair. Knockout screens are useful to identify essential gene functions, for example, gene functions related to drug and toxin sensitivities. One example of such functional genomics screening is presented in Example 12. In the example, a two-part sn-casRNA (sn1-casRNA and sn2-casRNA) system is used to create a lentiviral library of sn1-casRNAs. The library is used in a knockout method to identify candidate genes important in resistance to drug treatment. This procedure provides data to verify that the sn-casPNs/Cas9 systems of the present invention can be used in functional screening to interrogate gene-function on a genome-wide scale.

Another method of the present invention is the use of sn-casPNs/dCas systems to isolate or purify regions of genomic DNA (gDNA). In an embodiment of the method, a dCas9 protein is fused to an epitope (e.g., a FLAG® epitope, Sigma-Aldrich, St. Louis, Mo.) and a sn-casPN directs DNA target binding of a sn-casPNs/dCas9 protein-epitope complex to DNA sequences within the region of genomic DNA to be isolated or purified. An affinity agent is used to bind the epitope and the associated gDNA bound to the sn-casPNs/dCas9 protein-epitope complex.

In further aspect, the present invention includes kits comprising sn-casPNs or polynucleotides encoding sn-casPNs and instructions. Kits can comprise one or more of the following: sn-casPNs and cognate Cas9 protein; polynucleotides encoding sn-casPNs and cognate protein; recombinant cells comprising sn-casPNs; recombinant cells comprising sn-casPNs and cognate protein; and the like. Any kits of the present invention can further comprise other components such as solutions, buffers, substrates, cells, instructions, vectors (e.g., targeting vectors), and so on.

The invention also includes the use of T7E1 assays to evaluate and compare the percent cleavage in vivo of sn-casPNs/Cas9 systems relative to selected double-stranded DNA target sequences (Example 9). Also, the invention also includes methods for Identification and Screening of Trans-Activating CRISPR RNA (Example 8), which can be modified for use in the sn-casPNs/Cas9 systems and methods of the present invention. Furthermore, the invention includes methods of generating and testing split nexus modifications in tracrRNAs (Example 10), for example, based on crRNA/tracrRNAs know in the art or identified by methods described in Example 8.

The present invention also includes pharmaceutical compositions comprising sn-casPNs/Cas9 protein systems, or one or more polynucleotides encoding sn-casPNs and a Cas9 protein. Pharmaceutical composition, for example, the nanoparticle compositions comprising sn-casPNs/Cas9 systems described above, may further comprise pharmaceutically acceptable excipients.

A pharmaceutical composition can comprise a combination of any of the sn-casPNs/Cas9 systems described herein with other components, for example, excipients (e.g., carriers, stabilizers, diluents, suspending agents, thickening agents, and others as described herein). The compositions facilitate administration of the sn-casPNs/Cas9 systems to a subject. Pharmaceutical compositions can be administered in therapeutically effective amounts by various forms and routes including, for example, intravenous, subcutaneous, or inhalation.

Methods for the preparation of pharmaceutical compositions comprising the sn-casPNs/Cas9 systems can include formulating them with one or more inert, pharmaceutically acceptable excipient. For example, the pharmaceutical compositions can be liquid solutions or suspensions. Typical excipients useful in the practice of the present invention include, but are not limited to, the following: carrier or vehicle (e.g., water or buffered aqueous solutions); buffer systems (e.g., comprising acetate, phosphate, citrate, borate, tartrate, histidine, succinate, and mixtures thereof); antioxidants (e.g., sodium thiosulfate, ethylenediaminetetraacetic acid, citric acid, cysteins, thioglycerol, thioglycolic acid, thiosorbitol, butylated hydroxanisol, butylated hydroxyltoluene, and propyl gallate, and mixtures thereof); agents to maintain isotonicity (e.g., sodium chloride, sugars, polyols (sugar alcohols), boric acid, sodium tartrate, propylene glycol, and mixtures thereof); one or more sugar (e.g., trehalose, maltose, sucrose, lactose, mannose, dextrose, fructose, etc.) or sugar alcohol (e.g., sorbitol, maltitol, lactitol, mannitol, glycerol, etc.), alcohol (e.g., ethanol, t-butanol, etc.); and preservatives (alcohols, benzoic acid, salicylic acid, phenol and its derivatives (e.g., cresol, p-cresol, m-cresol and o-cresol), cetrimide, BHA (butylated hydroxytoluene), BHA (butylated hydroxyanisole); and mixtures thereof).

Advantages of the sn-casPNs/Cas9 systems of the present invention include, but are not limited to, the following. Use of a multipart sn-casPNs/Cas9 system allows improved control of activity for in vivo systems. Expression control of all parts of the system provides further layers of regulation over assembly of the specific components needed to constitute a functional sn-casPNs/Cas9 system, for example, relative to an sgRNA/Cas9 system.

The split nexus element, accessory, auxiliary, and adjunct polynucleotides of the sn-casPNs of the present invention provide additional sites (relative to crRNA/tracrRNA/Cas9 and sgRNA/Cas9 complexes) for adding and/or tethering functional moieties (e.g., polypeptides, small molecules, labels, and the like).

In some embodiments of the present invention, for example, a three polynucleotide engineered CRISPR-Cas9 system, the shorter length of the sn-casPNs (relative to the longer lengths of crRNA/tracrRNA and sgRNA) allows for higher quality and more rapid chemical synthesis of the sn-casPNs. Furthermore, the shorter length of the sn-casPNs facilitates packaging into virus-based vectors.

Furthermore, a three polynucleotide engineered CRISPR-Cas9 system of the present invention (e.g., as illustrated in FIG. 3A) can be used to provide partially preformed Cas9 complexes in an in vivo system to allow rapid activation. For example, sn1-casRNA, sn3-casRNA, and Cas9 protein are expressed in a cell. These components form a sn1RNA/sn3-casRNA/Cas9 protein complex, which is not active for binding or cleaving a target. When the sn2 component is expressed or introduced into the cell, the sn1-casRNA/sn2-casRNA/sn3-casRNA/Cas9 protein complex is rapidly activated, which enables temporal control over site-specific targeting.

Additional advantages of the present invention will be apparent to one of ordinary skill in the art in view of the teachings of the present specification.

While preferred embodiments of the present invention have been shown and described herein, it will be obvious to those skilled in the art that such embodiments are provided by way of example only. From the above description and the following Examples, one skilled in the art can ascertain essential characteristics of this invention, and without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are further illustrated in the following Examples. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric. It should be understood that these Examples, while indicating some embodiments of the invention, are given by way of illustration only.

The following examples are not intended to limit the scope of what the inventors regard as various aspects of the present invention.

Materials and Methods

Oligonucleotide sequences (e.g., the primer sequences shown in FIG. 13) were provided to commercial manufacturers for synthesis (Integrated DNA Technologies, Coralville, Iowa; or Eurofins, Luxembourg).

sn-casPNs are assembled by PCR using 3' overlapping primers containing the corresponding DNA sequences to the sn-casPNs. Furthermore, DNA sequences encoding the sn-casPNs can be cloned in a suitable vector for propagation and subsequent isolation of sn-casPN sequences (e.g., using restriction enzyme cleavage of the vector to yield the sn-casPN).

Example 1

Production of sn-casRNA Components

This example described production of a split-nexus Cas9-associated three polynucleotide system (e.g., similar to the system illustrated in FIG. 3A).

RNA components were produced by in vitro transcription (e.g., T7 Quick High Yield RNA Synthesis Kit, New England Biolabs, Ipswich, Mass.) from double-stranded DNA template incorporating a T7 promoter at the 5' end of the DNA sequences.

The double-stranded DNA template for the specific sn2-casRNA component, used in the examples (referred to herein as sn2-casRNA$^{EX}$), was assembled by PCR using 3' overlapping primers containing the corresponding DNA sequences to the sn2-casRNA$^{EX}$ component. The oligonucleotides used in the assembly are presented in Table 8.

TABLE 8

Overlapping Primers for Generation of sn2-casRNA Component Templates

| Type of sn-casPN Component | Target for DNA-binding Sequence | Oligonucleotides* |
|---|---|---|
| sn2-casRNA$^{EX}$ | n/a | A, B, C |

*DNA primer oligonucleotide sequences are shown in FIG. 13

The DNA primers were present at a concentration of 2 nM each. Two outer DNA primers corresponding to the T7 promoter (forward primer: Oligonucleotide A, Table 8), and the 3'end of the RNA sequence (reverse primers: Oligonucleotides C, Table 8) were used at 640 nM to drive the amplification reaction. PCR reactions were performed using Q5 Hot Start High-Fidelity 2X Master Mix (New England Biolabs, Ipswich, Mass.) as following the manufacturer's instructions. PCR assembly reactions were carried out using the following thermal cycling conditions: 98° C. for 2 minutes, 35 cycles of 15 seconds at 98° C., 15 seconds at 62° C., 15 seconds at 72° C., and a final extension at 72° C. for 2 min. DNA quality was evaluated by agarose gel electrophoresis (1.5%, SYBR® Safe, Life Technologies, Grand Island, N.Y.).

The double-stranded DNA templates for the specific sn1-casRNA and sn3-casRNA components, used in the examples, were assembled by complexing two complementary oligonucleotide sequences (referred to as sn1-casRNA$^{EX}$ and sn3-casRNA$^{EX}$) The oligonucleotides used in the assembly are presented in Table 9.

TABLE 9

Overlapping Primers for Generation of sn-casRNAs Component Templates

| Type of sn-casPN Component | Target for DNA-binding Sequence | Oligonucleotide[2] |
|---|---|---|
| sn1-casRNA$^{EX}$ | n/a | D, E |
| sn3-casRNA$^{EX}$-AAVS-1 | AAVS-1[1] | F, G |

[1]AAVS-1, Adeno-Associated Virus Integration Site 1 - Human Genome;
[2]DNA primer sequences are shown in FIG. 13.

The DNA primers were present at a concentration of 10 µM each, 10 uL of each primer were mixed together and incubated for 2 minutes at 95° C., removed from thermocycler and allowed to equilibrate to room temperature.

Between 0.25-0.5 mg of the DNA template for each sn-casRNA component was transcribed using T7 High Yield RNA Synthesis Kit (New England Biolabs, Ipswich, Mass.) for approximately 16 hours at 37° C. Transcription reactions were treated with DNAse I (New England Biolabs, Ipswich, Mass.) and purified using GeneJet RNA Cleanup and Concentration Kit (Life Technologies, Grand Island, N.Y.). RNA yield was quantified using the Nanodrop™ 2000 System (Thermo Scientific, Wilmington Del.). The quality of the transcribed RNA was checked by agarose gel electrophoresis (2%, SYBR® Safe, Life Technologies, Grand Island, N.Y.). The sn-casRNA sequences are as shown in Table 10.

TABLE 10 sn-casRNA Sequences

| | | |
|---|---|---|
| sn2-casRNA$^{EX}$ | 5'-GUCCGUUAUC AACUUGAAAA AGUGGCACCG AGUCGGUGCU U-3' | SEQ ID NO: 68 |
| sn1-casRNA$^{EX}$ | 5'-GCAGGACAGC AUAGCAAGUU GAGAUAAGGC UA-3' | SEQ ID NO: 69 |
| sn3-casRNA$^{EX}$-AAVS1 | 5'-GGGGCCACUA GGGACAGGAU GUCUCAGAGC UAUGCUGU-3' | SEQ ID NO: 70 |

This method for production of sn1-casRNA$^{EX}$, sn2-casRNA$^{EX}$, and sn3-casRNA$^{EX}$ can be applied to the production of other sn-casRNAs as described herein.

Example 2

Production of Double-Stranded DNA Target Regions for Use in Cas9 Cleavage Assays Target double stranded DNA for use in an in vitro Cas9 cleavage assays were produced using PCR amplification of the target region from genomic DNA.

Double-stranded DNA target regions (e.g., AAVS-1) for biochemical assays were amplified by PCR from phenol-chloroform prepared human cell line K562 (ATCC, Manassas, Va.) genomic DNA (gDNA). PCR reactions were carried out with Q5 Hot Start High-Fidelity 2X Master Mix (New England Biolabs, Ipswich, Mass.) following the manufacturer's instructions. 20 ng/µL gDNA in a final volume of 25 µl were used to amplify the selected target region under the following conditions: 98° C. for 2 minutes, 35 cycles of 20 s at 98° C., 20 s at 60° C., 20 s at 72° C., and a final extension at 72° C. for 2 min. PCR products were purified using Spin Smart™ PCR purification tubes (Denville Scientific, South Plainfield N.J.) and quantified using Nanodrop™ 2000 UV-Vis spectrophotometer (Thermo Scientific, Wilmington Del.).

The forward and reverse primers used for amplification of selected targeted sequences from gDNA were as follows: AAVS-1, oligonucleotides H and I (FIG. 13). The amplified double-stranded DNA target for AAVS-1 was 495 bp.

Other suitable double-stranded DNA target regions are obtained using essentially the same method. For non-human target regions, genomic DNA from the selected organism (e.g., plant, bacteria, yeast, algae) is used instead of DNA derived from human cells. Furthermore, polynucleotide sources other than genomic DNA can be used (e.g., vectors and gel isolated DNA fragments).

Example 3

Cas9 Cleavage Assays

This example illustrates the use of a split-nexus Cas9-associated three polynucleotide system of the present invention in in vitro Cas9 cleavage assays to evaluate and compare the percent cleavage of selected sn-casRNAs/Cas9 protein complexes relative to selected double-stranded DNA target sequences.

The cleavage of double-stranded DNA target sequences was determined for sn-casRNA$^{EX}$ components of Example 2 against a double-stranded DNA target (AAVS-1; Example 2).

All three sn-casPN$^{EX}$ components in equimolar amounts were mixed in an annealing buffer (1.25 mM HEPES, 0.625 mM MgCl$_2$, 9.375 mM KCl at pH7.5), incubated for 2 minutes at 95° C., removed from thermocycler and allowed to equilibrate to room temperature. Additional combinations of two of the three sn-casRNAs$^{EX}$ were tested as described below with reference to the data presented in FIG. 8. When only two components of the polynucleotide system were used water was added instead of the third sn-casRNA$^{EX}$ component.

The sn-casRNAs$^{EX}$ were added to a Cas9 reaction mix. The Cas9 reaction mix comprised Cas9 protein diluted to a final concentration of 200 µM in reaction buffer (20 mM HEPES, 100 mM KCl, 5 mM MgCl$_2$, 1 mM DTT, and 5% glycerol at pH 7.4). In the reaction mix the final concentration of each sn-casRNA$^{EX}$ was 500 nM in each reaction mix. Each reaction mix was incubated at 37° C. for 10 minutes. The cleavage reaction was initiated by the addition of target DNA to a final concentration of 15 nM. Samples were mixed and centrifuged briefly before being incubated for 15 minutes at 37° C. Cleavage reactions were terminated by the addition of Proteinase K (Denville Scientific, South Plainfield, N.J.) at a final concentration of 0.2 mg/mL and 0.44 mg/ml RNase A Solution (SigmaAldrich, St. Louis, Mo.).

Samples were incubated for 25 minutes at 37° C. and 25 minutes at 55° C. 12 µL of the total reaction were evaluated for cleavage activity by agarose gel electrophoresis (2%, SYBR® Gold, Life Technologies, Grand Island, N.Y.). For the AAVS-1 double-stranded DNA target, the appearance of DNA bands at approximately 316 bp and approximately 179 bp indicated that cleavage of the target DNA had occurred. Cleavage percentages were calculated using area under the curve values as calculated by FIJI (ImageJ; an open source Java image processing program) for each cleavage fragment and the target DNA, and dividing the sum of the cleavage fragments by the sum of both the cleavage fragments and the target DNA.

FIG. 8 presents the results of the Cas9 cleavage assay using the AAVS-1 target double-stranded DNA. In the figure, replicates of three are shown for each combination of sn-casRNAs$^{EX}$. At the top of each panel is a graphical representation of the sn-casRNAs$^{EX}$ used in the assay. FIG. 8, Panel A shows the biochemical activity of sn1-casRNA$^{EX}$, sn2-casRNA$^{EX}$, sn3-casRNA$^{EX}$-AAVS1. FIG. 8, Panel B shows the biochemical activity of sn1-casRNA$^{EX}$ and sn2-casRNA$^{EX}$. FIG. 8, Panel C shows the biochemical activity of sn2-casRNA$^{EX}$ and sn3-casRNA$^{EX}$-AAVS1, FIG. 8, Panel D shows the biochemical activity of sn1-casRNA$^{EX}$ and sn3-casRNA$^{EX}$-AAVS1. The last lane of FIG. 8, Panel D contains molecular weight standards. Cleavage percentages are shown at the bottom of each lane. As can be seen from the data in the FIG. 8, sn1-casRNA$^{EX}$, sn2-casRNA$^{EX}$, and sn3-casRNA$^{EX}$-AAVS1 had an average percent cleavage of 46.9% (standard deviation of 0.3%). For all reactions where only two sn-casRNA$^{EX}$ components were present (e.g. FIG. 8, Panel B, FIG. 8, Panel C, FIG. 8, Panel D) no cleavage activity was observed (for lanes indicated as LOD, any cleavage activity was below the limit of detection.).

The data presented in FIG. 8 demonstrate that the split-nexus Cas9-associated polynucleotide systems of the present invention facilitate Cas mediated site-specific cleavage of target double-stranded DNA. The data also show that all three sn-casRNA components of the split-nexus Cas9-associated three polynucleotide system are needed to support Cas mediated site-specific cleavage activity.

Following the guidance of the present specification and examples, the Cas9 cleavage assay described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 4

Deep Sequencing Analysis for Detection of Target Modifications in Eukaryotic Cells This example illustrates the use of deep sequencing analysis to evaluate and compare the percent cleavage in vivo of selected sn-casRNA/Cas9 protein complexes relative to selected double-stranded DNA target sequences.

A. Formation of RNP Complexes of sn1-casRNA$^{EX}$, sn2-casRNA$^{EX}$, sn3-casRNA$^{EX}$-AAVS1 and Cas9 protein.

S. pyogenes Cas9 was C-terminally tagged with two nuclear localization sequences (NLS) and recombinantly expressed in E. coli. Ribonucleoprotein (RNP) complexes were set up at two concentrations, 50 pmol Cas9:150 pmols sn-casRNAs$^{EX}$ and 200 pmols Cas9:600 pmols sn-casRNAs$^{EX}$, in triplicate. All three sn-casRNAs$^{EX}$ (sn1-casRNA$^{EX}$, sn2-casRNA$^{EX}$, sn3-casRNA$^{EX}$-AAVS1) components in equimolar amounts were mixed in an annealing buffer (1.25 mM HEPES, 0.625 mM MgCl$_2$, 9.375 mM KCl at pH7.5) to the desired concentration (150 pmols or 600 pmols) in a final volume of 54, incubated for 2 minutes at 95° C., removed from the thermocycler and allowed to equilibrate to room temperature: Cas9 protein was diluted to an appropriate concentration in binding buffer (20 mM HEPES, 100 mM KCl, 5 mM MgCl$_2$, 1 mM DTT, and 5% glycerol at pH 7.4) to a final volume of 54 and mixed with the 5 µL of heat-denatured sn-casRNAs$^{EX}$ followed by incubation at 37° C. for 30 minutes.

B. Cell Transfections Using Sn-casRNAs$^{EX}$/Cas9 Protein RNPs

RNP complexes were transfected into K562 cells (ATCC, Manassas Va.), using the Nucleofector® 96-well Shuttle System (Lonza, Allendale, N.J.) and the following protocol. RNP complexes were dispensed in a 104 final volume into individual wells of a 96-well plate. K562 cells suspended in media were transferred from a culture flask to a 50 mL conical tube. Cells were pelleted by centrifugation for 3 minutes at 200×g, the culture medium aspirated, and the cells washed once with calcium and magnesium-free PBS. K562 cells were then pelleted by centrifugation for 3 minutes at 200×g, the PBS aspirated and cell pellet was resuspended in 10 mL of calcium and magnesium-free PBS.

The cells were counted using the Countess® II Automated Cell Counter (Life Technologies, Grand Island, N.Y.). 2.2× 10$^7$ cells were transferred to a 50 ml tube and pelleted. The PBS was aspirated and the cells were resuspended in Nucleofector™ SF (Lonza, Allendale, N.J.) solution to a density of 1×10$^7$ cells/mL. 20 µL of the cell suspension are then added to individual wells containing 10 µL of RNP complexes and the entire volume was transferred to the wells of a 96-well Nucleocuvette™ Plate (Lonza, Allendale, N.J.). The plate was loaded onto the Nucleofector™ 96-well Shuttle™ (Lonza, Allendale, N.J.) and cells were nucleofected using the 96-FF-120 Nucleofector™ program (Lonza, Allendale, N.J.). Post-nucleofection, 70 µL Iscove's Modified Dulbecco's Media (IMDM; Life Technologies, Grand Island, N.Y.), supplemented with 10% FBS (Fisher Scientific, Pittsburgh, Pa.), penicillin and streptomycin (Life Technologies, Grand Island, N.Y.), was added to each well and 504 of the cell suspension were transferred to a 96-well cell culture plate containing 1504 pre-warmed IMDM complete culture medium. The plate was then transferred to a tissue culture incubator and maintained at 37° C. in 5% CO$_2$ for 48 hours.

C. Target Double-Stranded DNA Generation for Deep Sequencing gDNA was isolated from K562 cells 48 hours after RNP transfection using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. The isolated gDNA was then diluted with 50 µL water and samples were stored at −80° C.

Using the isolated gDNA, a first PCR was performed using Q5 Hot Start High-Fidelity 2X Master Mix (New England Biolabs, Ipswich, Mass.) at 1× concentration, primers at 0.5 µM each (FIG. 13, oligonucleotides H & I), 3.75 µL of gDNA in a final volume of 10 L and amplified 98° C. for 1 minute, 35 cycles of 10 s at 98° C., 20 s at 60° C., 30 s at 72° C., and a final extension at 72° C. for 2 min. PCR reaction was diluted 1:100 in water.

A "barcoding" PCR was set up using unique primers for each sample to facilitate multiplex sequencing. The primer pairs are shown in Table 11.

TABLE 11

| | Barcoding Primers | |
|---|---|---|
| ID | Sample | Primers* |
| BARCODING PRIMER set-1 | 50 pmol Cas9:150 pmol sn-casRNA rep-1 | L, M |

TABLE 11-continued

Barcoding Primers

| ID | Sample | Primers* |
|---|---|---|
| BARCODING PRIMER set-2 | 50 pmol Cas9:150 pmol sn-casRNA rep-2 | L, N |
| BARCODING PRIMER set-3 | 50 pmol Cas9:150 pmol sn-casRNA rep-3 | L, O |
| BARCODING PRIMER set-4 | 200 pmol Cas9:600 pmol sn-casRNA rep-1 | L, P |
| BARCODING PRIMER set-5 | 200 pmol Cas9:600 pmol sn-casRNA rep-2 | L, Q |
| BARCODING PRIMER set-6 | 200 pmol Cas9:600 pmol sn-casRNA rep-3 | L, R |

*Primer sequences are shown in FIG. 13

The barcoding PCR was performed using Q5 Hot Start High-Fidelity 2X Master Mix (New England Biolabs, Ipswich, Mass.) at 1× concentration, primers at 0.5 µM each (Table 11), 1 µL of 1:100 diluted first PCR, in a final volume of 10 µL and amplified 98° C. for 1 minutes, 12 cycles of 10 s at 98° C., 20 s at 60° C., 30 s at 72° C., and a final extension at 72° C. for 2 min.

D. SPRIselect Clean-Up

PCR reactions were pooled into a single microfuge tube for SPRIselect (Beckman Coulter, Pasadena, Calif.) bead-based clean up of amplicons for sequencing.

To the pooled amplicons, 0.9× volumes of SPRIselect beads were added, and mixed and incubated at room temperature (RT) for 10 minutes. The microfuge tube was placed on magnetic tube stand (Beckman Coulter, Pasadena, Calif.) until solution had cleared. Supernatant was removed and discarded, and the residual beads were washed with 1 volume of 85% ethanol, and incubated at RT for 30 s. After incubation ethanol was aspirated and beads were air dried at RT for 10 min. The microfuge tube was then removed from the magnetic stand and 0.25× volumes of Qiagen EB buffer (Qiagen, Venlo, Limburg) was added to the beads, mixed vigorously, and incubated for 2 min. at room temperature. The microfuge tube was returned to the magnet, incubated until solution had cleared, and supernatant containing the purified amplicons was dispensed into a clean microfuge tube. The purified amplicon library was quantified using the Nanodrop™ 2000 System (Thermo Scientific, Wilmington Del.) and library-quality analyzed using the Fragment Analyzer™ System (Advanced Analytical Technologies, Inc., Ames, Iowa) and the DNF-910 Double-stranded DNA Reagent Kit (Advanced Analytical Technologies, Inc. Ames, Iowa).

E. Deep Sequencing Set-Up

The amplicon library was normalized to a 4 nmolar concentration as calculated from Nanodrop values and size of the amplicons. The library was analyzed on MiSeq Sequencer (Illumina, San Diego) with MiSeq Reagent Kit v2 (Illumina, San Diego) for 300 cycles with two 151-cycle paired-end run plus two eight-cycle index reads.

F. Deep Sequencing Data Analysis

The identity of products in the sequencing data was determined based on the index barcode sequences adapted onto the amplicons in the barcoding round of PCR. A computational script was used to process the MiSeq data by executing the following tasks:

Reads were aligned to the human genome (build GRCh38/38) using Bowtie (bowtie-bio.sourceforge.net/index.shtml) software.

Aligned reads were compared to the expected wild-type AAVS-1 locus sequence, reads not aligning to any part of the AAVS-1 locus were discarded (Table 12, "other").

Reads matching wild-type AAVS-1 sequence (Table 12, "WT") were tallied.

Reads with indels (insertion or the deletion of bases) were categorized by indel type and tallied (Table 12, "indel").

Total indel reads were divided by the sum of wild-type reads and indel reads gave percent-mutated reads.

The results of this analysis are presented in Table 12.

TABLE 12

Deep Sequencing Data

| Sample Type[1] | Total[2] | Aligned[3] | WT[4] | indel[5] | Other[6] |
|---|---|---|---|---|---|
| 50 pmol Cas9:150 pmol sn-casRNAs$^{EX}$ rep 1 | 33807 | 33680 | 18119 | 15561 | 3 |
| 50 pmol Cas9:150 pmol sn-casRNAs$^{EX}$ rep2 | 33070 | 32991 | 18225 | 14766 | 2 |
| 50 pmol Cas9:150 pmol sn-casRNAs$^{EX}$ rep3 | 33062 | 32986 | 18580 | 14406 | 5 |
| 200 pmol Cas9:650 pmol sn-casRNAs$^{EX}$ rep1 | 34089 | 33993 | 9321 | 24672 | 1 |
| 200 pmol Cas9:650 pmol sn-casRNAs$^{EX}$ rep2 | 28691 | 28600 | 7100 | 26893 | 2 |
| 200 pmol Cas9:650 pmol sn-casRNAs$^{EX}$ rep3 | 28573 | 28509 | 12184 | 16325 | 1 |

[1]Sample type;
[2]Total MiSeq reads;
[3]Total reads aligns to target locus (AAVS-1);
[4]Total wt reads (i.e. unmodified sequence);
[5]Mutated reads (cas9 cleavaged);
[6]Reads not aligning to AAVS-1 locus.

As can be seen from the measured indels across replicates in Table 12, sn-casPNs/Cas9 systems are capable of in vivo modification of a target locus. Additionally the increased indel frequency as a result of increased transfected sn-casPNs/Cas9 concentration is indicative of dose dependent sn-casPNs/Cas9 system mediated cleavage. The data presented in Table 12 demonstrate that the split-nexus Cas9-associated polynucleotide systems of the present invention facilitate in vivo Cas9-mediated site-specific cleavage of a genomic locus.

Following the guidance of the present specification and examples, the analysis described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 5

Csy4* Facilitated Sn-casRNA/Cas9 Cleavage

This example illustrates the use of sn-casRNAs of the present invention and an effector protein, the nuclease deficient *P. aeruginosa* Csy4 protein possessing the H29A mutation (Csy4*), to increase association of two sn-casR-NAs augmented with a Csy4 RNA binding sequence.

A. Generation of sn-casRNA Components

The double-stranded DNA templates for the specific sn-casRNA$^{EXCsy}$ components comprising a Csy4 binding sequence were assembled by PCR using 3' overlapping primers containing the corresponding DNA sequences to the sn-casRNA$^{EXCsy}$ components. The oligonucleotide used in the assembly are presented in Table 13.

TABLE 13

Overlapping Primers for Generation of sn-casRNA$^{EXCsy}$s with Csy4 RNA Binding Sequence

| Type of Cas RNA Component | DNA Target Binding Sequence | Oligonucleotides* |
|---|---|---|
| first polynucleotide w/Csy4 binding sequence 3' of split nexus (sn1-casRNA$^{EXCsy}$-Csy) | AAVS-1 | A, Y, S, T |
| first polynucleotide w/Csy4 binding sequence 3' of split nexus (sn1-casRNA$^{EXCsy}$-Csy) | CD34 | A, Z, S, T |
| first polynucleotide w/Csy4 binding sequence 3' of split nexus (sn1-casRNA$^{EXCsy}$-Csy) | CD151 | A, AA, S, T |
| first polynucleotide w/Csy4 binding sequence 3' of split nexus (sn1-casRNA$^{EXCsy}$-Csy) | JAK-1 | A, AB, S, T |
| Second polynucleotide w/Csy4 binding sequence 3' of split nexus (sn2-casRNA$^{EXCsy}$-Csy) | n/a | A, U, AC |
| AAVS first polynucleotide w/linker + Csy4 binding sequence 3' of split nexus (sn1-casRNA$^{EXCsy}$-lnkCsy) | AAVS-1 | A, Y, V, W |
| CD34 first polynucleotide w/linker + Csy4 binding sequence 3' of split nexus (sn1-casRNA$^{EXCsy}$-lnkCsy) | CD34 | A, Z, V, W |
| CD151 first polynucleotide w/linker + Csy4 binding sequence 3' of split nexus (sn1-casRNA$^{EXCsy}$-lnkCsy) | CD151 | A, AA, V, W |
| JAK-1 first polynucleotide w/linker + Csy4 binding sequence 3' of split nexus (sn1-casRNA$^{EXCsy}$-lnkCsy) | JAK-1 | A, AB, V, W |
| Second polynucleotide w/linker + Csy4 binding sequence 3' of split nexus (sn2-casRNA$^{EXCsy}$-lnkCsy) | n/a | A, X, AC |

*DNA primer sequences are shown in FIG. 13

The DNA primers were present at a concentration of 2 nM each. Two outer DNA primers corresponding to the T7 promoter (forward primer: Oligonucleotide A, Table 13, and the 3'end of the RNA sequence (reverse primers: Oligonucleotides T, AC, or W, Table 13) were used at 640 nM to drive the amplification reaction. PCR and transcription was preformed as described in Example 1 described in this specification. Transcribed sn-casRNA$^{EXCsy}$ sequences are shown in Table 14.

TABLE 14 sn-casRNA$^{EXCsy}$ Sequences

| Type of Cas RNA Component | RNA sequence | SEQ ID NO |
|---|---|---|
| sn1-casRNA$^{EXCsy}$-Csy-AAVS1 | 5'-GGGGCCACUA GGGACAGGAU GUCUCAGAGC UAUGCUGUCC UGGAAACAGG ACAGCAUAGC AAGUUGAGAU AAGGCUACUG CC-3' | SEQ ID NO: 71 |
| sn1-casRNA$^{EXCsy}$-Csy-CD34 | 5'-GUUUGUGUUU CCAUAAACUG GUCUCAGAGC UAUGCUGUCC UGGAAACAGG ACAGCAUAGC AAGUUGAGAU AAGGCUACUG CC-3' | SEQ ID NO: 72 |
| sn1-casRNA$^{EXCsy}$-Csy-CD151 | 5'-GCCCGCCACC ACCAGGAUGU GUCUCAGAGC UAUGCUGUCC UGGAAACAGG ACAGCAUAGC AAGUUGAGAU AAGGCUACUG CC-3' | SEQ ID NO: 73 |
| sn1-casRNA$^{EXCsy}$-Csy-JAK-1 | 5'-GGCAGCCAGC AUGAUGAGAC GUCUCAGAGC UAUGCUGUCC UGGAAACAGG ACAGCAUAGC AAGUUGAGAU AAGGCUACUG CC-3' | SEQ ID NO: 74 |
| sn2-casRNA$^{EXCsy}$-Csy | 5'-GGCAGGUCCG UUAUCAACUU GAAAAGUGG CACCGAGUCG GUGCUU-3' | SEQ ID NO: 75 |
| sn1-casRNA$^{EXCsy}$-lnkCsy-AAVS1 | 5'-GGGGCCACUA GGGACAGGAU GUCUCAGAGC UAUGCUGUCC UGGAAACAGG ACAGCAUAGC AAGUUGAGAU AAGGCUAGUU CACUGCC-3' | SEQ ID NO: 76 |
| sn1-casRNA$^{EXCsy}$-lnkCsy-CD34 | 5'-GUUUGUGUUU CCAUAAACUG GUCUCAGAGC UAUGCUGUCC UGGAAACAGG ACAGCAUAGC AAGUUGAGAU AAGGCUAGUU CACUGCC-3' | SEQ ID NO: 77 |
| sn1-casRNA$^{EXCsy}$-lnkCsy-CD151 | 5'-GCCCGCCACC ACCAGGAUGU GUCUCAGAGC UAUGCUGUCC UGGAAACAGG ACAGCAUAGC AAGUUGAGAU AAGGCUAGUU CACUGCC-3' | SEQ ID NO: 78 |
| sn1-casRNA$^{EXCsy}$-lnkCsy-JAK-1 | 5'-GGCAGCCAGC AUGAUGAGAC GUCUCAGAGC UAUGCUGUCC UGGAAACAGG ACAGCAUAGC AAGUUGAGAU AAGGCUAGUU CACUGCC-3' | SEQ ID NO: 79 |
| sn2-casRNA$^{EXCsy}$-lnkCsy | 5'-GGGCAGUGAA CUAGCCUUAU CUCAACUUGC UAUGCUGUCC UGUUUCCAGG ACAGCAUAGC UCUGAGAC-3' | SEQ ID NO: 80 |

B. Generation of Double-Stranded DNA Targets for Biochemical Assay

Target double-stranded DNA for use in the in vitro Cas9 cleavage assays were produced using PCR amplification as described in Example 2 herein. The forward and reverse primers used for amplification from gDNA were as follows: AAVS-1 oligonucleotides were J and K (FIG. 13), the amplified double-stranded DNA target for AAVS-1 was 288 bp; CD34 (Hematopoietic Progenitor Cell Antigen) oligonucleotides were AD and AE (FIG. 13), the amplified double-stranded DNA target for CD34 was 258 bp; CD151 (Platelet-Endothelial Cell Tetraspanin Antigen) oligonucleotides were AF and AG (FIG. 13), the amplified CD151 double-stranded DNA target was 272 bp; and, JAK-1 (Janus Kinase 1) oligonucleotides were AH and AI, the amplified JAK-1 double-stranded DNA target was 298 bp.

C. Csy4* Supported Cas9 Cleavage Biochemical Assay sn-casRNAs$^{EXCsy}$ were prepared for use in the biochemical assay as described in Example 3 herein. With the modification that prior to the addition of Cas9, 250 nM of Csy* protein was added to the reaction and sn-casRNAs$^{EXCsy}$ and Csy4* were incubated at 37° C. for 5 min. After the incubation, Cas9 was added and biochemical reactions were carried out as described in Example 3. A non-Csy4* control was included.

For the AAVS-1 double-stranded DNA target, the appearance of DNA bands at approximately 174 bp and approximately 114 bp indicated that cleavage of the target DNA had occurred. For the CD34 double-stranded DNA target, the appearance of DNA bands at approximately 105 bp and approximately 153 bp indicated that cleavage of the target DNA had occurred. For the CD151 double-stranded DNA target, the appearance of DNA bands at approximately 109 bp and approximately 163 bp indicated that cleavage of the target DNA had occurred. For the JAK-1 double-stranded DNA target, the appearance of DNA bands at approximately 204 bp and approximately 94 bp indicated that cleavage of the target DNA had occurred.

FIG. 9 presents the results of the Cas9 cleavage assay using the Csy4* protein and the sn-casRNAs$^{EXCsy}$. The cleavage assays used two different split-nexus Cas9-associated two polynucleotide systems that were variants of the system present in FIG. 3B. In the first system the sn1-casRNAs$^{EXCsy}$ further comprised a first auxiliary polynucleotide comprising a Csy4 binding element nucleotide sequence I (sn1-casRNA$^{EXCsy}$-Csy) and the sn2-casRNA comprised a second auxiliary polynucleotide comprising a Csy4 binding element nucleotide sequence II (sn2-casRNA$^{EXCsy}$-Csy), wherein the first auxiliary polynucleotide and the second auxiliary polynucleotide associate to form a Csy4 RNA binding element (sn1-casRNA/sn2-casRNA/Csy4RNA). In the second system the sn1-casRNA further comprised a first auxiliary polynucleotide comprising a linker element nucleotide sequence I and a Csy4 binding element nucleotide sequence I (sn1-casRNA$^{EXCsy}$-lnkCsy) and the sn2-casRNA comprised a second auxiliary polynucleotide comprising a linker element nucleotide sequence II and a Csy4 binding element nucleotide sequence II (sn2-casRNA$^{EXCsy}$-lnkCsy), wherein the first auxiliary polynucleotide and the second auxiliary polynucleotide associate to form a linker element and a Csy4 RNA binding element (see, e.g., the general representations in FIG. 6A and FIG. 6B). Each of the two systems was used to target cleavage to four different targets, where the sn-casRNAs$^{EXCsy}$ each comprised a spacer complementary to one of the four targets: AAVS-1, CD-34, CD-151, and JAK-1 (see Table 13 above). In the figure, the cleavage activity is shown at the bottom of each lane (except for lanes 1 and 10, which are molecular weight standards). For lanes indicated as LOD, any cleavage activity was below the limit of detection. The systems used in each of the Cas9 cleavage assay reactions were as shown in Table 5/FIG. 9 (see Brief Description of the Figures, FIG. 9).

As can be seen from the data in the figure, the addition of Csy4* enhanced the cleavage activity of the sn-casRNAs$^{EXCsy}$ system for multiple double-stranded DNA target sequences: for AAVS-1 compare lanes 2/3 (no Csy4* protein) to lanes 4/5, respectively; for CD-34 compare lanes 6/7 (no Csy4* protein) to lanes 8/9; for CD-151 compare lanes 11/12 (no Csy4* protein) to 13/14; and, for JAK-1 compare lanes 15/16 (no Csy4* protein) to lanes 17/18.

The data presented in FIG. 9 demonstrate that an effector protein (here Csy4*) enhanced cleavage of target double-stranded DNA by split-nexus Cas9-associated polynucleotide systems of the present invention comprising auxiliary polynucleotides having an effector binding element (here the Csy RNA binding sequence).

Following the guidance in the present specification and examples, increasing the association of two sn-casRNAs comprising a Csy4 RNA binding sequence with a nuclease deficient *P. aeruginosa* Csy4 protein as described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element. Furthermore, in view of the guidance in the present specification and examples one of ordinary skill in the art can use other effector protein/effector binding sequence combinations as exemplified herein by the Csy* protein/Csy RNA binding sequence.

Example 6

Sn1-CasRNA/Sn2-casRNA/Cas9 Cleavage Activity

This example illustrates the use of a split-nexus Cas9-associated two polynucleotide system of the present invention in in vitro Cas9 cleavage assays to evaluate and compare the percent cleavage of selected sn1-casRNA/sn2-casRNA/Cas9 protein complexes relative to selected double-stranded DNA target sequences.

The double-stranded DNA templates for the sn-casRNA$^{EX2}$ components used in this example were assembled by PCR using 3' overlapping primers containing the corresponding DNA sequences to the sn-casRNA$^{EX2}$ components. A graphical representation of the sn-casRNA$^{EX2}$ components is presented in FIG. 10. The oligonucleotide used in the assembly are presented in Table 15.

TABLE 15

Overlaping Primers for Generation of sn1-casRNA and sn2-casRNA

| Type of sn-casRNA$^{EX2}$ Component | Oligonucleotides* |
| --- | --- |
| AAVS-1 sn1-casRNA | Y, AJ |
| CD151 sn1-casRNA | AA, AJ |
| JAK-1 sn1-casRNA | AB, AJ |
| sn2-casRNA | A, C, B |

*DNA primer sequences are shown in FIG. 13

Generation of double-stranded DNA template for RNA transcription was performed as described in Example 1 herein. Transcribed sn-casRNAs$^{EX2}$ sequences are shown in Table 16.

TABLE 16 sn-casRNA Sequences

| Type of Cas RNA Component | RNA sequence | SEQ ID NO |
| --- | --- | --- |
| sn1-casRNAs$^{EX2}$-AAVS1 | 5'-GGGGCCACUA GGGACAGGAU GUCUCAGAGC UAUGCUGUCC UGGAAACAGG ACAGCAUAGC AAGUUGAGAU AAGGCUA-3' | SEQ ID NO: 81 |
| sn1-casRNAs$^{EX2}$-CD151 | 5'-GCCCGCCACC ACCAGGAUGU GUCUCAGAGC UAUGCUGUCC UGGAAACAGG ACAGCAUAGC AAGUUGAGAU AAGGCUA-3' | SEQ ID NO: 82 |
| sn1-casRNAs$^{EX2}$-JAK-1 | 5'-GGCAGCCAGC AUGAUGAGAC GUCUCAGAGC UAUGCUGUCC UGGAAACAGG ACAGCAUAGC AAGUUGAGAU AAGGCUA-3' | SEQ ID NO: 83 |
| sn2-casRNAs$^{EX2}$ | 5'-GUCCGUUAUC AACUUGAAAA AGUGGCACCG AGUCGGUGCU U-3' | SEQ ID NO: 84 |

Target double-stranded DNA for use in the in vitro Cas9 cleavage assays were produced using PCR amplification as described in Example 2 herein. The forward and reverse primers used for amplification from gDNA were as follows:

AAVS-1 oligonucleotides were J and K (FIG. 13), the amplified double-stranded DNA target for AAVS-1 was 288 bp; CD151 oligonucleotides were AF and AG (FIG. 13), the amplified CD151 double-stranded DNA target was 272 bp; and, JAK-1 oligonucleotides were AH and AI, the amplified JAK-1 double-stranded DNA target was 298 bp. In vitro cleavage was performed as described in Example 3 herein.

FIG. 10 presents the result of the Cas9 cleavage assay using the sn1-casRNAs$^{EX2}$ and sn2-casRNA$^{EX2}$ described above. Cleavage percentages are shown at the bottom of each lane except for lane 1, which is a molecular weight standard. FIG. 10, lane 2, presents cleavage results for a sn1-casRNA$^{EX2}$-AAVS1 and sn2-casRNA$^{EX2}$ system, which demonstrated a cleavage activity of 97.6%. FIG. 10, lane 3, presents cleavage results for a sn1-casRNA$^{EX2}$-CD151 and sn2-casRNA$^{EX2}$ system, which demonstrated a cleavage activity of 48.8%. FIG. 10, lane 4, presents the results for a sn1-casRNA$^{EX2}$-JAK1 and sn2-casRNA$^{EX2}$ system, which demonstrated a cleavage activity of 60.0%.

The data presented in FIG. 10 demonstrated that the sn1-casRNA and sn2-casRNA constructs as described herein facilitate the in vitro Cas mediated site-specific cleavage of a double-stranded DNA target. These data support that the split-nexus Cas9-associated polynucleotide systems of the present invention facilitate in vivo Cas9-mediated site-specific cleavage of genomic loci.

Following the guidance of the present specification and examples, the Cas9 cleavage assay described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 7 sn1-CasRNA$^{Ex3Csy}$/sn2-casRNA$^{EX3Csy}$/Cas9 Cleavage Activity

This example illustrates the use of two different split-nexus Cas9-associated two polynucleotide systems of the present invention to evaluate and compare their percent cleavage activities relative to selected double-stranded DNA target sequences.

The two different split-nexus Cas9-associated two polynucleotide systems were as follows: one was the system illustrated in FIG. 7A (sn1-casRNA$^{EX3Csy}$-Csy-AAVS1/sn2-casRNA$^{EX3Csy}$-Csy); and the second was a variant of the system present in FIG. 7A. In the second system the sn1-casRNA$^{EX3Csy}$-lnkCsy-AAVS1 comprised, 5' to 3', a split nexus stem element nucleotide sequence I, a first auxiliary polynucleotide (having a linker element nucleotide sequence I and a hairpin forming polynucleotide), and the sn2-casRNA$^{EX3Csy}$-lnkCsy-AAVS1 comprised, 5' to 3', a second auxiliary polynucleotide (having a hairpin forming polynucleotide and a linker element nucleotide sequence II) and a split nexus stem element nucleotide sequence II. Each of the two systems was used to target cleavage of an AAVS-1 target, where the sn1-casRNA$^{EX3Csy}$-AAVS1 and sn1-casRNA$^{EX3Csy}$-lnkCsy-AAVS1 each comprised a spacer complementary to the AAVS-1.

The double-stranded DNA templates for sn-casRNA$^{EX3-Cys}$ components used in this example were assembled by PCR using 3' overlapping primers containing the corresponding DNA sequences to the sn-casRNA$^{EX3-Cys}$ components. The oligonucleotides used in the assemblies are presented in Table 17.

TABLE 17

Overlaping Primers for Generation of sn-casRNA$^{EX3-Cys}$ Components

| Type of sn-casRNA$^{EX3-Cys}$ Component | Oligonucleotides* |
|---|---|
| sn1-casRNA$^{EX3Csy}$-Csy-AAVS1 | A, AK, AL, AM |
| sn2-casRNA$^{EX3Csy}$-Csy | A, AN, AO, AC |
| sn1-casRNA$^{EX3Csy}$-lnkCsy-AAVS1 | A, AK, AP, AQ |
| sn2-casRNA$^{EX3Csy}$-lnkCsy | A, AR, AS, AC |

*DNA primer sequences are shown in FIG. 13

Generation of double-stranded DNA template for RNA transcription was performed as described in Example 1. Transcribed sn-casRNA$^{EX3-Cys}$ sequences are shown in Table 18.

TABLE 18 sn-casRNA Sequences

| Type of Cas9 RNA Component | RNA sequence | SEQ ID NO |
|---|---|---|
| sn1-casRNA$^{EX3Csy}$-Csy-AAVS1 | 5'-GGGGCCACUA GGGACAGGAU GUCUCAGAGC UAUGCAGUCC UGGAAACAGG ACUGCAUAGC AAGUUGAGAU AAGGCUACUG CCGUAUAGGC AG-3' | SEQ ID NO: 85 |
| sn2-casRNA$^{EX3Csy}$-Csy | 5'-CUGCCGUAUA GGCAGGUCCG UUAUCAACUU GAAAAAGUGG CACCGAGUCG GUGCUU-3' | SEQ ID NO: 86 |
| sn1-casRNA$^{EX3Csy}$-lnkCsy-AAVS1 | 5'-GGGGCCACUA GGGACAGGAU GUCUCAGAGC UAUGCAGUCC UGGAAACAGG ACUGCAUAGC AAGUUGAGAU AAGGCUAGAC ACUGCCGUAU AGGCAG-3' | SEQ ID NO: 87 |
| sn2-casRNA$^{EX3Csy}$-lnkCsy | 5'-CUGCCGUAUA GGCAGAGACA GUCCGUUAUC AACUUGAAAA AGUGGCACCG AGUCGGUGCUU-3' | SEQ ID NO: 88 |

Target double-stranded DNA for use in the in vitro Cas9 cleavage assays was produced using PCR amplification as described in Example 2. The forward and reverse primers used for amplification from gDNA were as follows: AAVS-1, oligonucleotides H and I (FIG. 13). The amplified double-stranded DNA target for AAVS-1 was 495 bp. In vitro cleavage was performed as described in Example 3.

FIG. 11 presents the results of the Cas9 cleavage assay using the sn-casRNAs described above. In the figure, the cleavage activity is shown at the bottom of each lane (except for lanes 1 and 10, which are molecular weight standards). For lanes indicated as LOD, any cleavage activity was below the limit of detection. The systems used in each of the Cas9 cleavage assay reactions were as shown in Table 6 (see Brief Description of the Figures, FIG. 11).

As can be seen from the data presented in FIG. 11, both sn1-casRNA$^{EX3Csy}$-Csy-AAVS1 and sn2-casRNA$^{EX3Csy}$-Csy (FIG. 11, lanes 2 and 3) or sn1-casRNA$^{EX3Csy}$-lnkCsy-AAVS1 and sn2-casRNA$^{EX3Csy}$-lnkCsy are necessary for detectable cleavage activity (FIG. 11, lanes 6 and 7). Furthermore, enhanced cleavage was detectable when a linker element nucleotide sequence was introduced between the split nexus element (FIG. 11, lane 8 compared to lane 4). Additionally, when Csy4* protein is introduced enhanced cleavage is observed with sn1-casRNA$^{EX3Csy}$-lnkCsy-AAVS1 and sn2-casRNA$^{EX3Csy}$-lnkCsy (FIG. 11 lane 9 compared to lane 8), but not in the absence of the linker sequences (sn1-casRNA$^{EX3\,Csy}$-Csy-AAVS1 and sn2-casRNA$^{EX3\,Csy}$-Csy; FIG. 11 lane 5 compared to lane 4).

The data presented in FIG. 11 demonstrate that the sn1-casRNA and sn2-casRNA constructs as described herein facilitate the in vitro Cas9 mediated site-specific cleavage of a double-stranded DNA target. These data support that the split-nexus Cas9-associated polynucleotide systems of the present invention facilitate in vivo Cas9-mediated site-specific cleavage of genomic loci.

Following the guidance of the present specification and examples, the Cas9 cleavage assay described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 8

Identification and Screening of Trans-Activating CRISPR RNA

This example illustrates the method through which trans-activating CRISPR RNAs (tracrRNAs) of species having CRISPR-Cas9 Type II system may be identified. The method presented here is adapted from Chylinski, et. al. ("The tracrRNA and Cas9 families of type II CRISPR-Cas immunity systems," RNA Biol. 2013 May; 10(5):726-37.). Not all of the following steps are required for screening nor must the order of the steps be as presented.

A. Identify a Species Containing a CRISPR-Cas9 Type-II System

Using the Basic Local Alignment Search Tool (BLAST, blast.ncbi.nlm.nih.gov/Blast.cgi), a search of various species' genomes is conducted to identify Cas9 or Cas9-like proteins. CRISPR-Cas9 system exhibit a high diversity in sequence across species, however Cas9 orthologs exhibit conserved domain architecture of central HNH endonuclease domain and a split RuvC/RNase H domain. Primary BLAST results are filtered for identified domains; incomplete or truncated sequences are discarded and Cas9 orthologs identified.

When a Cas9 ortholog is identified in a species, sequences adjacent to the Cas9 ortholog coding sequence are probed for other Cas proteins and an associated repeat-spacer array to identify all sequences belonging to the CRISPR-Cas9 locus. This may be done by alignment to other CRISPR-Cas9 Type-II loci already known in the public domain, with the knowledge that closely related species exhibit similar CRISPR-Cas9 locus architecture (i.e., Cas protein composition, size, orientation, location of array, location of tracrRNA, etc.). The tracrRNA element is typically contained within the CRISPR-Cas9 Type-II locus and is readily identified by its sequence complementarity to the repeat elements in the repeat-spacer array (tracr anti-repeat sequence).

Once the sequence of the CRISPR-Cas9 locus for the Cas9 ortholog is identified for the species, in silico predictive screening is used to extract the anti-repeat sequence to identify the associated tracrRNA. Putative anti-repeats are screened, for example, as follows.

If the repeat sequence is from a known species, it is identified in and retrieved from the CRISPRdb database (crispr.u-psud.fr/crispr/). If the repeat sequence is not known to be associated with a species, repeat sequences are predicted using CRISPRfinder software (crispr.u-psud.fr/Server/) using the CRISPR-Cas9 Type-II locus for the species as described above.

The identified repeat sequence for the species is used to probe the CRISPR-Cas9 locus for the anti-repeat sequence (e.g., using the BLASTp algorithm or the like). The search is typically restricted to intronic regions of the CRISPR-Cas9 locus.

An identified anti-repeat region is validated for complementarity to the identified repeat sequence.

A putative anti-repeat region is probed both 5' and 3' of the putative anti-repeat for a Rho-independent transcriptional terminator (TransTerm HP, transterm.cbcb.umd.edu/).

Thus, the identified sequence comprising the anti-repeat element and the Rho-independent transcriptional terminator is determined to be the putative tracrRNA of the given species.

B. Preparation of RNA-Seq Library

The putative tracrRNA that was identified in silico is further validated using RNA sequencing (RNAseq).

Cells from species from which the putative tracrRNA was identified are procured from a commercial repository (e.g., ATCC, Manassas Va.; DSMZ, Braunschweig, Germany).

Cells are grown to mid-log phase and total RNA prepped using Trizol reagent (Sigma-Aldrich, St. Louis, Mo.) and treated with DNaseI (Fermentas, Vilnius, Lithuania).

10 ug of the total RNA is treated with Ribo-Zero rRNA Removal Kit (Illumina, San Diego, Cas) and the remaining RNA purified using RNA Clean and Concentrators (Zymo Research, Irvine, Calif.).

A library is then prepared using TruSeq Small RNA Library Preparation Kit (Illumina, San Diego, Calif.) following the manufacturer's instructions, which results in the presence of adapter sequences associated with the cDNA.

The resulting cDNA library is sequenced using MiSeq Sequencer (Illumina, San Diego, Calif.).

C. Processing of Sequencing Data

Sequencing reads of the cDNA library are processed using the following method.

Adapter sequences are removed using cutadapt 1.1 (pypi.python.org/pypi/cutadapt/1.1) and 15nt are trimmed from the 3'end of the read to improve read quality.

Reads are aligned back to respective species' genome (from which the putative tracrRNA was identified) with a mismatch allowance of 2 nucleotides.

Read coverage is calculated using BedTools (bedtools.readthedocs.org/en/latest/).

Integrative Genomics Viewer (TGV, www.broadinstitute.org/igv/) is used to map the starting (5') and ending (3') position of reads. Total reads retrieved for the putative tracrRNA are calculated from the SAM file of alignments.

The RNA-seq data is used to validate that a putative tracrRNA element is actively transcribed in vivo. Confirmed hits from the composite of the in silico and RNA-seq screens are validated for functional ability of the identified tracrRNA sequence and its cognate crRNA to support Cas9 mediated cleavage of a double-stranded DNA target using methods outline herein (see Examples 1, 2, and 3).

Following the guidance of the present specification and the examples herein, the identification of novel tracrRNA sequences can be practiced by one of ordinary skill in the art.

Example 9

T7E1 Assay for Detection of Target Modifications in Eukaryotic Cells

This example illustrates the use of T7E1 assays to evaluate and compare the percent cleavage in vivo of sn-casPNs/Cas9 systems relative to selected double-stranded DNA target sequences.

A. Cell Transfections Using Cas Polynucleotide Components sn-casPNs are transfected into HEK293 cells constitutively expressing SpyCas9-GFP fusion (HEK293-Cas9-GFP), using the Nucleofector® 96-well Shuttle System (Lonza, Allendale, N.J.) and the following protocol. Equal molar amounts of Cas polynucleotide components are prepared in an annealing buffer (1.25 mM HEPES, 0.625 mM $MgCl_2$, 9.375 mM KCl at pH 7.5), are incubated for 2 minutes at 95° C., are removed from thermocycler, allowed to equilibrate to room temperature, and dispensed in a 104 final volume in a 96-well plate. Culture medium is aspirated from HEK293-Cas9-GFP cells, and the cells are washed once with calcium and magnesium-free PBS then are trypsinized by the addition of TrypLE (Life Technologies, Grand Island, N.Y.) followed by incubation at 37° C. for 3-5 minutes. Trypsinized cells are gently pipetted up and down to form a single cell suspension and added to DMEM complete culture medium composed of DMEM culture medium (Life Technologies, Grand Island, N.Y.) containing 10% FBS (Fisher Scientific, Pittsburgh, Pa.) and supplemented with penicillin and streptomycin (Life Technologies, Grand Island, N.Y.).

The cells are then pelleted by centrifugation for 3 minutes at 200×g, the culture medium aspirated and cells are resuspended in PBS. The cells are counted using the Countess® II Automated Cell Counter (Life Technologies, Grand Island, N.Y.). $2.2 \times 10^7$ cells are transferred to a 50 ml tube and pelleted. The PBS is aspirated and the cells are resuspended in Nucleofector™ SF (Lonza, Allendale, N.J.) solution to a density of $1 \times 10^7$ cells/mL. 20 µL of the cell suspension are then added to individual wells containing 10 uL of Cas polynucleotide components and the entire volume is transferred to the wells of a 96-well Nucleocuvette™ Plate (Lonza, Allendale, N.J.). The plate is loaded onto the Nucleofector™ 96-well Shuttle™ (Lonza, Allendale, N.J.) and cells are nucleofected using the 96-CM-130 Nucleofector™ program (Lonza, Allendale, N.J.). Post-nucleofection, 70 µL DMEM complete culture medium is added to each well and 50 µL of the cell suspension are transferred to a collagen coated 96-well cell culture plate containing 150 µL pre-warmed DMEM complete culture medium. The plate is then transferred to a tissue culture incubator and maintained at 37° C. in 5% $CO_2$ for 48 hours.

B. Target Double-Stranded DNA Generation for T7E1 Assay gDNA is isolated from HEK-293-SpyCas9 cells 48 hours after Cas polynucleotide component transfection using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. gDNA is then diluted with 150 µL water and samples are stored at −80° C.

DNA for T7E1 is generated by PCR amplification of a target double-stranded DNA sequence (e.g., AAVS-1) from isolated gDNA. PCR reactions are set up using 8 mL gDNA as template with KAPA HiFi Hot Start polymerase and containing 0.5 U of polymerase, 1× reaction buffer, 0.4 mM dNTPs and 300 nM forward and reverse primers directed to the target double-stranded DNA (e.g., AAVS-1, oligonucleotides K and L (FIG. 4)) in a total volume of 25 mL. Target DNA is amplified using the following conditions: 95° C. for 5 minutes, 4 cycles of 20 s at 98° C., 20 s at 70° C., minus 2° C./cycle, 30 s at 72° C., followed by 30 cycles of 15 s at 98° C., 20 s at 62° C., 20 s at 72° C., and a final extension at 72° C. for 1 minute.

C. T7E1 Assay

PCR amplified target double-stranded DNA for T7E1 assays is denatured at 95° C. for 10 minutes and then allowed to re-anneal by cooling to 25° C. at −0.5° C./s in a thermal cycler. The re-annealed DNA is incubated with 0.5 mL T7 Endonuclease 1 in 1×NEBuffer 2 buffer (New England Biolabs, Ipswich, Mass.) in a total volume of 15 mL for 25 minutes at 37° C. T7E1 reactions are analyzed using the Fragment Analyzer™ System (Advanced Analytical Technologies, Inc., Ames, Iowa) and the DNF-910 Double-stranded DNA Reagent Kit (Advanced Analytical Technologies, Inc., Ames, Iowa). The Fragment Analyzer™ System provides the concentration of each cleavage fragment and of the target double-stranded DNA that remains after cleavage.

Cleavage percentages of the target double-stranded DNA are calculated from the concentration of each cleavage fragment and the target double-stranded DNA, which remains after cleavage has take place, using the following formula:

$$\%\text{cleavage} = \left(1 - \sqrt{\left(1 - \frac{(frag1 + frag2)}{(frag1 + frag2 + \text{parent})}\right)}\right) \quad \text{EQUATION 1}$$

In Equation 1, "frag1" and "frag2" concentrations correspond to the concentration of Cas9 cleavage fragments of the double-stranded DNA target and "parent" corresponds to the target double-stranded DNA that remains after cleavage has take place.

The T7E1 assay for detection of target modifications in eukaryotic cells provides data to demonstrate that the sn-casPNs/Cas9 systems as described herein facilitate Cas9-mediated site-specific in vivo cleavage of target double-stranded DNA. sgRNA and/or tracrRNA/crRNA polynucleotides having the same DNA target binding sequence as the sn-casPNs can also be included in the assay to compare the Cas9-mediated site-specific cleavage percentages between the constructs.

Following the guidance of the present specification and examples, the T7E1 assay described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 10

Split Nexus Testing of Identified tracrRNAs

This example describes the generation and testing of split nexus modifications in tracrRNAs, for example, based on crRNA/tracrRNAs know in the art or identified by methods described in Example 8.

A tracrRNA sequence and its cognate crRNA sequences are joined, with the crRNA sequence placed 5' of the tracrRNA sequence maintaining 5' to 3' polarity, with a linker sequence to generate a sgRNA. A suitable linker sequence is 5'-GAAA-3'.

The sgRNA is analyzed for secondary structural motifs using publically available RNA folding software. One such software is RNAstructure (ma.urmcsochester.edu/RNA-structureWeb/Servers/Predict1/Predict1.html).

The secondary structures of the sgRNA are analyzed for secondary structure similar to known sgRNA that support Cas9 directed cleavage activity, traditionally comprising, in a 5' to 3' direction, a first stem element, a hairpin element that comprises a second stem element (herein referred to as a nexus element), and zero, one, or two, hairpin elements 3' of the nexus element.

The sgRNA is then split at the nexus element into at least two polynucleotides: a first polynucleotide (e.g., a sn1-casPN, FIG. 3B) comprising in a 5' to 3' direction a selected DNA targeting binding sequence, the first stem element, and first portion of the nexus (i.e., a split nexus stem element nucleotide sequence I); and a second polynucleotide (e.g., a sn2-casPN, FIG. 3B) comprising in a 5' to 3' direction a second portion of the nexus (i.e., a split nexus stem element nucleotide sequence II), and the zero, one, or two 3' hairpins.

A library of first polynucleotide sequences and second polynucleotide sequences is constructed, using method describe in Example 1 of the present specification, wherein a split in the nexus of the sgRNA is made at each nucleotide position of the sequence comprising the native nexus.

The library is then tested for the ability of each split nexus first polynucleotide sequence and its cognate split nexus second polynucleotide sequence to support Cas9 mediated cleavage of a selected double-stranded DNA target following the methods described in Example 2 through 4 of the present specification.

Putative split nexus arrangements of known tracrRNA sequences from various species are shown in FIG. 12. In the figure, the first column is an identifying number for the bacterial species (see Table 7, Brief Description of the Figures), the second column is the sequence of the sn1-casRNA/sn2-casRNA. A split nexus of a *S. pyogenes* sn1-casRNA/sn2-casRNA of the present invention is shown for reference (FIG. 12, row 1).

It is known that a single species can have more than one CRISPR locus of the same Type, or more than one CRISPR locus of different Types (e.g., Type-I and Type-II). Typically repeat elements of one CRISPR locus are only usable to identify the anti-repeat element (and therefore the tracrRNA sequences) contained within the same CRISPR locus.

Following the guidance of the present specification and examples, the testing described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 11

Screening of Multiple Sn-casRNAs Comprising DNA Target-Binding Sequences

This example illustrates the use of sn-casRNAs of the present invention to modify targets present in human genomic DNA and measure the level of cleavage activity at those sites. Target sites are first selected from genomic DNA and then sn-casRNAs are designed to target those selected sequences. Measurements are then carried out to determine the level of target cleavage that has taken place. Not all of the following steps are required for every screening nor must the order of the steps be as presented, and the screening can be coupled to other experiments, or form part of a larger experiment.

A. Select a DNA Target Region from Genomic DNA

Identify all PAM sequences (e.g. 'NGG') within the selected genomic region.

Identify and select one or more 20 nucleotide sequence long sequences (target DNA sequence) that is 5' adjacent to PAM sequences.

Selection criteria can include but are not limited to: homology to other regions in the genome; percent G-C content; melting temperature; presences of homopolymer within the spacer; and other criteria known to one skilled in the art.

Append an appropriate sn-casRNA sequence (e.g., an sn1-casRNA, as illustrated in FIG. 3B, with the spacer sequence removed) to the 3' end of the identified target DNA sequence (sn-casRNA-DNAtbs (DNA target binding sequence)). A sn-casRNA-DNAtbs construct is typically synthesized by a commercial manufacturer or produced as described in Example 1 by in vitro transcription.

A sn-casRNA-DNAtbs as described herein is used with cognate sn-casRNA(s) to complete a sn-casRNA system (e.g., a sn1-casRNA-DNAtbs/sn2-casRNA two polynucleotide split nexus system) for use with a cognate Cas protein.

B. Determination of Cleavage Percentages and Specificity

In vitro cleavage percentages and specificity associated with a sn-casRNA-DNAtbs/sn-casRNA(s) system are compared, for example, using the Cas9 cleavage assays of Example 3, as follows:

(a) If only a single target DNA sequence is identified or selected, the cleavage percentage and specificity for the DNA target region is determined. if so desired, cleavage percentage and/or specificity are altered in further experiments using methods of the present invention including but not limited to modifying the RNA, introducing effector proteins/effector protein-binding sequences or ligand/ligand binding moieties.

(b) The percentage cleavage data and site-specificity data obtained from the cleavage assays is compared between different DNAs comprising the target binding sequence to identify the target DNA sequences having the best cleavage percentage and highest specificity. Cleavage percentage data and specificity data provide criteria on which to base choices for a variety of applications. For example, in some situations the activity of the sn-casRNA may be the most important factor. In other situations, the specificity of the cleavage site may be relatively more important than the cleavage percentage. If so desired, cleavage percentage and/or specificity are altered in further experiments using methods of the present invention including but not limited to modifying the RNA, introducing effector proteins/effector protein-binding sequences or ligand/ligand binding moieties.

Optionally, or instead of, the in vitro analysis, in vivo cleavage percentages and specificity associated with a sn-casRNA-DNAtbs/sn-casRNA(s) system are compared, for example, using Deep Sequencing Analysis for Detection of Target Modifications in Eukaryotic Cells of Example 5, as follows:

(a) If only a target DNA sequence is identified the cleavage percentage and specificity for the DNA target region is determined. If so desired, cleavage percentage and/or specificity are altered in further experiments using methods of the present invention including but not limited to modifying the RNA, introducing effector proteins/effector protein-binding sequences or ligand/ligand binding moieties.

(b) The percentage cleavage data and site specificity data obtained from the cleavage assays is compared between different target DNAs to identify the sn-casRNA sequences that resulting the highest percentage cleavage or target DNA and the highest specificity for the target DNA. Cleavage percentage data and specificity data provide criteria on which to base choices for a variety of applications. For example, in some situations the activity of the sn-casRNA may be the most important factor. In other situations, the specificity of the cleavage site may be relatively more important than the cleavage percentage. If so desired, cleavage percentage and/or specificity are altered in further experiments using methods of the present invention including but not limited to modifying the RNA, introducing effector proteins/effector protein-binding sequences or ligand/ligand binding moieties.

Following the guidance of the present specification and examples, the screening described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 12

Functional Genomics Screening

This example describes use of the split-nexus Cas9-associated polynucleotides (sn-casPNs) of the present invention for identification of the functional role of genes utilizing a functional screening method and sequence data.

A two-part sn-casRNA (sn1-casRNA and sn2-casRNA) system (see, e.g., FIG. 3B) is used in a modification of the methods described in Shalem et al. ("Genome-scale CRISPR-Cas9 knockout screening in human cells," Science. 2014 Jan. 3; 343(6166):84-7.) and Zhou et al. ("High-throughput screening of a CRISPR/Cas9 library for functional genomics in human cells", Nature 509, 2014 May 22, 487-491) which used a single guide RNA having a continuous sequence. The screen described herein is designed around the vulnerability of the A375 melanoma cell line to the drug vemerafenib; when treated with vemurafenib, cells growth is arrested. A375 cells are transduced with a library of sn1-casRNA, and these cells are subsequently treated with vemerafenib. sn1-casRNA knockout of genes important for A375 sensitivity to vemerafenib will be enriched in the surviving cell population and can be sequenced and identified.

Examples of suitable vectors, media, culture conditions, etc. are described. Modifications of these components and conditions will be understood by one of ordinary skill in the art in view of the teachings of the present specification.

A. Lentiviral Library and Cas9 Constructs

A viral library of sn1-casRNAs is generated by synthesizing oligonucleotides containing the designed spacer sequences appended to universal tag sequences for cloning into a transfer plasmid for lentivirus production (e.g. pD2107-CMV-DNA 2.0, Menlo Park, Calif.). Oligonucleotide libraries are synthesized on programmable microarrays and cleaved from the microarray by the array manufacturer (e.g. Agilent technologies, Santa Clara, Calif.). Full-length oligonucleotides are amplified by PCR using Q5 polymerase (NEB) and primers designed to amplify DNA containing the universal tag sequences. Cloning into the transfer vector is carried out using standard techniques known to one skilled in the art. One example includes digesting the vector with a Type II restriction enzyme (e.g. Bsb1) to reveal single-stranded overhangs, treating with alkaline phosphatase (Fermentas) and purifying the cut vector from uncut by gel purification. Oligonucleotide libraries are digested with a restriction enzyme to reveal compatible ends, and ligated into the vector using DNA ligase (Fermentas).

The transfer vector can include a human codon optimized *S. pyogenes* Cas9 gene N-terminally and C-terminally tagged with a SV40 nuclear localization signal under the control of the elongation factor-1a short promoter (EFS) promoter. This NLS-Cas9-NLS sequence is joined to a 2A self-cleaving peptide and a selection maker suitable for mammalian cells (i.e. puromycin).

Alternatively, Cas9 can be delivered to the cells in a separate viral vector, or stable cell-lines can be generated that express Cas9 constitutively. Viral vector-expressed sn1-casRNA libraries can then be used to transduce the Cas9-expressing cell lines.

B. Lentivirus Production and Purification

HEK293T cells are seeded at approximately 40% confluence 24 hours before transfection in DMEM (Life Technologies, Grand Island, N.Y.) supplemented with 10% fetal bovine serum (FBS). Cells are transferred into reduced serum OptiMEM (Life Technologies, Grand Island, N.Y.) and transfected using Lipofectamine 2000 and Plus reagent according to manufacturer's instructions. For transfection, the lentiviral transfer vector is combined with plasmids for lentiviral packaging such as the Lenti-X™ HTX Packaging System (Takara Clontech, Mountain View, Calif.) according to manufacturer's instructions.

After 60 hours, media is removed and centrifuged at 3000 rpm to remove cell debris. Supernatant is filtered through a 0.45 um low protein binding membrane (e.g. Millipore Steriflip HV/PVDF). The pooled library can be concentrated by ultracentrifugation and then resuspended in DMEM supplemented with 10% FBS and 1% BSA (Sigma-Aldrich, St. Louis, Mo.).

C. Cell Culture

A375 (ATCC CRL-1619) cells are obtained from ATCC (Manassas, Va.) and cultured in R8758 medium (Sigma-Aldrich, St. Louis, Mo.), supplemented with 10% FBS (Life Technologies, Grand Island, N.Y.), 1% Penicillin-Streptomycin (Sigma-Aldrich, St. Louis, Mo.), 20 mM HEPES (Sigma-Aldrich, St. Louis, Mo.).

D. Lentiviral Transduction

Multiplicity of Infection (MOI) for the viral vector library is determined using standard methods based upon transduction of cells with predetermined virus volumes. Approximately $3 \times 10^6$ A375 cells are plated per well on a 12 well plate in appropriate media supplemented with 8 mg/ml polybrene (Sigma-Aldrich, St. Louis, Mo.). Cells are mixed with the predetermined virus volume to identify a multiplicity of infection (MOI) of between 0.3-0.5. Plated cells are centrifuged at 2,000 rpm for 2 hours at 37° C., after which the media is aspirated and fresh media for each cell type is added, without polybrene. Cells are incubated for 24 hours at 37° C., 5% CO2. A non-transduced control is included.

After 24 hours, cells are detached and counted, approximately $2.5 \times 10^6$ cells are re-plated into both a 'selection well' and a 'non-selection well'. Selection wells are put under selection specific to the lentiviral library construct (i.e. puromycin, Sigma-Aldrich, St. Louis, Mo.). Non-selection wells are not treated with puromycin. Cells are incubated until no surviving cells placed under selection in the non-transduced control remained. Cells are counted, and the number of cells in 'selection wells' divided by the number of cells in the corresponding 'non-selection wells' multiplied by 100 yields the MOI, with a MOI close to 0.4 being the ideal value.

E. Drug Resistance Screen

Cells are plated into wells of $2 \times 10^6$ cells per well for each condition to be tested. The cells in each well are transduced with 10 ul of the library to reach a transduction efficiency of 30% (minimum of 3-400 cells per clone in the library). Puromycin is added to the wells 24 hours post transduction and the cells are maintained for 7 days. Cells are split into drug conditions in duplicate with a minimum of $2\times10^7$ cells per replicate well. One well is supplemented with 2 uM drug compound (e.g. PLX4032, Thermo Fisher Scientific, South San Francisco, Calif.) and the other with DMSO (Thermo Fisher Scientific, South San Francisco, Calif.). Cells are incubated at 37° C., 5% CO2 for 14 days, and passaged every 2-3 days in to fresh media, supplemented with either PLX4032 or DMSO as appropriate. After 14 days, genomic DNA (gDNA) is prepared from cells using the QuickExtract DNA extraction solution (Illumina, San Diego, Calif.) as per manufacturer instructions.

F. gDNA Sequencing

PCR primers are designed to amplify lentiviral sn1-casPN target sequences from genomic DNA. Using isolated gDNA, a first PCR is performed using Herculase II Fusion DNA Polymerase (Agilent, Santa Clara, Calif.) with primers comprising an adapter sequences and a sequence specific to the lentiviral sn1-casPN cassette. A second PCR is performed using the amplicons of the first round as template at $\frac{1}{20}^{th}$ the volume of the second PCR reaction volume. The second PCR uses a second set of primers comprising: sequence complementary to the universal adapter sequence of the first primer pair, a barcode index sequence unique to each sample, and a flow cell adapter sequence. PCR reactions are pooled to ensure a 300× sequencing coverage of each transduced sample. Pooled PCR reactions are analyzed on a 2% TBE gel, bands of expected amplicon sizes are gel purified using the QIAEX II Gel Extraction Kit (Qiagen, Venlo, Limburg). The concentrations of purified amplicons are evaluated using the Double-strand DNA BR Assay Kit and Qubit System (Life Technologies, Grand Island, N.Y.) and library quality determined using the Agilent DNA100Chip and Agilent Bioanalyzer 2100 System (Agilent, Santa Clara, Calif.). Pooled library are sequenced on a MiSeq 2500 (Illumina, San Diego, Calif.).

G. Processing and Analysis of Sequencing Data

Raw sequencing reads are processed to only contain the sn1-casPN cassette sequence. sn1-casPN reads are aligned to the target sequences contained within the lentiviral screening library and the number of reads for each unique target sequence are counted. Counted reads per target sequence are normalized by dividing the reads per target by total aligned reads for all targets in the sample and multiplying by $10^6$ and adding 1.

Normalized target reads identified in drug-treated samples are compared to normalize targets reads identified in the DMSO control treated samples. Targets with high read count present in the drug treated sample that are absent or reduced in the DMSO control treated samples can be further evaluated as candidate genes, important in resistance to drug treatment.

Other functional genomic screens using a sn1-casRNA library and the method of screening outlined here can be used to identify candidate genes important in to those screens.

This procedure provides data to verify that the Cas9 sn1-casRNA/sn2-casRNA system of the present invention can be used in functional screening to interrogate gene-function on a genome-wide scale.

Following the guidance of the present specification and examples, the screening described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 13

Repression/Activation

This example describes use of the split-nexus Cas9-associated polynucleotides (sn-casPNs) of the present invention for the repression or activation of endogenous genes in human cells.

A two-part sn-casRNA (sn1-casRNA and sn2-casRNA) system (see, e.g., FIG. 3) is used in a modification of the methods described in Gilbert et al. (CRISPR-Mediated Modular RNA-Guided Regulation of Transcription in Eukaryotes," Cell. 2013 Jul. 18; 154(2):442-51. doi: 10.1016/j.cell.2013.06.044.) which used a single guide RNA having a continuous sequence.

Examples of suitable vectors, media, culture conditions, etc. are described. Modifications of these components and conditions will be understood by one of ordinary skill in the art in view of the teachings of the present specification.

A. dCas9 Activator and Repressor Constructs

The nuclease deficient *S. pyogenes* Cas9 (dCas9) with mutation D10A and H840A is codon optimized for expression in mammalian cells and C-terminally tagged with a SV40 nuclear localization signal and either the Kruppel associated box (KRAB) repression domain (dCas9-KRAB) or four copies of the transcriptional activator VP16 (dCas9-VP64). Both the dCas9-KRAB and dCas9-VP64 are inserted into a vector adjacent to a suitable mammalian promoter, such as the cytomegalovirus (CMV) promoter. One such vector, pJ607-03 (DNA2.0, Menlo Park, Calif.), is commercially available.

B. Sn-casPN Construction

The sn1-casRNA-CD71 sequence comprises a 20 nucleotide spacer sequence targeted toward the upstream untranslated region (UTR) of the of the transferrin receptor CD71. The sn1-casRNA-CD71 sequence is assembled into a suitable vector also comprising the independent sn2-casRNA sequence. Each sequence is under independent control by a human U6 promoter that directs transcription by RNA polymerase III. Once suitable vector backbone for the expression of sn1-casRNA and sn2-casRNA sequences is the pRSFDuet-1 vector (Novagen, Merck, Darmstadt, Germany).

C. Cell Culture

HeLa (ATCC CCL-2) cells are obtained from ATCC (Manassas, Va.) and cultured in Dulbecco's modified Eagle medium (DMEM, Life Technologies, Grand Island, N.Y.), supplemented with 10% FBS (Life Technologies, Grand Island, N.Y.), 1% Penicillin-Streptomycin (Sigma-Aldrich, St. Louis, Mo.), 2 mM glutamine (Life Technologies, Grand Island, N.Y.) and cultured at 37° C., 5% CO2.

D. Transfection and FACS Sorting

HeLa cells are transiently transfected with equal weight Cas9-containing plasmid and sn1-casRNA-CD71 vector using TransIT-LT1 (Minis, Madison, Wis.). A non-transfected control is included. 72 hours after transfection cells are trypsinized (Life Technologies, South San Francisco, Calif.) and dissociated with 10 nM EDTA-PBS (Lonza, Basel, Switzerland). Cells are incubated in the presents of an anti-human CD71-specific antibody conjugated to a FITC fluorophore (eBiosceince, San Diego, Calif.) in Flow Cytometry Staining Buffer (eBiosceince, San Diego, Calif.). Fluorescence-activated cell sorting (FACS) of transfected cells is preformed using the using blue laser (excitation 488 nm) and the LSR II flow cytometer (BD Biosciences, Franklin Lakes, N.J.) for detection of the CD71-FITC antibody.

Activation of CD71 expression in dCas9-VP64 transfected samples is measured by the increase in detected fluorescence (a.u. $Log_{10}$) compared to the measured fluorescence of a non-transfected control population of HeLa cells as detected by FACS sorting.

Repression of CD71 expression in dCas9-KRAB transfected samples is measured by the decrease in detected fluorescence (a.u. $Log_{10}$) compared to the measured fluorescence of a non-transfected control population of HeLa cells as detected by FACS sorting.

Other genes are similarly activated or repressed using the sn-casPN of the present invention and the methods outlined here. As apparent to one skilled in the art, other activation and repression domain can be fused to a dCas9 to achieve a similar result to the methods describe here.

This procedure provides data to verify that the Cas9 sn1-casRNA/sn2-casRNA system of the present invention can be used in the activation of repression of endogenous genes.

Following the guidance of the present specification and examples, the repression/activation assays described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 14

Modification of CHO Cells for Industrial Application

This example describes use of the split-nexus Cas9-associated polynucleotides (sn-casPNs) of the present invention for modifying the genome of a Chinese Hamster Ovary cell (CHO cell). Also contained in this example is an outline for the sequence validation and selection of sn-casPN modified cells for future uses in industrial applications (i.e. production of antibodies).

A two-part sn-casRNA (sn1-casRNA and sn2-casRNA) system (see, e.g., FIG. 3) is used in a modification of the method described in Ronda et al. ("Accelerating genome editing in CHO cells using CRISPR Cas9 and CRISPy, a web-based target finding tool," Biotechnology and Bioengineering. Volume 111, Issue 8, pages 1604-1616, August 2014), which used a single guide RNA having a continuous sequence.

Examples of suitable vectors, media, culture conditions, etc. are described. Modifications of these components and conditions will be understood by one of ordinary skill in the art in view of the teachings of the present specification.

A. Plasmid Construction

The *S. pyogenes* Cas9 sequence is codon optimized for expression in CHO cells and C-terminally tagged with a SV40 nuclear localization signal and inserted into a vector adjacent to a suitable mammalian promoter, such as the cytomegalovirus (CMV) promoter. One such vector, pJ607-03 (DNA2.0, Menlo Park, Calif.), is commercially available.

The sn1-casRNA-FUT8 sequence comprises a 20 nucleotide FUT8 spacer sequence. The sn1-casRNA-FUT8 sequence is assembled into a suitable vector also comprising the independent sn2-casRNA sequence. Each sequence is under independent control by a U6 promoter that directs transcription by RNA polymerase III. One suitable vector backbone for the expression of sn1-casRNA and sn2-casRNA sequences is the pRSFDuet-1 vector (Novagen, Merck, Darmstadt, Germany).

B. Cell Culture

CHO-K1 cells are obtained from ATCC (Manassas, Va.) and cultured in CHO-K1 F-12K medium (ATCC, Manassas, Va.), 10% FBS (Life Technologies, Grand Island, N.Y.) and 1% Penicillin-Streptomycin (Sigma-Aldrich, St. Louis, Mo.). CHO-K1 cells are transfected with equal weight Cas9 containing plasmid and sn1-casRNA-FUT8/sn2-casRNA comprising vector using the Nucleofector 2b Device (Lonza, Basel, Switzerland) and the Amaxa Cell line Nucleofector Kit V (Lonza, Basel, Switzerland) as per the manufacturers recommendations. Cells are incubated at 30° C. in 5% CO2 for the first 24 hours and then moved to 37° C., 5% CO2 for another 24 hour periods.

C. Selection of FUT8 Knockout Cells

FUT8 knockout cells are selected by the addition of 50 μg/mL *Lens culinaris* agglutinin (LCA, Vector Laboratories, Burlingame, Calif.) five days after transfection of Cas9 vector and the sn1-casRNA-FUT8. Cells are subject to 7 days of selection on LCA, cells are passaged and fresh medium added, with LCA, every 2-3 days or as necessary. Only cells that have disruptions in the Fut8 gene, caused by the Cas9 sn-casPN system, will have resistance to the LCA.

To confirm FUT8 knockout, selected cells are re-seeded into complete media without LCA, and incubated for 48 hours. After re-seeding, genomic DNA (gDNA) is prepped using the QuickExtract DNA extraction solution (Illumina, San Diego, Calif.) as per manufacturer instructions.

D. Sequence Validation of Cas9 Modification & Myseq Library Construction

Sequencing amplicons of between 150 bp-200 bp are designed to span the sn1-casRNA-FUT8 target site. Using previously isolated gDNA, a first PCR is performed using Herculase II Fusion DNA Polymerase (Agilent, Santa Clara, Calif.) with primers comprising an adapter sequences and a sequence specific to the region flanking the FUT8 target site. A second PCR is performed using the amplicons of the first round of PCR as template at $\frac{1}{20}^{th}$ the volume of the PCR reaction volume. The second PCR uses a second set of primers comprising: sequence complementary to the adapter sequence of the first primer pair, a barcode index sequence unique to a each sample, and a flow cell adapter sequence. Amplicons are pooled and analyzed on a 2% TBE gel, bands of expected amplicon sizes are gel purified using the QIAEX II Gel Extraction Kit (Qiagen, Venlo, Netherlands). The concentrations of purified amplicons are evaluated using the Double-strand DNA BR Assay Kit and Qubit System (Life Technologies, Grand Island, N.Y.) and library quality determined using the Agilent DNA100Chip and Agilent Bioanalyzer 2100 System (Agilent, Santa Clara, Calif.). After validation of library quality, the library is sequenced on a MiSeq Benchtop Sequencer (Illumina, San Diego, Calif.) with the MiSeq Reagent Kit v2 (300 cycles, Illumina, San Diego, Calif.) per manufacturer instructions for 151 bp paired end reads.

E. Deep Sequencing Data Analysis

The identity of products in the sequencing data is analyzed based upon the index barcode sequence adapted onto the amplicon in the second round of PCR. A computational script is used to process the MiSeq data by executing the following tasks:

1. Joining of paired end reads with the aid of fastq-join (Aronesty 2011: code.google.com/p/ea-utils)

2. Validation of the sequence reads for appropriate primer sequences being present at both 5' and 3' ends of the read sequence using fastx_barcode_splitter (hannonlab.cshl.edu/fastx_toolkit/index.html). Reads lacking correct primer sequences at both ends are discarded.

3. Compare Read sequences to expected wild type FUT8 sequence, identical read sequences are classified as having the same indel modification.

Other chromosomal loci within CHO cells are similarly modified by selection of appropriate spacer sequence for the sn1-casRNA. Selection is specific to a specific gene target and the procedure outlined in this example is readily modifiable by one of ordinary skill in the art for other gene targets.

This procedure provides data to verify the Cas9 sn1-casRNA/sn2-casRNA system of the present invention provides sequence specific RNA-directed endonuclease activity at targeted loci in CHO cell and outlines the methods for selection of said modified CHO cells for continued use.

Following the guidance of the present specification and examples, the assay described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 15

Genome Engineering in *Saccharomyces cerevisiae*

This example describes use of the split-nexus Cas9-associated polynucleotides (sn-casPNs) of the present invention for modifying the genome of the yeast *S. cerevisiae*.

A two-part sn-casRNA (sn1-casRNA and sn2-casRNA) system (see, e.g., FIG. 3) is used in a modification of the method of DiCarlo, et al. ("Genome engineering in *Saccharomyces cerevisiae* using CRISPR-Cas systems," Nucleic Acids Res. 2013 April; 41(7): 4336-4343), which used a single guide RNA having a continuous sequence.

Examples of suitable vectors, media, culture conditions, etc. are described. Modifications of these components and conditions will be understood by one of ordinary skill in the art in view of the teachings of the present specification.

A. Site-Specific Genomic Mutations

A *Streptococcus pyogenes* Cas9 gene, codon-optimized for expression in yeast cells, is C-terminally tagged with a SV40 nuclear localization signal and inserted into a low copy number vector adjacent an inducible promoter, for example, GalL promoter sequences. The vector also contains a selectable marker, such as a URA3 selectable marker. One such vector, p415-GalL-Cas9-CYC1t (Addgene, Cambridge, Mass.), is commercially available. Expression of the Cas9 gene is under the inducible control of the GalL promoter.

The sn1-casRNA-CAN1.Y sequence comprises a 20 nucleotide CAN1.Y spacer sequence. The sn1-casRNA-CAN1.Z comprises a 20 nucleotide CAN1.Z spacer sequence. Expression cassettes are assembled comprising each sn1-casRNA, the SNR52 promoter, and SUP4 30 flanking sequence. Each expression cassette is assembled into a vector comprising a 2 micron replication origin and a selectable marker, for example, p426. DNA sequences encoding sn1-casRNA expression cassette are inserted into a vector containing a HIS3 selectable marker. DNA sequences encoding sn2-casRNA expression cassette are inserted into a vector containing a LEU2 selectable marker. One suitable backbone vector for the sn-casRNA encoding sequences is p426 GPD (American Type Culture Collection, Manassas, Va.), wherein the URA3 coding sequences are mutated or deleted and the appropriate selectable marker is inserted. Expression of the sn-casRNA sequences is under the constitutive control of the SNR52 promoter that directs transcription by RNA polymerase III.

The Cas9 vector and each sn1-casRNA/sn2-casRNA vector pair are transformed using standard methods into ATCC 200895 (MATa his3delta200 leu2delta0 met15delta0 trp1delta63 ura3delta0) (American Type Culture Collection, Manassas, Va.) and presence of the vectors is selected for using SC dropout media without uracil, histidine or leucine. Negative control yeast strains are also constructed by transformation of the individual vectors comprising sn1-casRNA-CAN1.Y, sn1-casRNA-CAN1.Z, sn2-casRNA, and Cas9 into ATCC 200895. Appropriate selection media are used for each vector.

Cells comprising Cas9 and sn1-casRNA/sn2-casRNA are cultured in liquid SC dropout media without uracil, histidine and leucine, and containing 2% galactose and 1% raffinose. Cells are grown for approximately 16 hours, pelleted and plated on YPAD, SC-uracil-histidine-leucine plates containing 60 mg/ml L-canavanine (Sigma-Aldrich, St. Louis, Mo.), and SC-lysine containing 100 mg/ml thialysine (S-2-aminoethyl-1-cysteine, Sigma-Aldrich, St. Louis, Mo.). Approximately $10^7$-$10^8$ cells are plated on canavanine and thialysine containing media, and cells are diluted appropriately for plating on rich media.

The ratio of the colony count on canavanine or thialysine plates divided by the colony count on rich media (YPAD) plates for each culture is used as a measure of mutation frequency. Negative control strains are similarly cultured and plated.

To control for a potential genome-wide mutator phenotype, the mutation frequency of the non-targeted endogenous LYP1 gene, a lysine permease, is monitored by selecting for lyp1 mutants using a toxic lysine analogue, thialysine.

LYP1 and CAN1 genes are on separate chromosomes. Accordingly, local mutation frequency in each locus should be independent in the absence of a genome-wide mutator.

The sn1-casRNA-CAN1.Y/sn2-casRNA directs Cas9 endonuclease activity to a target site located 207 bp downstream of the start codon of the CAN1 gene. The sn1-casRNA-CAN1.Z/sn2-casRNA directs Cas9 endonuclease activity to a target site located 58 bp downstream of the ATG start codon of the CAN1 gene.

When expression of Cas9 is induced by galactose, a decrease in cell viability on SC-uracil-histidine-leucine plates containing 60 mg/ml L-canavanine versus YPAD media indicates a higher mutation frequency in the CAN1 gene. The mutation rate in the LYP1 gene provides an indication of the background mutation rate. When the LYP1 gene mutation rate remains constant across all strains it suggests that the sn1-casRNA/sn2-casRNA and Cas9 system does not induce random mutations genome-wide. To further validate that mutations are caused by the sn1-casRNA/sn2-casRNA and Cas9 system, the CAN1 gene can be isolated and sequenced from canavanine resistant populations. The sequences are then aligned to identify the location and types of mutations in the CAN1 gene relative to the target binding sequence (i.e., the spacer sequence) present in the sn1-casRNA.

Other chromosomal loci in *S. cerevisiae* are similarly targeted for modification by selection of appropriate spacer sequences for sn1-casRNA.

This analysis provides data to verify that the Cas9 and sn1-casRNA/sn2-casRNA systems of the present invention provide specific RNA-directed endonuclease activity at targeted endogenous genomic loci in yeast.

B. Site-Specific Homologous Recombination with Donor DNA

A KanMX oligonucleotide sequence is PCR amplified with 50 bp homology arms to the CAN1 locus from the pFA6α-KanMX6 plasmid, which is commonly used for creation of gene knockouts in yeast. The KanMX is used as a donor DNA. The KanMX oligonucleotide confers G418 resistance and is designed to disrupt the CAN1.Y associated PAM sequence. Upon integration, this donor DNA results in canavanine resistance and G418 resistance.

Cells containing the sn1-casRNA-CAN1.Y, sn2-casRNA, Cas9 expression vectors are grown to saturation in SC dropout media without uracil, histidine and leucine. This culture is used to inoculated liquid SC media without uracil, histidine and leucine and the culture is grown to approximately OD600 of 1.8. Cells are collected via centrifugation and donor oligonucleotides are transformed into the cells by electroporation. Electroporated cells are transferred into SC-ura-his-leu media containing 2% galactose and 1% raffinose and grown for approximately 12 hours. Negative control strains are similarly treated but no donor oligonucleotide is provided.

Approximately $10^6$-$10^7$ cells are plated on selective media, and cells are diluted appropriately on rich media. Negative control strains are similarly cultured and plated.

Colonies containing the plasmids are replica plated to canavanine media as well as rich media with G418 to select for the KanMX integration event. The ratio of colony count on selective plates (i.e., colonies that are both canavanine and G418 resistant) over colony count on rich plates is used as a measure of correction frequency which suggests homologous recombination of the KanMX sequences at the site of sn1-casRNA/sn2-casRNA directed cleavage. To further validate that the integration events are directed by the sn1-casRNA/sn2-casRNA and Cas9 system, the CAN1 gene including the integrated KanMX sequences can be isolated and sequenced from canavanine/G418 resistant populations. The sequences are then aligned to identify the location and types of insertions in the CAN1 gene relative to the target binding sequence (i.e., the spacer sequence) present in the sn1-casRNA.

Other chromosomal loci in *S. cerevisiae* are similarly targeted for modification by selection of appropriate spacer sequences for sn1-casRNA and donor oligonucleotides. Functional genes can be introduced into the *S. cerevisiae* genome without disruption of endogenous genes. Also, introduction of selectable markers into endogenous target genes can be used to provide selectable knock-out mutations of the target genes.

This analysis provides data to verify that the Cas9 and sn1-casRNA/sn2-casRNA systems of the present invention provide specific RNA-directed endonuclease activity at targeted endogenous genomic loci in yeast and can stimulate homologous recombination events at such loci using donor DNA.

Following the guidance of the present specification and examples, the methods described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 16

Targeted Mutagenesis in *Zea mays*

This example describes use of the split-nexus Cas9-associated polynucleotides (sn-casPNs) of the present invention for creating genomic modifications in plants. Although a two component sn-casRNA polynucleotide system is described, other embodiments of the present invention can be used as well (e.g., a three component sn-casRNA polynucleotide system).

A three-part sn-casRNA (sn1-casRNA, sn-2-casRNA and sn3-casRNA) system (see, e.g., FIG. 3A) is used in a modification of the method of Cigan, A. M., et al., "Genome modification using guide polynucleotide/cas endonuclease systems and methods of use," U.S. Patent Publication No. 20150059010, published Feb. 26, 2015, which used guide RNAs each having a continuous sequence.

Examples of suitable vectors, media, culture conditions, etc. are described. Modifications of these components and conditions will be understood by one of ordinary skill in the art in view of the teachings of the present specification.

A. Expression Cassettes

The Cas9 gene from *Streptococcus pyogenes* M1 GAS (SF370) is maize codon optimized per standard techniques known in the art. The potato ST-LS 1 intron is introduced in order to eliminate its expression in *E. coli* and *Agrobacterium*. Nuclear localization of the Cas9 protein in maize cells is facilitated by simian virus 40 (SV40) monopartite and *Agrobacterium tumefaciens* bipartite VirD2 T-DNA border endonuclease nuclear localization signals incorporated at the amino and carboxyl-termini of the Cas9 open reading frame, respectively. The Cas9 gene was operably linked to a maize constitutive (e.g. a plant Ubiquitin promoter) or regulated promoter by standard molecular biological techniques.

Expression cassettes for the expression of the sn1-casRNA, sn2-casRNA, and sn3-casRNA utilize the maize U6 polymerase HI promoter (5' of each sn-casRNA coding sequence) and maize U6 polymerase III terminator (3' of each sn-casRNA coding sequence) operably linked to sn-casRNA DNA coding sequences using standard molecular biology techniques to create sn-casRNA expression cassettes. As shown in FIG. 3A, sn3-casRNA comprises a 20 spacer region complementarity to the DNA target (VT domain). A target region upstream of a PAM sequence is selected for target site recognition and cleavage.

The expression cassettes for the Cas9 protein and sn-casRNAs can be placed in suitable backbone vectors (e.g., as described by Belhaj, K., et al., (2013) "Plant genome editing made easy: targeted mutagenesis in model and crop plants using the CRISPR/Cas system," Plant Methods. 9(1): 39; Weber E., et al., (2011) "A Modular Cloning System for Standardized Assembly of Multigene Constructs," PLoS ONE 6(2): e16765) using standard molecular biology techniques.

B. Generating Mutations

Three different maize genomic target sequences are targeted for cleavage using the sn1-casRNA/sn2-casRNA/sn3-casRNA/Cas9 system. The three target sequences are located at the LIG locus (approximately 600 bp upstream of the Liguleless 1 gene start codon) and examined by deep sequencing for the presence of mutations. Spacer sequences for each target site (LIGCas-1, LIGCas-2, and LIGCas3) are as described in U.S. Patent Publication No. 20150059010 (see, VT domains complementary to the antisense strand of the maize genomic target sequences listed in Table 1 of U.S. Patent Publication No. 20150059010). The resulting sn-casRNAs are as follows: sn1-casRNA/sn2-casRNA/sn3-casRNA-LIGCas-1; sn1-casRNA/sn2-casRNA/sn3-casRNA-LIGCas-2; and sn1-casRNA/sn2-casRNA/sn3-casRNA-LIGCas-3.

Expression cassettes comprising the three component sn-casRNA systems and Cas expression cassettes are code-livered to 60-90 Hi-II immature maize embryos by particle-mediated delivery. Hi-II maize embryos are transformed with the Cas9 and long guide RNA expression cassettes (as described in U.S. Published Patent Application 20150082478, published Mar. 19, 2015) targeting the LIG-Cas-3 genomic target site for cleavage to provide a positive control. Hi-II maize embryos transformed with only the Cas9 expression cassette provides a negative control.

Maize cars are husked and surface sterilized and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment.

Vectors comprising the sn1-casRNA/sn2-casRNA/sn3-casRNA/Cas9 systems are co-bombarded with vectors containing the developmental genes ODP2 (Ovule development protein 2, an AP2 domain transcription factor; see, e.g., U.S. Published Patent Application No. 20090328252, published Dec. 31, 2009) and Wushel (U.S. Published Patent Application No. 20110167516, published Jul. 7, 2011).

For each sn1-casRNA/sn2-casRNA/sn3-casRNA/Cas9 system, the corresponding vectors are precipitated onto 0.6 μm (average diameter) gold pellets using a water-soluble cationic lipid transfection reagent. DNA solution is prepared on ice using sn1-casRNA/sn2-casRNA/sn3-casRNA/Cas9 vectors and plasmids containing the developmental genes ODP2 and Wushel. Prepared gold particles are added to the pre-mixed DNA. The water-soluble cationic lipid transfection reagent is added in water and mixed carefully. Gold particles are pelleted in a microfuge the supernatant is removed. The resulting pellet is carefully rinsed with ethanol (EtOH) without resuspending the pellet and the EtOH rinse is carefully removed. 100% EtOH is added and the particles are resuspended by brief sonication. Then, the mixture is spotted onto the center of each macrocarrier and allowed to dry about 2 minutes before bombardment (Kikkert J. R., et al., (2005) "Stable transformation of plant cells by particle bombardmentlbiolistics," Methods Mol Biol. 286:61-78).

Plates with the embryos are bombarded at level #4 with a Helios® Gene Gun System (Biorad, Hercules Calif.). All samples receive a single shot at 450 PSI of prepared particles/DNA. Following bombardment, the embryos are incubated on maintenance medium for 12 to 48 hours at temperatures ranging from 26° C. to 37° C., and are then placed at 26° C.

After 7 days, approximately 30 of the most uniformly transformed embryos from each treatment are pooled and total genomic DNA is extracted. The region surrounding the intended target site is PCR amplified with Phusion® High-Fidelity PCR Master. Mix (New England Biolabs, Ipswich, Mass.). The PCR amplification is also used to add amplicon-specific barcodes and Illumnia sequencing primers (Illumina, Madison Wis.). The resulting PCR amplification products are purified with a PCR purification spin column (Qiagen, Valencia Calif.), concentration measured with a Hoechst dye-based fluorometric assay, combined in an equimolar ratio, and single-read 100 nucleotide-length deep sequencing was performed on MiSeq Personal Sequencer (Illumina, Madison Wis.).

The frequencies of NHEJ mutations recovered by deep sequencing for the sn1-casRNA/sn2-casRNA/sn3-casRNA/Cas9 systems targeting the three LIGCas targets compared to the single long guide RNA/Cas9 endonuclease system targeting the corresponding locus are determined. These data are to demonstrate that the sn1-casRNA/sn2-casRNA/sn3-casRNA/Cas9 systems as described herein cleaves maize chromosomal DNA and generates NHEJ-mediated mutations.

Following the guidance of the present specification and examples, the methods described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 17

Generation of Transgenic Mice

This example describes use of the split-nexus Cas9-associated polynucleotides (sn-casPNs) of the present invention for creating genomic modifications in animals.

A two-part sn-casRNA (sn1-casRNA and sn2-casRNA) system (see, e.g., FIG. 3) is used in a modification of the method of Wang, et al. ("One-step generation of mice carrying mutations in multiple genes by CRISPR/Cas-mediated genome engineering," Cell (2013) 153(4):910-918), which used a single guide RNAs each having a continuous sequence.

Examples of suitable vectors, media, culture conditions, etc. are described. Modifications of these components and conditions will be understood by one of ordinary skill in the art in view of the teachings of the present specification.

A. Production of Cas9 mRNA and sn1-casRNA/sn2-casRNA

A T7 promoter is added to Cas9 coding region optimized for mammalian expression (e.g., the Cas9 coding sequence can be PCR amplified from pX330-U6-Chimeric_BB-CBh-hSpCas9; Addgene, Cambridge, Mass.). The T7 promoter is added by PCR amplification. The T7-Cas9 PCR product is gel purified and used as the template for in vitro transcription using mMESSAGE mMACHINE T7 ULTRA Kit (Life Technologies, Grand Island, N.Y.). The Cas9-mRNA is purified using MEGAclear Kit (Life Technologies, Grand Island, N.Y.) and eluted in RNase-free water.

DNA sequences encoding the sn1-casRNAs and sn2-casRNAs (see, e.g., FIG. 3B) are chemically synthesized. The 20 nucleotide spacer sequences for the sn1-casRNAs are as follows: sn1-casRNA-Tet1, GGCTGCTGTC AGGGAGCTCA (SEQ ID NO:89); and sn1-casRNA-Tet 2, GAAAGTGCCA ACAGATATCC (SEQ ID NO:90) (see, FIG. 1A of Wang, et al., Cell (2013) 153(4):910-918)). The T7 promoter is added to each of the sn1-casRNA and sn2-casRNA templates by PCR amplification. The T7-sn-casRNA PCR products are gel purified and used as the template for in vitro transcription using MEGAshortscript T7 Kit (Life Technologies, Grand Island, N.Y.). The sn-casRNAs are purified using MEGAclear Kit (Life Technologies, Grand Island, N.Y.) and eluted in RNase-free water.

B. One-Cell Embryo Injection

All animal procedures are performed according to NIH guidelines. B6D2F1 (C57BL/6 X DBA2) female mice are used as embryo donors. ICR mouse strains are used as foster mothers. Superovulated, seven to eight week old female B6D2F1 mice are mated to B6D2F1 males. Fertilized embryos are collected from oviducts. Cas9 mRNAs (administered to individual embryos over a range of approximately 20 ng/ml to approximately 200 ng/ml), sn1-casRNA/sn2-casRNA (administered to individual embryos over a range of from 20 ng/ml to 50 ng/ml) are injected into the cytoplasm of fertilized embryos (having well recognized pronuclei) in M2 medium (Sigma-Aldrich, St. Louis, Mo.).

When a donor oligonucleotide is also being injected the concentration of the split-nexus Cas9-associated polynucleotides/Cas9 protein system components are as follows: Cas9 mRNA (approximately 100 ng/ml), sn1-casRNA/sn2-casRNA (50 ng/ml); and donor oligonucleotide (100 ng/ml). The components are mixed and injected into zygotes at the pronuclei stage. Injected zygotes are cultured in PrimeQ™ KSOM Embryo Culture Medium, w/Amino Acids and Phenol Red (MTI-GlobalStem, Gaithersburg, Md.) at 37° C. under 5% $CO_2$ in air for about 3.5 days (until blastocyst stage). 15-25 blastocysts are transferred into the uteri of pseudopregnant ICR females at approximately 2.5 days postcoitum.

C. Double-Gene Mutant Mice sn1-casRNA-Tet1/sn2-casRNA and sn1-casRNA-Tet2/sn2-casRNA are coinfected as described above into zygotes. The genomic DNA of pups is evaluated by RFLP (restriction fragment length polymorphism analysis), Southern blot analysis, and sequencing analysis to identify mice carrying targeted mutations at all four alleles of the Tet1 and Tet2 genes. The results of these analyses are to demonstrate that postnatal mice carrying bi-allelic mutations in two different genes (i.e., the Tet1 and Tet2 genes) can be efficiently generated.

In vivo off-target effects are also evaluated. Previous work in vitro, in bacteria, and in cultured human cells suggests that the protospacer-adjacent motif sequence NGG and the 8 to 12 base "seed sequence" of the spacer sequence is important for determining the DNA cleavage specificity (Cong, L., et al., (2013) "Multiplex genome engineering using CRISPR/Cas systems," Science 339:819-82; Jiang, W., et al., (2013) "RNA-guided editing of bacterial genomes using CRISPR-Cas systems," Nat. Biotechnol. 31:233-239; and Jinek, M., et al., (2012) "A programmable dual-RNA-guided DNA endonuclease in adaptive bacterial immunity," Science 337:816-821). Using this rule, Wang, et al., identified that only three Tet1 and four Tet2 potential off-target sites exist in the mouse genome. Off-target effects are evaluated using the Surveyor Assay (Guschin, D. Y., et al., (2010) "A rapid and general assay for monitoring endogenous gene modification," Methods Mol. Biol. 649: 247-256). The number of off-target effects provides an estimate of in vivo targeting accuracy of the sn1-casRNA/sn-2-casRNA/Cas9 protein complex.

D. In Vivo Gene Repair Modification

To evaluate in vivo gene repair using the sn1-casRNA and sn2-casRNA system, a donor oligonucleotide is used to target Tet1 to change two base pairs of a SacI restriction site to create an EcoRI site (Tet1 oligonucleotide; 126 bp, for sequence see FIG. 3A of Wang, et al.). A second donor oligonucleotide is used to target Tet2 to change two base pairs of an EcoRV site into an EcoRI site (Tet2 oligonucleotide; 126 bp, for sequence see FIG. 3A of Wang, et al.). Blastocysts are derived from zygotes injected with Cas9 mRNA, sn1-casRNA-Tet1/sn2-casRNA, and Tet1 oligonucleotide, Cas9 mRNA, sn1-casRNA-Tet2/sn2-casRNA, and Tet2 oligonucleotide, and Cas9 mRNA, sn1-casRNA-Tet1/sn2-casRNA, Tet1 oligonucleotide, sn1-casRNA-Tet2/sn2-casRNA, and Tet2 oligonucleotide.

DNA is isolated from the Cas9 mRNA, sn1-casRNA-Tet1/sn2-casRNA, and Tet1 oligonucleotide blastocysts, amplified, and digested with EcoRI to detect oligonucleotide-mediated gene repair events. DNA is isolated from the Cas9 mRNA, sn1-casRNA-Tet2/sn2-casRNA, and Tet2 oligonucleotide blastocysts, amplified, and digested with EcoRI to detect oligonucleotide-mediated gene repair events. DNA is isolated from the Cas9 mRNA, sn1-casRNA-Tet1/sn2-casRNA, Tet1 oligonucleotide, sn1-casRNA-Tet2/sn2-casRNA, and Tet2 oligonucleotide blastocysts, amplified, and digested with EcoRI to detect oligonucleotide-mediated gene repair events. The genomic DNA from the blastocysts is evaluated by RFLP, Southern blot analysis, and sequencing analysis to identify blastocysts carrying modified restriction sites of the Tet1 and Tet2 genes. The results of these analyses are to demonstrate that in vivo repair of mouse genes (i.e., the Tet1 and Tet2 genes) can be efficiently carried out.

RFLP analyses using SacI and EcoRV cleavage to evaluate the Tet1 and Tet2 loci, respectively, are used to demonstrate that alleles not targeted by a selected Cas9 mRNA, sn1-casRNA-Tet1 or Tet2/sn2-casRNA, and oligonucleotide (in each of the above listed combinations) are not affected.

Furthermore, blastocysts with double oligonucleotide injections are implanted into, foster mothers. The genomic DNA from resulting pups is evaluated by RFLP, Southern blot analysis, and sequencing analysis to identify blastocysts carrying modified restriction sites of the Tet1 and Tet2 genes. The results of these analyses are to demonstrate that mice with genomic repair modifications in multiple genes can be generated.

Following the guidance of the present specification and examples, the methods described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

Example 18

Sn-casRNAs/Cas9 Complexes in Delivery Vectors Comprising Cationic Molecules

A. Production of Cas9 mRNA and sn1-casRNA/sn2-casRNA/sn3-casRNA

A T7 Promoter is Added to Cas9 Coding Region Optimized for Mammalian expression and tagged at the C-terminal with two nuclear localization sequences (NLS). The T7 promoter is added by PCR amplification. The T7-Cas9 PCR product is gel purified and cloned into a vector for cell free protein expression (e.g., pT7CFE1-NFtag Vector for Mammalian Cell-Free Protein Expression, Life Technologies, Grand Island N.Y.). Cas9 protein is expressed and isolated using a cell free protein expression system (e.g., 1-Step CHO High-Yield 1VT Kit, Life Technologies, Grand Island N.Y.) and suspended in RNase-free water.

DNA sequences encoding the sn1-casRNA, sn2-casRNA, and sn3-casRNA-AAVS-1 are prepared as described in Example 1. The T7-sn-casRNA PCR products are gel purified and used as the template for in vitro transcription using T7 High Yield RNA Synthesis Kit (New England Biolabs, Ipswich, Mass.). The sn-casRNAs are purified using GeneJet RNA Cleanup and Concentration Kit (Life Technologies, Grand Island, N.Y.) and eluted in RNase-free water.

B. Formation of Ribonucleoprotein Complexes

Ribonucleoprotein (RNP) complexes are prepared at two concentrations, 50 pmol Cas9:150 pmols sn-casRNAs and 200 pmols Cas9:600 pmols sn-casRNAs. All three sn-casRNA components in equimolar amounts are mixed in an annealing buffer (1.25 mM HEPES, 0.625 mM MgCl2, 9.375 mM KCl at pH7.5) to desired concentration (150 pmols or 600 pmols) in a final volume of 5 µL, are incubated for 2 minutes at 95° C., are removed from thermocycler and are allowed to equilibrate to room temperature. Cas9 protein is diluted to appropriate concentration in binding buffer (20 mM HEPES, 100 mM KCl, 5 mM MgCl2, 1 mM DTT, and 5% glycerol at pH 7.4) in a final volume of 5 µL and is mixed with the 5 µL of heat-denatured sn-casRNAs followed by incubation at 37° C. for 30 minutes to form the sn-casRNAs/Cas9 complexes.

C. Preparation of SC12CDClickpropylamine Vector sn-casRNAs/Cas9 Complexes

SC12CDClickpropylamine (a cationic betacyclodextrin; O'Mahony A. M., et al., (2013) "Cationic and PEGylated Amphiphilic Cyclodextrins: Co-Formulation Opportunities for Neuronal Sirna Delivery," PLoS ONE 8(6): e66413) is weighed out and dissolved in chloroform (approximately 1 mg/ml), then mixed together in appropriate volumes to provide molar ratios of cationic to PEGylated-Cyclodextrin (U.S. Patent Application Publication No. 20140079770, published Mar. 20, 2014, "Vector for Pulmonary Delivery, Inducing Agent, and Uses"). The solvent is removed under a stream of nitrogen to provide a dry cyclodextrin (CD) composition.

The CD composition is rehydrated with binding buffer (final concentration approximately 1 mg/ml) and is sonicated for one hour at room temperature followed by the immediate addition of the sn-casRNAs/Cas9 complexes in binding buffer. The sn-casRNAs/Cas9 complexes in binding buffer are added in an equal volume. The solution is mixed and is incubated for 20-30 minutes at room temperature to produce a CD composition comprising the sn-casRNAs/Cas9 complexes (CD-sn-casRNAs/Cas9).

D. Preparation of Liposomal Entrapped Sn-casRNAs/Cas9 Complexes

Liposomes are formed without the casRNAs/Cas9 complexes to provide negative controls (empty liposomes).

In a suitably sized round bottom flask the liposome components are added and solubilized in a suitable solvent or solvent mixture. Example liposome components are as follows:

Liposome 1: EPC (EtOH solution) and Cholesterol (EtOH solution) are prepared in a molar ratio of 70/30.

Liposome 1-PEG: Stearylated PEG2000 (EtOH solution) is added to be 5 mol % with respect to the total lipid amount of liposome 1 (EPC+Cholesterol).

Liposome 2: DOTMA (EtOH solution), Cholesterol (EtOH solution), and EPC (EtOH solution) are prepared in a molar ratio of 30/40/30.

Liposome 2-PEG: Stearylated PEG2000 (EtOH solution) is added to be 5 mol % with respect to the total lipid amount of liposome 2 (DOTMA+Cholesterol+EPC).

Liposome 3: DODAP (EtOH solution), Cholesterol (EtOH solution), and EPC (EtOH solution) were added at a molar ratio of 30/40/30.

Liposome 3-PEG: Stearylated PEG2000 (EtOH solution) is added to be 5 mol % with respect to the total lipid amount of liposome 3 (DODAP+Cholesterol+EPC).

An amount of EtOH is added to solubilize all components. The flask is attached to a rotary evaporator spinning at 50-100 rpm and immersed in a water bath set above the highest gel-liquid crystal phase transition (Tc) temperature of the lipids used. The flask is allowed to rotate in the water bath for approximately 1 minute to equilibrate. A slow vacuum is pulled, to as low as <10 Torr, to obtain a thin dry film on the walls of the flask without precipitation. To remove any residual solvent, the flask is subjected to high vacuum at room temperature for a few hours or overnight.

A solution of either sn-casRNAs/Cas9 complexes or CD-sn-casRNAs/Cas9 is added to obtain a final lipid concentration of between about 2 mM to about 0.5 mM. Lipid rehydration is conducted at room temperature for 15 minutes or longer. Liposomes are prepared by ultrasonication for approximately 1 minute.

The above methods produce the particle compositions and liposome compositions shown in Table 19.

TABLE 19

Particle and Liposome Compositions

| | |
|---|---|
| Particle | sn-casRNAs/Cas9 complex |
| Particle | CD-sn-casRNAs/Cas9 complex |
| Liposome 1 | sn-casRNAs/Cas9 complex |
| Liposome 1 | CD-sn-casRNAs/Cas9 complex |
| Liposome 1-PEG | sn-casRNAs/Cas9 complex |
| Liposome 1-PEG | CD-sn-casRNAs/Cas9 complex |
| Liposome 2 | sn-casRNAs/Cas9 complex |
| Liposome 2 | CD-sn-casRNAs/Cas9 complex |
| Liposome 2-PEG | sn-casRNAs/Cas9 complex |
| Liposome 2-PEG | CD-sn-casRNAs/Cas9 complex |
| Liposome 3 | sn-casRNAs/Cas9 complex |
| Liposome 3 | CD-sn-casRNAs/Cas9 complex |
| Liposome 3-PEG | sn-casRNAs/Cas9 complex |
| Liposome 3-PEG | CD-sn-casRNAs/Cas9 complex |

E. Characterization of Particle Compositions and Liposomes Compositions

The particle compositions and liposome compositions described above are characterized (see e.g., Laouini, A., et al., (2012) "Preparation, Characterization and Applications of Liposomes: State of the Art," Journal of Colloid Science and Biotechnology Vol. 1, 147-168, 2012) using standard methods as follows.

(i) Size Analysis

The sizes of the particles and liposomes are evaluated by standard techniques. Several techniques are available for assessing liposome size and size distribution including microscopy techniques, size-exclusion chromatography (SEC), field-flow fractionation and static or dynamic light scattering. Furthermore, particle sizes can be evaluated using non-denaturing agarose gels (e.g., 1.5% agarose gels, SYBR® Safe, Life Technologies, Grand. Island, N.Y.). Different sizes of particles and liposomes are useful for different applications, for example, cell transfection in culture or therapeutic administration to an animal.

(ii) Charge Measurements

The average size and charge the particles and liposomes are measured with a Zetasizer Nano ZS (Malvern, Westborough Mass.) using dynamic light scattering (DLS). If all the particles in a suspension have a large negative or large positive zeta potential they tend to repel each other. Thus reducing or eliminating the tendency to aggregation. However, particles with low zeta potential value have no force to prevent the particles flocculating.

(iii) Morphology

The morphologies of the compositions are evaluated using transmission electron microscopy (TEM), for example, a JEOL 2000 FXII transmission electron microscope (Jeol Ltd., Tokyo, Japan). Generally compositions having uniform particle or liposome morphology is most desirable.

(iv) Aggregation Studies

The effects of salt-containing medium and serum on the aggregation of the particles and liposomes is evaluated by incubating complexes in either Opti-MEM® transfection media (Life Technologies, Grand Island, N.Y.) or fetal bovine serum for 24 hours at 37° C. Size measurements are carried out using the Zetasizer Nano ZS. The absence of aggregation is often a desirable quality. However, in some applications (for example, transfection experiments) some aggregation may be desirable.

(v) Encapsulation Efficiency

The liposome preparations are a mixture of encapsulated and unencapsulated CD-sn-casRNAs/Cas9 or sn-casRNAs/Cas9 fractions. Several techniques are know for the determination of the encapsulation efficiency including HPLC and field-flow fractionation. Typically, the encapsulation percent is expressed as the ratio of the unencapsulated peak area to that of a reference standard at the same initial concentration. This method can be applied if the liposomes do not undergo any purification following preparation. General a high degree of encapsulation efficiency is an important parameter for liposomes in therapeutic applications. Low encapsulation efficiency necessitates the incorporation of a post encapsulation separation step (such as dialysis, size exclusion chromatography or ultrafiltration) to remove unencapsulated complexes. Typically an encapsulation efficiency of greater than 45%, more preferably greater than 80%, and most preferably greater than 95% is desirable.

(v) In Vivo Activity

The particle compositions and liposome compositions comprising the sn1-casRNA, sn2-casRNA, and sn3-casRNA-AAVS-1 are evaluated for their relative abilities to deliver the sn-casRNAs/Cas9 complexes into cells for gene repair. For this experiment a donor DNA molecule is included in the preparation of each of the particle compositions and liposome compositions. The donor DNA is an EGFP fragment for use with the AAVS1 Positive Control EGIP 293T Reporter Cell Line (System Biosciences, Mountain View, Calif.). Other reporter systems are suitable for use in this analysis. Liposome compositions are concentrated as necessary using standard techniques.

The particle compositions and liposome compositions are transfected into cells. One day before transfection, the cells are plated in growth medium without antibiotics. The cells should be at confluence at the time of transfection. The particle compositions and liposome compositions are diluted into Opti-MEM® I Medium (Life Technologies, Grand Island N.Y.) without serum to provide a range of concentration for the sn-casRNAs/Cas9 complexes. Typically a volume of about 200 µl of these suspensions is applied to cells in multiwell plates. The cells and suspensions are gently mixed by rocking the plates back and forth. The cells are incubated at 37° C. in a $CO_2$ incubator for 5-24 hours. The following day, complete growth medium is added to the cells. The cells are incubated cells at 37° C. in a $CO_2$ incubator for 24-48 hours prior to testing.

Gene repair is evaluated using the AAVS1 Positive Control EGIP 293T Reporter Cell Line for monitoring HDR efficiency of EGFP donor DNA. The sn3-casRNA-AAVS1 RNA sequence directs the sn-casRNA/Cas9 complex to target and cleave a 53 bp AAVS1 sequence integrated in a Enhanced Green Fluorescent Inhibited Protein (EGIP) reporter cell line. The EGIP comprises a stop codon in the middle to inactivate expression of the Enhanced Green Fluorescent Protein (EGFP). In the presence of an active sn-casRNA/Cas9 complex, the EGFP donor DNA recombines at the target site and restores the open reading of the EGFP gene by homologous recombination. Cleavage efficiency of the sn-casRNAs/Cas99 complex targeting the AAVS1 locus is measured using the Surveyor Assay. Efficiency of restoration of EGFP expression is monitored using fluorescence microscopy. Results are expressed as a percent EGFP gene expression relative to particle composition (sn-casRNAs/Cas9 and CD-sn-casRNA/Cas9) and the empty liposome controls. The results of the in vivo activity studies provide guidance for the selection of optimal particle and/or liposome components and compositions.

Taken together, these data provide information that allows establishing criteria for selecting optimal liposomal compositions for encapsulation of sn-casRNAs/Cas9 complexes of the present invention according to their advantages and limitations.

Following the guidance of the present specification and examples, the methods described in this example can be practiced by one of ordinary skill in the art with other Type II CRISPR Cas9 proteins including, but not limited to, Cas9 and Cas9 fusions combined with their cognate polynucleotide components modified as described herein to comprise a split nexus element.

As is apparent to one of skill in the art, various modification and variations of the above embodiments can be made without departing from the spirit and scope of this invention. Such modifications and variations are within the scope of this invention.

What is claimed is:

1. A Type II CRISPR-Cas9-associated polynucleotide composition comprising:
   a first Type II CRISPR-Cas9-associated split-nexus polynucleotide having a 5' end and a 3' end (sn1-casPN) comprising, in the 5' to 3' direction, a first stem element nucleotide sequence I and a nexus stem element nucleotide sequence I;
   a second Type II CRISPR-Cas9-associated split-nexus polynucleotide having a 5' end and a 3' end (sn2-casPN) comprising, in the 5' to 3' direction, a nexus stem element nucleotide sequence II and a second stem element nucleotide sequence I wherein the nexus stem element nucleotide sequence I of the sn1-casPN and the nexus stem element nucleotide sequence II of the sn2-casPN are capable of forming a nexus stem element by base-pair hydrogen bonding between the nexus stem element nucleotide sequence I and the nexus stem element nucleotide sequence II;
   a third Type II CRISPR-Cas9-associated polynucleotide having a 5' end and a 3' end (sn3-casPN) comprising, in the 5' to 3' direction, a DNA target binding sequence and a first stem element nucleotide sequence II, wherein the first stem element nucleotide sequence I of the sn1-casPN and the first stem element nucleotide sequence II of the sn3-casPN are capable of forming a first stem element by base-pair hydrogen bonding between the first stem element nucleotide sequence I and the first stem element nucleotide sequence II, and
   a first adjunct polynucleotide having a 5' end and a 3' end comprising a second stem element nucleotide sequence II;
   wherein the second stem element nucleotide sequence I of the sn2-casPN and the second stem element nucleotide sequence II of the first adjunct polynucleotide are capable of forming a second stem element by base-pair hydrogen bonding between the second stem element nucleotide sequence I and the second stem element nucleotide sequence II;
   wherein the 5' end of the sn1-casPN is covalently bonded to the 3' end of the sn3-casPN.

2. The composition of claim 1, wherein
   the first stem element nucleotide sequence I of the sn1-casPN further comprises, in the 5' to 3' direction, an upper stem element nucleotide sequence I, a bulge element nucleotide sequence I, and a lower stem element nucleotide sequence I, and
   the first stem element nucleotide sequence II of the sn3-casPN further comprises, in the 5' to 3' direction, a lower stem element nucleotide sequence II, a bulge element nucleotide sequence II, and an upper stem element nucleotide sequence II, wherein the upper stem element nucleotide sequence I of the sn1-casPN and the upper stem element nucleotide sequence II of the sn3-casPN are capable of forming an upper stem element by base-pair hydrogen bonding between the upper stem element nucleotide sequence I and the upper stem element nucleotide sequence II, and the lower stem element nucleotide sequence I of the sn1-casPN and the lower stem element nucleotide sequence II of the sn3-casPN are capable of forming a lower stem element by base-pair hydrogen bonding between the lower stem element nucleotide sequence I and the lower stem element nucleotide sequence II.

3. The composition of claim 1, wherein the first adjunct polynucleotide further comprises, in the 5' to 3' direction, a loop element nucleotide sequence and the second stem element nucleotide sequence II, and wherein the 5' end of the first adjunct polynucleotide is covalently bonded to the 3' end of the sn2-casPN.

4. The composition of claim 3, further comprising:
   a second adjunct polynucleotide having a 5' end and a 3' end comprising third stem element nucleotide sequence II; wherein
   the first adjunct polynucleotide comprises, in the 5' to 3' direction, the loop element nucleotide sequence, the second stem element nucleotide sequence II, and a third stem element nucleotide sequence I, and
   the third stem element nucleotide sequence I of the first adjunct polynucleotide and the third stem element nucleotide sequence II of the second adjunct polynucleotide are capable of forming a third stem element by base-pair hydrogen bonding between the third stem element nucleotide sequence I and third stem element nucleotide sequence II.

5. The composition of claim 4, wherein the second adjunct polynucleotide further comprises, in the 5' to 3' direction, a loop element nucleotide sequence and the third stem element nucleotide sequence II, wherein 5' end of the second adjunct polynucleotide is covalently bonded to the 3' end of the first adjunct polynucleotide.

6. The composition of claim 1, wherein the sn1-casPN further comprises a first auxiliary polynucleotide 3' adjacent the nexus stem element nucleotide sequence I.

7. The composition of claim 6, wherein the sn2-casPN further comprises a second auxiliary polynucleotide 5' adjacent the nexus stem element nucleotide sequence II.

8. The composition of claim 1, wherein the sn2-casPN further comprises an auxiliary polynucleotide 5' adjacent the nexus stem element nucleotide sequence II.

9. The composition of claim 7, wherein
   the first auxiliary polynucleotide further comprises an effector binding element nucleotide sequence I,
   the second auxiliary polynucleotide further comprises an effector binding element nucleotide sequence II, and
   the effector binding element nucleotide sequence I of the first auxiliary polynucleotide and the effector binding element nucleotide sequence II of the second auxiliary polynucleotide are capable of forming an effector binding element by base-pair hydrogen bonding between the effector binding element nucleotide sequence I and the effector binding element nucleotide sequence II.

10. The composition of claim 9, wherein
    the first auxiliary polynucleotide further comprises, in the 5' to 3' direction, a linker element nucleotide sequence I and the effector binding element nucleotide sequence I, the second auxiliary polynucleotide comprises, in the 5' to 3' direction, the effector binding element nucleotide sequence II and a linker element nucleotide sequence II, and the linker element nucleotide sequence I of the first auxiliary polynucleotide and the linker element nucleotide sequence II of the second auxiliary polynucleotide are capable of forming a linker element by base-pair hydrogen bonding between the linker element nucleotide sequence I and the linker element nucleotide sequence II.

11. The composition of claim 6, wherein the first auxiliary polynucleotide comprises a hairpin.

12. The composition of claim 7, wherein the first auxiliary polynucleotide comprises a hairpin and the second auxiliary polynucleotide comprises a hairpin.

13. The composition of claim 8, wherein the auxiliary polynucleotide comprises a hairpin.

14. The composition of claim 12, wherein the first auxiliary polynucleotide further comprises, in the 5' to 3' direction, a linker element nucleotide sequence I and the hairpin, the second auxiliary polynucleotide further comprises, in the 5' to 3' direction, the hairpin and a linker element nucleotide sequence II, and the linker element nucleotide sequence I of the first auxiliary polynucleotide and the linker element nucleotide sequence II of the second auxiliary polynucleotide are capable of forming linker element by base-pair hydrogen bonding between the linker element nucleotide sequence I and the linker element nucleotide sequence II.

15. A Type II CRISPR-Cas9-associated split-nexus polynucleotide composition comprising:

a first Type II CRISPR-Cas9-associated split-nexus polynucleotide having a 5' end and a 3' end (sn1-casPN) comprising, in the 5' to 3' direction, an upper stem element nucleotide sequence I, a bulge element nucleotide sequence I, a lower stem element nucleotide sequence I, and a nexus stem element nucleotide sequence I;

a second Type II CRISPR-Cas9-associated split-nexus polynucleotide having a 5' end and a 3' end (sn2-casPN) comprising, in the 5' to 3' direction, a nexus stem element nucleotide sequence II, a second stem element comprising a hairpin, and a third stem element comprising a hairpin, wherein the nexus stem element nucleotide sequence I of the sn1-casPN and the nexus stem element nucleotide sequence II of the sn2-casPN are capable of forming a nexus stem element by base-pair hydrogen bonding between the nexus stem element nucleotide sequence I and the nexus stem element nucleotide sequence II; and a third Type II CRISPR-Cas9-associated polynucleotide having a 5' end and a 3' end (sn3-casPN) comprising, in the 5' to 3' direction, a DNA target binding sequence, a lower stem element nucleotide sequence II, a bulge element nucleotide sequence II, and an upper stem element nucleotide sequence II, wherein the upper stem element nucleotide sequence I of the sn1-casPN and the upper stem element nucleotide sequence II of the sn3-casPN are capable of forming an upper stem element by base-pair hydrogen bonding between the upper stem element nucleotide sequence I and the upper stem element nucleotide sequence II, and the lower stem element nucleotide sequence I of the sn1-casPN and the lower stem element nucleotide sequence II of the sn3-casPN are capable of forming a lower stem element by base-pair hydrogen bonding between the lower stem element nucleotide sequence I and the lower stem element nucleotide sequence II;

wherein the 5' end of the sn1-casPN is covalently bonded to the 3' end of the sn3-casPN.

16. The composition of claim 15, wherein the first Type II sn1-casPN further comprises a first auxiliary polynucleotide 3' adjacent the nexus stem element nucleotide sequence I, and the sn2-casPN further comprises a second auxiliary polynucleotide 5' adjacent the nexus stem element nucleotide sequence II.

17. A Type II CRISPR-Cas9 system, comprising:

the Type II CRISPR-Cas9-associated polynucleotide composition of claim 1; and a Cas9 protein or a DNA sequence encoding a Cas9 protein.

18. The composition of claim 9, wherein the effector binding element is a double-stranded RNA, and the effector binding element comprises a Csy4 protein binding site.

19. The composition of claim 16, wherein the first auxiliary polynucleotide further comprises an effector binding element nucleotide sequence I, the second auxiliary polynucleotide further comprises an effector binding element nucleotide sequence II, and the effector binding element nucleotide sequence I of the first auxiliary polynucleotide and the effector binding element nucleotide sequence II of the second auxiliary polynucleotide are capable of forming an effector binding element by base-pair hydrogen bonding between the effector binding element nucleotide sequence I and the effector binding element nucleotide sequence II.

* * * * *

UNITED STATES PATENT AND TRADEMARK OFFICE
CERTIFICATE OF CORRECTION

PATENT NO.         : 9,580,727 B1
APPLICATION NO.    : 14/835675
DATED              : February 28, 2017
INVENTOR(S)        : Paul Daniel Donohoue et al.

It is certified that error appears in the above-identified patent and that said Letters Patent is hereby corrected as shown below:

In the Specification

In Column 17, Line 4, delete "H", and insert --II--, therefor.

In Column 32, Line 19, delete "sequence II", and insert --sequence I--, therefor.

In Column 47, Line 45, delete "GALT", and insert --GAL7--, therefor.

In Column 56, Line 32, delete "(3-beta-N—(N',N'-dimethyl", and insert --(3-beta-N-(N',N'-dimethyl--, therefor.

In Column 74, Line 4, delete "Using Sn-cas", and insert --Using sn-cas--, therefor.

In Column 74, Line 53, delete "volume of 10 L", and insert --volume of 10 µL--, therefor.

In Column 76, Line 53, delete "Sn-casRNA/Cas9 Cleavage", and insert --sn-casRNA/Cas9 Cleavage--, therefor.

In Column 80, Line 10, delete "Sn1-CasRNA/Sn2-casRNA/Cas9 Cleavage Activity", and insert --sn1-casRNA/sn2-casRNA/Cas9 Cleavage Activity--, therefor.

In Column 87, Line 51, delete "Sn-casRNAs", and insert --sn-casRNAs--, therefor.

In Column 89, Line 56, delete "Agilent technologies", and insert --Agilent Technologies--, therefor.

In Column 92, Line 36, delete "Sn-casPN Construction", and insert --sn-casPN Construction--, therefor.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)

In Column 92, Line 59, delete "Minis", and insert --Mirus--, therefor.

In Column 96, Line 12, delete "his3delta200 leu2delta0 met15delta0", and insert --his3Δ200 leu2Δ0 met15Δ0--, therefor.

In Column 96, Line 13, delete "trp1delta63 ura3delta0", and insert --trp1Δ63 ura3Δ0--, therefor.

In Column 102, Line 44, delete "Sn-casRNAs/Cas9", and insert --sn-casRNAs/Cas9--, therefor.

In Column 102, Line 49, delete "T7 Promoter is Added to Cas9 Coding Region Opti-", and insert --T7 promoter is added to Cas9 coding region opti- --, therefor.

In Column 102, Line 50, delete "for Mammalian expression", and insert --for mammalian expression--, therefor.

In Column 103, Line 40, delete "Sn-casRNAs/", and insert --sn-casRNAs/--, therefor.

In the Claims

In Column 136, Line 22, delete "comprising third", and insert --comprising a third--, therefor.

In Column 136, Line 34, delete "and third", and insert --and the third--, therefor.

In Column 136, Line 39, delete "wherein 5' end", and insert --wherein the 5' end--, therefor.

In Column 137, Line 29, delete "forming linker", and insert --forming a linker--, therefor.

In Column 138, Line 24, delete "wherein the first Type II", and insert --wherein the--, therefor.

SEQUENCE LISTING

```
<160> NUMBER OF SEQ ID NOS: 90

<210> SEQ ID NO 1
<211> LENGTH: 31
<212> TYPE: RNA
<213> ORGANISM: Artificial Sequence
<220> FEATURE:
<223> OTHER INFORMATION: Derived from Streptococcus pyogenes

<400> SEQUENCE: 1
caaaacagca uagcaaguua aaauaaggcu a                                  31

<210> SEQ ID NO 2
<211> LENGTH: 46
```

```
<212> TYPE: RNA
<213> ORGANISM: Artificial Sequence
<220> FEATURE:
<223> OTHER INFORMATION: Derived from Streptococcus pyogenes

<400> SEQUENCE: 2
guccguuauc aacuugaaaa aguggcaccg agucggugcu uuuuuu            46

<210> SEQ ID NO 3
<211> LENGTH: 34
<212> TYPE: RNA
<213> ORGANISM: Artificial Sequence
<220> FEATURE:
<223> OTHER INFORMATION: Derived from Streptococcus thermophilus
      CRISPR-I

<400> SEQUENCE: 3
uaaaucuugc agaagcuaca acgauaaggc uuca                         34

<210> SEQ ID NO 4
<211> LENGTH: 53
<212> TYPE: RNA
<213> ORGANISM: Artificial Sequence
<220> FEATURE:
<223> OTHER INFORMATION: Derived from Streptococcus thermophilus
      CRISPR-I

<400> SEQUENCE: 4
ugccgaaauc aacacccugu cauuuuaugg caggguguuu ucguuauuuu uuu    53

<210> SEQ ID NO 5
<211> LENGTH: 32
<212> TYPE: RNA
<213> ORGANISM: Artificial Sequence
<220> FEATURE:
<223> OTHER INFORMATION: Derived from Listeria innocua

<400> SEQUENCE: 5
caaaauaaca uagcaaguua aaauaaggcu uu                           32

<210> SEQ ID NO 6
<211> LENGTH: 48
<212> TYPE: RNA
<213> ORGANISM: Artificial Sequence
<220> FEATURE:
<223> OTHER INFORMATION: Derived from Listeria innocua

<400> SEQUENCE: 6
guccguuauc aacuuuuaau uaaguagcgc uguuucggcg cuuuuuuu          48

<210> SEQ ID NO 7
<211> LENGTH: 45
<212> TYPE: RNA
<213> ORGANISM: Artificial Sequence
<220> FEATURE:
<223> OTHER INFORMATION: Derived from Neisseria meningitidis

<400> SEQUENCE: 7
cugcgaaaug agaaccguug cuacaauaag gccgucugaa aagau             45

<210> SEQ ID NO 8
<211> LENGTH: 35
<212> TYPE: RNA
<213> ORGANISM: Artificial Sequence
<220> FEATURE:
<223> OTHER INFORMATION: Derived from Neisseria meningitidis
```

<400> SEQUENCE: 8
gugccgcaac gcucugcccc uuaaagcuuc ugcuu          35

<210> SEQ ID NO 9
<211> LENGTH: 43
<212> TYPE: RNA
<213> ORGANISM: Artificial Sequence
<220> FEATURE:
<223> OTHER INFORMATION: Derived from Streptococcus gallolyticus

<400> SEQUENCE: 9
uuggagcuau ucgaaacaac acagcgaguu aaauaaggc uuu          43

<210> SEQ ID NO 10
<211> LENGTH: 49
<212> TYPE: RNA
<213> ORGANISM: Artificial Sequence
<220> FEATURE:
<223> OTHER INFORMATION: Derived from Streptococcus gallolyticus

<400> SEQUENCE: 10
guccguacac aacuuguaaa aguggcaccc gauucgggug cguuuuuu          49

<210> SEQ ID NO 11
<211> LENGTH: 46
<212> TYPE: RNA
<213> ORGANISM: Artificial Sequence
<220> FEATURE:
<223> OTHER INFORMATION: Derived from Staphylococcus aureus

<400> SEQUENCE: 11
auuguacuua uaccuaaaau uacagaaucu acuaaaacaa ggcaaa          46

<210> SEQ ID NO 12
<211> LENGTH: 39
<212> TYPE: RNA
<213> ORGANISM: Artificial Sequence
<220> FEATURE:
<223> OTHER INFORMATION: Derived from Staphylococcus aureus

<400> SEQUENCE: 12
augccguguu uaucucguca acuuguuggc gagauuuuu          39

<210> SEQ ID NO 13
<211> LENGTH: 48
<212> TYPE: RNA
<213> ORGANISM: Artificial Sequence
<220> FEATURE:
<223> OTHER INFORMATION: Derived from Corynebacterium diphtheriae

<400> SEQUENCE: 13
agucacuaac uuaauuaaau agaacugaac cucaguaagc auuggcuc          48

<210> SEQ ID NO 14
<211> LENGTH: 58
<212> TYPE: RNA
<213> ORGANISM: Artificial Sequence
<220> FEATURE:
<223> OTHER INFORMATION: Derived from Corynebacterium diphtheriae

<400> SEQUENCE: 14
guuuccaaug uugauugcuc cgccggugcu ccuuauuuuu aagggcgccg gcuuucuu          58

<210> SEQ ID NO 15
<211> LENGTH: 46

<212> TYPE: RNA
<213> ORGANISM: Artificial Sequence
<220> FEATURE:
<223> OTHER INFORMATION: Derived from Parvibaculum lavamentivorans

<400> SEQUENCE: 15
uagcaaaucg agaggcgguc gcuuucgca agcaaauuga ccccuu         46

<210> SEQ ID NO 16
<211> LENGTH: 77
<212> TYPE: RNA
<213> ORGANISM: Artificial Sequence
<220> FEATURE:
<223> OTHER INFORMATION: Derived from Parvibaculum lavamentivorans

<400> SEQUENCE: 16
gugcgggcuc ggcaucccaa ggucagcugc cgguuauuau cgaaaaggcc caccgcaagc         60
agcgcguggg ccuuuuu         77

<210> SEQ ID NO 17
<211> LENGTH: 51
<212> TYPE: RNA
<213> ORGANISM: Artificial Sequence
<220> FEATURE:
<223> OTHER INFORMATION: Derived from Campylobacter lari

<400> SEQUENCE: 17
aauucuugcu aaagaaauuu aaaaagagac uaaauaagu gguuuuggu c         51

<210> SEQ ID NO 18
<211> LENGTH: 73
<212> TYPE: RNA
<213> ORGANISM: Artificial Sequence
<220> FEATURE:
<223> OTHER INFORMATION: Derived from Campylobacter lari

<400> SEQUENCE: 18
auccacgcag gguuacaauc ccuuuaaaac cauuaaaauu caaauaaacu agguuguauc         60
aacuuaguuu uuu         73

<210> SEQ ID NO 19
<211> LENGTH: 54
<212> TYPE: RNA
<213> ORGANISM: Artificial Sequence
<220> FEATURE:
<223> OTHER INFORMATION: Derived from Neisseria cinerea

<400> SEQUENCE: 19
auugucgcac ugcgaaauga gaaccguugc uacaauaagg ccgucgaaa agau         54

<210> SEQ ID NO 20
<211> LENGTH: 85
<212> TYPE: RNA
<213> ORGANISM: Artificial Sequence
<220> FEATURE:
<223> OTHER INFORMATION: Derived from Neisseria cinerea

<400> SEQUENCE: 20
gugccgcaac gcucugcccc uuaaagcuuc ugcuuuaagg ggcaucguuu auucgguua         60 aaaaugccgu cugaaaccgg uuuuu         85

<210> SEQ ID NO 21
<211> LENGTH: 47
<212> TYPE: RNA

<213> ORGANISM: Artificial Sequence
<220> FEATURE:
<223> OTHER INFORMATION: Derived from Streptococcus pasteurianus

<400> SEQUENCE: 21
cuugcacggu acuuaaauc uugcugagcc uacaaagaua aggcuuu        47

<210> SEQ ID NO 22
<211> LENGTH: 43
<212> TYPE: RNA
<213> ORGANISM: Artificial Sequence
<220> FEATURE:
<223> OTHER INFORMATION: Derived from Streptococcus pasteurianus

<400> SEQUENCE: 22
augccgaauu caagcacccc auguuuugac augaggugcu uuu        43

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 23
agtaataata cgactcacta tag        23

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 24
aagcaccgac tcggtgccac tttt        24

<210> SEQ ID NO 25
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 25
taatacgact cactatagtc cgttatcaac ttgaaaaagt ggcaccgagt cggtgctt        58

<210> SEQ ID NO 26
<211> LENGTH: 49
<212> TYPE: DNA
<213> ORGANISM: Artificial Sequence
<220> FEATURE:
<223> OTHER INFORMATION: Oligonucleotide Primer

<400> SEQUENCE: 26
taatacgact cactatagca ggacagcata gcaagttgag ataaggcta        49

<210> SEQ ID NO 27
<211> LENGTH: 49
<212> TYPE: DNA
<213> ORGANISM: Artificial Sequence
<220> FEATURE:
<223> OTHER INFORMATION: Oligonucleotide Primer

<400> SEQUENCE: 27
tagccttatc tcaacttgct atgctgtcct gctatagtga gtcgtatta        49

<210> SEQ ID NO 28
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 28
taatacgact cactataggg gccactaggg acaggatgtc tcagagctat gctgt        55

<210> SEQ ID NO 29
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 29
acagcatagc tctgagacat cctgtcccta gtggcccta tagtgagtcg tatta        55

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 30
ccccgttctc ctgtggattc                                              20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 31
atcctctctg gctccatcgt                                              20

<210> SEQ ID NO 32
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 32
cactctttcc ctacacgacg ctcttccgat cttctggcaa ggagagagat gg           52

<210> SEQ ID NO 33
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 33
ggagttcaga cgtgtgctct tccgatctta tattcccagg gccggtta               48

<210> SEQ ID NO 34
<211> LENGTH: 57
<212> TYPE: DNA
<213> ORGANISM: Artificial Sequence
<220> FEATURE:

<223> OTHER INFORMATION: Oligonucleotide Primer

<400> SEQUENCE: 34
caagcagaag acggcatacg agattacgtg atgtgactgg agttcagacg tgtgctc    57

<210> SEQ ID NO 35
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 35
aatgatacgg cgaccaccga gatctacacc gtctaataca ctctttccct acacgacg    58

<210> SEQ ID NO 36
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 36
aatgatacgg cgaccaccga gatctacact ctctccgaca ctctttccct acacgacg    58

<210> SEQ ID NO 37
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 37
aatgatacgg cgaccaccga gatctacact cgactagaca ctctttccct acacgacg    58

<210> SEQ ID NO 38
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 38
aatgatacgg cgaccaccga gatctacact tctagctaca ctctttccct acacgacg    58

<210> SEQ ID NO 39
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 39
aatgatacgg cgaccaccga gatctacacc ctagagtaca ctctttccct acacgacg    58

<210> SEQ ID NO 40
<211> LENGTH: 58
<212> TYPE: DNA
<213> ORGANISM: Artificial Sequence
<220> FEATURE:
<223> OTHER INFORMATION: Oligonucleotide Primer

<400> SEQUENCE: 40
aatgatacgg cgaccaccga gatctacacc tattaagaca ctctttccct acacgacg    58

```
<210> SEQ ID NO 41
<211> LENGTH: 62
<212> TYPE: DNA
<213> ORGANISM: Artificial Sequence
<220> FEATURE:
<223> OTHER INFORMATION: Oligonucleotide Primer

<400> SEQUENCE: 41
ggcagtagcc ttatctcaac ttgctatgct gtcctgtttc caggacagca tagctctgag     60
ac                                                                    62

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 42
ggcagtagcc ttatctcaac                                                 20

<210> SEQ ID NO 43
<211> LENGTH: 63
<212> TYPE: DNA
<213> ORGANISM: Artificial Sequence
<220> FEATURE:
<223> OTHER INFORMATION: Oligonucleotide Primer

<400> SEQUENCE: 43
taatacgact cactataggc aggtccgtta tcaacttgaa aaagtggcac cgagtcggtg     60
ctt                                                                   63

<210> SEQ ID NO 44
<211> LENGTH: 67
<212> TYPE: DNA
<213> ORGANISM: Artificial Sequence
<220> FEATURE:
<223> OTHER INFORMATION: Oligonucleotide Primer

<400> SEQUENCE: 44
ggcagtgaac tagccttatc tcaacttgct atgctgtcct gtttccagga cagcatagct     60
ctgagac                                                               67

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 45
ggcagtgaac tagccttatc                                                 20

<210> SEQ ID NO 46
<211> LENGTH: 68
<212> TYPE: DNA
<213> ORGANISM: Artificial Sequence
<220> FEATURE:
<223> OTHER INFORMATION: Oligonucleotide Primer

<400> SEQUENCE: 46
taatacgact cactataggc agctaaggtc cgttatcaac ttgaaaaagt ggcaccgagt     60
cggtgctt                                                              68
```

<210> SEQ ID NO 47
<211> LENGTH: 56
<212> TYPE: DNA
<213> ORGANISM: Artificial Sequence
<220> FEATURE:
<223> OTHER INFORMATION: Oligonucleotide Primer

<400> SEQUENCE: 47
taatacgact cactataggg gccactaggg acaggatgtc tcagagctat gctgtc         56

<210> SEQ ID NO 48
<211> LENGTH: 56
<212> TYPE: DNA
<213> ORGANISM: Artificial Sequence
<220> FEATURE:
<223> OTHER INFORMATION: Oligonucleotide Primer

<400> SEQUENCE: 48
taatacgact cactatagtt tgtgtttcca taaactggtc tcagagctat gctgtc         56

<210> SEQ ID NO 49
<211> LENGTH: 56
<212> TYPE: DNA
<213> ORGANISM: Artificial Sequence
<220> FEATURE:
<223> OTHER INFORMATION: Oligonucleotide Primer

<400> SEQUENCE: 49
taatacgact cactatagcc cgccaccacc aggatgtgtc tcagagctat gctgtc         56

<210> SEQ ID NO 50
<211> LENGTH: 56
<212> TYPE: DNA
<213> ORGANISM: Artificial Sequence
<220> FEATURE:
<223> OTHER INFORMATION: Oligonucleotide Primer

<400> SEQUENCE: 50
taatacgact cactataggc agccagcatg atgagacgtc tcagagctat gctgtc         56

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 51
aagcaccgac tcggtgccac                                                 20

<210> SEQ ID NO 52
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 52
cactctttcc ctacacgacg ctcttccgat ctacatgcac acccatgttt tg             52

<210> SEQ ID NO 53
<211> LENGTH: 48
<212> TYPE: DNA
<213> ORGANISM: Artificial Sequence
<220> FEATURE:
<223> OTHER INFORMATION: Oligonucleotide Primer

```
<400> SEQUENCE: 53
ggagttcaga cgtgtgctct tccgatctaa catttccagg tgacaggc                48

<210> SEQ ID NO 54
<211> LENGTH: 50
<212> TYPE: DNA
<213> ORGANISM: Artificial Sequence
<220> FEATURE:
<223> OTHER INFORMATION: Oligonucleotide Primer

<400> SEQUENCE: 54
cactctttcc ctacacgacg ctcttccgat ctgttccgac gctccttgaa              50

<210> SEQ ID NO 55
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 55
ggagttcaga cgtgtgctct tccgatctca gatgcgatga cctttgtg               48

<210> SEQ ID NO 56
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 56
cactctttcc ctacacgacg ctcttccgat ctaagaaagg caagaagcct gg          52

<210> SEQ ID NO 57
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 57
ggagttcaga cgtgtgctct tccgatctgc tggcctgaga cattccta               48

<210> SEQ ID NO 58
<211> LENGTH: 57
<212> TYPE: DNA
<213> ORGANISM: Artificial Sequence
<220> FEATURE:
<223> OTHER INFORMATION: Oligonucleotide Primer

<400> SEQUENCE: 58
tagccttatc tcaacttgct atgctgtcct gtttccagga cagcatagct ctgagac     57

<210> SEQ ID NO 59
<211> LENGTH: 57
<212> TYPE: DNA
<213> ORGANISM: Artificial Sequence
<220> FEATURE:
<223> OTHER INFORMATION: Oligonucleotide Primer

<400> SEQUENCE: 59
taatacgact cactataggg gccactaggg acaggatgtc tcagagctat gcagtcc     57

<210> SEQ ID NO 60
```

<210> SEQ ID NO 60
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 60
cagtagcctt atctcaactt gctatgcagt cctgtttcca ggactgcata gctctgagac    60

<210> SEQ ID NO 61
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 61
ctgcctatac ggcagtagcc ttatctcaac ttgctatgca    40

<210> SEQ ID NO 62
<211> LENGTH: 57
<212> TYPE: DNA
<213> ORGANISM: Artificial Sequence
<220> FEATURE:
<223> OTHER INFORMATION: Oligonucleotide Primer

<400> SEQUENCE: 62
taatacgact cactatagct gccgtatagg caggtccgtt atcaacttga aaaagtg    57

<210> SEQ ID NO 63
<211> LENGTH: 43
<212> TYPE: DNA
<213> ORGANISM: Artificial Sequence
<220> FEATURE:
<223> OTHER INFORMATION: Oligonucleotide Primer

<400> SEQUENCE: 63
aagcaccgac tcggtgccac ttttcaagt tgataacgga cct    43

<210> SEQ ID NO 64
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 64
gtctagcctt atctcaactt gctatgcagt cctgtttcca ggactgcata gctctgagac    60

<210> SEQ ID NO 65
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 65
ctgcctatac ggcagtgtct agccttatct caacttgcta    40

<210> SEQ ID NO 66
<211> LENGTH: 57
<212> TYPE: DNA
<213> ORGANISM: Artificial Sequence
<220> FEATURE:
<223> OTHER INFORMATION: Oligonucleotide Primer

<400> SEQUENCE: 66

```
taatacgact cactatagct gccgtatagg cagagacagt ccgttatcaa cttgaaa      57
```

<210> SEQ ID NO 67
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 67

```
aagcaccgac tcggtgccac tttttcaagt tgataacgga ctgtctct              48
```

<210> SEQ ID NO 68
<211> LENGTH: 41
<212> TYPE: RNA
<213> ORGANISM: Artificial Sequence
<220> FEATURE:
<223> OTHER INFORMATION: Split-nexus Cas9-associated RNA

<400> SEQUENCE: 68

```
guccguuauc aacuugaaaa aguggcaccg agucggugcu u                     41
```

<210> SEQ ID NO 69
<211> LENGTH: 32
<212> TYPE: RNA
<213> ORGANISM: Artificial Sequence
<220> FEATURE:
<223> OTHER INFORMATION: Split-nexus Cas9-associated RNA

<400> SEQUENCE: 69

```
gcaggacagc auagcaaguu gagauaaggc ua                               32
```

<210> SEQ ID NO 70
<211> LENGTH: 38
<212> TYPE: RNA
<213> ORGANISM: Artificial Sequence
<220> FEATURE:
<223> OTHER INFORMATION: Split-nexus Cas9-associated RNA

<400> SEQUENCE: 70

```
ggggccacua gggacaggau gucucagagc uaugcugu                         38
```

<210> SEQ ID NO 71
<211> LENGTH: 82
<212> TYPE: RNA
<213> ORGANISM: Artificial Sequence
<220> FEATURE:
<223> OTHER INFORMATION: Split-nexus Cas9-associated RNA

<400> SEQUENCE: 71

```
ggggccacua gggacaggau gucucagagc uaugcugucc uggaaacagg acagcauagc  60
aaguugagau aaggcuacug cc                                          82
```

<210> SEQ ID NO 72
<211> LENGTH: 82
<212> TYPE: RNA
<213> ORGANISM: Artificial Sequence
<220> FEATURE:
<223> OTHER INFORMATION: Split-nexus Cas9-associated RNA

<400> SEQUENCE: 72

```
guuuguguuu ccauaaacug gucucagagc uaugcugucc uggaaacagg acagcauagc  60
aaguugagau aaggcuacug cc                                          82
```

```
<210> SEQ ID NO 73
<211> LENGTH: 82
<212> TYPE: RNA
<213> ORGANISM: Artificial Sequence
<220> FEATURE:
<223> OTHER INFORMATION: Split-nexus Cas9-associated RNA

<400> SEQUENCE: 73
gcccgccacc accaggaugu gucucagagc uaugcugucc uggaaacagg acagcauagc    60
aaguugagau aaggcuacug cc                                             82

<210> SEQ ID NO 74
<211> LENGTH: 82
<212> TYPE: RNA
<213> ORGANISM: Artificial Sequence
<220> FEATURE:
<223> OTHER INFORMATION: Split-nexus Cas9-associated RNA

<400> SEQUENCE: 74
ggcagccagc augaugagac gucucagagc uaugcugucc uggaaacagg acagcauagc    60
aaguugagau aaggcuacug cc                                             82

<210> SEQ ID NO 75
<211> LENGTH: 46
<212> TYPE: RNA
<213> ORGANISM: Artificial Sequence
<220> FEATURE:
<223> OTHER INFORMATION: Split-nexus Cas9-associated RNA

<400> SEQUENCE: 75
ggcagguccg uuaucaacuu gaaaaagugg caccgagucg gugcuu                   46

<210> SEQ ID NO 76
<211> LENGTH: 87
<212> TYPE: RNA
<213> ORGANISM: Artificial Sequence
<220> FEATURE:
<223> OTHER INFORMATION: Split-nexus Cas9-associated RNA

<400> SEQUENCE: 76
ggggccacua gggacaggau gucucagagc uaugcugucc uggaaacagg acagcauagc    60
aaguugagau aaggcuaguu cacugcc                                        87

<210> SEQ ID NO 77
<211> LENGTH: 87
<212> TYPE: RNA
<213> ORGANISM: Artificial Sequence
<220> FEATURE:
<223> OTHER INFORMATION: Split-nexus Cas9-associated RNA

<400> SEQUENCE: 77
guuuguguuu ccauaaacug gucucagagc uaugcugucc uggaaacagg acagcauagc    60
aaguugagau aaggcuaguu cacugcc                                        87

<210> SEQ ID NO 78
<211> LENGTH: 87
<212> TYPE: RNA
<213> ORGANISM: Artificial Sequence
<220> FEATURE:
<223> OTHER INFORMATION: Split-nexus Cas9-associated RNA

<400> SEQUENCE: 78
gcccgccacc accaggaugu gucucagagc uaugcugucc uggaaacagg acagcauagc    60
```

```
aaguugagau aaggcuaguu cacugcc                                   87

<210> SEQ ID NO 79
<211> LENGTH: 87
<212> TYPE: RNA
<213> ORGANISM: Artificial Sequence
<220> FEATURE:
<223> OTHER INFORMATION: Split-nexus Cas9-associated RNA

<400> SEQUENCE: 79
ggcagccagc augaugagac gucucagagc uaugcugucc uggaaacagg acagcauagc  60
aaguugagau aaggcuaguu cacugcc                                    87

<210> SEQ ID NO 80
<211> LENGTH: 68
<212> TYPE: RNA
<213> ORGANISM: Artificial Sequence
<220> FEATURE:
<223> OTHER INFORMATION: Split-nexus Cas9-associated RNA

<400> SEQUENCE: 80
gggcagugaa cuagccuuau cucaacuugc uaugcugucc uguuccagg acagcauagc   60 ucugagac                                                         68

<210> SEQ ID NO 81
<211> LENGTH: 77
<212> TYPE: RNA
<213> ORGANISM: Artificial Sequence
<220> FEATURE:
<223> OTHER INFORMATION: Split-nexus Cas9-associated RNA

<400> SEQUENCE: 81
ggggccacua gggacaggau gucucagagc uaugcugucc uggaaacagg acagcauagc  60
aaguugagau aaggcua                                               77

<210> SEQ ID NO 82
<211> LENGTH: 77
<212> TYPE: RNA
<213> ORGANISM: Artificial Sequence
<220> FEATURE:
<223> OTHER INFORMATION: Split-nexus Cas9-associated RNA

<400> SEQUENCE: 82
gcccgccacc accaggaugu gucucagagc uaugcugucc uggaaacagg acagcauagc  60
aaguugagau aaggcua                                               77

<210> SEQ ID NO 83
<211> LENGTH: 77
<212> TYPE: RNA
<213> ORGANISM: Artificial Sequence
<220> FEATURE:
<223> OTHER INFORMATION: Split-nexus Cas9-associated RNA

<400> SEQUENCE: 83
ggcagccagc augaugagac gucucagagc uaugcugucc uggaaacagg acagcauagc  60
aaguugagau aaggcua                                               77

<210> SEQ ID NO 84
<211> LENGTH: 41
<212> TYPE: RNA
<213> ORGANISM: Artificial Sequence
<220> FEATURE:
```

```
<223> OTHER INFORMATION: Split-nexus Cas9-associated RNA

<400> SEQUENCE: 84
guccguuauc aacuugaaaa aguggcaccg agucggugcu u                  41

<210> SEQ ID NO 85
<211> LENGTH: 92
<212> TYPE: RNA
<213> ORGANISM: Artificial Sequence
<220> FEATURE:
<223> OTHER INFORMATION: Split-nexus Cas9-associated RNA

<400> SEQUENCE: 85
ggggccacua gggacaggau gucucagagc uaugcagucc uggaaacagg acugcauagc   60
aaguugagau aaggcuacug ccguauaggc ag                               92

<210> SEQ ID NO 86
<211> LENGTH: 56
<212> TYPE: RNA
<213> ORGANISM: Artificial Sequence
<220> FEATURE:
<223> OTHER INFORMATION: Split-nexus Cas9-associated RNA

<400> SEQUENCE: 86
cugccguaua ggcagguccg uuaucaacuu gaaaagugg caccgagucg gugcuu        56

<210> SEQ ID NO 87
<211> LENGTH: 96
<212> TYPE: RNA
<213> ORGANISM: Artificial Sequence
<220> FEATURE:
<223> OTHER INFORMATION: Split-nexus Cas9-associated RNA

<400> SEQUENCE: 87
ggggccacua gggacaggau gucucagagc uaugcagucc uggaaacagg acugcauagc   60
aaguugagau aaggcuagac acugccguau aggcag                             96

<210> SEQ ID NO 88
<211> LENGTH: 61
<212> TYPE: RNA
<213> ORGANISM: Artificial Sequence
<220> FEATURE:
<223> OTHER INFORMATION: Split-nexus Cas9-associated RNA

<400> SEQUENCE: 88
cugccguaua ggcagagaca guccguuauc aacuugaaaa aguggcaccg agucggugcu   60
u                                                                   61

<210> SEQ ID NO 89
<211> LENGTH: 20
<212> TYPE: DNA
<213> ORGANISM: Artificial Sequence
<220> FEATURE:
<223> OTHER INFORMATION: Tet1-Spacer

<400> SEQUENCE: 89
ggctgctgtc agggagctca                                              20

<210> SEQ ID NO 90
<211> LENGTH: 20
<212> TYPE: DNA
<213> ORGANISM: Artificial Sequence
<220> FEATURE:
<223> OTHER INFORMATION: Tet2-Spacer
```

```
<400> SEQUENCE: 90
gaaagtgcca acagatatcc                                              20
```